US012751977B2

(12) United States Patent
von Maltzahn et al.

(10) Patent No.: US 12,751,977 B2
(45) Date of Patent: Oct. 6, 2026

(54) METHODS AND COMPOSITIONS OF CHONDRISOMES

(71) Applicants: Sana Biotechnology, Inc., Seattle, WA (US); The Children's Medical Center Corporation, Boston, MA (US)

(72) Inventors: Geoffrey A. von Maltzahn, Somerville, MA (US); John Miles Milwid, Denver, CO (US); Michael Travis Mee, Montreal (CA); Jacob Rosenblum Rubens, Cambridge, MA (US); David Chess, Waltham, MA (US); Kyle Marvin Trudeau, Boston, MA (US); Kiana Mahdaviani, Chestnut Hill, MA (US); Jacob Feala, Franklin, MA (US); James D. McCully, Marblehead, MA (US); Douglas B. Cowan, Brighton, MA (US)

(73) Assignees: Sana Biotechnology, Inc., Seattle, WA (US); The Children's Medical Center Corporation, Boston, MA (US)

( * ) Notice: Subject to any disclaimer, the term of this patent is extended or adjusted under 35 U.S.C. 154(b) by 1272 days.

(21) Appl. No.: 17/651,056

(22) Filed: Feb. 14, 2022

(65) Prior Publication Data

US 2022/0160784 A1 May 26, 2022

Related U.S. Application Data

(63) Continuation of application No. 16/252,369, filed on Jan. 18, 2019, now abandoned, which is a continuation of application No. 15/365,239, filed on Nov. 30, 2016, now abandoned.

(60) Provisional application No. 62/261,169, filed on Nov. 30, 2015, provisional application No. 62/261,157, filed on Nov. 30, 2015, provisional application No. 62/261,170, filed on Nov. 30, 2015.

(51) Int. Cl.

| | |
|---|---|
| ***A61P 3/00*** | (2006.01) |
| ***A61K 35/12*** | (2015.01) |
| ***A61K 35/14*** | (2015.01) |
| ***A61K 35/19*** | (2015.01) |
| ***A61K 35/33*** | (2015.01) |
| ***A61K 35/34*** | (2015.01) |
| ***A61K 35/35*** | (2015.01) |
| ***A61K 38/17*** | (2006.01) |
| ***C12N 15/87*** | (2006.01) |
| ***G01N 33/15*** | (2006.01) |
| *A61K 9/00* | (2006.01) |

(52) U.S. Cl.

CPC .............. *A61K 35/35* (2013.01); *A61K 35/12* (2013.01); *A61K 35/14* (2013.01); *A61K 35/19* (2013.01); *A61K 35/33* (2013.01); *A61K 35/34* (2013.01); *A61K 38/1709* (2013.01); *A61P 3/00* (2018.01); *C12N 15/87* (2013.01); *G01N 33/15* (2013.01); *A61K 9/0029* (2013.01)

(58) Field of Classification Search

None

See application file for complete search history.

(56) References Cited

U.S. PATENT DOCUMENTS

| | | | |
|---|---|---|---|
| 2,561,043 | A | 7/1951 | Ayers |
| 4,279,890 | A | 7/1981 | Harris et al. |
| 5,460,940 | A | 10/1995 | Yves et al. |
| 5,830,445 | A | 11/1998 | Bouillon et al. |
| 6,562,864 | B1 | 5/2003 | Larson |
| 6,693,086 | B1 | 2/2004 | Dow et al. |
| 6,777,227 | B2 | 8/2004 | Ricci et al. |
| 6,867,197 | B1 | 3/2005 | Davis et al. |
| 7,279,326 | B2 | 10/2007 | Weissig et al. |
| 7,745,651 | B2 | 6/2010 | Heyes et al. |
| 7,799,565 | B2 | 9/2010 | MacLachlan et al. |
| 7,803,397 | B2 | 9/2010 | Heyes et al. |
| 7,838,658 | B2 | 11/2010 | MacLachlan et al. |
| 7,901,708 | B2 | 3/2011 | MacLachlan et al. |
| 7,915,399 | B2 | 3/2011 | MacLachlan et al. |
| 7,923,984 | B2 | 4/2011 | Philbert |
| 7,982,027 | B2 | 7/2011 | MacLachlan et al. |
| 8,058,069 | B2 | 11/2011 | Yaworski et al. |
| 8,084,599 | B2 | 12/2011 | Rossi et al. |
| 8,101,741 | B2 | 1/2012 | MacLachlan et al. |
| 8,188,263 | B2 | 5/2012 | MacLachlan et al. |
| 8,236,943 | B2 | 8/2012 | Lee et al. |
| 8,283,333 | B2 | 10/2012 | Yaworski et al. |
| 8,349,809 | B2 | 1/2013 | Brown et al. |
| 8,513,207 | B2 | 8/2013 | Brown et al. |
| 8,697,359 | B1 | 4/2014 | Zhang |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang et al. |

(Continued)

FOREIGN PATENT DOCUMENTS

| | | |
|---|---|---|
| EP | 1519714 | 4/2005 |
| EP | 1664316 | 6/2006 |

(Continued)

OTHER PUBLICATIONS

"Chondrisome" Merriam-Webster.com Dictionary, Merriam-Webster https://www.merriam-webster.com/dictionary/chondriosome, accessed Feb. 3, 2021.

(Continued)

*Primary Examiner* — Evelyn Y Pyla

(74) *Attorney, Agent, or Firm* — Morrison & Foerster LLP

(57) ABSTRACT

Therapeutic chondrisome compositions and related methods are described.

22 Claims, 10 Drawing Sheets

Specification includes a Sequence Listing.

(56) References Cited

U.S. PATENT DOCUMENTS

| | | | |
|---|---|---|---|
| 8,889,418 | B2 | 11/2014 | Zhang et al. |
| 8,895,308 | B1 | 11/2014 | Zhang et al. |
| 8,906,616 | B2 | 12/2014 | Zhang et al. |
| 8,932,814 | B2 | 1/2015 | Cong et al. |
| 8,945,839 | B2 | 2/2015 | Zhang |
| 8,993,233 | B2 | 3/2015 | Zhang et al. |
| 8,999,641 | B2 | 4/2015 | Zhang et al. |
| 9,315,773 | B2 | 4/2016 | Schiedner et al. |
| 10,370,458 | B2 | 8/2019 | McCully et al. |
| 2004/0131641 | A1 | 7/2004 | Mikszta et al. |
| 2004/0161421 | A1 | 8/2004 | Komowski et al. |
| 2004/0171809 | A1 | 9/2004 | Korsmeyer |
| 2007/0128726 | A1 | 6/2007 | Koob et al. |
| 2008/0014144 | A1 | 1/2008 | Saltzman et al. |
| 2008/0260637 | A1 | 10/2008 | Dickman |
| 2008/0275005 | A1 | 11/2008 | Murphy |
| 2011/0008310 | A1 | 1/2011 | Cataldo et al. |
| 2011/0130309 | A1 | 6/2011 | Cardone |
| 2011/0177051 | A1 | 7/2011 | Galski-Lorberoum |
| 2011/0321200 | A1 | 12/2011 | Hyde et al. |
| 2012/0039810 | A1 | 2/2012 | Gorenstein et al. |
| 2012/0107285 | A1 | 5/2012 | Hyde et al. |
| 2012/0110683 | A1 | 5/2012 | Shomura et al. |
| 2012/0171716 | A1 | 7/2012 | Sun et al. |
| 2013/0022666 | A1 | 1/2013 | Brzezinska et al. |
| 2013/0149778 | A1 | 6/2013 | Chang et al. |
| 2013/0287748 | A1 | 10/2013 | June et al. |
| 2014/0051174 | A1 | 2/2014 | Burke et al. |
| 2014/0086886 | A1 | 3/2014 | Westenfelder |
| 2014/0106004 | A1 | 4/2014 | Wong et al. |
| 2014/0178993 | A1 | 6/2014 | Chang et al. |
| 2014/0193511 | A1 | 7/2014 | Yivgi-Ohana et al. |
| 2014/0314879 | A1 | 10/2014 | Lawendy |
| 2015/0026833 | A1 | 1/2015 | Ande et al. |
| 2015/0079193 | A1 | 3/2015 | Yivgi-Ohana et al. |
| 2015/0344912 | A1 | 12/2015 | Kim et al. |
| 2016/0020823 | A1 | 1/2016 | Kuipers et al. |
| 2016/0138008 | A1 | 5/2016 | Doudna et al. |
| 2016/0208243 | A1 | 7/2016 | Zhang et al. |
| 2017/0120237 | A1 | 5/2017 | McCully et al. |
| 2017/0151287 | A1 | 6/2017 | Von Maltzahn et al. |
| 2017/0290763 | A1 | 10/2017 | Su |
| 2018/0057610 | A1 | 3/2018 | McCully et al. |
| 2019/0374582 | A1 | 12/2019 | Von Maltzahn et al. |
| 2020/0123273 | A1 | 4/2020 | McCully et al. |
| 2021/0023143 | A1 | 1/2021 | Yivgi-Ohana et al. |
| 2022/0160782 | A1 | 5/2022 | McCully |

FOREIGN PATENT DOCUMENTS

| | | |
|---|---|---|
| EP | 1766035 | 3/2007 |
| EP | 1781593 | 5/2007 |
| WO | WO 1988/07580 | 3/1988 |
| WO | WO 2006/059329 | 6/2006 |
| WO | WO 2008/137035 | 11/2008 |
| WO | WO 2008/152626 | 12/2008 |
| WO | WO 2013/035101 | 3/2013 |
| WO | WO 2013/171752 | 11/2013 |
| WO | WO 2015/192020 | 12/2015 |
| WO | WO 2016/135723 | 9/2016 |
| WO | WO 2017/095940 | 6/2017 |
| WO | WO 2017/095944 | 6/2017 |
| WO | WO 2017/095946 | 6/2017 |
| WO | WO 2017/124037 | 7/2017 |

OTHER PUBLICATIONS

Ahmad et al (2014) Miro1 regulated intercellular mitochondrial transport and enhances mesenchymal stem cell rescue efficacy. EMBO Journal 33(9):994-1010.

Akurathi et al., "Preliminary Evaluation of 18F-Rhodamine 6G as a Tumor-Imaging Agent," J Nucl Med, May 2013, 54 (Supplement 2): 1148.

Alfonzo et al. (2009). Mitochondrial tRNA import-the challenge to understand has just begun. Biol. Chem. 390(8): 717-722.

Allen et al., "Angiopellosis as an Alternative Mechanism of Cell Extravasation," Stem Cells, Jan. 2017, 35:170-180.

Altschul, et al "Basic Local Alignment Search Tool" J_ Mal. Biol. (1990) 215:403-410.

Amarzguioui et al. (Feb. 18, 2004), "An algorithm for selection of functional siRNA sequences," *Biochemical and Biophysical Research Communications*, 316, 1050-1058.

Angsutararux et al., "Chemotherapy-Induced Cardiotoxicity: Overview of the Roles of Oxidative Stress," Oxid Med Cell Longev, Oct. 2015, 795602, 13 pages.

Arora "Cell Culture Media: A Review" Mater Methods (2013) vol. 3, No. 175, pp. 1-21.

Augustin et al. (2005). Characterization of peptides released from mitochondria: evidence for constant proteolysis and peptide efflux. J_ Biol. Chem. 280(4): 2691-2699.

Bacman et al. (2013). Specific elimination of mutant mitochondrial genomes in patient-derived cells by mito TALENs. Nat. Med. 19(9): 1111-1113.

Bansal et al., "Photocontrolled nanoparticle delivery systems for biomedical applications," Accounts of Chemical Research, Oct. 2014, 47(10), 3052-3060.

Barhoumi et al., "Ultraviolet light-mediated drug delivery: Principles, applications, and challenges," Journal of Controlled Release, Dec. 2015, 219, 40 pages.

Bartel (2004). MicroRNAs: genomics, biogenesis, mechanism, and function. Cell 116(2): 281-297.

Bartholoma et al, "Biological characterzation of F 18-labeled Rhodamine B, a potential position emission tomography perfusion tracer," Nuclear Medicine and Biology, Nov. 1, 2013, 40(8): 1043-8.

Bartholomä et al., "18F-labeled rhodamines as potential myocardial perfusion agents: comparison of pharmacokinetic properties of several rhodamines," Nuclear Medicine and Biology, Oct. 1, 2015, 42(10):796-803.

Bershteyn et al. (2008). Polymer-supported lipid shells, onions, and flowers. Safi Matter 4:1787-1787.

Birmingham et al. (2006). 3' UTR seed matches, but not overall identity, are associated with RNAi off-targets. Nat. Methods 3(3): 199-204.

Birsoy et al., "An Essential Role of the Mitochondrial Electron Transport Chain in Cell Proliferation Is to Enable Aspartate Synthesis," Cell, Jul. 2015, 162: 540-551.

Black et al., "Microarray and proteomic analysis of the cardioprotective effects of cold blood cardioplegia in the mature and aged male and female," Physiological Genomics, Nov. 1, 2012, 44(21):1027-41.

Boezeman et al., "Systematic review of clinical applications of monitoring muscle tissue oxygenation with near-infrared spectoscopy in vascular diease," Microvasc Res, Mar. 2016, 104, 47 pages.

Boldogh et al. (2007). Cell-free assays for mitochondria-cytoskeleton interactions. Methods Cell Biol. 80: 683-706.

Bolender et al. (2008). Multiple pathways for sorting mitochondrial precursor proteins. EMBO Rep. 9: 42-49.

Boudreau et al. (2014). Platelets release mitochondria serving as substrate for bactericidal group !IA-secreted phospholipase A2 to promote inflammation. Blood 124(14): 2173-2183.

Brand et al., "Assessing mitochondrial dysfunction in cells", Biochemistry Journal (Apr. 15, 2011), vol. 435 p. 297-312.

Calvo et al. (2015). MitoCarta2.0: an updated inventory of mammalian mitochondrial proteins. Nucleic Acids Res. 44 D1): D1251-D1257.

Cameron et al. (2016). Development of Therapeutics That Induce Mitochondrial Biogenesis for the Treatment of Acute and Chronic Degenerative Diseases. J_ Med. Chem. 59(23): 10411-10434.

Cannon et al., "Brown Adipose Tissue: Function and Physiological Significance," Physiol Rev, Jan. 2004, 84: 277-359.

Cavers "Chondrisomes (Mitochondria) and Their Significance" The New Phytologist (1914) vol. 13, No. 3, pp. 96-106.

Cedikova et al., "Mitochrondia in white, brown, and beige adipocytes," Stem cells international, 2016: 1-11, Jan. 2016.

(56) References Cited

OTHER PUBLICATIONS

Chalk et al. (Apr. 26, 2004), "Improved and automated prediction of effective siRNA," *Biochemical and Biophysical Research Communications*, 319, 264-274.
Chance et al (1961). The interaction of energy and electron transfer reactions in mitochondria. VI. The efficiency of the eaction. J_ Biol. Chem. 236: 1577-1584.
Chance et al. (1955). A simple and rapid assay of oxidative phosphorylation. Nature 175(4469): 1120-1121.
Chang et al., "Treatment of human cells derived from MERRF syndrome by peptide-mediated mitochondrial delivery," Cryotherapy, Dec. 1, 2013, 15(12): 1580-96.
Chattopadhyay et al., T3 fails to restore mitochondrial thiol redox status altered by experimental hypothyroidism in at testis, General and Comparative Endocrinology (2010) vol. 169, pp. 39-47.
Chen et al. (2016). Absolute Quantification of Matrix Metabolites Reveals the Dynamics of Mitochondrial Metabolism. Cell 166(5): 1324-1337.
Cheng et al., "Brief Report: Mechanism of extravasation of infused stem cells," Stem cells, 2012, 30: 2835-2842.
Colman, "Effects of amino acid sequence changes on antibody-antigen interactions," Research in Immunology, Jan. 1, 1994, 145(1): 33-6.
Cong et al. (2013) Multiplex Genome Engineering Using CRISPR/Cas Systems. Science 339:819-823.
Cowan et al., "Intracoronary delivery of mitochondria to the ischemic heart for cardioprotection." PloS one, Aug. 2016, 11(8): e0160889, 19 pages.
Cypress et al., "Brown fat as a therapy for obesity and diabetes," Current Opinion in Endocrinology, Diabetes, and Obesity, Apr. 2010, 17: 143-149.
Dare et al., "The mitochondria-targeted anti-oxidant MitoQ decreasesischemia-reperfusion injury in a murine sygeneic heart transplant model," J Heart Lung Transplant, Nov. 2015, 34(11): 1471-80.
Doench et al. (2003). siRNAs can function as miRNAs. Genes Dev. 17(4): 438-442.
Dolezal et al. (2006). Evolution of the molecular machines for protein import into mitochondria. Science 313: 314-318.
Ejsing et al. (2009). Global analysis of the yeast lipidome by quantitative shotgun mass spectrometry. PNAS 106 7):2136-2141.
Eliott et al. "Mitochondria organelle transplantation: introduction of normal epithelial mitochondria into human cancel cells inhibits proliferation and increases drug sensitivity" Breast Cancer Res Treat (2012) vol. 136, pp. 347-354.
Faulk et al., "Magnesium cardioplegia enhances mRNA levels and the maximal velocity of cytochrome oxidase I in the senescent myocardium during global ischemia," Circulation, Nov. 1, 1995, 92(9):405-12.
Faulk et al., "Myocardial mitochondrial calcium accumulation modulates nuclear calcium accumulation and DNA fragmentation," The Annals of thoracic surgery, Aug. 1, 1995, 60(2):338-44.
Flaquer et al., "Mitochondrial genetic variants identified to be associated with posttraumalic stress disorder," ranslalional Psychiatry, Mar. 2015, 5(3):e524.
Frezza et al., "Organelle isolation: functional mitochondria from mouse liver, muscle and cultured filroblasls," Nature Protocols, 2007, 2(2): 287-295.
Friehs et al., "Pressure-overload hypertrophy of the developing heart reveals activation of divergent gene and protein pathways in the left and right ventricular myocardium," American Journal of Physiology-Heart and Circulatory Physiology, Mar. 1, 2013, 304(5):H697-708.
Gabriel (2007). The mitochondrial machinery for import of precursor proteins. Methods Mol. Biol. 390: 99-117.
Gasteiger et al., "Protein Identification and Analysis Tools on the ExPASy Server," The Proteomics Protocols Handbook (2005) 571-607.
Geng et al (2013). Microfluidic electroporation for cellular analysis and delivery. Lab Chip. 13(19):3803-3821.
Glancy et al. (2013). Effect of calcium on the oxidative phosphorylation cascade in skeletal muscle mitochondria. Biochemistry 52(16): 2793-2809.
Gram et al., "Skeletal muscle mitochondrial H202 emission increases with immobilization and decreases after aerobic raining in young and older men," J Physiol. (2015) 593(17): 4011-4027.
Green et al. Metabolic, enzymatic, and transporter responses in human muscle during three consecutive days of exercise and recovery. Am J Physiol Regul Integr Comp Physiol (2008) 295(4): R12380-R12350.
Gross et al., "Isolation of functional mitochondria from rat kidney and skeletal muscle without manual homogenization," Anal Biochem, Nov. 2011, 418:213-223.
Guo et al., "Cardiovascular toxicities from systemic breast cancer therapy," Front Oncol, Dec. 4, 2014, 10 pages.
Hamilton, "The hidden risks for 'three-person' babies," Nature, Sep. 2015, 525(7570):444-6.
Han et al., "An unexpectedly labile mitochondrially encoded protein is required for Mia expression," Immunogenetics, Jul. 1989, 29: 258-264.
Hao et al. "Hydroxytyrosol promotes mitochondrial biogenesis and mitochondrial function in 3T3-L 1 adipocytes" Journal of Nutritional Biochemistry (2010) vol. 21, pp. 634-644.
Harms et al., "Brown and beige fat: development, function and therapeutic potential," Nature Medicine, Oct. 2013, 19: 1252-1263.
Hartwig et al., "A critical comparison between two classical and a kit-based method for mitochondria isolation" Droteomics (2009) vol. 9, pp. 13209-3214.
Heale et al. (Feb. 18, 2005), "siRNA target site secondary structure predictions using local stable substructures," *Nucleic Acids Research*, 2005, vol. 33(3), e30, 1-10.
Hendel et al. (2015). Chemically modified guide RNAs enhance CRISPR-Cas genome editing in human primary cells. Nature Biotechnol. 33:985-989.
Herzog et al. (2011). A novel informatics concept for high-throughput shotgun lipidomics based on the molecular ragmentation query language. Genome Biol. 12(1): R8.
Herzog et al., "LipidXplorer: a software for consensual cross-platform lipidomics," PLoS One. (2012) 7(1):e29851.
Ikon et al., "Exogenous cardiolipin localizes to mitochondria and prevents TAZ knockdown-induced apoptosis in myeloid progenitor cells," Biochem Biophys Res Commun, Aug. 2015, 464(2):580-5.
Islam et al., "Mitochondrial transfer from bone-marrow-derived stromal cells to pulmonary alveoli protects against cute lung injury," Nature Medicine, May 2012, 18: 759-765.
Jo et al. (2015). Efficient Mitochondrial Genome Editing by CRISPR/Cas9. Biomed Res. Int. 2015:305716.
Kadnenbach et al., "A second mechanism of respiratory control," FEBS Letters (Mar. 26, 1999), vol. 447, Issue 2-3, p. 131-134.
Kalogeris et al. (2012). Cell biology of ischemia/reperfusion injury. Int Rev Cell Mal Biol. 298:229-317.
Kaul et al., "Insulin resistance in type 1 diabetes mellitus," Metabolism, Dec. 2015, 64(12), 39 pages.
Kaza et al., "Myocardial rescue with autologous mitochondrial transplantation in a porcine model of ischemia/ reperfusion," The Journal of Thoracic and Cardiovascular Surgery, Apr. 2017, 153(4), 934-943.
Keeney et al., "Mitochondrial Gene Therapy Augments Mitochondrial Physiology in a Parkinson's Disease Cell Model" Hum Gene Ther (2009) vol. 20, pp. 897-907.
Khvorova et al. (Oct. 17, 2003), "Functional siRNAs and miRNAs Exhibit Strand Bias," *Cell*, 115, 209-216.
Kirby et al. (2007). Biochemical assays of respiratory chain complex activity. Methods Cell Biol. 80: 93-119.
Kishida et al., "Reprogrammed Functional Brown Adipocytes Ameliorate Insulin Resistance and Dyslipidemia in Diel-Induced Obesity and Type 2 Diabetes," Stem Cell Reports, Oct. 2015, 5(4):569-81.
Kitani et al., "Internalization of isolated functional mitochondria: involvement of micropinocytosis," Journal of Cellular and Molecular Medicine, Aug. 2014, 18(8):1694-703.

(56) References Cited

OTHER PUBLICATIONS

Kunze et al. (2015) The similarity between N-terminal targeting signals for protein import into different organelles and ts evolutionary relevance. Frontiers in Physiology 6: 259.
Kusminski et al., "Mitochondrial dysfunction in while adipose tissue," Trends in endocrinology & metabolism, 23 9):435-43, Sep. 2012.
Levitsky et al., "Mitochondrial DNA deletions in coronary artery bypass grafting patients," European Journal of Cardio-thoracic Surgery, Nov. 2003, 24: 777-784.
Lim et al. (2005). Microarray analysis shows that some microRNAs downregulate large numbers of target mRNAs. Nature 433(7027): 769-773.
Lim et al., "Cold-induced activation of brown adipose tissue and adipose angiogenesis in mice," Nature Protocols, Mar. 2012, 7: 606-615.
Lim et al., "Levosimendan Reduces Mortality in Adults with Left Ventricular Dysfunction Undergoing Cardiac Surgery: A Systematic Review and Meta-analysis," J Card Surg, Jul. 2015, 30(7):547-54.
Lin et al "Incorporation of VSV-G produces fusogenic plasma membrane vesicles capable of efficient transfer of bioactive macromolecules and mitochondria" Biomed Microdevices (2016) 18(3): 41.
Lin et al., "Human white adipose tissue vasculature contains endothelial colony-forming cells with robust in vivo vasculogenic potential," Angiogenesis, Oct. 2013, 16(4): 735-744.
Lin et al., "Isolated mitochondria infusion mitigates ischemia-reperfusion injury of the liver in rats," Shock, Mar. 2013, 39: 304-310.
Liu et al., "Disrupted Renal Mitochondrial Homeostasis after Liver Transplantation in Rats," PLoS One, Oct. 2015, 10(10): e0140906.
Maniataki et al., "Human mitochondrial tRNAMet is exported to the cytoplasm and associates with the Argonaute 2 protein. Rna," Jun. 1, 2005, 11(6):849-52.
Masuzawa et al., "Transplantation of autologously derived mitochondria protects the heart from ischemia-reperfusion injury," Amer J Physiol Heart Circ Physiol, Apr. 2013, 304:H966-H982.
Matsuda et al., "Developmental Differences in Cytosolic Calcium Accumulation Associated With Global Ischemia Evidence for Differential Intracellular Calcium Channel Receptor Activity," Circulation, Nov. 1997, 96[suppl 11]:11-233-11-239.
McCully et al "Mitochondrial transplantation for therapeutic use." Clin Transl Med. (2016) vol. 5, No. 1, pp. 16.
McCully et al. "Injection of isolated mitochondria during early reperfusion for cardioprotection" Am J Physiol Heart:; ir Physiol (2009) vol. 296, pp. H94-H105.
McCully et al., "Adenosine-enhanced ischemic preconditioning: adenosine receptor involvement during ischemia and reperfusion," Am J Heart Cir Physiol, Feb. 2001, 280: H591-H602.
McCully et al., "Age- and Gender-Related Differences in Mitochondrial Oxygen Consumption and Calcium With Cardioplegia and Diazoxide," Ann Thorac Surg, Mar. 2007, 83: 1102-9.
McCully et al., "Mitochrondial Transplantation for Cardioprotection," Scientific Sessions (Oct. 16, 2007), vol. 116, No. 16, Supplemental II, Abstract 2272.
MCully et al., "Diazoxide Amelioration of Myocardial Injury and Mitochondrial Damage During Cardiac Surgery," Ann Thorac Surg, Dec. 2002, 74: 2138-46.
Melero-Martin et al., "In vivo vasculogenic potential of human blood-derived endothelial progenitor cells," Blood, Jun. J007, 109(11), 4761-4768.
Mumtaz et al. (1991). Design of liposomes for circumventing the reticuloendothelial cells. Glycobiol. 1 (5): 505-510.
Nechad et al. (1983). Development of brown fat cells in monolayer culture. Exp Cell Res. 149(1):105-118.
Nishikawa et al. (2001) Nonviral vectors in the new millennium: delivery barrers in gene transfer. Hum. Gene Ther. 12 (8): 861-870.
Novobrantseva et al. (2012). Systemic RNAi-medialed Gene Silencing in Nonhuman Primate and Rodent Myeloid: Cells. Mol. Ther. Nuc. Acids 1: e4.
Olson et al., "Changes in endogenous substrates of isolated rabbit heart mitochondria during storage," Journal of Biological Chemistry, Jan. 25, 1967, 242(2):325-32.
Orme-Johnson (2007) Appendix 2. Direct and indirect inhibitors of mitochondrial ATP synthesis. Methods Cell Biol. 80:813-826.
Orive et al. (2015). Cell encapsulation: technical and clinical advances. Trends Pharmacol. Sci. 36(8):537-546.
Pacak et al., "Actin-dependent mitochondrial internalization in cardiomyocytes: evidence for rescue of mitochondrial function," Biology Open, Jul. 2015, 4: 622-626.
Pacak et al., "Superparamagnetic iron oxide nanoparticles function as a long-term, multi-modal imaging label for non-Invasive tracking of implanted progenitor cells," PLoS One, Sep. 24, 2014, 9(9): e108695.
Pallotti et al. (2007). Isolation and subfractionation of mitochondria from animal cells and tissue culture lines. Methods n Cell Biology 80: 3-44.
Peschechera et al., "Browning of adipose tissue-regulation and therapeutic perspectives," Archives of physiology and biochemistry, 119(4):151-60, Oct. 2013.
Pfanner et al. "Assembling the mitochondrial outer membrane". Nat. Strucl. Mol. Biol. (2004) vol. 11, pp. 1044-1048.
Phinney et al. (2015). Mesenchymal stem cells use extracellular vesicles to outsource mitophagy and shuttle rnicroRNAs. Nature Communications 6:8472.
Pinton et al. (2007) Biosensors for the detection of calcium and pH. Methods Cell Biol. 80: 297-325.
Preble et al. "Rapid Isolation and Purification of Mitochondria for Transplantation by Tissue Dissociation and Differential Filtration" Journal of Visualized Experiments (2014) vol. 91, e51682, pp. 1-6.
Preble et al., "Quality Control Parameters for Mitochondria Transplant in Cardiac Tissue," Mal. Biol., Jun. 2, 2014, 2 1):1008.
Preble et al., "Rapid isolation and purification of mitochondria for transplantation by tissue dissociation and differential filtration." J Vis Exp (2014) 91: e51682.
Quiros et al. (2015) New roles for mitochondrial proteases in health, ageing and disease. Nat. Rev. Mol. Cell Biol. 16 6): 345-359.
Rahman et al. "Demarcating the membrane damage for the extraction of functional mitochondria" Microsystems & Nanoengineering (2018) vol. 4, No. 39, pp. 1-12.
Rajewsky (2006). microRNA target predictions in animals. Nat. Genet. 38: S8-S13.
Ran et al. (2013). Double nicking by RNA-guided CRISPR Cas9 for enhanced genome editing specificity. Cell 154:1380-1389.
Ran et al. (2013). Genome engineering using the CRISPR-Cas9 system. Nature Protocols, 8:2281-2308.
Rogers et al., "When Cells Become Organelle Donors," Physiology, Nov. 2013, 28: 414-422.
Rosner et al. (2013). Merging high-quality biochemical fractionation with a refined flow cytometry approach to monitor nucleocytoplasmic protein expression throughout the unperturbed mammalian cell cycle. Nature Protocols 8:602-626.
Roucou et al., "A cytochrome c-GFP fusion is not released from mitochondria into the cytoplasm upon expression of Bax in yeast cells," FEBS letters, Apr. 14, 2000, 471(2-3):235-9.
Rousou et al., "Opening of mitochondrial KATP channels enhances cardioprotection through the modulation of mitochondrial matrix volume calcium accumulation, and respiration," American Journal of Physiology-Heart and Circulatory Physiology.
Rowley et al. (2012). Meeting Loi-Size Challenges of Manufacturing Adherent Cells for Therapy. BioProcess nternational 10(3) Supplement.
Rubino et al. (2012). HmIDB, a genomic resource for mitochondrion-based human variability studies. Nuc. Acids Res. 10: D1150-D1159.
Rudikoff et al., Single amino acid substitution altering antigen-binding specificity,: Proceedings of the National Academy of Sciences, Mar. 1, 1982, 79(6):1979-83.
Rustom et al., "Nanotubular Highways for Intercellular Organelle Transport," Science, Feb. 2004, 303: 1007-1010.
Sampaio et al. (2011). Membrane lipidome of an epithelial cell line. PNAS 108(5): 1903-1907.

(56) References Cited

OTHER PUBLICATIONS

Sass et al., "Folding of Fumarase during Mitochondrial Import Determines its Dual Targeting in Yeast," The Journal of Biological Chemistry, Nov. 2008, 278: 45109-45116.
Seyfried, "Cancer as a mitochondrial metabolic disease," Frontiers in Cell and Developmental Biology, Jul. 2015, 3: 43 (12 pages).
Sharei et al. (2013). A vector-free microfluidic platform for intracellular delivery. PNAS 110(6): 2082-2087.
Sims et al., "Isolation of mitochondria from rat brain using Percoll density gradient centrifugation," Nature Protocols (2008) vol. 3, No. 7, pp. 1228-1239.
Sivitz and Yorek, "Mitochondrial dysfunction in diabetes: from molecular mechanisms to functional significance and therapeutic opportunities," Antioxidants & Redox Signaling, 2010, 12: 537-577.
Slinde et al. "On the polydispersity of mitochondria in tissue homogenates and the determination of the average sedimentation coefficients of mixed populations of mitochondria," Anal Biochem, 1978, 90(2): 516-24.
Soubannier et al. (2012). A vesicular transport pathway shuttles cargo from mitochondria to lysosomes. Current Biology 22: 135-141.
Spees et al., "Mitochondrial transfer between cells can rescue aerobic respiration," PNAS, Jan. 2006, 103: 1283-1288.
Spinazzi et al. "Assessment of mitochondrial respiratory chain enzymatic activities on tissue and cultured cells" Nature Protocols (2012) vol. 7, No. 6, pp. 1235-1246.
Spuch et al (2011). Liposomes for Targeted Delivery of Active Agents against Neurodegenerative Diseases Alzheimer's Disease and Parkinson's Disease). J. Drug Deliv. (2011):469679, 12 pages. doi:10.1155/2011/469679.
Starkov "Measurement of mitochondrial ROS production" Methods Mol Biol (2010) vol. 648, pp. 245-255.
Stojanovski et al. (2007) Import of proteins into mitochondria. Methods in Cell Biology, 80:783-806.
Sun et al. "Systemic combined melatonin-mitochondria treatment improves acute respiratory distress syndrome in the at," Journal of Pineal Research, 2015, 58: 137-150.
Surma et al. (2015). An automated shotgun lipidomics platform for high throughput, comprehensive, and quantitative analysis of blood plasma intact lipids. Eur J lipid Sci Technol. 117(10):1540-1549.
Templeton et al. "Improved DNA: liposome complexes for increased systemic delivery and gene expression" Nat. Biotechnol. (1997) vol. 15, No. 7, pp. 647-652.
Titov et al. (2016). Complementation of mitochondrial electron transport chain by manipulation of the NAD+/NADH atio. Science 352(6282):231-235.
Toyoda et al., "Opening of Mitochondrial ATP-Sensitive Potassium Channels Enhances Cardioplegic Protection," Ann Thorac Surg, 2001, 71: 1281-9.
Trudeau et al. (2016). Lysosome acidification by photoactivated nanoparticles restores autophagy under lipotoxicity. Journal of Cell Biol. 214(1): 25-34.
Tsukube et al., Amelioration of ischemic calcium overload correlates with high-energy phosphates in senescent myocardium, Am J Physiol Heart Cir Physiol, 1997, 273: H418-H425.
Tsukube et al., "Developmental Differences in Cytosolic Calcium Accumulation Associated With Surgically Induced Global Ischemia: Optimization of Cardioplegic Protection and Mechanism of Action," The Journal of Thoracic and Cardiovascular Surgery, Jul. 1996, 112: 175-184.
Ui-Tei et al. (2000) Sensitive assay of RNA interference in *Drosophila* and Chinese hamster cultured cells using firefly uciferase gene as target. FEBS Letters 479: 79-82.
Vander Heiden et al. "Bcl-xL Regulates the Membrane Potential and Volume Homeostasis of Mitochondria" Cell 1997) vol. 91, pp. 627-637.
Varkouhi et al. (2011) Endosomal escape pathways for delivery of biologicals. J_ Control. Release 151(3): 220-228.
Vlieghe et al. (2010) Synthetic therapeutic peptides: science and market. Drug Discov. Today 15: 40-56.
Wakiyama et al., "Selective opening of mitochondrial ATP-sensitive potassium channels during surgically induced myocardial ischemia decreases necrosis and apoptosis," Eur J Cardiothorac Surg,21:424-433.
Wang et al. (2012). Correcting human mitochondrial mutations with targeted RNA import. PNAS 109(13): 4840-4845.
Weber-Lotfi et al. (2014) DNA import competence and mitochondrial genetics. Biopolymers and Cell. 30(1): 71-73.
Wibom et al. (2002). Measurement of ATP production and respiratory chain enzyme activities in mitochondria isolated rom small muscle biopsy samples. Anal. Biochem. 311(2): 139-151.
Wu et al. (2006) MicroRNAs direct rapid deadenylation of mRNA. PNAS 103(11) 4034-4039.
Wu et al., "Covalent labeling of mitochondria with a photostable fluorescent thiol-reactive rhodamine-based probe," Analytical Methods, Mar. 2012, 4(6):1699-703.
Yin et al. (2014). Non-viral vectors for gene-based therapy. Nat. Rev. Genet. 15(8): 541-555.
Yin et al., "Adipocyte mitochondrial function is reduced in human obesity independent of fat cell size," The Journal of Clinical Endocrinology & Metabolism, Feb. 1, 2014, 99(2): E209-16.
Yu et al., Investigative Ophthalmology & Visual Science 49(2): 522-527, Feb. 2008.
Zeng et al. (2002). Both natural and designed micro RNAs can inhibit the expression of cognate mRNAs when expressed in human cells. Mol. Cell 9(6): 1327-1333.
Zetsche et al. "Cpf1 is a single RNA-guided endonuclease of a class 2 CRISPR-Cas system" Cell (2015). 163:759-771.
Zhao et al., "Glutathione selectively modulates the binding of platinum drugs to human copper chaperone Cox17," Biochem J, Dec. 2015, 472(2):217-23.
Zhou et al., "Progress in the Field of Constructing Near-Infrared Light-Responsive Drug Delivery Platforms," Journal of Nanoscience and Nanotechnology, 2016, 16: 2111-2125.
Scanlon et al., "Pharmacological investigation of mitochondrial ca(2+) transport in central neurons: studies with CGP-37157, an inhibitor of the mitochondrial Na(+)—Ca(2+) exchanger," Cell Calcium (Nov.-Dec. 2000), vol. 28 (5-6), p. 317-327.

FIG. 5

| | IL-1-beta (pg/ml) | IL-6 (pg/ml) | GM-CSF (pg/ml) | TNF-alpha (pg/ml) |
|---|---|---|---|---|
| Chondrisome Treatment, IV | < 23.56 | < 28.13 | < 15.33 | <23.26 |
| Vehicle Treatment, IV | < 23.56 | < 28.13 | < 15.33 | <23.26 |
| Chondrisome Treatment, SC | < 23.56 | < 28.13 | < 15.33 | <23.26 |
| Vehicle Treatment, SC | < 23.56 | < 28.13 | < 15.33 | <23.26 |

METHODS AND COMPOSITIONS OF CHONDRISOMES

CROSS-REFERENCE TO RELATED APPLICATIONS

This application is a continuation of U.S. application Ser. No. 16/252,369, filed Jan. 18, 2019, which is a continuation of U.S. application Ser. No. 15/365,239, filed Nov. 30, 2016, which claims priority to U.S. Provisional Application Nos. 62/261,157, 62/261,169, and 62/261,170, all filed on Nov. 30, 2015, the contents of each of which are hereby incorporated herein by reference in their entirety.

SEQUENCE LISTING

The present application is being filed along with a Sequence Listing in electronic format. The Sequence Listing is provided as a file entitled 186152001202SubSeqList.xml, created Apr. 14, 2026, which is 34,912 bytes in size. The information in the electronic format of the Sequence Listing is incorporated by reference in its entirety.

BACKGROUND

Mitochondria are membrane bound subcellular structures found in eukaryotic cells. Sometimes described as the power plants of cells, mitochondria generate most of the energy of the cell in the form of adenosine triphosphate (ATP) through respiration. Damage and subsequent dysfunction of mitochondria are important factors in a range of human diseases.

SUMMARY OF THE INVENTION

Described herein are novel preparations of chondrisomes derived from mitochondria, and related methods, that have advantageous and surprising qualities for use in human pharmaceutical and in veterinary applications. Chondrisome preparations and methods described herein have beneficial structural characteristics, yield, concentration, stability, viability, integrity, or function, e.g., a bioenergetic or biological function, for use in therapeutic applications.

Accordingly, in one aspect, the invention features a pharmaceutical preparation comprising isolated chondrisomes, derived from a cellular source of mitochondria. In one embodiment, the preparation (or the chondrisomes of the preparation) has one or more (2, 3, 4, 5, 6 or more) of the following characteristics:

- the chondrisomes of the preparation have a mean average size between 150-1500 nm, e.g., between 200-1200 nm, e.g., between 500-1200 nm, e.g., 175-950 nm;
- the chondrisomes of the preparation have a polydispersity (D90/D10) between 1.1 to 6, e.g., between 1.5-5. In embodiments, chondrisomes of a preparation from a cultured cell source (e.g., cultured fibroblasts) have a polydispersity (D90/D10) between 2-5, e.g., between 2.5-5;
- outer chondrisome membrane integrity wherein the preparation exhibits<20% (e.g., <15%, <10%, <5%, <4ˆ, <3%, <2%, <1%) increase in oxygen consumption rate over state 4 rate following addition of reduced cytochrome c;
- complex I level of 1-8 mOD/ug total protein, e.g., 3-7 mOD/ug total protein, 1-5 mOD/ug total protein. In embodiments, chondrisomes of a preparation from a cultured cell source (e.g., cultured fibroblasts) have a complex I level of 1-5 mOD/ug total protein;

- complex II level of 0.05-5 mOD/ug total protein, e.g., 0.1-4 mOD/ug total protein, e.g., 0.5-3 mOD/ug total protein. In embodiments, chondrisomes of a preparation from a cultured cell source (e.g., cultured fibroblasts) have a complex II level of 0.05-1 mOD/ug total protein;
- complex III level of 1-30 mOD/ug total protein, e.g., 2-30, 5-10, 10-30 mOD/ug total protein.

In embodiments, chondrisomes of a preparation from a cultured cell source (e.g., cultured fibroblasts) have a complex III level of 1-5 mOD/ug total protein;

- complex IV level of 4-50 mOD/ug total protein, e.g., 5-50, e.g., 10-50, 20-50 mOD/ug total protein. In embodiments, chondrisomes of a preparation from a cultured cell source (e.g., cultured fibroblasts) have a complex IV level of 3-10 mOD/ug total protein;
- genomic concentration 0.001-2 (e.g., .001-1, .01-1, .01-.1, .01-.05, .1-.2) mtDNA ug/mg protein;
- membrane potential of the preparation is between −5 to −200 mV, e.g., between −100 to −200 mV, −50 to −200 mV, −50 to −75 mV, −50 to −100 mV. In some embodiments, membrane potential of the preparation is less than −150 mV, less than −100 mV, less than −75 mV, less than −50 mV, e.g., −5 to −20 mV;
- a protein carbonyl level of less than 100 nmol carbonyl/mg chondrisome protein (e.g., less than 90 nmol carbonyl/mg chondrisome protein, less than 80 nmol carbonyl/mg chondrisome protein, less than 70 nmol carbonyl/mg chondrisome protein, less than 60 nmol carbonyl/mg chondrisome protein, less than 50 nmol carbonyl/mg chondrisome protein, less than 40 nmol carbonyl/mg chondrisome protein, less than 30 nmol carbonyl/mg chondrisome protein, less than 25 nmol carbonyl/mg chondrisome protein, less than 20 nmol carbonyl/mg chondrisome protein, less than 15 nmol carbonyl/mg chondrisome protein, less than 10 nmol carbonyl/mg chondrisome protein, less than 5 nmol carbonyl/mg chondrisome protein, less than 4 nmol carbonyl/mg chondrisome protein, less than 3 nmol carbonyl/mg chondrisome protein;
- <20% mol/mol ER proteins (e.g., >15%, >10%, >5%, >3%, >2%, >1%) mol/mol ER proteins;
- >5% mol/mol mitochondrial proteins (proteins identified as mitochondrial in the MitoCarta database (Calvo et al., NAR 20151 doi: 10.1093/nar/gkv1003)), e.g., >10%, >15%, >20%, >25%, >30%,
- >35%, >40%; >50%, >55%, >60%, >65%, >70%, >75%, >80%; >90% mol/mol mitochondrial proteins);
- >0.05% mol/mol of MT-CO2, MT-ATP6, MT-ND5 and MT-ND6 protein (combined) (e.g., >0.1%; >05%, >1%, >2%, >3%, >4%, >5%, >7, >8%, >9%, >10, >15% mol/mol of MT-CO2, MT-ATP6, MT-ND5 and MT-ND6 protein);
- Genetic quality>80%, e.g., >85%, >90%, >95%, >97%, >98%, >99%;
- Relative ratio mtDNA/nuclear DNA is >1000 (e.g., >1,500, >2000, >2,500, >3,000, >4,000, >5000, >10,000, >25,000, >50,000, >100,000, >200,000, >500,000);
- Endotoxin level<0.2 EU/ug protein (e.g., <0.1, 0.05, 0.02, 0.01 EU/ug protein);
- Substantially absent exogenous non-human serum;
- Glutamate/malate RCR 3/2 of 1-15, e.g., 2-15, 5-15, 2-10, 2-5, 10-15;
- Glutamate/malate RCR 3/40 of 1-30, 1-20, 2-20, 5-20, 3-15, 10-30;

Succinate/rotenone RCR 3/2 of 1-15, 2-15, 5-15, 1-10, 10-15;

Succinate/rotenone RCR 3/40 of 1-30, 1-20, 2-20, 5-20, 3-15, 10-30;

complex I activity of 0.05-100 nmol/min/mg total protein (e.g., .05-50, .05-20, .5-10, .1-50, 1-50, 2-50, 5-100, 1-20 nmol/min/mg total protein);

complex II activity of 0.05-50 nmol/min/mg total protein (e.g., .05-50, .05-20, .5-10, .1-50, 1-50, 2-50, 5-50, 1-20 nmol/min/mg total protein);

complex III activity of 0.05-20 nmol/min/mg total protein (e.g., .05-50, .05-20, .5-10, .1-50, 1-50, 2-50, 5-100, 1-20 nmol/min/mg total protein);

complex IV activity of 0.1-50 nmol/min/mg total protein (e.g., .05-50, .05-20, .5-10, .1-50, 1-50, 2-50, 5-50, 1-20 nmol/min/mg total protein);

complex V activity of 1-500 nmol/min/mg total protein (e.g., 10-500, 10-250, 10-200, 100-500 nmol/min/mg total protein);

reactive oxygen species (ROS) production level of 0.01-50 μmol H2O2/ug protein/hr (e.g., .05-40, .05-25, 1-20, 2-20, .05-20, 1-20 μmol H2O2/ug protein/hr);

Citrate Synthase activity of 0.05-5 (e.g., .5-5, .5-2, 1-5, 1-4) mOD/min/ug total protein;

Alpha ketoglutarate dehydrogenase activity of 0.05-10 (e.g., .1-10, .1-8, .5-8, .1-5, .5-5, .5-3, 1-3) mOD/min/ug total protein;

Creatine Kinase activity of 0.1-100 (e.g., .5-50, 1-100, 1-50, 1-25, 1-15, 5-15) mOD/min/ug total protein;

Pyruvate dehydrogenase activity of 0.1-10 (e.g., .5-10, .5-8, 1-10, 1-8, 1-5, 2-3) mOD/min/ug total protein;

Aconitase activity of 0.1-50 (e.g., 5-50, .1-2, .1-20, .5-30) mOD/min/ug total protein. In embodiments, aconitase activity in a chondrisome preparation from platelets is between .5-5 mOD/min/ug total protein. In embodiments, aconitase activity in a chondrisome preparation from cultured cells, e.g., fibroblasts, is between 5-50 mOD/min/ug total protein;

Maximal fatty acid oxidation level of 0.05-50 (e.g., .05-40, .05-30, .05-10, .5-50, .5-25, .5-10, 1-5) pmol O2/min/ug chondrisome protein;

Palmitoyl carnitine & Malate RCR3/2 state 3/state 2 respiratory control ratio (RCR 3/2) of 1-10 (e.g., 1-5);

electron transport chain efficiency of 1-1000 (e.g., 10-1000, 10-800, 10-700, 50-1000, 100-1000, 500-1000, 10-400, 100-800) nmol 02/min/mg protein/ΔGATP (in kcal/mol);

total lipid content of 50,000-2,000,000 μmol/mg (e.g., 50,000-1,000,000; 50,000-500,000 pmol/mg);

double bonds/total lipid ratio of 0.8-8 (e.g., 1-5, 2-5, 1-7, 1-6) pmol/pmol;

phospholipid/total lipid ratio of 50-100 (e.g., 60-80, 70-100, 50-80) 100*pmol/pmol;

phosphosphingolipid/total lipid ratio of 0.2-20 (e.g., .5-15, .5-10, 1-10, .5-10, 1-5, 5-20) 100*pmol/pmol;

ceramide content 0.05-5 (e.g., .1-5, .1-4, 1-5, .05-3) 100*pmol/pmol total lipid;

cardiolipin content 0.05-25 (0.1-20, .5-20, 1-20, 5-20, 5-25, 1-25, 10-25, 15-25) 100*pmol/pmol total lipid;

lyso-phosphatidylcholine (LPC) content of 0.05-5 (e.g., .1-5, 1-5, .1-3, 1-3, .05-2) 100*pmol/pmol total lipid;

Lyso-Phosphatidylethanolamine (LPE) content of 0.005-2 (e.g., .005-1, .05-2, .05-1) 100*pmol/pmol total lipid;

Phosphatidylcholine (PC) content of 10-80 (e.g., 20-60, 30-70, 20-80, 10-60m 30-50) 100*pmol/pmol total lipid;

Phosphatidylcholine-ether (PC O—) content 0.1-10 (e.g., .5-10, 1-10, 2-8, 1-8) 100*pmol/pmol total lipid;

Phosphatidylethanolamine (PE) content 1-30 (e.g., 2-20, 1-20, 5-20) 100*pmol/pmol total lipid; Phosphatidylethanolamine-ether (PE O—) content 0.05-30 (e.g., .1-30, .1-20, 1-20, .1-5, 1-10, 5-20) 100*pmol/pmol total lipid;

Phosphatidylinositol (PI) content 0.05-15 (e.g., .1-15, .1-10, 1-10, .1-5, 1-10, 5-15) 100*pmol/pmol total lipid;

Phosphatidylserine (PS) content 0.05-20 (e.g., .1-15, .1-20, 1-20, 1-10, .1-5, 1-10, 5-15) 100*pmol/pmol total lipid;

Sphingomyelin (SM) content 0.01-20 (e.g., .01-15, .01-10, .5-20, .5-15, 1-20, 1-15, 5-20) 100*pmol/pmol total lipid;

Triacylglycerol (TAG) content 0.005-50 (e.g., .01-50, .1-50, 1-50, 5-50, 10-50, .005-30, .01-25, . 1-30) 100*pmol/pmol total lipid;

PE: LPE ratio 30-350 (e.g., 50-250, 100-200, 150-300);

PC: LPC ratio 30-700 (e.g., 50-300, 50-250, 100-300, 400-700, 300-500, 50-600, 50-500, 100-500, 100-400);

PE 18: n (n>0) content 0.5-20% (e.g., 1-20%, 1-10%, 5-20%, 5-10%, 3-9%) pmol AA/pmol lipid class;

PE 20:4 content 0.05-20% (e.g., 1-20%, 1-10%, 5-20%, 5-10%) pmol AA/pmol lipid class;

PC 18: n (n>0) content 5-50% (e.g., 5-40%, 5-30%, 20-40%, 20-50%) pmol AA/pmol lipid class;

PC 20:4 content 1-20% (e.g., 2-20%, 2-15%, 5-20%, 5-15%) pmol AA/pmol lipid class.

In certain embodiments, the preparation or composition has one or more of the following characteristics upon administration to a recipient cell, tissue or subject (a control may be a negative control (e.g., a control tissue or subject that has not been treated or administered a preparation), or a baseline prior to administration, e.g., a cell, tissue or subject prior to administration of the preparation or composition):

Increases basal respiration of recipient cells at least 10% (e.g., >15%, >20%, >30%, >40%, >50%, >60%, >70%, >80%, >90%) relative to a control;

Chondrisomes of the preparation are taken up by at least 1% (e.g., at least 2%, 5%, 10%, 20%, 30%, 40%, 50%, 60%, 70%) of recipient cells;

Chondrisomes of the preparation are taken up and maintain membrane potential in recipient cells; Chondrisomes of the preparation persist in recipient cells at least 6 hours, e.g., at least 12 hours, 18 hours, 24 hours, 2 days, 3 days, 4 days, a week, 2 weeks, a month, 2 months, 3 months, 6 months;

increase ATP levels in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

decrease apotosis in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

decrease cellular lipid levels in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

increase membrane potential in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

increase uncoupled respiration in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);

increase PI3K activity in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);

reduce reductive stress in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);

decrease reactive oxygen species (e.g. H2O2) in the cell, tissue of subject (e.g., in serum of a target subject) (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);

Decrease cellular lipid levels of recipient cells at least 5% (e.g., >10%, >15%, >20%, >30%, >40%, >50%, >60%, >70%, >80%, >90%) relative to a control;

increases uncoupled respiration of recipient cells at least 5% (e.g., >10%, >15%, >20%, >30%, >40%, >50%, >60%, >70%, >80%, >90%) relative to a control;

decrease mitochondrial permeability transition pore (MPTP) formation in recipient cells at least 5% and does not increase more than 10% relative to a control;

increase Akt levels in recipient cells at least 10% (e.g., >10%, >15%, >20%, >30%, >40%, >50%, >60%, >70%, >80%, >90%) relative to a control;

decrease total NAD/NADH ratio in recipient cells at least 5% (e.g., >10%, >15%, >20%, >30%, >40%, >50%, >60%, >70%, >80%, >90%) relative to a control;

Reduce ROS levels in recipient cells at least 5% (e.g., >10%, >15%, >20%, >30%, >40%, >50%, >60%, >70%, >80%, >90%) relative to a control;

Increase fractional shortening in subject with cardiac ischemia at least 5% (e.g., >10%, >15%, >20%, >30%, >40%, >50%, >60%, >70%, >80%, >90%) relative to a control;

Increase end diastolic volume in subject with cardiac ischemia at least 5% (e.g., >10%, >15%, >20%, >30%, >40%, >50%, >60%, >70%, >80%, >90%) relative to a control;

decrease end systolic volume in subject with cardiac ischemia at least 5% (e.g., >10%, >15%, >20%, >30%, >40%, >50%, >60%, >70%, >80%, >90%) relative to a control;

decrease infarct area of ischemic heart at least 5% (e.g., >10%, >15%, >20%, >30%, >40%, >50%, >60%, >70%, >80%, >90%) relative to a control;

increase stroke volume in subject with cardiac ischemia at least 5% (e.g., >10%, >15%, >20%, >30%, >40%, >50%, >60%, >70%, >80%, >90%) relative to a control;

increase ejection fraction in subject with cardiac ischemia at least 5% (e.g., >10%, >15%, >20%, >30%, >40%, >50%, >60%, >70%, >80%, >90%) relative to a control;

increase cardia output in subject with cardiac ischemia at least 5% (e.g., >10%, >15%, >20%, >30%, >40%, >50%, >60%, >70%, >80%, >90%) relative to a control;

increase cardiac index in subject with cardiac ischemia at least 5% (e.g., >10%, >15%, >20%, >30%, >40%, >50%, >60%, >70%, >80%, >90%) relative to a control;

decrease serum CKNB levels in subject with cardiac ischemia at least 5% (e.g., >10%, >15%, >20%, >30%, >40%, >50%, >60%, >70%, >80%, >90%) relative to a control;

decrease serum cTnI levels in subject with cardiac ischemia at least 5% (e.g., >10%, >15%, >20%, >30%, >40%, >50%, >60%, >70%, >80%, >90%) relative to a control;

decrease serum hydrogen peroxide in subject with cardiac ischemia at least 5% (e.g., >10%, >15%, >20%, >30%, >40%, >50%, >60%, >70%, >80%, >90%) relative to a control;

decrease serum cholesterol levels and/or triglycerides in a subject at least 5% (e.g., >10%, >15%, >20%, >30%, >40%, >50%, >60%, >70%, >80%, >90%) relative to a control.

In embodiments, the pharmaceutical preparation is stable for at least 6 hours, 12 hours, 24 hours, 48 hours, 72 hours, 96 hours, 5 days, 7 days, 10 days, 14 days, 21 days, 30 days, 45 days, 60 days, 90 days, 120 days, 180 days, or longer (for example, at 4° C., 0° C., −4° C., or −20° C., −80° C.).

In embodiments, the chondrisomes in the preparation may be encapsulated, e.g., in a natural, synthetic or engineered encapsulation material such as a lipid based material, e.g., a micelle, synthetic or natural vesicle, exosome, lipid raft, clathrin coated vesicle, or platelet (mitoparticle), MSC or astrocyte microvesicle membrane.

In embodiments, the preparation may be configured for systemic or local delivery, e.g., for enteral, parenteral (e.g., IV, SC, IM), or transdermal delivery.

In embodiments, the concentration of the preparation or composition is between 150-20,000 μg protein/ml; between 150-15,000 μg/ml; 200-15,000 μg/ml; 300-15,000 μg/ml; 500-15,000 μg/ml; 200-10,000 μg/ml; 200-5,000 μg/ml; 300-10,000 μg/ml; >200 μg/ml; >250 μg/ml; >300 μg/ml; >350 μg/ml; >400 μg/ml; >450 μg/ml; >500 μg/ml; >600 μg/ml; >700 μg/ml; >800 μg/ml; >900 μg/ml; >1 mg/ml;>2 mg/ml; >3 mg/ml; >4 mg/ml; >5 mg/ml; >6 mg/ml; >7 mg/ml; >8 mg/ml; >9 mg/ml; >10 mg/ml; >11 mg/ml; >12 mg/ml; >14 mg/ml; >15 mg/ml (and, e.g., ≤20 mg/ml).

In embodiments, the preparation does not produce an undesirable immune response in a recipient animal, e.g., a recipient mammal such as a human (e.g., does not significantly increase levels of IL-1-beta, IL-6, GM-CSF, TNF-alpha, or lymph node size, in the recipient).

In certain embodiments, the chondrisomes of the preparation express a metabolite transporter, e.g., UCP1, UCP2, UCP3, UCP4 or UCP5. The expressed transporter may be endogenous or heterologous to the source mitochondria (e.g., the transporter may be naturally expressed, or the mitochondria or chondrisomes may be modified (e.g., genetically modified or loaded) to express or over-express the transporter. In one embodiment, the chondrisomes are engineered to express a protein at least 85%, 90%, 95%, 97%, 98%, 100% identical to the sequence of human UCP1 (SEQ ID NO:1), human UCP2 (SEQ ID NO:2), human UCP3 (SEQ ID NO:3), human UCP4 (SEQ ID NO:4) or human UCP5 (SEQ ID NO:5), wherein the protein has transporter activity.

In other embodiments, the mitochondria of the preparation have reduced expression, or lack expression, of a metabolite transporter, e.g., UCP1, UCP2, UCP3, UCP4 or UCP5. The transporter may be knocked down or knocked-out in the source mitochondria and/or in the chondrisomes, e.g., using routine methods in the art, such as CRISPR or RNAi.

In embodiments, the source of the mitochondria is selected from epithelial, connective, muscular, or nervous tissue.

In embodiments, the cellular source of mitochondria is a plurality of tissue types or cell types.

In some embodiments, the preparation is made using a method of making a pharmaceutical composition described herein.

In certain embodiments, the chondrisomes of the preparation are modified, e.g., the source mitochondria or chondrisomes are (a) genetically engineered to overexpress or knock-down or knock-out an endogenous gene product (e.g., an endogenous mitochondrial or nuclear gene product); (b) engineered to express a heterologous gene product (e.g., a heterologous, e.g., allogeneic or xenogeneic, mitochondrial or nuclear gene product), or (c) loaded with a heterologous cargo agent, such as a polypeptide, nucleic acid or small molecule (e.g., a dye, a drug, a metabolite) or an agent listed in Table 4. In embodiments, the chondrisomes of the preparation are modified as described herein.

In another aspect, the invention features a pharmaceutical preparation comprising isolated, modified chondrisomes derived from a cellular source of mitochondria. Chondrisomes may be modified by a modification made to the source mitochondria (e.g., a modification to the cell, tissue or subject that provides the source mitochondria), or by a modification made to the chondrisome preparation after isolation from the source. For example, the source mitochondria or chondrisomes of the preparation are (a) subjected to or combined with an external condition or agent (e.g., a stress condition or agent that induces one or more mitochondrial activity to compensate), (b) genetically engineered to overexpress or knock-down or knock-out an endogenous gene product (e.g., an endogenous mitochondrial or nuclear gene product, e.g., an endogenous mitochondrial or nuclear gene product described herein); (c) engineered to express a heterologous gene product (e.g., a heterologous, e.g., allogeneic or xenogeneic, mitochondrial or nuclear gene product, e.g., an exogenous mitochondrial or nuclear gene product described herein), or (d) loaded with a heterologous cargo agent, such as a polypeptide, nucleic acid or small molecule (e.g., a dye, a drug, a metabolite or other cargo described herein), or an agent listed in Table 4.

In embodiments, the source of mitochondria is modified. For example, the source is subjected to an external condition or agent, such as a stress condition or agent. In embodiments, the source of mitochondria is subjected to a temperature change. In embodiments, the source of mitochondria is subjected to hypoxia or hyperoxia. In another embodiment, chondrisomes are obtained from a source exposed to stressed nutrient conditions, e.g., lack of glucose or other sugar substrate, amino acids, or a combination thereof. In another embodiment, the source of mitochondria is exposed to different concentrations of one or more nutrients, e.g., reduced concentration of glucose or other sugar substrate, amino acids, or a combination thereof. In another embodiment, chondrisomes are obtained from a source exposed to osmotic stress, e.g., increase or decrease in solute concentration. In some embodiments, chondrisomes are obtained from a source that has been injured or a source undergoing a wound healing process. In embodiments, the source of mitochondria may be treated with a toxin, e.g., metformin. In another embodiment, a source of mitochondria may be treated with one or more infectious agents, such as a virus or bacteria (e.g., hepatitis C virus (HCV) and hepatitis B virus (HBV)).

In some embodiments, the source mitochondrial genome is engineered, e.g., to express, overexpress or knock-down or knock-out a mitochondrial gene, e.g., a gene listed in Table 2 or any other gene described herein.

In some embodiments, the source may be engineered to express a cytosolic enzyme (e.g., a protease, phosphatase, kinase, demethylase, methyltransferase, acetylase) that targets a mitochondrial protein. For example, the source mitochondria or chondrisomes are engineered to express a protein at least 85%, 90%, 95%, 97%, 98%, 99%, 100% identical to the sequence of human SIRT3 (SEQ ID NO:7). For example, the source mitochondria or chondrisomes are engineered to express a protein at least 85%, 90%, 95%, 97%, 98%, 99%, 100% identical to the sequence of human pyruvate dehydrogenase kinase (SEQ ID NO:8). For example, the source mitochondria or chondrisomes are engineered to express a protein at least 85%, 90%, 95%, 97%, 98%, 99%, 100% identical to the sequence of human O-GlcNAc transferase (SEQ ID NO:9) or to an alternative splice variant thereof (e.g., comprising amino acid 177-1046 of SEQ ID NO:9; amino acid 23-1046 of SEQ ID NO:9; or amino acid 382-1046 of SEQ ID NO:9).

In some embodiments, the source is modified to modulate a mitochondrial transporter, e.g., by phosphorylation, e.g., the mitochondrial source is treated with dephosphorylated pyruvate dehydrogenase to catabolize glucose and gluconeogenesis precursors. In another embodiment, the source is treated with phosphorylated pyruvate dehydrogenase to shift metabolism toward fat utilization.

In some embodiments, the source of mitochondria has altered distribution and/or quantity of nuclear encoded mitochondrial targeted proteins. For example, the source is engineered to express a mitochondrial import signal appended to an RNA encoding a target protein, or a fusion that includes a protein mitochondrial import signal and a non-mitochondrial target protein. In other examples, the source may be modified to target cytosolic proteins, such as proteases or enzymes, to the source mitochondria. Import into mitochondria can be effected by N-terminal targeting sequences (presequences) or internal targeting sequences.

In embodiments, the isolated chondrisomes are modified. For example, a chondrisome preparation comprises an exogenous agent, e.g., has been loaded with an exogenous agent such as a nucleic acid (e.g., DNA, RNA), protein, or chemical compound. In some embodiments, the exogenous agent is a cargo or payload, e.g., a payload for administration to a cell, tissue or subject, e.g., an agent listed in Table 4.

In some embodiments, the exogenous agent is a modified protein, e.g., a modified protein described herein.

In embodiments, the modified chondrisome preparation has one or more of the following characteristics:

- the chondrisomes of the preparation have a mean average size between 150-1500 nm, e.g., between 200-1200 nm, e.g., between 500-1200 nm, e.g., 175-950 nm;
- the chondrisomes of the preparation have a polydispersity (D90/D10) between 1.1 to 6, e.g., between 1.5-5. In embodiments, chondrisomes of a preparation from a cultured cell source (e.g., cultured fibroblasts) have a polydispersity (D90/D10) between 2-5, e.g., between 2.5-5;

- outer chondrisome membrane integrity wherein the preparation exhibits<20% (e.g., <15%, <10%, <5%, <4ˆ, <3%, <2%, <1%) increase in oxygen consumption rate over state 4 rate following addition of reduced cytochrome c;
- complex I level of 1-8 mOD/ug total protein, e.g., 3-7 mOD/ug total protein, 1-5 mOD/ug total protein. In embodiments, chondrisomes of a preparation from a cultured cell source (e.g., cultured fibroblasts) have a complex I level of 1-5 mOD/ug total protein;
- complex II level of 0.05-5 mOD/ug total protein, e.g., 0.1-4 mOD/ug total protein, e.g., 0.5-3 mOD/ug total protein. In embodiments, chondrisomes of a preparation from a cultured cell source (e.g., cultured fibroblasts) have a complex II level of 0.05-1 mOD/ug total protein;
- complex III level of 1-30 mOD/ug total protein, e.g., 2-30, 5-10, 10-30 mOD/ug total protein. In embodiments, chondrisomes of a preparation from a cultured cell source (e.g., cultured fibroblasts) have a complex III level of 1-5 mOD/ug total protein;
- complex IV level of 4-50 mOD/ug total protein, e.g., 5-50, e.g., 10-50, 20-50 mOD/ug total protein. In embodiments, chondrisomes of a preparation from a cultured cell source (e.g., cultured fibroblasts) have a complex IV level of 3-10 mOD/ug total protein;
- genomic concentration 0.001-2 (e.g., .001-1, .01-1, .01-.1, .01-.05, .1-.2) mtDNA ug/mg protein;
- membrane potential of the preparation is between −5 to −200 mV, e.g., between −100 to −200 mV, −50 to −200 mV, −50 to −75 mV, −50 to −100 mV. In some embodiments, membrane potential of the preparation is less than −150 mV, less than −100 mV, less than −75 mV, less than −50 mV, e.g., −5 to −20 mV;
- a protein carbonyl level of less than 100 nmol carbonyl/mg chondrisome protein (e.g., less than 90 nmol carbonyl/mg chondrisome protein, less than 80 nmol carbonyl/mg chondrisome protein, less than 70 nmol carbonyl/mg chondrisome protein, less than 60 nmol carbonyl/mg chondrisome protein, less than 50 nmol carbonyl/mg chondrisome protein, less than 40 nmol carbonyl/mg chondrisome protein, less than 30 nmol carbonyl/mg chondrisome protein, less than 25 nmol carbonyl/mg chondrisome protein, less than 20 nmol carbonyl/mg chondrisome protein, less than 15 nmol carbonyl/mg chondrisome protein, less than 10 nmol carbonyl/mg chondrisome protein, less than 5 nmol carbonyl/mg chondrisome protein, less than 4 nmol carbonyl/mg chondrisome protein, less than 3 nmol carbonyl/mg chondrisome protein;
- <20% mol/mol ER proteins (e.g., >15%, >10%, >5%, >3%, >2%, >1%) mol/mol ER proteins;
- >5% mol/mol mitochondrial proteins (proteins identified as mitochondrial in the MitoCarta database (Calvo et al., NAR 20151 doi: 10.1093/nar/gkv1003)), e.g., >10%, >15%, >20%, >25%, >30%,
- >35%, >40%; >50%, >55%, >60%, >65%, >70%, >75%, >80%; >90% mol/mol mitochondrial proteins);
- >0.05% mol/mol of MT-CO2, MT-ATP6, MT-ND5 and MT-ND6 protein (e.g., >0.1%; >05%,
- >1%, >2%, >3%, >4%, >5%, >7, >8%, >9%, >10, >15% mol/mol of MT-CO2, MT-ATP6, MT-ND5 and MT-ND6 protein);
- Genetic quality>80%, e.g., >85%, >90%, >95%, >97%, >98%, >99%;
- Relative ratio mtDNA/nuclear DNA is >1000 (e.g., >1,500, >2000, >2,500, >3,000, >4,000, >5000, >10,000, >25,000, >50,000, >100,000, >200,000, >500,000);
- Endotoxin level<0.2 EU/ug protein (e.g., <0.1, 0.05, 0.02, 0.01 EU/ug protein); Substantially absent exogenous non-human serum;
- Glutamate/malate RCR 3/2 of 1-15, e.g., 2-15, 5-15, 2-10, 2-5, 10-15;
- Glutamate/malate RCR 3/40 of 1-30, 1-20, 2-20, 5-20, 3-15, 10-30; Succinate/rotenone RCR 3/2 of 1-15, 2-15, 5-15, 1-10, 10-15;
- Succinate/rotenone RCR 3/40 of 1-30, 1-20, 2-20, 5-20, 3-15, 10-30;
- complex I activity of 0.05-100 nmol/min/mg total protein (e.g., .05-50, .05-20, .5-10, .1-50, 1-50, 2-50, 5-100, 1-20 nmol/min/mg total protein);
- complex II activity of 0.05-50 nmol/min/mg total protein (e.g., .05-50, .05-20, .5-10, .1-50, 1-50, 2-50, 5-50, 1-20 nmol/min/mg total protein);
- complex III activity of 0.05-20 nmol/min/mg total protein (e.g., .05-50, .05-20, .5-10, .1-50, 1-50, 2-50, 5-100, 1-20 nmol/min/mg total protein);
- complex IV activity of 0.1-50 nmol/min/mg total protein (e.g., .05-50, .05-20, .5-10, .1-50, 1-50, 2-50, 5-50, 1-20 nmol/min/mg total protein);
- complex V activity of 1-500 nmol/min/mg total protein (e.g., 10-500, 10-250, 10-200, 100-500 nmol/min/mg total protein);
- reactive oxygen species (ROS) production level of 0.01-50 μmol H2O2/ug protein/hr (e.g., .05-40, .05-25, 1-20, 2-20, .05-20, 1-20 μmol H2O2/ug protein/hr);
- Citrate Synthase activity of 0.05-5 (e.g., .5-5, .5-2, 1-5, 1-4) mOD/min/ug total protein; Alpha ketoglutarate dehydrogenase activity of 0.05-10 (e.g., .1-10, .1-8, .5-8, .1-5, .5-5, .5-3, 1-3) mOD/min/ug total protein;
- Creatine Kinase activity of 0.1-100 (e.g., .5-50, 1-100, 1-50, 1-25, 1-15, 5-15) mOD/min/ug total protein;
- Pyruvate dehydrogenase activity of 0.1-10 (e.g., .5-10, .5-8, 1-10, 1-8, 1-5, 2-3) mOD/min/ug total protein;
- Aconitase activity of 0.1-50 (e.g., 5-50, .1-2, .1-20, .5-30) mOD/min/ug total protein. In embodiments, aconitase activity in a chondrisome preparation from platelets is between .5-5 mOD/min/ug total protein. In embodiments, aconitase activity in a chondrisome preparation from cultured cells, e.g., fibroblasts, is between 5-50 mOD/min/ug total protein;
- Maximal fatty acid oxidation level of 0.05-50 (e.g., .05-40, .05-30, .05-10, .5-50, .5-25, .5-10, 1-5) pmol O2/min/ug chondrisome protein;
- Palmitoyl carnitine & malate RCR3/2 state 3/state 2 respiratory control ratio (RCR 3/2) of 1-10 (e.g., 1-5);
- electron transport chain efficiency of 1-1000 (e.g., 10-1000, 10-800, 10-700, 50-1000, 100-1000, 500-1000, 10-400, 100-800) nmol 02/min/mg protein/ΔGATP (in kcal/mol);
- total lipid content of 50,000-2,000,000 μmol/mg (e.g., 50,000-1,000,000; 50,000-500,000 pmol/mg);
- double bonds/total lipid ratio of 0.8-8 (e.g., 1-5, 2-5, 1-7, 1-6) pmol/pmol;
- phospholipid/total lipid ratio of 50-100 (e.g., 60-80, 70-100, 50-80) 100*pmol/pmol;
- phosphosphingolipid/total lipid ratio of 0.2-20 (e.g., .5-15, .5-10, 1-10, .5-10, 1-5, 5-20) 100*pmol/pmol;
- ceramide content 0.05-5 (e.g., .1-5, .1-4, 1-5, .05-3) 100*pmol/pmol total lipid;

cardiolipin content 0.05-25 (0.1-20, .5-20, 1-20, 5-20, 5-25, 1-25, 10-25, 15-25) 100*pmol/pmol total lipid;

lyso-phosphatidylcholine (LPC) content of 0.05-5 (e.g., .1-5, 1-5, .1-3, 1-3, .05-2) 100*pmol/pmol total lipid;

Lyso-Phosphatidylethanolamine (LPE) content of 0.005-2 (e.g., .005-1, .05-2, .05-1) 100*pmol/pmol total lipid;

Phosphatidylcholine (PC) content of 10-80 (e.g., 20-60, 30-70, 20-80, 10-60m 30-50) 100*pmol/pmol total lipid;

Phosphatidylcholine-ether (PC O—) content 0.1-10 (e.g., .5-10, 1-10, 2-8, 1-8) 100*pmol/pmol total lipid;

Phosphatidylethanolamine (PE) content 1-30 (e.g., 2-20, 1-20, 5-20) 100*pmol/pmol total lipid; Phosphatidylethanolamine-ether (PE O—) content 0.05-30 (e.g., .1-30, .1-20, 1-20, .1-5, 1-10, 5-20) 100*pmol/pmol total lipid;

Phosphatidylinositol (PI) content 0.05-15 (e.g., .1-15, .1-10, 1-10, .1-5, 1-10, 5-15) 100*pmol/pmol total lipid;

Phosphatidylserine (PS) content 0.05-20 (e.g., .1-15, .1-20, 1-20, 1-10, .1-5, 1-10, 5-15) 100*pmol/pmol total lipid;

Sphingomyelin (SM) content 0.01-20 (e.g., .01-15, .01-10, .5-20, .5-15, 1-20, 1-15, 5-20) 100*pmol/pmol total lipid;

Triacylglycerol (TAG) content 0.005-50 (e.g., .01-50, .1-50, 1-50, 5-50, 10-50, .005-30, .01-25, . 1-30) 100*pmol/pmol total lipid;

PE: LPE ratio 30-350 (e.g., 50-250, 100-200, 150-300); PC: LPC ratio 30-700 (e.g., 50-300, 50-250, 100-300, 400-700, 300-500, 50-600, 50-500, 100-500, 100-400);

PE 18: n (n>0) content 0.5-20% (e.g., 1-20%, 1-10%, 5-20%, 5-10%, 3-9%) pmol AA/pmol lipid class;

PE 20:4 content 0.05-20% (e.g., 1-20%, 1-10%, 5-20%, 5-10%) pmol AA/pmol lipid class;

PC 18: n (n>0) content 5-50% (e.g., 5-40%, 5-30%, 20-40%, 20-50%) pmol AA/pmol lipid class;

PC 20:4 content 1-20% (e.g., 2-20%, 2-15%, 5-20%, 5-15%) pmol AA/pmol lipid class.

In certain embodiments, the preparation or composition has one or more of the following characteristics upon administration to a recipient cell, tissue or subject (a control may be a negative control (e.g., a control tissue or subject that has not been treated or administered a preparation), or a baseline prior to administration, e.g., a cell, tissue or subject prior to administration of the preparation or composition):

Increases basal respiration of recipient cells at least 10% (e.g., >15%, >20%, >30%, >40%, >50%, >60%, >70%, >80%, >90%) relative to a control;

Chondrisomes of the preparation are taken up by at least 1% (e.g., at least 2%, 5%, 10%, 20%, 30%, 40%, 50%, 60%, 70%) of recipient cells;

Chondrisomes of the preparation are taken up and maintain membrane potential in recipient cells; Chondrisomes of the preparation persist in recipient cells at least 6 hours, e.g., at least 12 hours, 18 hours, 24 hours, 2 days, 3 days, 4 days, a week, 2 weeks, a month, 2 months, 3 months, 6 months;

increase ATP levels in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

decrease apoptosis in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

decrease cellular lipid levels in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

increase membrane potential in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

increase uncoupled respiration in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);

increase PI3K activity in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);

reduce reductive stress in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);

decrease reactive oxygen species (e.g. $H_2O_2$) in the cell, tissue of subject (e.g., in serum of a target subject) (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);

Decrease cellular lipid levels of recipient cells at least 5% (e.g., >10%, >15%, >20%, >30%, >40%, >50%, >60%, >70%, >80%, >90%) relative to a control;

increases uncoupled respiration of recipient cells at least 5% (e.g., >10%, >15%, >20%, >30%, >40%, >50%, >60%, >70%, >80%, >90%) relative to a control;

decrease mitochondrial permeability transition pore (MPTP) formation in recipient cells at least 5% and does not increase more than 10% relative to a control;

increase Akt levels in recipient cells at least 10% (e.g., >10%, >15%, >20%, >30%, >40%, >50%, >60%, >70%, >80%, >90%) relative to a control;

decrease total NAD/NADH ratio in recipient cells at least 5% (e.g., >10%, >15%, >20%, >30%, >40%, >50%, >60%, >70%, >80%, >90%) relative to a control;

Reduce ROS levels in recipient cells at least 5% (e.g., >10%, >15%, >20%, >30%, >40%, >50%, >60%, >70%, >80%, >90%) relative to a control;

Increase fractional shortening in subject with cardiac ischemia at least 5% (e.g., >10%, >15%, >20%, >30%, >40%, >50%, >60%, >70%, >80%, >90%) relative to a control;

Increase end diastolic volume in subject with cardiac ischemia at least 5% (e.g., >10%, >15%, >20%, >30%, >40%, >50%, >60%, >70%, >80%, >90%) relative to a control;

decrease end systolic volume in subject with cardiac ischemia at least 5% (e.g., >10%, >15%, >20%, >30%, >40%, >50%, >60%, >70%, >80%, >90%) relative to a control;

decrease infarct area of ischemic heart at least 5% (e.g., >10%, >15%, >20%, >30%, >40%, >50%, >60%, >70%, >80%, >90%) relative to a control;

- increase stroke volume in subject with cardiac ischemia at least 5% (e.g., >10%, >15%, >20%, >30%, >40%, >50%, >60%, >70%, >80%, >90%) relative to a control;
- increase ejection fraction in subject with cardiac ischemia at least 5% (e.g., >10%, >15%, >20%, >30%, >40%, >50%, >60%, >70%, >80%, >90%) relative to a control;
- increase cardia output in subject with cardiac ischemia at least 5% (e.g., >10%, >15%, >20%, >30%, >40%, >50%, >60%, >70%, >80%, >90%) relative to a control;
- increase cardiac index in subject with cardiac ischemia at least 5% (e.g., >10%, >15%, >20%, >30%, >40%, >50%, >60%, >70%, >80%, >90%) relative to a control;
- decrease serum CKNB levels in subject with cardiac ischemia at least 5% (e.g., >10%, >15%, >20%, >30%, >40%, >50%, >60%, >70%, >80%, >90%) relative to a control;
- decrease serum cTnI levels in subject with cardiac ischemia at least 5% (e.g., >10%, >15%, >20%, >30%, >40%, >50%, >60%, >70%, >80%, >90%) relative to a control;
- decrease serum hydrogen peroxide in subject with cardiac ischemia at least 5% (e.g., >10%, >15%, >20%, >30%, >40%, >50%, >60%, >70%, >80%, >90%) relative to a control;
- decrease serum cholesterol levels and/or triglycerides in a subject at least 5% (e.g., >10%, >15%, >20%, >30%, >40%, >50%, >60%, >70%, >80%, >90%) relative to a control.

In another aspect, the invention features a process of making a chondrisome preparation. The process includes obtaining or providing a tissue or cellular source of mitochondria (e.g., fresh tissue, frozen tissue, suspension tissue such as blood or blood products, cultured cells, frozen cultured cells, from a living or cadaver donor); manipulating the tissue (e.g., dissociating or activating the tissue or cellular source) to produce a subcellular composition; separating the subcellular composition into a cellular debris fraction and a chondrisome enriched fluid fraction; separating the chondrisome enriched fraction into a fraction containing chondrisomes and a fraction substantially lacking chondrisomes; and suspending the fraction containing chondrisomes in a solution, thereby preparing a chondrisome preparation. The solution may be, e.g., a storage buffer or a formulation for administration. In some embodiments, the preparation may be stored in storage solution for a period of time and changed into a formulation for administration before use. A storage or formulation solution may include, e.g., an osmotic regulator, e.g., a sugar such as mannitol, sucrose, trehalose; a physiological salt, e.g., a salt of sodium, chloride or potassium; a pH buffer).

In embodiments, the dissociating comprises applying to the tissue or cellular source a plurality of different shear forces, e.g., a first shear force (e.g., with a dounce device) followed by a second, higher shear force (e.g., passing through a needle). The separating steps may be performed by, e.g., differential centrifugation or differential size filtration.

In embodiments, the dissociating step is performed in no more than 10 fold (no more than 8-fold, 6-fold, 5-fold, 4-fold, 3-fold, 2-fold) the volume of buffer relative to the volume of the tissue or cellular source. Likewise, the final fraction containing mitochondria is suspended in no more than 10-fold (no more than 8-fold, 6-fold, 5-fold, 4-fold, 3-fold, 2-fold) the volume of buffer relative to the volume of the fraction containing mitochondria.

In embodiments, the dissociating and subsequent steps are performed in the absence of an exogenous protease.

In certain embodiments, the yield of the preparation is >0.05 (e.g., >0.1, >0.2, >0.5, >1, >2, >3, >5, >6, >7, >8, >8, >10, >20, >30, >40, >50, >60, >80, >90, >100, >150, >200, >300) ug protein/10E6 cells. In certain embodiments, the yield of the preparation is >100 (e.g., >200, >300, >400, >500, >600, >700, >800, >900, >1,000, >2,000, >3,000, >5,000, >7000, >10,000) ug protein/g tissue. In embodiments, the yield is 1E9 to 9E12 (e.g., >1E9, >5E9, >1E10, >5E10, >1E11, >5E11, >1E12, >5E12) particles/mg total protein.

The tissue or cellular source may be exposed to one or more modulator before or during the preparation. The modulator may be, e.g., a mitochondrial biogenesis agent (e.g., a mitochondrial biogenesis agent described herein); a modulator of metabolic activity (e.g., modulator of metabolic activity described herein); an environmental modulator such as hypoxia, a temperature change.

In another aspect, the invention features a preparation of chondrisomes made by a process described herein.

In another aspect, the invention features a method of delivering a chondrisome preparation to a subject in-vivo, e.g., to a human in need thereof. The method includes administering to the subject a pharmaceutical composition or chondrisome preparation described herein.

In embodiments the composition or preparation is administered locally to a target tissue of the subject. In other embodiments, the composition or preparation is administered systemically. The composition may be configured for local administration, or for systemic administration.

In embodiments, the administration may be for a time and in an amount sufficient to enhance a cell or tissue function in the subject; for a time and in an amount sufficient to improve function of an injured or diseased cell or tissue in the subject; for a time and in an amount sufficient to increase mitochondrial content and/or activity in a cell or tissue of the subject; for a time and in an amount sufficient to induce or decrease (e.g., block) cellular differentiation, de-differentiation, or trans-differentiation of the cell or tissue of the subject. The administration may be for a time and in an amount sufficient to effect one or more of:

- Increases basal respiration of recipient cells at least 10% (e.g., >15%, >20%, >30%, >40%, >50%, >60%, >70%, >80%, >90%) relative to a control;
- Chondrisomes of the preparation are taken up by at least 1% (e.g., at least 2%, 5%, 10%, 20%, 30%, 40%, 50%, 60%, 70%) of recipient cells;
- Chondrisomes of the preparation are taken up and maintain membrane potential in recipient cells;
- Chondrisomes of the preparation persist in recipient cells at least 6 hours, e.g., at least 12 hours, 18 hours, 24 hours, 2 days, 3 days, 4 days, a week, 2 weeks, a month, 2 months, 3 months, 6 months;
- increase ATP levels in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);
- decrease apoptosis in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

decrease cellular lipid levels in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

increase membrane potential in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

increase uncoupled respiration in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);

increase PI3K activity in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);

reduce reductive stress in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);

decrease reactive oxygen species (e.g. H2O2) in the cell, tissue of subject (e.g., in serum of a target subject) (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control) Decrease cellular lipid levels of recipient cells at least 5% (e.g., >10%, >15%, >20%, >30%, >40%, >50%, >60%, >70%, >80%, >90%) relative to a control;

increases uncoupled respiration of recipient cells at least 5% (e.g., >10%, >15%, >20%, >30%, >40%, >50%, >60%, >70%, >80%, >90%) relative to a control;

decrease mitochondrial permeability transition pore (MPTP) formation in recipient cells at least 5% and does not increase more than 10% relative to a control;

increase Akt levels in recipient cells at least 10% (e.g., >10%, >15%, >20%, >30%, >40%, >50%, >60%, >70%, >80%, >90%) relative to a control;

decrease total NAD/NADH ratio in recipient cells at least 5% (e.g., >10%, >15%, >20%, >30%, >40%, >50%, >60%, >70%, >80%, >90%) relative to a control;

Reduce ROS levels in recipient cells at least 5% (e.g., >10%, >15%, >20%, >30%, >40%, >50%, >60%, >70%, >80%, >90%) relative to a control;

Increase fractional shortening in subject with cardiac ischemia at least 5% (e.g., >10%, >15%, >20%, >30%, >40%, >50%, >60%, >70%, >80%, >90%) relative to a control;

Increase end diastolic volume in subject with cardiac ischemia at least 5% (e.g., >10%, >15%, >20%, >30%, >40%, >50%, >60%, >70%, >80%, >90%) relative to a control;

decrease end systolic volume in subject with cardiac ischemia at least 5% (e.g., >10%, >15%, >20%, >30%, >40%, >50%, >60%, >70%, >80%, >90%) relative to a control;

decrease infarct area of ischemic heart at least 5% (e.g., >10%, >15%, >20%, >30%, >40%, >50%, >60%, >70%, >80%, >90%) relative to a control;

increase stroke volume in subject with cardiac ischemia at least 5% (e.g., >10%, >15%, >20%, >30%, >40%, >50%, >60%, >70%, >80%, >90%) relative to a control;

increase ejection fraction in subject with cardiac ischemia at least 5% (e.g., >10%, >15%, >20%, >30%, >40%, >50%, >60%, >70%, >80%, >90%) relative to a control;

increase cardia output in subject with cardiac ischemia at least 5% (e.g., >10%, >15%, >20%, >30%, >40%, >50%, >60%, >70%, >80%, >90%) relative to a control;

increase cardiac index in subject with cardiac ischemia at least 5% (e.g., >10%, >15%, >20%, >30%, >40%, >50%, >60%, >70%, >80%, >90%) relative to a control;

decrease serum CKNB levels in subject with cardiac ischemia at least 5% (e.g., >10%, >15%, >20%, >30%, >40%, >50%, >60%, >70%, >80%, >90%) relative to a control;

decrease serum cTnI levels in subject with cardiac ischemia at least 5% (e.g., >10%, >15%, >20%, >30%, >40%, >50%, >60%, >70%, >80%, >90%) relative to a control;

decrease serum hydrogen peroxide in subject with cardiac ischemia at least 5% (e.g., >10%, >15%, >20%, >30%, >40%, >50%, >60%, >70%, >80%, >90%) relative to a control;

decrease serum cholesterol levels and/or triglycerides in a subject at least 5% (e.g., >10%, >15%, >20%, >30%, >40%, >50%, >60%, >70%, >80%, >90%) relative to a control.

In another aspect, the invention features a method of delivering a chondrisome preparation to a cell or tissue ex-vivo. The method includes contacting the cell or tissue with a pharmaceutical composition or chondrisome preparation described herein. The composition or preparation may be delivered to an isolated or cultured cell or a population thereof (e.g., a cell therapy preparation), an isolated or cultured tissue (e.g., a tissue explant or tissue for transplantation, e.g., a human vein, a musculoskeletal graft such as bone or tendon, cornea, skin, heart valves, nerves), an isolated or cultured organ (e.g., an organ to be transplanted into a human, e.g., a human heart, liver, lung, kidney, pancreas, intestine, thymus, eye).

In embodiments, the contacting may be for a time and in an amount sufficient to enhance a function of the cell or tissue; for a time and in an amount sufficient to improve function of an injured or diseased cell or tissue; for a time and in an amount sufficient to improve or enhance viability (e.g., reduce cell death, e.g., reduce apoptosis or ferroptosis) of the cell or tissue; for a time and in an amount sufficient to increase mitochondrial content and/or activity in the cell or tissue; for a time and in an amount sufficient to induce or decrease (e.g., block) cellular differentiation, de-differentiation, or trans-differentiation of the cell or tissue. The administration may be for a time and in an amount sufficient to modulate one or more of these parameters in the subject, e.g., at least 5%, 10%, 15%, 20%, 30%, 40%, 50%, 60%, 70%, 80% or greater, e.g., compared to a reference (e.g., compared to a control cell or tissue, or compared to prior to the administration).

The contacting may be for a time and in an amount sufficient to modulate, e.g., at least 5%, 10%, 15%, 20%, 30%, 40%, 50%, 60%, 70%, 80% or greater, e.g., compared to a reference (e.g., compared to a control cell or tissue, or compared to prior to the administration), one or more of:

Increases basal respiration of recipient cells at least 10% (e.g., >15%, >20%, >30%, >40%, >50%, >60%, >70%, >80%, >90%) relative to a control;

Chondrisomes of the preparation are taken up by at least 1% (e.g., at least 2%, 5%, 10%, 20%, 30%, 40%, 50%, 60%, 70%) of recipient cells;

Chondrisomes of the preparation are taken up and maintain membrane potential in recipient cells;

Chondrisomes of the preparation persist in recipient cells at least 6 hours, e.g., at least 12 hours, 18 hours, 24 hours, 2 days, 3 days, 4 days, a week, 2 weeks, a month, 2 months, 3 months, 6 months; increase ATP levels in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

decrease apoptosis in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

decrease cellular lipid levels in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

increase membrane potential in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

increase uncoupled respiration in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);

increase PI3K activity in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);

reduce reductive stress in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);

decrease reactive oxygen species (e.g. H2O2) in the cell, tissue of subject (e.g., in serum of a target subject) (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control)

Decrease cellular lipid levels of recipient cells at least 5% (e.g., >10%, >15%, >20%, >30%, >40%, >50%, >60%, >70%, >80%, >90%) relative to a control;

increases uncoupled respiration of recipient cells at least 5% (e.g., >10%, >15%, >20%, >30%, >40%, >50%, >60%, >70%, >80%, >90%) relative to a control;

decrease mitochondrial permeability transition pore (MPTP) formation in recipient cells at least 5% and does not increase more than 10% relative to a control;

increase Akt levels in recipient cells at least 10% (e.g., >10%, >15%, >20%, >30%, >40%, >50%, >60%, >70%, >80%, >90%) relative to a control;

decrease total NAD/NADH ratio in recipient cells at least 5% (e.g., >10%, >15%, >20%, >30%, >40%, >50%, >60%, >70%, >80%, >90%) relative to a control;

Reduce ROS levels in recipient cells at least 5% (e.g., >10%, >15%, >20%, >30%, >40%, >50%, >60%, >70%, >80%, >90%) relative to a control;

In another aspect, the invention features a method of enhancing function (e.g., enhancing respiratory function, enhancing viability), of a target cell or tissue. The method includes delivering or administering to the target cell or tissue a composition described herein. The target cell or tissue may be in an injured state, e.g., from trauma or disease. The composition may be delivered to the target cell or tissue ex-vivo, in vitro, or in-vivo in a human subject.

In embodiments, the contacting may be for a time and in an amount sufficient to enhance a cell or tissue function; for a time and in an amount sufficient to improve function of an injured or diseased cell or tissue; for a time and in an amount sufficient to increase mitochondrial content and/or activity in the cell or tissue; for a time and in an amount sufficient to induce or decrease (e.g., block) cellular differentiation, de-differentiation, or trans-differentiation of the cell or tissue. The administration may be for a time and in an amount sufficient to modulate one or more of these parameters in the subject, e.g., at least 5%, 10%, 15%, 20%, 30%, 40%, 50%, 60%, 70%, 80% or greater, e.g., compared to a reference (e.g., compared to a control subject, or compared to prior to the administration). The contacting may be for a time and in an amount sufficient to modulate, e.g., at least 5%, 10%, 15%, 20%, 30%, 40%, 50%, 60%, 70%, 80% or greater, e.g., compared to a reference (e.g., compared to a control subject, or compared to prior to the administration) one or more of:

Increases basal respiration of recipient cells at least 10% (e.g., >15%, >20%, >30%, >40%, >50%, >60%, >70%, >80%, >90%) relative to a control;

Chondrisomes of the preparation are taken up by at least 1% (e.g., at least 2%, 5%, 10%, 20%, 30%, 40%, 50%, 60%, 70%) of recipient cells;

Chondrisomes of the preparation are taken up and maintain membrane potential in recipient cells; Chondrisomes of the preparation persist in recipient cells at least 6 hours, e.g., at least 12 hours, 18 hours, 24 hours, 2 days, 3 days, 4 days, a week, 2 weeks, a month, 2 months, 3 months, 6 months;

increase ATP levels in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

decrease apoptosis in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

decrease cellular lipid levels in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

increase membrane potential in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

increase uncoupled respiration in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);

increase PI3K activity in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);

reduce reductive stress in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);

decrease reactive oxygen species (e.g. H2O2) in the cell, tissue of subject (e.g., in serum of a target subject) (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control)

Decrease cellular lipid levels of recipient cells at least 5% (e.g., >10%, >15%, >20%, >30%, >40%, >50%, >60%, >70%, >80%, >90%) relative to a control;

increases uncoupled respiration of recipient cells at least 5% (e.g., >10%, >15%, >20%, >30%, >40%, >50%, >60%, >70%, >80%, >90%) relative to a control;

decrease mitochondrial permeability transition pore (MPTP) formation in recipient cells at least 5% and does not increase more than 10% relative to a control;

increase Akt levels in recipient cells at least 10% (e.g., >10%, >15%, >20%, >30%, >40%, >50%, >60%, >70%, >80%, >90%) relative to a control;

decrease total NAD/NADH ratio in recipient cells at least 5% (e.g., >10%, >15%, >20%, >30%, >40%, >50%, >60%, >70%, >80%, >90%) relative to a control;

Reduce ROS levels in recipient cells at least 5% (e.g., >10%, >15%, >20%, >30%, >40%, >50%, >60%, >70%, >80%, >90%) relative to a control;

In another aspect, the invention features a method of increasing mitochondrial content and/or activity in a target cell or tissue, comprising delivering to the target cell or tissue a composition described herein. The composition may be delivered to the target cell or tissue in-vivo in a human subject, or ex-vivo to a human target cell or tissue. Mitochondrial content and/or activity may be increased e.g., at least 5%, 10%, 15%, 20%, 30%, 40%, 50%, 60%, 70%, 80% or greater, e.g., compared to a reference (e.g., compared to a control subject, or compared to prior to the administration).

In embodiments, the contacting may be for a time and in an amount sufficient to enhance a cell or tissue function; for a time and in an amount sufficient to improve function of an injured or diseased cell or tissue; for a time and in an amount sufficient to increase mitochondrial content and/or activity in the cell or tissue; for a time and in an amount sufficient to induce or decrease (e.g., block) cellular differentiation, de-differentiation, or trans-differentiation of the cell or tissue. The administration may be for a time and in an amount sufficient to modulate one or more of these parameters in the subject, e.g., at least 5%, 10%, 15%, 20%, 30%, 40%, 50%, 60%, 70%, 80% or greater, e.g., compared to a reference (e.g., compared to a control subject, or compared to prior to the administration). The contacting may be for a time and in an amount sufficient to modulate, e.g., at least 5%, 10%, 15%, 20%, 30%, 40%, 50%, 60%, 70%, 80% or greater, e.g., compared to a reference (e.g., compared to a control subject, or compared to prior to the administration):

Increases basal respiration of recipient cells at least 10% (e.g., >15%, >20%, >30%, >40%, >50%, >60%, >70%, >80%, >90%) relative to a control;

Chondrisomes of the preparation are taken up by at least 1% (e.g., at least 2%, 5%, 10%, 20%, 30%, 40%, 50%, 60%, 70%) of recipient cells;

Chondrisomes of the preparation are taken up and maintain membrane potential in recipient cells; Chondrisomes of the preparation persist in recipient cells at least 6 hours, e.g., at least 12 hours, 18 hours, 24 hours, 2 days, 3 days, 4 days, a week, 2 weeks, a month, 2 months, 3 months, 6 months;

increase ATP levels in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

decrease apotosis in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

decrease cellular lipid levels in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

increase membrane potential in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);

increase uncoupled respiration in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);

increase PI3K activity in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);

reduce reductive stress in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);

decrease reactive oxygen species (e.g. H2O2) in the cell, tissue of subject (e.g., in serum of a target subject) (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);

Decrease cellular lipid levels of recipient cells at least 5% (e.g., >10%, >15%, >20%, >30%, >40%, >50%, >60%, >70%, >80%, >90%) relative to a control;

increases uncoupled respiration of recipient cells at least 5% (e.g., >10%, >15%, >20%, >30%, >40%, >50%, >60%, >70%, >80%, >90%) relative to a control;

decrease mitochondrial permeability transition pore (MPTP) formation in recipient cells at least 5% and does not increase more than 10% relative to a control;

increase Akt levels in recipient cells at least 10% (e.g., >10%, >15%, >20%, >30%, >40%, >50%, >60%, >70%, >80%, >90%) relative to a control;

- decrease total NAD/NADH ratio in recipient cells at least 5% (e.g., >10%, >15%, >20%, >30%, >40%, >50%, >60%, >70%, >80%, >90%) relative to a control;
- Reduce ROS levels in recipient cells at least 5% (e.g., >10%, >15%, >20%, >30%, >40%, >50%, >60%, >70%, >80%, >90%) relative to a control.

In another aspect, the invention features a method of increasing tissue ATP levels, comprising delivering to a target cell or tissue a composition described herein. The composition may be delivered to the target cell or tissue in-vivo in a human subject, or ex-vivo to a human target cell or tissue. Tissue ATP levels may be increased e.g., at least 5%, 10%, 15%, 20%, 30%, 40%, 50%, 60%, 70%, 80% or greater, e.g., compared to a reference (e.g., compared to a control subject, or compared to prior to the administration).

In embodiments, the contacting may be for a time and in an amount sufficient to enhance a cell or tissue function; for a time and in an amount sufficient to improve function of an injured or diseased cell or tissue; for a time and in an amount sufficient to increase mitochondrial content and/or activity in the cell or tissue; for a time and in an amount sufficient to induce or decrease (e.g., block) cellular differentiation, de-differentiation, or trans-differentiation of the cell or tissue. The administration may be for a time and in an amount sufficient to modulate one or more of these parameters in the subject, e.g., at least 5%, 10%, 15%, 20%, 30%, 40%, 50%, 60%, 70%, 80% or greater, e.g., compared to a reference (e.g., compared to a control subject, or compared to prior to the administration). The contacting may be for a time and in an amount sufficient to modulate, e.g., at least 5%, 10%, 15%, 20%, 30%, 40%, 50%, 60%, 70%, 80% or greater, e.g., compared to a reference (e.g., compared to a control subject, or compared to prior to the administration):

- Increases basal respiration of recipient cells at least 10% (e.g., >15%, >20%, >30%, >40%, >50%, >60%, >70%, >80%, >90%) relative to a control;
- Chondrisomes of the preparation are taken up by at least 1% (e.g., at least 2%, 5%, 10%, 20%, 30%, 40%, 50%, 60%, 70%) of recipient cells;
- Chondrisomes of the preparation are taken up and maintain membrane potential in recipient cells; Chondrisomes of the preparation persist in recipient cells at least 6 hours, e.g., at least 12 hours, 18 hours, 24 hours, 2 days, 3 days, 4 days, a week, 2 weeks, a month, 2 months, 3 months, 6 months;
- increase ATP levels in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);
- decrease apoptosis in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);
- decrease cellular lipid levels in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);
- increase membrane potential in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);
- increase uncoupled respiration in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);
- increase PI3K activity in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);
- reduce reductive stress in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);
- decrease reactive oxygen species (e.g. H2O2) in the cell, tissue of subject (e.g., in serum of a target subject) (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control) Decrease cellular lipid levels of recipient cells at least 5% (e.g., >10%, >15%, >20%, >30%, >40%, >50%, >60%, >70%, >80%, >90%) relative to a control;
- increases uncoupled respiration of recipient cells at least 5% (e.g., >10%, >15%, >20%, >30%, >40%, >50%, >60%, >70%, >80%, >90%) relative to a control;
- decrease mitochondrial permeability transition pore (MPTP) formation in recipient cells at least 5% and does not increase more than 10% relative to a control;
- increase Akt levels in recipient cells at least 10% (e.g., >10%, >15%, >20%, >30%, >40%, >50%, >60%, >70%, >80%, >90%) relative to a control;
- decrease total NAD/NADH ratio in recipient cells at least 5% (e.g., >10%, >15%, >20%, >30%, >40%, >50%, >60%, >70%, >80%, >90%) relative to a control;
- Reduce ROS levels in recipient cells at least 5% (e.g., >10%, >15%, >20%, >30%, >40%, >50%, >60%, >70%, >80%, >90%) relative to a control.

In another aspect, the invention features a method of delivering a payload or cargo to a subject in need thereof. The method includes administering to the subject a composition described herein, wherein the chondrisomes of the composition comprise the payload. A payload may be a nucleic acid, a small molecule, a polypeptide, e.g., an agent listed in Table 4.

In embodiments, the contacting may be for a time and in an amount sufficient to enhance a cell or tissue function; for a time and in an amount sufficient to improve function of an injured or diseased cell or tissue; for a time and in an amount sufficient to increase mitochondrial content and/or activity in the cell or tissue; for a time and in an amount sufficient to induce or decrease (e.g., block) cellular differentiation, de-differentiation, or trans-differentiation of the cell or tissue. The administration may be for a time and in an amount sufficient to modulate one or more of these parameters in the subject, e.g., at least 5%, 10%, 15%, 20%, 30%, 40%, 50%, 60%, 70%, 80% or greater, e.g., compared to a reference (e.g., compared to a control subject, or compared to prior to the administration). The contacting may be for a time and in an amount sufficient to modulate, e.g., at least 5%, 10%, 15%, 20%, 30%, 40%, 50%, 60%, 70%, 80% or greater, e.g., compared to a reference (e.g., compared to a control subject, or compared to prior to the administration):

- Increases basal respiration of recipient cells at least 10% (e.g., >15%, >20%, >30%, >40%, >50%, >60%, >70%, >80%, >90%) relative to a control;

- Chondrisomes of the preparation are taken up by at least 1% (e.g., at least 2%, 5%, 10%, 20%, 30%, 40%, 50%, 60%, 70%) of recipient cells;
- Chondrisomes of the preparation are taken up and maintain membrane potential in recipient cells; Chondrisomes of the preparation persist in recipient cells at least 6 hours, e.g., at least 12 hours, 18 hours, 24 hours, 2 days, 3 days, 4 days, a week, 2 weeks, a month, 2 months, 3 months, 6 months;
- increase ATP levels in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);
- decrease apoptosis in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);
- decrease cellular lipid levels in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);
- increase membrane potential in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);
- increase uncoupled respiration in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);
- increase PI3K activity in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);
- reduce reductive stress in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);
- decrease reactive oxygen species (e.g. H2O2) in the cell, tissue of subject (e.g., in serum of a target subject) (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control)
- Decrease cellular lipid levels of recipient cells at least 5% (e.g., >10%, >15%, >20%, >30%, >40%, >50%, >60%, >70%, >80%, >90%) relative to a control;
- increases uncoupled respiration of recipient cells at least 5% (e.g., >10%, >15%, >20%, >30%, >40%, >50%, >60%, >70%, >80%, >90%) relative to a control;
- decrease mitochondrial permeability transition pore (MPTP) formation in recipient cells at least 5% and does not increase more than 10% relative to a control;
- increase Akt levels in recipient cells at least 10% (e.g., >10%, >15%, >20%, >30%, >40%, >50%, >60%, >70%, >80%, >90%) relative to a control;
- decrease total NAD/NADH ratio in recipient cells at least 5% (e.g., >10%, >15%, >20%, >30%, >40%, >50%, >60%, >70%, >80%, >90%) relative to a control;
- Reduce ROS levels in recipient cells at least 5% (e.g., >10%, >15%, >20%, >30%, >40%, >50%, >60%, >70%, >80%, >90%) relative to a control.

In another aspect, the invention features a method of treating a subject, e.g., a human, in need thereof. The method includes administering to the subject (e.g., a subject identified as having, or diagnosed with, a condition or disease described herein) a pharmaceutical composition or chondrisome preparation described herein.

In one embodiment, the subject is treated for a mitochondrial disease, e.g., a mitochondrial disease characterized by a mutation in the mitochondrial genome, or a mitochondrial disease characterized by a mutation in a nuclear gene associated with mitochondrial structure or function. In some embodiments, the subject is treated for a disease or condition associated with mitochondrial function.

In one embodiment, the subject is treated for a metabolic disease or condition, e.g., metabolic syndrome, high blood pressure (e.g., 130/80 or higher), high blood sugar, excess body fat, obesity, high cholesterol (e.g., HDL cholesterol 50 mg/dl or lower in men or 40 mg/dl or lower in women) or triglyceride levels (e.g., serum triglycerides 150 mg/dl or above).

In one embodiment, the subject is treated for a cardiovascular disorder (e.g. atherosclerosis, hypercholesterolemia, thrombosis, clotting disorder, myocardial infarction, sudden cardiac arrest, heart failure, angiogenic disorder such as macular degeneration, pulmonary hypertension, critical limb ischemia, critical organ ischemia (e.g. liver, lung, heart, spleen, pancreas, mesentery, brain), or traumatic brain injury).

In one embodiment, the subject is treated for a neurodegenerative disorder (e.g. Alzheimer's disease, Huntington's disease, Parkinson's disease, Friedreich's ataxia and other ataxias, amyotrophic lateral sclerosis (ALS) and other motor neuron diseases, autism, Duchenne muscular dystrophy);

In one embodiment, the subject is treated for a neuropsychiatric disease (e.g., bipolar disorder, depression, schizophrenia, Rett's syndrome).

In one embodiment, the subject is treated for a neuropathy or myopathy, such as Leber's hereditary optic neuropathy (LHON), encephalopathy, lactacidosis, myoclonic epilepsy with ragged red fibers (MERFF); epilepsy; and mitochondrial myopathy.

In one embodiment, the subject is treated for an infectious disease (e.g. a viral infection (e.g., HIV, HCV, RSV), a bacterial infection, a fungal infection, sepsis).

In other embodiments, the subject is treated for an autoimmune disorder (e.g. diabetes, lupus, multiple sclerosis, psoriasis, rheumatoid arthritis); an inflammatory disorder (e.g. arthritis, pelvic inflammatory disease); a proliferative disorder (e.g. cancer, benign neoplasms); a respiratory disorder (e.g. chronic obstructive pulmonary disease); a digestive disorder (e.g. inflammatory bowel disease, ulcer); a musculoskeletal disorder (e.g. fibromyalgia, arthritis); an endocrine, metabolic, or nutritional disorder (e.g. diabetes, osteoporosis); an urological disorder (e.g. renal disease); a psychological disorder (e.g. depression, schizophrenia); a skin disorder (e.g. wounds, eczema); or a blood or lymphatic disorder (e.g. anemia, hemophilia); an optical disorder (e.g., glaucoma, optic neuropathy).

In each of the above embodiments, the method includes administering the pharmaceutical composition or chondrisome preparation in combination with a second therapeutic agent, e.g., a standard-of-care agent for treatment of the disease or condition.

The administration may be for a time and in an amount sufficient to enhance a cell or tissue function in the subject. The administration may be for a time and in an amount sufficient to improve function of an injured cell or diseased tissue in the subject. The administration may be for a time and in an amount sufficient to increase mitochondrial content and/or activity in a cell or tissue of the subject. The administration may be for a time and in an amount sufficient to increase tissue ATP levels in the subject. The administration may be for a time and in an amount sufficient to induce or decrease (e.g., block) cellular differentiation, de-differentiation, or trans-differentiation.

The administration may be for a time and in an amount sufficient to effect one or more of:

- Increases basal respiration of recipient cells at least 10% (e.g., >15%, >20%, >30%, >40%, >50%, >60%, >70%, >80%, >90%) relative to a control;
- Chondrisomes of the preparation are taken up by at least 1% (e.g., at least 2%, 5%, 10%, 20%, 30%, 40%, 50%, 60%, 70%) of recipient cells;
- Chondrisomes of the preparation are taken up and maintain membrane potential in recipient cells;
- Chondrisomes of the preparation persist in recipient cells at least 6 hours, e.g., at least 12 hours, 18 hours, 24 hours, 2 days, 3 days, 4 days, a week, 2 weeks, a month, 2 months, 3 months, 6 months;
- increase ATP levels in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);
- decrease apotosis in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);
- decrease cellular lipid levels in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);
- increase membrane potential in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);
- increase uncoupled respiration in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);
- increase PI3K activity in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);
- reduce reductive stress in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);
- decrease reactive oxygen species (e.g. H2O2) in the cell, tissue of subject (e.g., in serum of a target subject) (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control)
- Decrease cellular lipid levels of recipient cells at least 5% (e.g., >10%, >15%, >20%, >30%, >40%, >50%, >60%, >70%, >80%, >90%) relative to a control;
- increases uncoupled respiration of recipient cells at least 5% (e.g., >10%, >15%, >20%, >30%, >40%, >50%, >60%, >70%, >80%, >90%) relative to a control;
- decrease mitochondrial permeability transition pore (MPTP) formation in recipient cells at least 5% and does not increase more than 10% relative to a control;
- increase Akt levels in recipient cells at least 10% (e.g., >10%, >15%, >20%, >30%, >40%, >50%, >60%, >70%, >80%, >90%) relative to a control;
- decrease total NAD/NADH ratio in recipient cells at least 5% (e.g., >10%, >15%, >20%, >30%, >40%, >50%, >60%, >70%, >80%, >90%) relative to a control;
- Reduce ROS levels in recipient cells at least 5% (e.g., >10%, >15%, >20%, >30%, >40%, >50%, >60%, >70%, >80%, >90%) relative to a control;

In one aspect, the invention features a pharmaceutical composition comprising a preparation of chondrisomes expressing an exogenous protein. In another aspect, the invention features a pharmaceutical composition comprising a preparation of chondrisomes expressing an uncoupling protein.

In one embodiment, the pharmaceutical preparation of chondrisomes expresses an uncoupling protein, e.g., UCP1, UCP2, UCP3, UCP4 or UCP5. The uncoupling protein may be endogenous or heterologous (exogenous) to the source mitochondria (e.g., the uncoupling protein may be naturally expressed, or the source mitochondria or chondrisomes may be modified (e.g., genetically modified or loaded) to express or over-express the protein. The source mitochondria or chondrisomes may be genetically modified by, e.g., the introduction of modified RNA, or DNA, encoding the protein.

In one embodiment, the source mitochondria or chondrisomes are engineered to express a protein at least 85%, 90%, 95%, 97%, 98%, 100% identical to the sequence of human UCP1 (SEQ ID NO:1), human UCP2 (SEQ ID NO:2), human UCP3 (SEQ ID NO:3), human UCP4 (SEQ ID NO:4) or human UCP5 (SEQ ID NO:5), wherein the protein has transporter activity in the chondrisomes.

In one embodiment, the chondrisomes are derived from brown fat of a subject, e.g., a human. In one embodiment, the chondrisomes are derived from a non-brown fat source.

In another aspect, the invention features a method of increasing thermogenesis in a subject, reducing fat tissue mass in a subject, and/or increasing mitochondrial number or function in the fat tissue of a subject (e.g., in a target cell or tissue of a subject). The method includes delivering to the target cell or tissue a composition described herein. The composition may be delivered to the target cell or tissue in-vivo, e.g., in a human subject, or ex-vivo to a human target cell or tissue.

In embodiments, the target cell or tissue is white adipocytes.

In embodiments, the mitochondria of the composition express a transporter, e.g., UCP1, UCP2, UCP3, UCP4 or UCP5. The expressed transporter may be endogenous or heterologous to the source mitochondria (e.g., the transporter may be naturally expressed, or the mitochondria may be modified (e.g., genetically modified or loaded) to express or over-express the transporter. In one embodiment, the mitochondria are engineered to express a protein at least 85%, 90%, 95%, 97%, 98%, 100% identical to the sequence of human UCP1 (SEQ ID NO:1), human UCP2 (SEQ ID NO:2), human UCP3 (SEQ ID NO: 3), human UCP4 (SEQ ID NO:4) or human UCP5 (SEQ ID NO:5), wherein the protein has transporter activity in the chondrisomes.

In embodiments, the chondrisomes of the composition are isolated at least in part from brown adipocytes, e.g., from a live or deceased donor subject. In other embodiments, the chondrisomes of the composition are isolated at least in part from brown adipocytes in culture (e.g., a primary culture of brown adipocytes, or an immortalized brown adipocyte cell line).

In embodiments, the source mitochondria or chondrisomes of the composition are autologous to the subject. In other embodiments, the source mitochondria or chondrisomes of the composition are allogeneic.

In embodiments, the composition is administered to fat tissue, e.g., to white adipocytes, of the subject.

In embodiments, thermogenesis may be increased, and/or fat tissue mass or volume is reduced, and/or mitochondrial number or function may increase e.g., at least 5%, 10%, 15%, 20%, 30%, 40%, 50%, 60%, 70%, 80% or greater compared to a reference (e.g., compared to a control subject, or compared to prior to the administration).

The administration may be for a time and in an amount sufficient to promote weight loss in the subject.

In another aspect, the invention features a method of modulating one or more serum composition, e.g., modulating one or more serum metabolites, e.g., decreasing serum cholesterol and/or triglycerides in a subject in need thereof. The method includes administering to the subject a pharmaceutical composition described herein. The method includes delivering to the target cell or tissue a composition described herein. The composition may be delivered to the target cell or tissue in-vivo, e.g., in a human subject, or ex-vivo to a human target cell or tissue.

In embodiments, the target cell or tissue is a fat tissue of the subject, e.g., white adipocytes. In embodiments, the source mitochondria or chondrisomes of the composition express a transporter, e.g., UCP1, UCO2, UCP3, UCP4 or UCP5. The expressed transporter may be endogenous or heterologous to the source mitochondria (e.g., the transporter may be naturally expressed, or the mitochondria may be modified (e.g., genetically modified or loaded) to express or over-express the transporter. In one embodiment, the mitochondria are engineered to express a protein at least 85%, 90%, 95%, 97%, 98%, 100% identical to the sequence of human UCP1 (SEQ ID NO:1), human UCP2 (SEQ ID NO: 2), human UCP3 (SEQ ID NO:3), human UCP4 (SEQ ID NO:4) or human UCP5 (SEQ ID NO:5), wherein the protein has transporter activity in the mitochondria.

In embodiments, the chondrisomes of the composition are isolated at least in part from brown adipocytes.

In embodiments, the source mitochondria or chondrisomes of the composition are autologous to the subject. In other embodiments, the source mitochondria or chondrisomes of the composition are allogeneic.

In embodiments, the composition is administered to a fat tissue, e.g., white adipocytes of the subject.

In embodiments, serum cholesterol in the subject may be reduced e.g., at least 5%, 10%, 15%, 20%, 30%, 40%, 50%, 60%, 70%, 80% or greater compared to a reference (e.g., compared to a control subject, or compared to prior to the administration).

In embodiments, serum triglycerides may be reduced in the subject, e.g., at least 5%, 10%, 15%, 20%, 30%, 40%, 50%, 60%, 70%, 80% or greater compared to a reference (e.g., compared to a control subject, or compared to prior to the administration).

In another aspect, the invention features a method of making a pharmaceutical preparation suitable for administration to a human subject, comprising:

(a) providing a parent cell or tissue source of mitochondria, (b) isolating a preparation of chondrisomes from the parent cell or tissue source (e.g., as described herein), and (c) evaluating (e.g., testing or measuring) a sample of the preparation for one or more of the following characteristics:

the chondrisomes of the preparation have a mean average size between 150-1500 nm, e.g., between 200-1200 nm, e.g., between 500-1200 nm, e.g., 175-950 nm;

the chondrisomes of the preparation have a polydispersity (D90/D10) between 1.1 to 6, e.g., between 1.5-5. In embodiments, chondrisomes of a preparation from a cultured cell source (e.g., cultured fibroblasts) have a polydispersity (D90/D10) between 2-5, e.g., between 2.5-5;

outer chondrisome membrane integrity wherein the preparation exhibits<20% (e.g., <15%, <10%, <5%, <4ˆ, <3%, <2%, <1%) increase in oxygen consumption rate over state 4 rate following addition of reduced cytochrome c;

complex I level of 1-8 mOD/ug total protein, e.g., 3-7 mOD/ug total protein, 1-5 mOD/ug total protein. In embodiments, chondrisomes of a preparation from a cultured cell source (e.g., cultured fibroblasts) have a complex I level of 1-5 mOD/ug total protein;

complex II level of 0.05-5 mOD/ug total protein, e.g., 0.1-4 mOD/ug total protein, e.g., 0.5-3 mOD/ug total protein. In embodiments, chondrisomes of a preparation from a cultured cell source (e.g., cultured fibroblasts) have a complex II level of 0.05-1 mOD/ug total protein;

complex III level of 1-30 mOD/ug total protein, e.g., 2-30, 5-10, 10-30 mOD/ug total protein. In embodiments, chondrisomes of a preparation from a cultured cell source (e.g., cultured fibroblasts) have a complex III level of 1-5 mOD/ug total protein;

complex IV level of 4-50 mOD/ug total protein, e.g., 5-50, e.g., 10-50, 20-50 mOD/ug total protein. In embodiments, chondrisomes of a preparation from a cultured cell source (e.g., cultured fibroblasts) have a complex IV level of 3-10 mOD/ug total protein;

genomic concentration 0.001-2 (e.g., .001-1, .01-1, .01-.1, .01-.05, .1-.2) mtDNA ug/mg protein;

membrane potential of the preparation is between −5 to −200 mV, e.g., between −100 to −200 mV, −50 to −200 mV, −50 to −75 mV, −50 to −100 mV. In some embodiments, membrane potential of the preparation is less than −150 mV, less than −100 mV, less than −75 mV, less than −50 mV, e.g., −5 to −20 mV;

a protein carbonyl level of less than 100 nmol carbonyl/mg chondrisome protein (e.g., less than 90 nmol carbonyl/mg chondrisome protein, less than 80 nmol carbonyl/mg chondrisome protein, less than 70 nmol carbonyl/mg chondrisome protein, less than 60 nmol carbonyl/mg chondrisome protein, less than 50 nmol carbonyl/mg chondrisome protein, less than 40 nmol carbonyl/mg chondrisome protein, less than 30 nmol carbonyl/mg chondrisome protein, less than 25 nmol carbonyl/mg chondrisome protein, less than 20 nmol carbonyl/mg chondrisome protein, less than 15 nmol carbonyl/mg chondrisome protein, less than 10 nmol carbonyl/mg chondrisome protein, less than 5 nmol carbonyl/mg chondrisome protein, less than 4 nmol carbonyl/mg chondrisome protein, less than 3 nmol carbonyl/mg chondrisome protein;

<20% mol/mol ER proteins (e.g., >15%, >10%, >5%, >3%, >2%, >1%) mol/mol ER proteins;

>5% mol/mol mitochondrial proteins (proteins identified as mitochondrial in the MitoCarta database (Calvo et al., NAR 20151 doi: 10.1093/nar/gkv1003)), e.g., >10%, >15%, >20%, >25%, >30%, >35%, >40%; >50%, >55%, >60%, >65%, >70%, >75%, >80%; >90% mol/mol mitochondrial proteins);

>0.05% mol/mol of MT-CO2, MT-ATP6, MT-ND5 and MT-ND6 protein (e.g., >0.1%; >05%, >1%, >2%, >3%, >4%, >5%, >7, >8%, >9%, >10, >15% mol/mol of MT-CO2, MT-ATP6, MT-ND5 and MT-ND6 protein);

Genetic quality>80%, e.g., >85%, >90%, >95%, >97%, >98%, >99%;

Relative ratio mtDNA/nuclear DNA is >1000 (e.g., >1,500, >2000, >2,500, >3,000, >4,000, >5000, >10, 000, >25,000, >50,000, >100,000, >200,000, >500, 000);

Endotoxin level<0.2 EU/ug protein (e.g., <0.1, 0.05, 0.02, 0.01 EU/ug protein);

Substantially absent exogenous non-human serum;

Glutamate/malate RCR 3/2 of 1-15, e.g., 2-15, 5-15, 2-10, 2-5, 10-15;

Glutamate/malate RCR 3/40 of 1-30, 1-20, 2-20, 5-20, 3-15, 10-30;

Succinate/rotenone RCR 3/2 of 1-15, 2-15, 5-15, 1-10, 10-15;

Succinate/rotenone RCR 3/40 of 1-30, 1-20, 2-20, 5-20, 3-15, 10-30;

complex I activity of 0.05-100 nmol/min/mg total protein (e.g., .05-50, .05-20, .5-10, .1-50, 1-50, 2-50, 5-100, 1-20 nmol/min/mg total protein);

complex II activity of 0.05-50 nmol/min/mg total protein (e.g., .05-50, .05-20, .5-10, .1-50, 1-50, 2-50, 5-50, 1-20 nmol/min/mg total protein);

complex III activity of 0.05-20 nmol/min/mg total protein (e.g., .05-50, .05-20, .5-10, .1-50, 1-50, 2-50, 5-100, 1-20 nmol/min/mg total protein);

complex IV activity of 0.1-50 nmol/min/mg total protein (e.g., .05-50, .05-20, .5-10, .1-50, 1-50, 2-50, 5-50, 1-20 nmol/min/mg total protein);

complex V activity of 1-500 nmol/min/mg total protein (e.g., 10-500, 10-250, 10-200, 100-500 nmol/min/mg total protein);

reactive oxygen species (ROS) production level of 0.01-50 µmol H2O2/ug protein/hr (e.g., .05-40, .05-25, 1-20, 2-20, .05-20, 1-20 µmol H2O2/ug protein/hr);

Citrate Synthase activity of 0.05-5 (e.g., .5-5, .5-2, 1-5, 1-4) mOD/min/ug total protein;

Alpha ketoglutarate dehydrogenase activity of 0.05-10 (e.g., .1-10, .1-8, .5-8, .1-5, .5-5, .5-3, 1-3) mOD/min/ug total protein;

Creatine Kinase activity of 0.1-100 (e.g., .5-50, 1-100, 1-50, 1-25, 1-15, 5-15) mOD/min/ug total protein;

Pyruvate dehydrogenase activity of 0.1-10 (e.g., .5-10, .5-8, 1-10, 1-8, 1-5, 2-3) mOD/min/ug total protein;

Aconitase activity of 0.1-50 (e.g., 5-50, .1-2, .1-20, .5-30) mOD/min/ug total protein. In embodiments, aconitase activity in a chondrisome preparation from platelets is between .5-5 mOD/min/ug total protein. In embodiments, aconitase activity in a chondrisome preparation from cultured cells, e.g., fibroblasts, is between 5-50 mOD/min/ug total protein;

Maximal fatty acid oxidation level of 0.05-50 (e.g., .05-40, .05-30, .05-10, .5-50, .5-25, .5-10, 1-5) pmol O2/min/ug chondrisome protein;

Palmitoyl carnitine & Malate RCR3/2 state 3/state 2 respiratory control ratio (RCR 3/2) of 1-10 (e.g., 1-5);

electron transport chain efficiency of 1-1000 (e.g., 10-1000, 10-800, 10-700, 50-1000, 100-1000, 500-1000, 10-400, 100-800) nmol 02/min/mg protein/ΔGATP (in kcal/mol) total lipid content of 50,000-2, 000,000 µmol/mg (e.g., 50,000-1,000,000; 50,000-500, 000 pmol/mg);

double bonds/total lipid ratio of 0.8-8 (e.g., 1-5, 2-5, 1-7, 1-6) pmol/pmol;

phospholipid/total lipid ratio of 50-100 (e.g., 60-80, 70-100, 50-80) 100*pmol/pmol;

phosphosphingolipid/total lipid ratio of 0.2-20 (e.g., .5-15, .5-10, 1-10, .5-10, 1-5, 5-20) 100*pmol/pmol.

ceramide content 0.05-5 (e.g., .1-5, .1-4, 1-5, .05-3) 100*pmol/pmol total lipid;

cardiolipin content 0.05-25 (0.1-20, .5-20, 1-20, 5-20, 5-25, 1-25, 10-25, 15-25) 100*pmol/pmol total lipid;

lyso-phosphatidylcholine (LPC) content of 0.05-5 (e.g., .1-5, 1-5, .1-3, 1-3, .05-2) 100*pmol/pmol total lipid;

Lyso-Phosphatidylethanolamine (LPE) content of 0.005-2 (e.g., .005-1, .05-2, .05-1) 100*pmol/pmol total lipid;

Phosphatidylcholine (PC) content of 10-80 (e.g., 20-60, 30-70, 20-80, 10-60m 30-50) 100*pmol/pmol total lipid;

Phosphatidylcholine-ether (PC O—) content 0.1-10 (e.g., .5-10, 1-10, 2-8, 1-8) 100*pmol/pmol total lipid;

Phosphatidylethanolamine (PE) content 1-30 (e.g., 2-20, 1-20, 5-20) 100*pmol/pmol total lipid; Phosphatidylethanolamine-ether (PE O—) content 0.05-30 (e.g., .1-30, .1-20, 1-20, .1-5, 1-10, 5-20) 100*pmol/pmol total lipid;

Phosphatidylinositol (PI) content 0.05-15 (e.g., .1-15, .1-10, 1-10, .1-5, 1-10, 5-15) 100*pmol/pmol total lipid;

Phosphatidylserine (PS) content 0.05-20 (e.g., .1-15, .1-20, 1-20, 1-10, .1-5, 1-10, 5-15) 100*pmol/pmol total lipid;

Sphingomyelin (SM) content 0.01-20 (e.g., .01-15, .01-10, .5-20, .5-15, 1-20, 1-15, 5-20) 100*pmol/pmol total lipid;

Triacylglycerol (TAG) content 0.005-50 (e.g., .01-50, .1-50, 1-50, 5-50, 10-50, .005-30, .01-25, .1-30) 100*pmol/pmol total lipid;

PE: LPE ratio 30-350 (e.g., 50-250, 100-200, 150-300); PC: LPC ratio 30-700 (e.g., 50-300, 50-250, 100-300, 400-700, 300-500, 50-600, 50-500, 100-500, 100-400);

PE 18: n (n>0) content 0.5-20% (e.g., 1-20%, 1-10%, 5-20%, 5-10%, 3-9%) pmol AA/pmol lipid class;

PE 20:4 content 0.05-20% (e.g., 1-20%, 1-10%, 5-20%, 5-10%) pmol AA/pmol lipid class; PC 18: n (n>0) content 5-50% (e.g., 5-40%, 5-30%, 20-40%, 20-50%) pmol AA/pmol lipid class;

PC 20:4 content 1-20% (e.g., 2-20%, 2-15%, 5-20%, 5-15%) pmol AA/pmol lipid class; and (d) processing the preparation for administration to a human subject if one or more (2, 3, 4, 5, 6, 7, 8, 9, 10 or more) of the characteristics meet a pre-determined reference value (e.g., a reference value recited above), thereby making a pharmaceutical preparation suitable for administration to a human subject.

In some embodiments, processing includes formulating, packaging, labeling or selling for human use.

In some embodiments, the pre-determined reference value is a quality control potency assay. In some embodiments, the pre-determined reference value is a quality control identity assay. In some embodiments, the pre-determined reference value is a manufacturing release assay.

In another aspect, the invention features methods of delivering a composition or preparation described herein to an ischemic tissue or subject, and methods of reducing, improving or treating ischemia in a tissue or subject.

In one embodiment, the methods include: providing to the tissue or subject (e.g., in-vivo or ex-vivo) a pharmaceutical composition comprising a preparation of chondrisomes described herein.

In one embodiment, the methods include: providing to the tissue or subject (e.g., in-vivo or ex-vivo) a pharmaceutical composition comprising a preparation of chondrisomes having at least one (e.g., 1, 2, 3, 4, 5, 6, 7, 8 or more) of the following characteristics:

(a) the chondrisomes of the preparation have a polydispersity (D90/D10) between 1.1 to 6, e.g., between 1.5-5, between 2-5, e.g., between 2.5-5;

(b) outer chondrisome membrane integrity wherein the preparation exhibits<20% (e.g., <15%, <10%, <5%, <4^, <3%, <2%, <1%) increase in oxygen consumption rate over state 4 rate following addition of reduced cytochrome c;

(c) a protein carbonyl level of less than 100 nmol carbonyl/mg chondrisome protein (e.g., less than 90 nmol carbonyl/mg chondrisome protein, less than 80 nmol carbonyl/mg chondrisome protein, less than 70 nmol carbonyl/mg chondrisome protein, less than 60 nmol carbonyl/mg chondrisome protein, less than 50 nmol carbonyl/mg chondrisome protein, less than 40 nmol carbonyl/mg chondrisome protein, less than 30 nmol carbonyl/mg chondrisome protein, less than 25 nmol carbonyl/mg chondrisome protein, less than 20 nmol carbonyl/mg chondrisome protein, less than 15 nmol carbonyl/mg chondrisome protein, less than 10 nmol carbonyl/mg chondrisome protein, less than 5 nmol carbonyl/mg chondrisome protein, less than 4 nmol carbonyl/mg chondrisome protein, less than 3 nmol carbonyl/mg chondrisome protein;

(d) cardiolipin content 0.05-25 (0.1-20, .5-20, 1-20, 5-20, 5-25, 1-25, 10-25, 15-25) 100*pmol/pmol total lipid;

(e) Sphingomyelin (SM) content 0.01-20 (e.g., .01-15, .01-10, .5-20, .5-15, 1-20, 1-15, 5-20) 100*pmol/pmol total lipid;

(f) substantially lacks detectable amounts of endotoxin, infectious agent, and exogenous serum.

In one embodiment, the methods include providing to the tissue or subject (e.g., in-vivo or ex-vivo) a pharmaceutical composition comprising a preparation of chondrisomes in an amount and for a time sufficient to modulate (e.g., decrease) a cardiac protein in the tissue or subject (e.g., in-vivo or ex-vivo) comprising: contacting the cell with a composition comprising a preparation of chondrisomes in an amount and for a time sufficient to modulate (e.g., decrease) the cardiac protein in the cell. In embodiments, the cardiac protein is troponin I, troponin T, creatine kinase (CK-MB) or combinations thereof. In embodiments, the composition further decreases at least one selected from the group consisting of myoglobin, B-type natriuretic peptide, and high-sensitivity C-reactive protein (hs-CRP). The composition is provided for a time and in an amount sufficient to reduce or improve ischemia in the tissue or subject.

In one embodiment, the methods include providing to the tissue or subject, a pharmaceutical composition comprising a composition or preparation of chondrisomes described herein in an amount and for a time sufficient to decrease apoptosis and/or ferroptosis in the cell or subject.

In one embodiment, the methods include providing to the tissue or subject, a pharmaceutical composition comprising a composition or preparation of chondrisomes described herein in an amount and for a time sufficient to decrease reactive oxygen species (e.g. H2O2) in the tissue or subject.

In one embodiment, the chondrisomes of the composition have a bioenergetic characteristic selected from the group consisting of:

electron transport chain efficiency of 1-1000 (e.g., 10-1000, 10-800, 10-700, 50-1000, 100-1000, 500-1000, 10-400, 100-800) nmol 02/min/mg protein/ΔGATP (in kcal/mol)

Alpha ketoglutarate dehydrogenase activity of 0.05-10 (e.g., .1-10, .1-8, .5-8, .1-5, .5-5, .5-3, 1-3) mOD/min/ug total protein;

Maximal fatty acid oxidation level of 0.05-50 (e.g., .05-40, .05-30, .05-10, .5-50, .5-25, .5-10, 1-5) pmol O2/min/ug chondrisome protein; Pyruvate dehydrogenase activity of 0.1-10 (e.g., .5-10, .5-8, 1-10, 1-8, 1-5, 2-3) mOD/min/ug total protein;

In embodiments where the subject or tissue has cardiac ischemia, the composition is administered in an amount and for a time sufficient to:

(a) Reduce ROS levels in recipient cells at least 5% (e.g., >10%, >15%, >20%, >30%, >40%, >50%, >60%, >70%, >80%, >90%) relative to a control;

(b) Increase fractional shortening in subject with cardiac ischemia at least 5% (e.g., >10%, >15%, >20%, >30%, >40%, >50%, >60%, >70%, >80%, >90%) relative to a control;

(c) Increase end diastolic volume in subject with cardiac ischemia at least 5% (e.g., >10%, >15%, >20%, >30%, >40%, >50%, >60%, >70%, >80%, >90%) relative to a control;

(d) decrease end systolic volume in subject with cardiac ischemia at least 5% (e.g., >10%, >15%, >20%, >30%, >40%, >50%, >60%, >70%, >80%, >90%) relative to a control;

(e) increase stroke volume in subject with cardiac ischemia at least 5% (e.g., >10%, >15%, >20%, >30%, >40%, >50%, >60%, >70%, >80%, >90%) relative to a control;

(f) increase ejection fraction in subject with cardiac ischemia at least 5% (e.g., >10%, >15%, >20%, >30%, >40%, >50%, >60%, >70%, >80%, >90%) relative to a control;

(g) increase cardia output in subject with cardiac ischemia at least 5% (e.g., >10%, >15%, >20%, >30%, >40%, >50%, >60%, >70%, >80%, >90%) relative to a control;

(h) increase cardiac index in subject with cardiac ischemia at least 5% (e.g., >10%, >15%, >20%, >30%, >40%, >50%, >60%, >70%, >80%, >90%) relative to a control;

(i) decrease serum CKNB levels in subject with cardiac ischemia at least 5% (e.g., >10%, >15%, >20%, >30%, >40%, >50%, >60%, >70%, >80%, >90%) relative to a control;

(j) decrease serum cTnI levels in subject with cardiac ischemia at least 5% (e.g., >10%, >15%, >20%, >30%, >40%, >50%, >60%, >70%, >80%, >90%) relative to a control;

(k) decrease serum hydrogen peroxide in subject with cardiac ischemia at least 5% (e.g., >10%, >15%, >20%, >30%, >40%, >50%, >60%, >70%, >80%, >90%) relative to a control;

(l) decrease serum cholesterol levels and/or triglycerides in a subject at least 5% (e.g., >10%, >15%, >20%, >30%, >40%, >50%, >60%, >70%, >80%, >90%) relative to a control.

(m) improve (e.g., increase) ejection fraction (e.g., at least 5%, 10%, 15%, 20%, 30%, 40%, 50%, 60%, 70%, 80% or greater compared to a reference (e.g., compared to a control subject, or compared to prior to the administration));

(n) decrease infarcted area (% IR/AAR) (e.g., at least 5%, 10%, 15%, 20%, 30%, 40%, 50%, 60%, 70%, 80% or greater compared to a reference (e.g., compared to a control subject, or compared to prior to the administration));

(o) decrease blood creatine kinase (e.g., CK-MB) levels (e.g., at least 5%, 10%, 15%, 20%, 30%, 40%, 50%, 60%, 70%, 80% or greater compared to a reference (e.g., compared to a control subject, or compared to prior to the administration)) and/or (p) decrease blood cTnI levels (e.g., at least 5%, 10%, 15%, 20%, 30%, 40%, 50%, 60%, 70%, 80% or greater compared to a reference (e.g., compared to a control subject, or compared to prior to the administration)

For all aspects described herein:

In embodiments of the compositions or methods described herein, chondrisomes of the preparation are associated with, e.g., internalized into, or partially fused with, the target tissue or cell. In some embodiments, chondrisomes of the preparation are internalized into the cytosol of a target cell (e.g., >5% e.g., >10%, >20%, >30%, >40%, >50%, >60%, >70%, >80% or >90% of associated chondrisomes are internalized into the cytosol of the target cell). In some embodiments, chondrisomes of the preparation are associated with the endogenous mitochondrial network of a target cell (e.g., >5% e.g., >10%, >20%, >30%, >40%, >50%, >60%, >70%, >80% or >90% of associated chondrisomes are internalized into the endogenous mitochondrial network of the target cell). In some embodiments, chondrisomes of the preparation are internalized into the lysosomes of a target cell (e.g., between 1-90%, e.g., <90%, <80%, <70%, <60%, <50%, <40%, <30%, <20%, <10% of associated chondrisomes are internalized into the cytosol of the target cell). In some embodiments, chondrisomes of the preparation are associated with the mitochondrial outer membrane of a target cell (e.g., >5% e.g., >10%, >20%, >30%,>40%, >50%, >60%, >70%, >80% or >90% of associated chondrisomes are associated with the mitochondrial outer membrane of the target cell).

In embodiments of the compositions or methods described herein, greater than 5%, 10%, 20%, 30%, 40%, 50%, 60%, 70%, 80% or more of the chondrisomes of a preparation are internalized into the target tissue or cell. In other embodiments, chondrisomes of the preparation are internalized into the cytosol of a target cell, e.g., greater than 5%, 10%, 20%, 30%, 40%, 50%, 60%, 70%, 80% or more of the chondrisomes are internalized into the cytosol. In some embodiments, less than 5%, 10%, 20%, 30%, 40%, 50%, 60%, 70%, 80% of the chondrisomes are internalized into lysosomes of the target cells.

In embodiments of the compositions or methods described herein, the target tissue or cell is selected from the group consisting of: epithelial, connective, muscular, and nervous tissue or cell.

In embodiments of the methods described herein, the chondrisome composition or preparation is delivered over a period of time, e.g., over a period of hours or days. In some embodiments, a chondrisome composition or preparation is contacted with a target cell, tissue or subject over a period of time, during which association of the chondrisomes with the target cell, tissue or subject increases over time, e.g., as measured by increased detection of a cargo or payload delivered to the target cell, tissue or subject by the preparation, over time.

In embodiments of the methods described herein, the chondrisome composition or preparation is treated with an agent, and/or administered in combination with an agent, to modulate subcellular targeting of the administered preparation. In embodiments, the agent enables endosomal/lysosomal escape and/or enhances cytosolic or non-lysosomal delivery of the preparation. In embodiments, the agent is a peptide or protein that enhances cytosolic or non-lysosomal delivery of the preparation, e.g., haemagglutinin, diINF-7, penton base, gp41, gp41/polyethylenimine, TAT, L2 from Papillomavirus, envelope protein (E) of West Nile virus, listeriolysin O (LLO), Pneumococcal pneumolysin (PLO), Streptococcal streptolysin O (SLO), Diphtheria toxin (DT), *Pseudomonas aeruginosa* exotoxin A (ETA), Shiga toxin, cholera toxin, ricin, saporin, gelonin, human calcitonin derived peptide, fibroblast growth factors receptor (FGFR3), melittin, (R-Ahx-R) (4) AhxB, glycoprotein H (gpH) from herpes simplex, KALA, GALA, a synthetic surfactant, penetratin (pAntp), R6-Penetratin with arginine-residues, EB1, bovine prion protein (bPrPp), Poly(L-histidine), Sweet Arrow Peptide (SAP). In other embodiments, the agent is a chemical that enhances cytosolic or non-lysosomal delivery of the preparation, e.g., polyethylenimine (PEI), Poly(amidoamine) s (PAAs), poly(propylacrylic acid) (PPAA), ammonium chloride, chloroquine, methylamine.

In embodiments of the compositions or methods described herein, the target tissue or cell is in the digestive system, the endocrine system, the excretory system, the lymphatic system, the skin, muscle, the nervous system, the reproductive system, the respiratory system, or the skeletal system.

In embodiments of the compositions or methods described herein, the chondrisomes are obtained from a human cell or tissue source, or from human cells in culture.

In embodiments of the compositions or methods described herein, the chondrisomes are obtained from a cell type different than the target tissue or cell type.

In embodiments of the compositions or methods described herein, the chondrisomes are obtained from the same cell type as the target tissue or cell type.

In any composition, preparation, or method described herein, the chondrisomes may be encapsulated.

In embodiments of the methods described herein, the chondrisomes are autologous to the subject. In other embodiments of the methods described herein, the chondrisomes are allogeneic to the subject. The subject may be an animal, e.g., a mammal, e.g., a human.

In embodiments of the methods described herein, the compositions or preparations are administered locally to a tissue or organ of a subject (e.g., by local injection or perfusion). In other embodiments, the compositions or preparations are administered systemically to a subject.

In embodiments of the compositions or methods described herein, the parent cell source is selected from the group consisting of: circulating cells (e.g., platelets, leukocytes), muscle cells (e.g., cardiomyocytes, skeletal muscle, smooth muscle), epidermal cells (e.g., keratinocytes, melanocytes), dermal cells, hypodermal cells (e.g., fibroblasts, brown adipocytes), stem cells (e.g., mesenchymal stem cells, hemapoietic stem cells, neural stem cells), liver cells, kidney cells, pancreas cells, spleen cells.

In embodiments of the compositions or methods described herein, the target cell or tissue is from, or the subject is, a subject who has or is at risk for: ischemia; a mitochondrial disease (e.g., a genetic mitochondrial disease); an infectious disease (e.g. a viral infection (e.g., HIV, HCV, RSV), a bacterial infection, a fungal infection, sepsis); cardiovascular disorder (e.g. atherosclerosis, hypercholesterolemia, thrombosis, clotting disorder, angiogenic disorder such as macular degeneration); an autoimmune disorder (e.g. diabetes, lupus, multiple sclerosis, psoriasis, rheumatoid arthritis); an inflammatory disorder (e.g. arthritis, pelvic inflammatory disease); a neurological disorder (e.g. Alzheimer's disease, Huntington's disease; autism; Duchenne muscular dystrophy); a proliferative disorder (e.g. cancer, benign neoplasms); a respiratory disorder (e.g. chronic obstructive pulmonary disease); a digestive disorder (e.g. inflammatory bowel disease, ulcer); a musculoskeletal disorder (e.g. fibromyalgia, arthritis); an endocrine, metabolic, or nutritional disorder (e.g. diabetes, osteoporosis); an urological disorder (e.g. renal disease); a psychological disorder (e.g. depression, schizophrenia); a skin disorder (e.g. wounds, eczema); or a blood or lymphatic disorder (e.g. anemia, hemophilia).

In embodiments of the compositions or methods described herein, the chondrisomes are modified, e.g.: (a) subjected to or combined with an external condition or agent (e.g., a stress condition or agent that induces one or more mitochondrial activity to compensate), (b) genetically engineered to overexpress or knock-down or knock-out an endogenous gene product (e.g., an endogenous mitochondrial or nuclear gene product); (c) engineered to express a heterologous gene product (e.g., a heterologous, e.g., allogeneic or xenogeneic, mitochondrial or nuclear gene product), or (d) loaded with a heterologous cargo agent, such as a polypeptide, nucleic acid or small molecule (e.g., a dye, a drug, a metabolite) e.g., an agent listed in Table 4.

In embodiments of the methods described herein, the composition is administered in an amount and for a time sufficient to effect, in the target cell, tissue or subject, one or more (e.g., 2, 3, 4, 5, 6, 7 or more) of the following:

a. delivery of cargo to target cells from the administered mitochondria of the preparation (e.g., UCP1) following delivery of the mitochondrial preparation;
b. Increases basal respiration of recipient cells at least 10% (e.g., >15%, >20%, >30%, >40%, >50%, >60%, >70%, >80%, >90%) relative to a control;
c. Chondrisomes of the preparation are taken up by at least 1% (e.g., at least 2%, 5%, 10%, 20%, 30%, 40%, 50%, 60%, 70%) of recipient cells;
d. Chondrisomes of the preparation are taken up and maintain membrane potential in recipient cells;
e. Chondrisomes of the preparation persist in recipient cells at least 6 hours, e.g., at least 12 hours, 18 hours, 24 hours, 2 days, 3 days, 4 days, a week, 2 weeks, a month, 2 months, 3 months, 6 months;
f. increase ATP levels in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);
g. decrease apotosis in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);
h. decrease cellular lipid levels in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);
i. increase membrane potential in a recipient cell, tissue or subject (e.g., by at least 5%, 10%, 15%, 20%, 25%, 30%, 35%, 40%, 45%, 50%, 60%, 70%, 80%, 90%, or more, e.g., compared to a reference value, e.g., a control value, e.g., an untreated control);
j. increase uncoupled respiration in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);
k. increase PI3K activity in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);
l. reduce reductive stress in a recipient cell, tissue or subject (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);
m. decrease reactive oxygen species (e.g. H2O2) in the cell, tissue of subject (e.g., in serum of a target subject) (e.g., by at least 5%, 10%, 15%, 20%, 25%, 30%, 35%, 40%, 45%, 509%, 60%, 70%, 80%, 90%, or more, e.g., compared to a reference value, e.g., a control value, e.g., an untreated control);
n. Decrease cellular lipid levels of recipient cells at least 5% (e.g., >10%, >15%, >20%, >30%, >40%, >50%, >60%, >70%, >80%, >90%) relative to a control;
o. increases uncoupled respiration of recipient cells at least 5% (e.g., >10%, >15%, >20%, >30%, >40%, >50%, >60%, >70%, >80%, >90%) relative to a control;
p. decrease mitochondrial permeability transition pore (MPTP) formation in recipient cells at least 5% and does not increase more than 10% relative to a control;
q. increase Akt levels in recipient cells at least 10% (e.g., >10%, >15%, >20%, >30%, >40%, >50%, >60%, >70%, >80%, >90%) relative to a control;
r. decrease total NAD/NADH ratio in recipient cells at least 5% (e.g., >10%, >15%, >20%, >30%, >40%, >50%, >60%, >70%, >80%, >90%) relative to a control;
s. Reduce ROS levels in recipient cells at least 5% (e.g., >10%, >15%, >20%, >30%, >40%, >50%, >60%, >70%, >80%, >90%) relative to a control;
t. Increase fractional shortening in subject with cardiac ischemia at least 5% (e.g., >10%, >15%, >20%, >30%, >40%, >50%, >60%, >70%, >80%, >90%) relative to a control;
u. Increase end diastolic volume in subject with cardiac ischemia at least 5% (e.g., >10%, >15%, >20%, >30%, >40%, >50%, >60%, >70%, >80%, >90%) relative to a control;
v. decrease end systolic volume in subject with cardiac ischemia at least 5% (e.g., >10%, >15%, >20%, >30%, >40%, >50%, >60%, >70%, >80%, >90%) relative to a control;

w. decrease infarct area of ischemic heart at least 5% (e.g., >10%, >15%, >20%, >30%, >40%, >50%, >60%, >70%, >80%, >90%) relative to a control;

x. increase stroke volume in subject with cardiac ischemia at least 5% (e.g., >10%, >15%, >20%, >30%, >40%, >50%, >60%, >70%, >80%, >90%) relative to a control;

y. increase ejection fraction in subject with cardiac ischemia at least 5% (e.g., >10%, >15%, >20%, >30%, >40%, >50%, >60%, >70%, >80%, >90%) relative to a control;

z. increase cardia output in subject with cardiac ischemia at least 5% (e.g., >10%, >15%, >20%, >30%, >40%, >50%, >60%, >70%, >80%, >90%) relative to a control;

aa. increase cardiac index in subject with cardiac ischemia at least 5% (e.g., >10%, >15%, >20%, >30%, >40%, >50%, >60%, >70%, >80%, >90%) relative to a control;

bb. decrease serum CKNB levels in subject with cardiac ischemia at least 5% (e.g., >10%, >15%, >20%, >30%, >40%, >50%, >60%, >70%, >80%, >90%) relative to a control;

cc. decrease serum cTnI levels in subject with cardiac ischemia at least 5% (e.g., >10%, >15%, >20%, >30%, >40%, >50%, >60%, >70%, >80%, >90%) relative to a control;

dd. decrease serum hydrogen peroxide in subject with cardiac ischemia at least 5% (e.g., >10%, >15%, >20%, >30%, >40%, >50%, >60%, >70%, >80%, >90%) relative to a control;

ee. decrease serum cholesterol levels in a subject at least 5% (e.g., >10%, >15%, >20%, >30%, >40%, >50%, >60%, >70%, >80%, >90%) relative to a control.

BRIEF DESCRIPTION OF THE FIGURES

The figures are meant to be illustrative of one or more features, aspects, or embodiments of the invention and are not intended to be limiting.

FIG. 5 is a table showing the concentration of plasma cytokines in mice 24 hours after intravenous (IV) or subcutaneous (SC) treatment with chondrisomes or Vehicle. The concentration of each cytokine is below the limit of detection.

DETAILED DESCRIPTION

Figure 1:
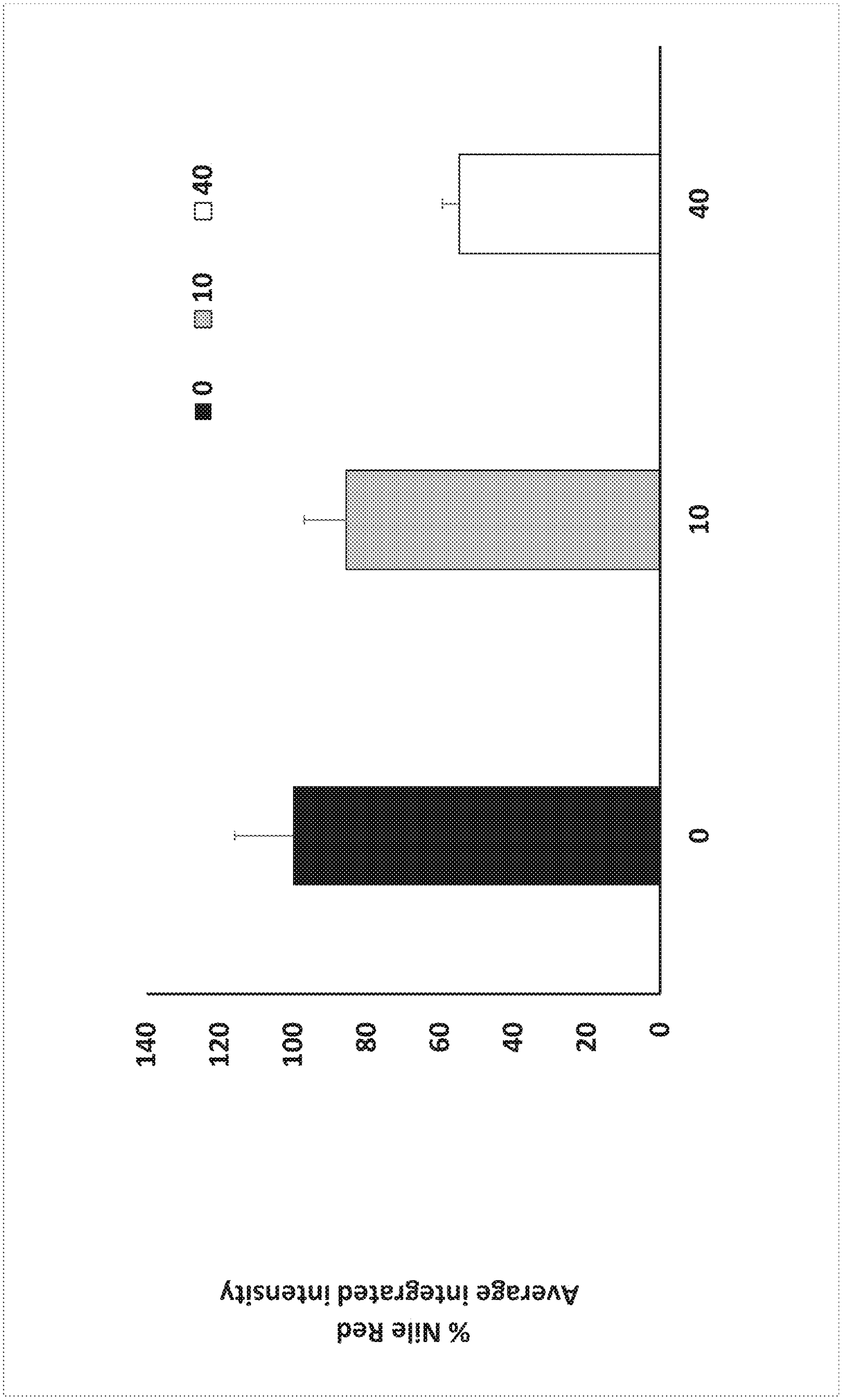
FIG. 1 is a graph showing quantification of lipid droplet content using nile red average integrated intensity in control INS1 cells and INS1 cells that received 10 or 40 μg BAT chondrisome protein/100K cells. Bar graphs represent average±SD of percent change form control group

The invention describes chondrisome preparations and pharmaceutical compositions that have beneficial characteristics suitable for administration to a target tissue or cell (e.g., ex vivo or in vivo), useful in methods to modify (e.g., modify the metabolic or cellular state of) a target tissue or cell (e.g., ex vivo or in vivo), and/or to treat a subject (e.g., a mammal such as a human). The preparations and compositions described herein may also be modified, e.g., may include a heterologous function or activity, e.g., may include a payload such as an effector molecule, a drug, a targeting agent; may overexpress or under express an endogenous mitochondrial or nuclear gene; may express a heterologous mitochondrial or nuclear gene.

Chondrisome Preparations

Chondrisome preparations of the invention may be produced from any eukaryotic source, e.g., from yeast, plant, mammalian (e.g., human or agricultural animal) tissue.

Tissue Sources

Mitochondrial preparations can be isolated from any mammalian (e.g., human) tissue or cell, e.g., from epithelial, connective, muscular, or nervous tissue or cells, and combinations thereof. Mitochondrial preparations can be isolated from any eukaryotic (e.g., mammalian) organ system, for example, from the cardiovascular system (heart, vasculature); digestive system (esophagus, stomach, liver, gallbladder, pancreas, intestines, colon, rectum and anus); endocrine system (hypothalamus, pituitary gland, pineal body or pineal gland, thyroid, parathyroids, adrenal glands); excretory system (kidneys, ureters, bladder); lymphatic system (lymph, lymph nodes, lymph vessels, tonsils, adenoids, thymus, spleen); integumentary system (skin, hair, nails); muscular system (e.g., skeletal muscle); nervous system (brain, spinal cord, nerves)'; reproductive system (ovaries, uterus, mammary glands, testes, vas deferens, seminal vesicles, prostate); respiratory system (pharynx, larynx, trachea, bronchi, lungs, diaphragm); skeletal system (bone, cartilage), and combinations thereof.

In embodiments, the source tissue is a source of stem cells or progenitor cells, e.g., bone marrow stromal cells, marrow-derived adult progenitor cells (MAPCs), endothelial progenitor cells (EPC), blast cells, intermediate progenitor cells formed in the subventricular zone, neural stem cells, muscle stem cells, satellite cells, liver stem cells, hematopoietic stem cells, bone marrow stromal cells, epidermal stem cells, embryonic stem cells, mesenchymal stem cells, umbilical cord stem cells, precursor cells, muscle precursor cells, myoblast, cardiomyoblast, neural precursor cells, glial precursor cells, neuronal precursor cells, hepatoblasts.

In some embodiments, the source tissue is a tissue sample from a mammal, e.g., a human. The tissue sample may be, e.g., from a living human or from a cadaver. The tissue may be fresh (used within days of harvest, typically stored at ≤4° C.), or may be frozen.

In embodiments, the tissue sample is from a highly mitotic tissue (e.g., a highly mitotic healthy tissue, such as epithelium, embryonic tissue, bone marrow, intestinal crypts). In embodiments, the tissue sample is a highly metabolic tissue (e.g., skeletal tissue, neural tissue, cardiomyocytes).

In some embodiments, the source tissue is from a young donor, e.g., a donor under 25 years, 20 years, 18 years, 16 years, 12 years, 10 years, 8 years of age or less.

In certain embodiments, the cells of the tissue have telomeres of average size greater than 3000, 4000, 5000, 6000, 7000, 8000, 9000, or 10000 nucleotides in length (e.g., between 4,000-10,000 nucleotides in length, between 6,000-10,000 nucleotides in length).

In certain embodiments, the mitochondrial mutation load of the source tissue is low, e.g., fewer than 0.001/17,000, 0.01/17,000, 0.1/17,000, 1/17,000, 2/17,000, 5/17,000, 10/17,000, 50/17,000, 100/17,000 of the genetic content deviates from the reference haplotype mitochondrial sequence of the source.

Blood Product Sources

Mitochondrial preparations of the invention are isolated from blood or blood fractions, e.g., whole blood, platelets, platelet mitoparticles, peripheral blood mononuclear cells (PBMCs), platelet rich plasma, or platelet free plasma.

Human blood can be generally obtained from healthy human volunteers under approved protocols, from blood banks, or form commercial sources.

Platelets are typically isolated from blood, e.g., by differential centrifugation. Briefly, platelet rich plasma (PRP) is prepared from whole blood through centrifugation at low g force, wherein the PRP remains in the supernatant and red blood cells and white blood cells pellet, followed by centrifugation at higher g force to pellet the platelets in the PRP. In some embodiments, platelets are activated before isolation of mitochondria or mitoparticles. In some embodiments, one or more platelet activation inhibitors may be used during isolation.

Activated platelets release mitochondria, both within membrane encapsulated microvesicles (referred to herein as "mitoparticles") and as free organelles. (*See Boudreau et al.* 2014. *Platelets release mitochondria serving as substrate for bactericidal group IIA-secreted phospholipase A*2 *to promote inflammation. Blood. Vol.* 24 *No.* 14:2173-2183.) Such mitoparticles may be isolated from platelets (e.g., through differential centrifugation or filtration), concentrated, and surprisingly may be used as a source of mitochondrial activity or chondrisomes in the methods described herein.

Platelet free plasma (PFP) may also be a source of mitochondria in the compositions and methods described herein.

The most common method for isolation of PBMCs, e.g., lymphocytes and monocytes, from blood is through a density gradient medium (e.g., Ficoll) based on the principle of differential migration of blood cells through the media during the centrifugation stage of the procedure. In brief, either anticoagulant or defibrinated blood specimens are layered on top of the gradient (e.g., Ficoll) solution, then briefly centrifuged to form different layers containing different types of cells. The bottom layer is made up of red blood cells (erythrocytes) which are collected or aggregated by the medium and sink completely through to the bottom. The next layer up from the bottom is primarily granulocytes, which also migrate down through the solution. The next layer toward to top is the lymphocytes, which are typically at the interface between the plasma and the Ficoll solution, along with monocytes and platelets. To recover the lymphocytes, this layer is carefully recovered, washed with a salt solution to remove platelets, Ficoll, and plasma, then centrifuged again.

The source of mitochondria may be an apheresis product, e.g., apheresis derived plasma, e.g., fresh frozen plasma; red blood cells; platelets; leukocytes.

Cultured Cell Sources

Preparations of chondrisomes are isolated from cells in culture, for example cultured mammalian cells, e.g., cultured human cells. The cells may be progenitor cells or non-progenitor (e.g., differentiated) cells. The cells may be primary cells or cell lines (e.g., a mammalian, e.g., human, cell line described herein).

In embodiments, the cells are from a highly mitotic tissue (e.g., a highly mitotic healthy tissue, such as epithelium, embryonic tissue, bone marrow, intestinal crypts). In embodiments, the tissue sample is a highly metabolic tissue (e.g., skeletal tissue, neural tissue, cardiomyocytes).

In some embodiments, the cells are from a young donor, e.g., a donor 25 years, 20 years, 18 years, 16 years, 12 years, 10 years, 8 years of age, 5 years of age, 1 year of age, or less. In some embodiments, the cells are from fetal tissue.

In certain embodiments, the cells have telomeres of average size greater than 3000, 4000, 5000, 6000, 7000, 8000, 9000, or 10000 nucleotides in length (e.g., between 4,000-10,000 nucleotides in length, between 6,000-10,000 nucleotides in length).

In certain embodiments, the mitochondrial mutation load of the source tissue is low, e.g., fewer than 0.001/17,000, 0.01/17,000, 0.1/17,000, 1/17,000, 2/17,000, 5/17,000, 10/17,000, 50/17,000, 100/17,000 of the genetic content deviates from the reference haplotype mitochondrial sequence of the source.

Chondrisomes may be prepared from the cultured cells after 1 or more passages. In some embodiments, chondrisomes are prepared from cells having undergone no more than 20, no more than 15 passages in culture, e.g., between 1-15 passages, between 1-10 passages, between 1-8 passages, between 1-6 passages, between 1-4 passages.

In embodiments, the cells are cultured induced pluripotent stem cells (iPS cells), bone marrow stromal cells, marrow-derived adult progenitor cells (MAPCs), endothelial progenitor cells (EPC), blast cells, intermediate progenitor cells formed in the subventricular zone, neural stem cells, muscle stem cells, satellite cells, liver stem cells, hematopoietic stem cells, bone marrow stromal cells, epidermal stem cells, embryonic stem cells, mesenchymal stem cells, umbilical cord stem cells, precursor cells, muscle precursor cells, myoblast, cardiomyoblast, neural precursor cells, glial precursor cells, neuronal precursor cells, hepatoblasts.

In one embodiment, the cells are iPS derived, e.g., iPS derived cardiomyocytes or neural stem cells.

In embodiments, chondrisomes are prepared from a human cell line. The production of permanent human cell lines is described, e.g., in U.S. Pat. No. 9,315,773. In embodiments, the cell line is HeLa or HEK293. In embodiments, chondrisomes are prepared from a cell line described in Table 1.

In embodiments, chondrisomes are prepared from cultured primary cells, e.g., cultured primary fibroblasts, skeletal muscle cells (e.g., cardiomyocytes), keratinocytes, epithelial cells, hepatocytes, neuronal, glial, or neural stem cells, skeletal myoblasts, smooth muscle cells, adipose tissue (e.g., brown adipose tissue) (see, e.g., *Néchad et al.* 1983. *Development of brown fat cells in monolayer culture Exp Cell Res.* 149 (1): 105-18).

TABLE 1

Cell lines for chondrisome production

| Species | Cell Type | Tissue/Cell line type | ATCC Number |
|---|---|---|---|
| Human | Cancerous tissue | Bladder Cancer | TCP-1020 ™ |
| | | Bone Cancer | TCP-1009 ™ |
| | | Breast Cancer | TCP-1004 ™ |
| | | Brain Cancer | TCP-1018 ™ |
| | | Colon Cancer | TCP-1006 ™ |
| | | Ovarian Cancer | TCP-1021 ™ |
| | | Leukemia | TCP-1010 ™ |
| | | Lymphoma | TCP-1025 ™ |
| | | Liver Cancer | TCP-1011 ™ |
| | | Lung Cancer | TCP-1016 ™ |
| | | Melanoma | TCP-1014 ™ |
| | | Pancreatic Cancer | TCP-1026 ™ |
| | Non-cancerous tissue | Cornea | CRL-11515 ™ |
| | | Mammary Gland | CRL-8798 ™ |
| | Epithelial | Colon | CRL-2302 ™ |
| | | Kidney | CRL-2190 ™ |
| | | Liver | CRL-11233 ™ |
| | Blood | B lymphoblast | CRL-1980 ™ |
| | Skin | Fibroblast | CRL-2072 ™ |
| | Lung | Fibroblast | CCL-204 ™ |
| | Bone | Marow Stromal | CRL-11882 ™ |
| | Endothelial | Vascular | CRL-1730 ™ |
| Murine | | Fibroblast | CRL-2817 ™ |
| Bovine | | Pulmonary Artery | CCL-209 ™ |
| Canine | | Kidney | CRL-2936 ™ |
| Hampster | | Ovary | CRL-9606 ™ |
| Monkey | | Kidney | CRL-1586 ™ |
| Rabbit | | Corneal Fibroblast | CCL-60 ™ |
| Rat | | Liver Epithelial | CRL-1439 ™ |
| Pig | | Lung Macrophage | CRL-2844 ™ |
| Cat | | Lymphocyte | CRL-11967 ™ |
| Chicken | | Embryonic Fribroblast | CRL-12203 ™ |
| Zebrafish | | Fibroblast | CRL-2296 ™ |
| Trout | | Ovaries & Testies | CCL-55 ™ |
| Fungi & Yeast | | Saccharomyces cerevisiae | 7754 ™ |

Methods of Culturing Cells

Cells are generally cultured according to methods known in the art. Culture media contain a mixture of amino acids, sugars, salts, vitamins, and other nutrients, and are available either as a powder or as a liquid form from commercial suppliers. Basal medium for cell culture may also include vitamins, lipids, proteins (e.g., rh-insulin and/or rh-transferrin). Amino acid ingredients which may be included in the media of the present invention include L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine and L-valine. These amino acids may be obtained commercially. Vitamin ingredients which may be included in the media of the present invention include biotin, choline chloride, D-Ca++-pantothenate, folic acid, i-inositol, niacinamide, pyridoxine, riboflavin, thiamine and vitamin $B_{12}$. These vitamins may be obtained commercially. Inorganic salt ingredients which may be used in the media include one or more calcium salts (e.g., $CaCl_2$)), $Fe(NO_3)_3$, KCl, one or more magnesium salts (e.g., $MgCl_2$ and/or $MgSO_4$), one or more manganese salts (e.g., $MnCl_2$), NaCl, $NaHCO_3$, $Na_2HPO_4$, and ions of the trace elements selenium, vanadium and zinc. These trace elements may be provided in a variety of forms, preferably in the form of salts such as $Na_2SeO_3$, $NH_4VO_3$ and $ZnSO_4$. Methods of selecting and using culture media for various cells are known and are described, e.g., in Arora. 2013. Cell Culture Media: A Review. Mater Methods 3:175.

In embodiments of the invention, the medium contains no non-human animal products, e.g., no non-human serum, e.g., no BSA or FBS. The medium may be a serum-free medium or may be a chemically defined medium. The medium may be completely protein-free. If protein is present, it is preferably a human protein such as a human recombinant protein (e.g., transferring or insulin). Transferrin may be replaced by ferric citrate chelates at a concentration of about 10-100 μM (preferably $FeCl_3$-sodium citrate chelate at about 60 μM) or ferrous sulfate chelates at a concentration of about 10-100 μM (preferably $FeSO_4$-EDTA chelate at about 40 μM). Insulin may be replaced by one or more zinc-containing compounds such alone or more zinc salts. Zinc-containing compounds which may be used include but are not limited to ZnCl, Zn $(NO_3)_2$, ZnBr, and $ZnSO_4$, any of which may be present in their anhydrous or hydrated (i.e., ".H2O") forms.

In one embodiment, the cultured cells are cultured in a serum free medium, e.g., a defined medium.

In some embodiments, the cells may be cultured in 2 or more "phases", e.g., a growth phase, wherein the cells are cultured under conditions to multiply and increase biomass of the culture, and a "production" phase, wherein the cells are cultured under conditions to increase mitochondrial quality (e.g., to maximize mitochondrial phenotype, to increase number or size of mitochondria, to increase oxidative phosphorylation status).

In embodiments, the cell culture media does not contain glucose. In embodiments, the cell culture media contains glucose during the growth phase but does not contain added glucose during the production phase.

In some embodiments, the cells may be synchronized, e.g., during a growth phase or the production phase. For example, cells may be synchronized at G1 phase by elimination of serum from the culture medium (e.g., for about 12-24 hours) or by the use in the culture media of DNA synthesis inhibitors such as thymidine, aminopterin, hydroxyurea and cytosine arabinoside. Additional methods for mammalian cell cycle synchronization are known and disclosed, e.g., in Rosner et al. 2013. *Nature Protocols* 8:602-626 (specifically Table 1 in Rosner).

In some embodiments, the cells can be evaluated and optionally enriched for a desirable phenotype or genotype for use as a source of a chondrisome preparation described herein. For example, cells can be evaluated and optionally enriched, e.g., before culturing, during culturing (e.g., during a growth phase or a production phase) or after culturing but before isolation of chondrisomes, for example, for one or more of: membrane potential (e.g., a membrane potential of −5 to −200 mV; cardiolipin content (e.g., between 1-20% of total lipid); genetic quality>80%, >85%, >90%.

In some embodiments, a cell clone is identified, chosen, or selected for culturing based on a desirable phenotype or genotype for use as a source of a chondrisome preparation described herein. For example, a cell clone is identified, chosen, or selected based on low mitochondrial mutation load, long telomere length, differentiation state, or a particular genetic signature (e.g., a genetic signature to match a recipient).

In some embodiments, cells are cultured in the presence of an exogenous agent that modulates mitochondrial structure, function or activity, e.g., a structure, function or activity described herein. In embodiments, one or a plurality (e.g., 2, 3, 4, 5 or more) of the agents or strategies described hereinbelow may be used to treat a cell culture for preparation of a mitochondrial preparation.

Mitochondrial Biogenesis (MB) Agents

The source subject, tissue or cell may be contacted with a mitochondrial biogenesis (MB) agent in an amount and for a time sufficient to increase mitochondrial biogenesis in the source subject tissue or cell (e.g., by at least 10%, 15%, 20%, 30%, 40%, 50%, 60%, 75%, 80%, 90% or more). Such MB agents are described, e.g., in *Cameron et al.* 2016. *Development of Therapeutics That Induce Mitochondrial Biogenesis for the Treatment of Acute and Chronic Degenerative Diseases.*

DOI: 10.1021/acs.jmedchem.6b00669. In embodiments, the MB agent is added to the cell culture during the growth phase and/or during the production phase. In embodiments, the MB agent is added when the cell culture has a predetermined target density.

In one embodiment, the MB agent is an agent extracted from a natural product or its synthetic equivalent, sufficient to increase mitochondrial biogenesis in the source subject, tissue or cell. Examples of such agents include resveratrol, epicatechin, curcumin, a phytoestrogen (e.g., genistein, daidzein, pyrroloquinoline, quinone, coumestrol and equol).

In one embodiment, the MB agent is a transcription factor modulator sufficient to increase mitochondrial biogenesis in the source subject, tissue or cell. Examples of such transcription factor modulators include: thiazolidinediones (e.g., rosiglitazone, pioglitazone, troglitazone and ciglitazone), estrogens (e.g., 17β-Estradiol, progesterone) and estrogen receptor agonists; SIRTI Activators (e.g., SRT1720, SRT1460, SRT2183, SRT2104).

In one embodiment, the MB agent is a kinase modulator sufficient to increase mitochondrial biogenesis in the source subject, tissue or cell. Examples include: AMPK and AMPK activators such as AICAR, metformin, phenformin, A769662; and ERK1/2 inhibitors, such as U0126, trametinib.

In one embodiment, the MB agent is a cyclic nucleotide modulator sufficient to increase mitochondrial biogenesis in the source subject, tissue or cell. Examples include modulators of the NO-cGMP-PKG pathway (for example nitric oxide (NO) donors, such as sodium nitroprusside, (±)S-nitroso-N-acetylpenicillamine (SNAP), diethylamine NONOate (DEA-NONOate), diethylenetriamine-NONOate (DETA-NONOate); sGC stimulators and activators, such as cinaciguat, riociguat, and BAY 41-2272; and phosphodiesterase (PDE) inhibitors, such as zaprinast, sildenafil, udenafil, tadalafil, and vardenafil) and modulators of the cAMP-PKA-CREB Axis, such as phosphodiesterase (PDE) inhibitors such as rolipram.

In one embodiment, the MB agent is a modulator of a G protein coupled receptor (GPCR) such as a GPCR ligand sufficient to increase mitochondrial biogenesis in the source subject, tissue or cell.

In one embodiment, the MB agent is a modulator of a cannabinoid-1 receptor sufficient to increase mitochondrial biogenesis in the source subject, tissue or cell. Examples include taranabant and rimonobant.

In one embodiment, the MB agent is a modulator of a 5-Hydroxytryptamine receptor sufficient to increase mitochondrial biogenesis in the source subject, tissue or cell. Examples include alpha-methyl-5-hydroxytryptamine, DOI, CP809101, SB242084, serotonin reuptake inhibitors such as fluoxetine, alpha-methyl 5HT, 1-(2,5-dimethoxy-4-iodophenyl)-2-aminopropane, LY334370, and LY344864.

In one embodiment, the MB agent is a modulator of a beta adrenergic receptor sufficient to increase mitochondrial biogenesis in the source subject, tissue or cell. Examples include epinephrine, norepinephrine, isoproterenol, metoprolol, formoterol, fenoterol and procaterol. E.g., BAT cells in culture express UCP1 following β-adrenergic stimulation.

In one embodiment, the cultured cells are modified, e.g., genetically modified, to express a transcriptional activator of mitochondrial biogenesis, e.g., a transcription factor or transcriptional coactivator such as PGC1α. In some embodiments, the cells express PGC1a (e.g., over express an endogenous, or express an exogenous, PGC1α).

Modulators of Metabolic Activity

The source subject, tissue or cell may be contacted with an agent that is a modulator of metabolic activity in an amount and for a time sufficient to increase metabolic activity in the source subject tissue or cell (e.g., by at least 10%, 15%, 20%, 30%, 40%, 50%, 60%, 75%, 80%, 90% or more, compared to without the agent). In embodiments, the agent is added to the cell culture during the growth phase and/or during the production phase. In embodiments, the agent is added when the cell culture has a predetermined target density.

In one embodiment, the agent is a respiratory substrate. Examples include ADP, carbohydrates, lipids and fatty acids, proteins and amino acids.

In one embodiment, the agent is a non-glucose carbon source. Examples include galactose, glutamine, fructose, maltose.

In some embodiments, the cells are cultured under low oxygen conditions, e.g., between 0.1-15% oxygen, between 0.5-10% oxygen, between 0.5-8% oxygen, between 0.5-6% oxygen, between 1-6% oxygen, between 2-6% oxygen, between 1-5% oxygen, between 2-5% oxygen. In embodiments, the cells are cultured under low oxygen conditions during the production phase but not the growth phase.

In one embodiment, the agent is an antioxidant. In one embodiment, the agent is an antireductant. In one embodiment, the agent is an uncoupler.

In some embodiments, the cells are cultured in combination with a second cell population (a co-culture), e.g., a feeder culture that provides the cultured source cells with desirable agents, e.g., metabolic substrates.

Bioreactors

Cell cultures described herein for preparation of chondrisome preparations may be cultured in a bioreactor.

For suspension cells, the bioreactor may be any scale or lot size, e.g., 100 mL, 500 mL, IL, 2L, 5L, 10L, 20L, 40L, 50L, 100L, or greater. For example, the bioreactor is between 1L-100 L, e.g., between 1L-50L, between 1L-20L, between 1L-10L. In some embodiments, the bioreactor is between 100 mL-100 L, e.g., between 100 mL-5L, 100 mL-1L.

For adherent cells, such as adult primary cell lines and human multipotent (MSCs) and pluripotent stem cells (hPSCs), a lot size of cultured cells for production of chondrisome preparations may be $1\text{-}10\times10^7$, $1\text{-}10\times10^8$, $1\text{-}10\times10^9$, $1\text{-}10\times10^{10}$, $1\text{-}10\times10^{11}$, $1\text{-}10\times10^{12}$. Adherent cells may be cultured in planar systems, e.g., flasks, or stacked-plate systems, parallel-plate vessels, or packed-bed bioreactors (PBRs). Honeycomb bioreactors may also be used, e.g., as described, e.g., in U.S. Pat. No. 6,777,227. Microcarriers can also be used in bioreactors to increase surface area. Microcarriers can be made, e.g., from polystyrene or from cross-linked dextran. Although most microcarriers are spherical and smooth, others have macroporous surfaces or may have other shapes such as rod-shaped carriers. Additional techniques include infusion of magnetic particles that help in cell separation from beads and chip-based microcarriers that provide a traditional flat surface for cell growth while maintaining the high SA: V ratio of traditional microcarriers. Surface chemistry modifications may improve cell adhesion in adherent systems. Such methods include, e.g., applying positive or negative charges and coating with extracellular matrix proteins such as laminin or vitronectin. See, e.g., Rowley et al. 2012. *Meeting Lot-Size Challenges of Manufacturing Adherent Cells for Therapy. BioProcess International* 10 (3) *Supplement.*

A chondrisome preparation described herein may be comprised of chondrisomes from one cellular or tissue source, or from a combination of sources. For example, a chondrisome preparation may comprise chondrisomes isolated from xenogeneic sources (plants, animals, tissue culture of the aforementioned species' cells), allogeneic, autologous, from specific tissues resulting in different protein concentrations and distributions (liver, skeletal, neural, adipose, etc.), from cells of different metabolic states (e.g., glycolytic, respiring). A preparation may also comprise chondrisomes in different metabolic states, e.g. coupled or uncoupled.

Isolation Methods

The basic steps of mitochondria isolation for research are described in Pallotti & Lenaz. 2007. *Isolation and subfractionation of mitochondria. Methods in Cell Biology Vol* 80. Generally, preparations of mitochondria are isolated from a donor tissue or cell culture (or combinations of donor tissues or cells) as follows: Tissue can be obtained by biopsy (solid tissue) or syringe draw (fluid tissue) and is typically maintained at 0-4° C. throughout the process of isolation. Solid tissue may be minced into small pieces. The tissue is ground, dissociated or homogenized in isolation buffer (IB). A typical IB contains one or more stabilizing agent such as sucrose or albumin (e.g., human serum albumin), a chelator such as EGTA, and a buffering system such as Tris. The resulting homogenized material is centrifuged and/or filtered (e.g., through a 5 μm filter) to remove cells or large cell debris. The filtrate is recovered and the mitochondria are washed and concentrated, e.g., by additional centrifugation, and resuspended in buffer.

In embodiments of the invention, preparing a chondrisome preparation includes the following steps (a)-(e):

(a) A tissue or cellular source of mitochondria (e.g., a tissue or cellular source described herein) is provided or obtained. The tissue or cellular source may be fresh or frozen, from a live or dead donor. In one embodiment, the source is a sample of frozen cultured cells. In one embodiment, the source is a blood product (e.g., whole blood, platelets, leucocytes).

(b) the tissue or cellular source is dissociated to produce a subcellular composition (e.g., a homogenate) or manipulated (e.g., activated) to release chondrisomes or mitochondria-containing vesicles. In embodiments, the dissociating step is performed in no more than 10 fold (no more than 7-fold, 5-fold, 4-fold, 3-fold, or 2-fold) the volume of buffer relative to the volume of the tissue or cellular source. The dissociating may be performed by any cellular dissociation device or method, e.g., by douncing (e.g., with a glass dounce, or by a dissociator device such as a Miltenyl GentleMACS Dissociator). In embodiments, the dissociating comprises applying a plurality of shear force steps to the tissue or cellular source, e.g., a first shear force followed by at least a second, higher shear force. For example, the first shear force is applied with a dounce device and the second, higher shear force is applied by passing the homogenate through one or more needle, e.g., passing the homogenate (e.g., 1-10 times, 1-8 times, 1-6 times, 1-4 times) through a series of needles having a gauge between 15-45, e.g., a gauge between 18-30. In embodiments, the dissociation to produce the subcellular homogenate is performed in the absence of added proteases. In some embodiments, if the tissue or cells have been previously treated with proteases (e.g., to dissociate adherent cultured cells from their substrate or to dissociate tissue into individual cells), the proteases may be washed away before this step. In embodiments, the dissociation technique (e.g., a douncing step) is optimized to produce a subcellular composition that results in a yield described herein.

(c) the subcellular composition is separated into a cellular debris fraction (e.g., a solid or pelleted fraction) and a chondrisome enriched fraction (e.g., a fluid fraction). Separation may be accomplished by known techniques, e.g., centrifugation or size filtration. The separation may include a plurality of centrifugation or size filtration steps.

(d) the chondrisome enriched fraction is separated into a fraction containing chondrisomes (e.g., a solid or pellet fraction) and a fraction (e.g., a supernatant) substantially lacking chondrisomes, e.g., by centrifugation or size filtration. This separation may include a plurality of centrifugation or size filtration steps, e.g., including one or more "wash" steps or repelleting steps.

(e) the fraction containing chondrisomes is suspended in solution. In embodiments, the suspension is performed in no more than 10 fold (no more than 7-fold, 5-fold, 4-fold, 3-fold, or 2-fold) the volume of buffer relative to the volume of the fraction. The solution may be a buffer, e.g., a storage buffer, or a pharmaceutically acceptable solution, e.g., suitable for delivery or administration to a subject.

In certain embodiments, the yield of the preparation is >0.05 (e.g., >0.1, >0.2, >0.5, >1, >2, >3, >5, >6, >7, >8, >8, >10, >20, >30, >40, >50, >60, >80, >90, >100, >150, >200, >300) ug protein/10E6 cells. In certain embodiments, the yield of the preparation is >100 (e.g., >200, >300, >400, >500, >600, >700, >800, >900, >1,000, >2,000, >3,000, >5,000, >7000, >10,000) ug protein/g tissue. In embodiments, the efficiency of chondrisome yield is 1E9 to 9E12 (e.g., >1E9, >5E9, >1E10, >5E10, >1E11, >5E11, >1E12, >5E12) particles/mg total protein.

Characterization

Chondrisome preparations can be assayed for structural and functional parameters e.g., physical, structural, bioenergetics and functional parameters, e.g., membrane integrity, purity, stability, morphology, protein content, lipid content, enzymatic activity, respiration rate, ATP production, concentration, protein content, fission capabilities and functional activity (or lack thereof), such as apoptotic modulation, internalization ability, endosomal escape, metabolic effects, cardiac-protective effects, e.g., as described in the Examples section herein.

Encapsulation

In some embodiments of the compositions and methods described herein, the chondrisomes can be encapsulated, e.g., in naturally derived or in engineered lipid membranes. Some cells are known to eject mitochondria in a membrane bound vesicle (Boudreau et al. 2014. Platelets release mitochondria serving as substrate for bactericidal group IIA-secreted phospholipase A2 to promote inflammation. *Blood.* 124 (14): 2173-83; Phinney et al. 2015. Mesenchymal stem cells use extracellular vesicles to outsource mitophagy and shuttle microRNAs. *Nature Communications.* 6:8472). Such vesicles can surprisingly be used in the methods of the invention. In other instances, this encapsulation takes the form of an autologous, allogeneic, xenogeneic or engineered cell such as is described in Ahmad et al. 2014. Mirol regulates intercellular mitochondrial transport & enhances mesenchymal stem cell rescue efficacy. *EMBO Journal.* 33 (9): 994-1010). In another embodiment the chondrisomes can be encapsulated in engineered substrates such as described in, e.g. in Orive. et al. 2015. Cell encapsulation: technical and clinical advances. *Trends in Pharmacology Sciences;* 36 (8): 537-46; and in Mishra. 2016. *Handbook of Encapsulation and Controlled Release*. CRC Press. In some embodiments, mitochondria can be encapsulated in naturally occurring vesicles themselves (McBride et al. 2012. A Vesicular Transport Pathway Shuttles Cargo from mitochondria to lysosomes. *Current Biology* 22:135-141).

In some embodiments, a composition described herein includes mitochondria encapsulated in naturally derived vesicles, e.g., membrane vesicles prepared from cells or tissues, which vesicles carry mitochondria. In one embodiment, the vesicle is a platelet mitoparticle. In one embodiment, the vesicle is a mitochondria-containing microvesicle from MSCs or astrocytes. In one embodiment, the vesicle is an exosome.

In some embodiments, a composition described herein includes chondrisomes encapsulated in synthetic vesicles, e.g., liposomes.

In some embodiments, a composition described herein includes chondrisomes encapsulated in nanoparticles or nanogels.

In some embodiments, a composition described herein includes mitochondria encapsulated in naturally derived vesicles, e.g., membrane vesicles prepared from cells or tissues, which vesicles carry mitochondria (McBride et al. 2012. A Vesicular Transport Pathway Shuttles Cargo from mitochondria to lysosomes. Current Biology 22:135-141). Some cells are known to eject mitochondria in a membrane bound vesicle (Boudreau et al. 2014. Platelets release mitochondria serving as substrate for bactericidal group IIA-secreted phospholipase A2 to promote inflammation. Blood. 124 (14): 2173-83; Phinney et al. 2015. Mesenchymal stem cells use extracellular vesicles to outsource mitophagy and shuttle microRNAs. Nature Communications. 6:8472). In other instances, this encapsulation takes the form of an autologous, allogeneic, xenogeneic or engineered cell such as is described in Ahmad et al. 2014. Mirol regulates intercellular mitochondrial transport & enhances mesenchymal stem cell rescue efficacy. EMBO Journal. 33 (9): 994-1010).

In another embodiment the chondrisomes can be encapsulated in engineered substrates such as described in, e.g. in Orive. et al. 2015. Cell encapsulation: technical and clinical advances. Trends in Pharmacology Sciences; 36 (8): 537-46; and in Mishra. 2016. Handbook of Encapsulation and Controlled Release. CRC Press. In some embodiments, a composition described herein includes chondrisomes encapsulated in synthetic vesicles, e.g., liposomes.

Liposomes are spherical vesicle structures composed of a uni- or multilamellar lipid bilayer surrounding internal aqueous compartments and a relatively impermeable outer lipophilic phospholipid bilayer. Liposomes may be anionic, neutral or cationic. Liposomes are biocompatible, nontoxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi: 10.1155/2011/469679 for review).

Vesicles can be made from several different types of lipids; however, phospholipids are most commonly used to generate liposomes as drug carriers. Vesicles may comprise without limitation DOPE (dioleoylphosphatidylethanolamine), DOTMA, DOTAP, DOTIM, DDAB, alone or together with cholesterol to yield DOPE and cholesterol, DOTMA and cholesterol, DOTAP and cholesterol, DOTIM and cholesterol, and DDAB and cholesterol. Methods for preparation of multilamellar vesicle lipids are known in the art (see for example U.S. Pat. No. 6,693,086, the teachings of which relating to multilamellar vesicle lipid preparation are incorporated herein by reference). Although vesicle formation can be spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi: 10.1155/2011/469679 for review). Extruded lipids can be prepared by extruding through filters of decreasing size, as described in Templeton et al., Nature Biotech, 15:647-652, 1997, the teachings of which relating to extruded lipid preparation are incorporated herein by reference.

As described herein, additives may be added to vesicles to modify their structure and/or properties. For example, either cholesterol or sphingomyelin may be added to the mixture in order to help stabilize the structure and to prevent the leakage of the inner cargo. Further, vesicles can be prepared from hydrogenated egg phosphatidylcholine or egg phosphatidylcholine, cholesterol, and dicetyl phosphate. (see, e.g., Spuch and Navarro, Journal of Drug Delivery, vol. 2011, Article ID 469679, 12 pages, 2011. doi: 10.1155/2011/469679 for review). Also vesicles may be surface modified during or after synthesis to include reactive groups complementary to the reactive groups on the carrier cells. Such reactive groups include without limitation maleimide groups. As an example, vesicles may be synthesized to include maleimide conjugated phospholipids such as without limitation DSPE-MaL-PEG2000.

A vesicle formulation may be mainly comprised of natural phospholipids and lipids such as 1,2-distearoryl-sn-glycero-3-phosphatidyl choline (DSPC), sphingomyelin, egg phosphatidylcholines and monosialoganglioside. Formulations made up of phospholipids only are less stable in plasma. However, manipulation of the lipid membrane with cholesterol reduces rapid release of the encapsulated bioactive compound into the plasma or 1,2-dioleoyl-sn-glycero-3-phosphoethanolamine (DOPE) increases stability (see, e.g., Spuch and Navarro, Journal of Drug Delivery, vol. 2011, Article ID 469679, 12 pages, 2011. doi: 10.1155/2011/469679 for review).

In another embodiment, lipids may be used to form lipid microparticles. Lipids include, but are not limited to, DLin-KC2-DMA4, C12-200 and colipids disteroylphosphatidyl choline, cholesterol, and PEG-DMG may be formulated (see, e.g., Novobrantseva, Molecular Therapy-Nucleic Acids (2012) 1, e4; doi: 10.1038/mtna.2011.3) using a spontaneous vesicle formation procedure. The component molar ratio may be about 50/10/38.5/1.5 (DLin-KC2-DMA or C12-200/disteroylphosphatidyl choline/cholesterol/PEG-DMG). Tekmira has a portfolio of approximately 95 patent families, in the U.S. and abroad, that are directed to various aspects of lipid microparticles and lipid microparticles formulations (see, e.g., U.S. Pat. Nos. 7,982,027; 7,799,565; 8,058,069; 8,283,333; 7,901,708; 7,745,651; 7,803,397; 8,101,741; 8,188,263; 7,915,399; 8,236,943 and 7,838,658 and European Pat. Nos. 1766035; 1519714; 1781593 and 1664316), all of which may be used and/or adapted to the present invention.

Some vesicles and lipid-coated polymer particles are able to spontaneously adsorb to cell surfaces.

In some embodiments, a composition described herein includes chondrisomes encapsulated in microparticles or microgels.

Microparticles are comprised of one or more solidified polymer(s) that is arranged in a random manner. The microparticles may be biodegradable. Biodegradable microparticles may be synthesized using methods known in the art including without limitation solvent evaporation, hot melt microencapsulation, solvent removal, and spray drying. Exemplary methods for synthesizing microparticles are described by Bershteyn et al., Soft Matter 4:1787-1787, 2008 and in US 2008/0014144 A1, the specific teachings of which relating to microparticle synthesis are incorporated herein by reference.

As discussed herein, some microparticles are biodegradable in nature and thus they gradually degrade in an aqueous environment such as occurs in vivo. Chondrisomes may be released from the microparticles as the microparticle degrades or chondrisome products may be released through pores within the microparticles. Release kinetic studies have been performed and they demonstrate that protein and small-molecule drugs can be released from such microparticles over time-courses ranging from 1 day to at least 2 weeks.

Exemplary synthetic polymers which can be used to form the biodegradable microparticles include without limitation aliphatic polyesters, poly(lactic acid) (PLA), poly(glycolic acid) (PGA), co-polymers of lactic acid and glycolic acid (PLGA), polycarprolactone (PCL), polyanhydrides, poly (ortho) esters, polyurethanes, poly(butyric acid), poly(valeric acid), and poly(lactide-co-caprolactone), and natural polymers such as albumin, alginate and other polysaccharides including dextran and cellulose, collagen, chemical derivatives thereof, including substitutions, additions of chemical groups such as for example alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

The microparticles' diameter ranges from 0.1-1000 micrometers (μm). In some embodiments, their diameter ranges in size from 1-750 μm, or from 50-500 μm, or from 100-250 μm. In some embodiments, their diameter ranges in size from 50-1000 μm, from 50-750 μm, from 50-500 μm, or from 50-250 μm. In some embodiments, their diameter ranges in size from .05-1000 μm, from 10-1000 μm, from 100-1000 μm, or from 500-1000 μm. In some embodiments, their diameter is about 0.5 μm, about 10 μm, about 50 μm, about 100 μm, about 200 μm, about 300 μm, about 350 μm, about 400 μm, about 450 μm, about 500 μm, about 550 μm, about 600 μm, about 650 μm, about 700 μm, about 750 μm, about 800 μm, about 850 μm, about 900 μm, about 950 μm, or about 1000 μm. As used in the context of microparticle diameters, the term "about" means +/−5% of the absolute value stated. Thus, it is to be understood that although these particles are referred to herein as microparticles, the invention intends to embrace nanoparticles as well.

In some embodiments, a ligand is conjugated to the surface of the microparticle via a functional chemical group (carboxylic acids, aldehydes, amines, sulfhydryls and hydroxyls) present on the surface of the particle and present on the ligand to be attached. Functionality may be introduced into the microparticles by, for example, during the emulsion preparation of microparticles, incorporation of stabilizers with functional chemical groups.

Another example of introducing functional groups to the microparticle is during post-particle preparation, by direct crosslinking particles and ligands with homo- or heterobifunctional crosslinkers. This procedure may use a suitable chemistry and a class of crosslinkers (CDI, EDAC, glutaraldehydes, etc. as discussed in more detail below) or any other crosslinker that couples ligands to the particle surface via chemical modification of the particle surface after preparation. This also includes a process whereby amphiphilic molecules such as fatty acids, lipids or functional stabilizers may be passively adsorbed and adhered to the particle surface, thereby introducing functional end groups for tethering to ligands.

In some embodiments, the microparticles may be synthesized to comprise one or more targeting groups on their exterior surface to target a specific cell or tissue type (e.g., cardiomyocytes). These targeting groups include without limitation receptors, ligands, antibodies, and the like. These targeting groups bind their partner on the cells' surface. In some embodiments, the microparticles will integrate into a lipid bilayer that comprises the cell surface and the chondrisomes are delivered to the cell.

The microparticles may also comprise a lipid bilayer on their outermost surface. This bilayer may be comprised of one or more lipids of the same or different type. Examples include without limitation phospholipids such as phosphocholines and phosphoinositols. Specific examples include without limitation DMPC, DOPC, DSPC, and various other lipids such as those described herein for liposomes.

In some embodiments, the vesicles or microparticles described herein are functionalized with a diagnostic agent. Examples of diagnostic agents include, but are not limited to, commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium.

Modified Preparations

Source Modification

In one aspect, a modification is made to the source, such as a subject, tissue or cell, that affects the mitochondria or chondrisome preparation, such as producing mitochondria with a heterologous function or a structural change in the mitochondria. Such modifications can be effective to, e.g., improve mitochondrial activity, function or structure. Modifications to the source can include, but are not limited to, changes to the cellular metabolic state (e.g. through different culture conditions or through transfected regulatory modulators); changes to the cellular regulatory state; and changes to the source cells' differentiation state.

Stress Treatment

The source may be treated to modulate mitochondrial activity, function or structure prior to isolation of chondrisomes. In some embodiments, chondrisomes are obtained from a source that has been stressed. A stress condition can include nutritional stress (reduction in carbon (e.g., sugar) and/or amino acid source), osmotic stress, hypoxia, temperature stress, injury. Such stress conditions may enhance mitochondrial biogenesis or function in the source.

In one embodiment, chondrisomes can be obtained from a source exposed to different temperatures: e.g., isolated chondrisomes from a source below freezing (e.g., at −20° C. or lower, −4° C. or lower, lower than 0° C.), a cold or chilled source (e.g., between 0° C.-10° C., e.g., 0° C., 4° C., 10° C.), a source at or around room temperature (between 15° C.-25° C., e.g., 15° C., 20° C., 25° C.) or a warmed source (between 25° C.-42° C., e.g., 32° C., 37° C.). In another embodiment, the invention includes a composition of chondrisomes isolated from a source exposed to a time and temperature sufficient to modulate mitochondrial activity, function, structure, or any combination thereof (e.g., by at least 10%, 15%, 20%, 30%, 40%, 50%, 60%, 75%, 80%, 90% or more). The source is exposed to the temperature difference for a time sufficient to modulate its mitochondrial activity, function, structure, or any combination thereof (e.g., by at least 10%, 15%, 20%, 30%, 40%, 50%, 60%, 75%, 80%, 90% or more).

In another example, chondrisomes are obtained from a source exposed to a reference oxygen concentrations, e.g., hypoxia (e.g., about 0% to about 4%), normoxia (e.g., about 1% to about 14%), hyperoxia (e.g., about 5% or higher), or any concentration therebetween. Normal O2 concentration varies significantly between tissues. In another embodiment, the invention includes a composition of chondrisomes isolated from a source exposed to an O2 concentration for a time sufficient to modulate its mitochondrial activity, function, structure, or any combination thereof (e.g., by at least 10%, 15%, 20%, 30%, 40%, 50%, 60%, 75%, 80%, 90% or more). O2 concentrations in parenchymal organs (liver, kidneys, heart) varies from about 4% to about 14%; in the brain, it varies from about 0.5% to about 7%; in the eye (retina, corpus vitreous), it varies from about 1 to about 5%; and in the bone marrow, it varies from almost 0% to about 4%. The source is exposed to an oxygen concentration that is sufficient to modulate mitochondrial activity, function, structure, or any combination thereof (e.g., by at least 10%, 15%, 20%, 30%, 40%, 50%, 60%, 75%, 80%, 90% or more). The source is exposed to the oxygen concentration for a time sufficient to modulate its mitochondrial activity, function, structure, or any combination thereof (e.g., by at least 10%, 15%, 20%, 30%, 40%, 50%, 60%, 75%, 80%, 90% or more).

In some embodiments, chondrisomes are obtained from a source exposed to starvation conditions, e.g., lack of added glucose or other sugar substrate, amino acids, or a combination thereof. In another embodiment, the invention includes a composition of chondrisomes isolated from a source exposed to starvation conditions for a time sufficient to modulate its mitochondrial activity, function, structure, or any combination thereof (e.g., by at least 10%, 15%, 20%, 30%, 40%, 50%, 60%, 75%, 80%, 90% or more). The source is exposed to starvation conditions that are sufficient to modulate its mitochondrial activity, function, structure, or any combination thereof (e.g., by at least 10%, 15%, 20%, 30%, 40%, 50%, 60%, 75%, 80%, 90% or more). The source is exposed to the starvation conditions for a time sufficient to modulate its mitochondrial activity, function, structure, or any combination thereof (e.g., by at least 10%, 15%, 20%, 30%, 40%, 50%, 60%, 75%, 80%, 90% or more).

In another embodiment, chondrisomes are obtained from a source exposed to specified concentrations of one or more nutrients, e.g., reduced concentration of glucose or other sugar substrate, amino acids, or a combination thereof. In another embodiment, the invention includes a composition of chondrisomes isolated from a source exposed to one or more nutrient concentrations for a time sufficient to modulate its mitochondrial activity, function, structure, or any combination thereof (e.g., by at least 10%, 15%, 20%, 30%, 40%, 50%, 60%, 75%, 80%, 90% or more). The source is exposed to a nutrient concentration or combination (e.g., ratio) of nutrients that is sufficient to modulate its mitochondrial activity, function, structure, or any combination thereof (e.g., by at least 10%, 15%, 20%, 30%, 40%, 50%, 60%, 75%, 80%, 90% or more). The source is exposed to the nutrient concentration or combination (e.g., ratio) of nutrients for a time sufficient to modulate its mitochondrial activity, function, structure, or any combination thereof (e.g., by at least 10%, 15%, 20%, 30%, 40%, 50%, 60%, 75%, 80%, 90% or more).

In another embodiment, chondrisomes are obtained from a source exposed to osmotic stress, e.g., increase or decrease in solute concentration. In another embodiment, the invention includes a composition of chondrisomes isolated from a source exposed to osmotic stress for a time sufficient to modulate its mitochondrial activity, function, structure, or any combination thereof (e.g., by at least 10%, 15%, 20%, 30%, 40%, 50%, 60%, 75%, 80%, 90% or more). The source is exposed to a solute concentration that is sufficient to modulate its mitochondrial activity, function, structure, or any combination thereof (e.g., by at least 10%, 15%, 20%, 30%, 40%, 50%, 60%, 75%, 80%, 90% or more). The source is exposed to the solute concentration for a time sufficient to modulate its mitochondrial activity, function, structure, or any combination thereof (e.g., by at least 10%, 15%, 20%, 30%, 40%, 50%, 60%, 75%, 80%, 90% or more).

In some embodiments, chondrisomes are obtained from a source that has been injured or a source undergoing the wound healing process. At least about 20% of the source may be injured, at least about 25%, 30%, 35%, 40%, 45%, 50%, 55%, 60%, 65%, 70%, 75%, 80%, 85%, 90%, 95%, or up to 100% of the source may be injured. Chondrisomes may be obtained from a source that has been injured within about 7 days, 6 days, 5 days, 4 days, 3 days, 2 days, 1 day, 20 hours, 18 hours, 16 hours, 15 hours, 14 hours, 13 hours, 12 hours, 11 hours, 10 hours, 9 hours, 8 hours, 7 hours, 6 hours, 5 hours, 4 hours, 3 hours, 2.5 hours, 2 hours, 1.5 hours, 1 hour, 50 mins, 40 mins, 30 mins, 25 mins, 20 mins, 15 mins, 10 mins, 5 mins, or less. The source may be injured by any physical, chemical, or other process described herein or known to cause injury to a source. In another embodiment, the invention includes a composition of chondrisomes isolated from a source exposed to injury for a time sufficient to modulate its mitochondrial activity, function, structure, or any combination thereof (e.g., by at least 10%, 15%, 20%, 30%, 40%, 50%, 60%, 75%, 80%, 90% or more).

Toxin Treatment

The source may be treated with a toxin to modulate its mitochondrial activity, function or structure. In some embodiments, chondrisomes are obtained from source that has been treated with or exposed to one or more toxins (e.g., a mitochondrial toxin), such as an inhibitor of complex 1 activity, e.g., metformin. Additional toxins are described in www.mitoaction.org/files/MitoToxins_0.pdf. Treating a source with a toxin or injury inducing chemical agent induces processes within the source, such as mechanisms to compensate for toxin injury, that may enhance mitochondrial biogenesis or activity or function.

In some embodiments, chondrisomes are obtained from a source that has been exposed to a toxin described herein. At least about 20% of the source may be exposed to the toxin, at least about 25%, 30%, 35%, 40%, 45%, 50%, 55%, 60%, 65%, 70%, 75%, 80%, 85%, 90%, 95%, or up to 100% of the source is exposed to the toxin. Chondrisomes may be obtained from a source that has been exposed to the toxin within about 7 days, 6 days, 5 days, 4 days, 3 days, 2 days, 1 day, 20 hours, 18 hours, 16 hours, 15 hours, 14 hours, 13 hours, 12 hours, 11 hours, 10 hours, 9 hours, 8 hours, 7 hours, 6 hours, 5 hours, 4 hours, 3 hours, 2.5 hours, 2 hours, 1.5 hours, 1 hour, 50 mins, 40 mins, 30 mins, 25 mins, 20 mins, 15 mins, 10 mins, 5 mins, or less. In another embodiment, the invention includes a composition of chondrisomes isolated from a source exposed to a toxin for a time sufficient to modulate its mitochondrial activity, function, structure, or any combination thereof (e.g., by at least 10%, 15%, 20%, 30%, 40%, 50%, 60%, 75%, 80%, 90% or more).

Infectious Agent Treatment

In another embodiment, a source may be treated with one or more infectious agents, such as a virus or bacteria (e.g., hepatitis C virus (HCV) and hepatitis B virus (HBV)). A viral infection causes many physiological alterations in a source and many of those alterations can directly affect its mitochondrial dynamics and mitophagy. For example, expression of HCV core and NS5a proteins perturb complex 1 activity and promote mitochondrial $Ca^{2+}$ uptake, ROS production, and mitochondrial permeability transition. In another example, source infection with an infectious agent, such as a virus or bacteria, may induce mitochondrial dysfunction that activates the innate immune response to fight the infection. In some embodiments, the source is exposed to an infectious agent that is sufficient to modulate its mitochondrial activity, function, structure, or any combination thereof (e.g., by at least 10%, 15%, 20%, 30%, 40%, 50%, 60%, 75%, 80%, 90% or more). The source is exposed to the infectious agent for a time sufficient to modulate its mitochondrial activity, function, structure, or any combination thereof (e.g., by at least 10%, 15%, 20%, 30%, 40%, 50%, 60%, 75%, 80%, 90% or more). In another embodiment, the invention includes a composition of chondrisomes isolated from a source exposed to an infectious agent for a time sufficient to modulate its mitochondrial activity, function, structure, or any combination thereof (e.g., by at least 10%, 15%, 20%, 30%, 40%, 50%, 60%, 75%, 80%, 90% or more).

Increasing Bioenergy in Source

In some embodiments, communication between the mitochondrion and the cytosol across the outer mitochondrial membrane and the remarkably high-resistance inner membrane is dependent on numerous transporters. Thus modulation of these transporters via protein phosphorylation affects the ability of the cytosol to influence mitochondrial reaction pathways via the exchange of metabolites and signaling molecules, as well as proteins. For example, phosphorylation of mitochondrial pyruvate dehydrogenase (PDH) is metabolically controlled by enzyme phosphorylation via the PDH kinase (PDHK) and PDH phosphatase (PDHP) system. In one embodiment, the source is treated with dephosphorylated pyruvate dehydrogenase to catabolize glucose and gluconeogenesis precursors. In another embodiment, the source is treated with phosphorylated pyruvate dehydrogenase to shift metabolism toward fat utilization. In another embodiment, the invention includes a composition of chondrisomes comprising phosphorylated mitochondrial pyruvate dehydrogenase (e.g., at least 10%, 15%, 20%, 30%, 40%, 50%, 60%, 75%, 80%, 90% or more pyruvate dehydrogenase is phosphorylated). In another embodiment, the invention includes a composition of chondrisomes isolated from a source exposed to pyruvate dehydrogenase kinase for a time sufficient to phosphorylate mitochondrial pyruvate dehydrogenase (e.g., increase phosphorylation by at least 10%, 15%, 20%, 30%, 40%, 50%, 60%, 75%, 80%, 90% or more).

Targeting to Mitochondria

Modifications to the source may also change the distribution and/or quantity of nuclearly encoded mitochondrial targeted proteins. In some embodiments, these modifications can involve targeting proteins or RNA not normally present in the mitochondria (including both endogenous and exogenous genes) to the mitochondria by the addition of a targeting sequence to non-mitochondrial proteins or a mitochondrial import signal appended to RNA. In one embodiment, the invention includes a composition of chondrisomes comprising non-mitochondrial proteins (e.g., at least 10%, 15%, 20%, 30%, 40%, 50%, 60%, 75%, 80%, 90% or more proteins are non-mitochondrial proteins).

Of the many proteins involved in mitochondrial function, only a handful are encoded by the mitochondrial genome and the rest are expressed by the nuclear genome and transported into the mitochondria. Mitochondrial proteins may be targeted to the mitochondrial matrix, inner membrane, outer membrane, or the intermembrane space. In one embodiment, the invention includes a composition of chondrisomes comprising non-mitochondrial proteins in the mitochondrial matrix, inner membrane, outer membrane, or the intermembrane space (e.g., at least 10%, 15%, 20%, 30%, 40%, 50%, 60%, 75%, 80%, 90% or more non-mitochondrial are located in the mitochondrial matrix, inner membrane, outer membrane, or the intermembrane space).

In addition, mitochondria import a modest number of RNAs (e.g., small noncoding RNAs, miRNAs, tRNAs, and possibly lncRNAs and viral RNAs). RNAs are processed within mitochondria and may have functions different from their cytosolic or nuclear counterparts. In some tissues, RNA splice-variants are differentially present in mitochondria or the cytosol. For example, variants that code for mitochondrial and cytosolic selenocysteine-containing isoforms possess identical glutaredoxin (Grx) and thioredoxin reductase (TR) domains but differ exclusively in their N termini. In one embodiment, the invention includes a composition of chondrisomes comprising cytosolic RNA or nuclear RNA. Alternative trans-splicing may create a long or a short spliced variant of trypanosomal isoleucyl-tRNA synthetase (IleRS). The protein product of the longer spliced variant possesses an amino-terminal presequence and is found exclusively in mitochondria. In contrast, the shorter spliced variant is translated to a cytosol-specific isoform lacking the presequence. In some embodiments, a distribution of alternative splice variants, such as in the cytosol or the mitochondria, is altered by increasing the presence of one or more forms or decreasing the presence of one or more forms. In one embodiment, the invention includes a composition of chondrisomes comprising an altered distribution of alternative splice variants (e.g., at least 10%, 15%, 20%, 30%, 40%, 50%, 60%, 75%, 80%, 90% or more of the distribution of the splice variants is altered). In another embodiment, the invention includes a composition of chondrisomes comprising an increase of the presence of one or more forms or a decrease in the presence of one or more forms e.g., at least 10%, 15%, 20%, 30%, 40%, 50%, 60%, 75%, 80%, 90% or more of the distribution of the splice variants is altered.

Import into mitochondria can be initiated by N-terminal targeting sequences (presequences) or internal targeting sequences. Import into the organelle may be mediated by a translocase in the outer membrane (TOM) complex, molecular chaperone proteins, and targeting sequences. A translocase in the inner membrane (TIM) complex mediates transit from the intermembrane space into the mitochondrial matrix, as well as embedding proteins into the inner membrane. A carrier translocase (TIM22) also is capable of embedding carrier proteins and N-terminal targeted inner membrane proteins. In one embodiment, the invention includes a composition of chondrisomes comprising a translocase with modulated activity e.g., an increase or a decrease in activity of at least 10%, 15%, 20%, 30%, 40%, 50%, 60%, 75%, 80%, 90% or more as compared to a non-modulated translocase. In one embodiment, the invention includes a composition of chondrisomes comprising a protein (or nucleic acid encoding) a fusion of a translocase and a cargo protein (e.g., a cargo protein described herein, e.g., an agent listed in Table 4).

Proteins destined for import into the mitochondria via the presequence import pathway may have a leader sequence or an N-terminal targeting sequence capable of forming an amphipathic helix. In some embodiments, a protein (e.g., a cargo protein) is engineered fused to a mitochondrial targeting sequence (MTS) described herein. Some MTS may be about 10 to about 80 amino acids in length, and generally able to form amphipathic helices. In one embodiment, a protein is engineered with a MTS between about 10 to 100 amino acids in length, about 10 to 75 amino acids in length, about 10 to 50 amino acids in length, about 10 to 40 amino acids in length, about 10 to about 30 amino acids in length, or any range therebetween. In one embodiment, the invention includes a composition of chondrisomes comprising an exogenous protein (e.g., a exogenous protein described herein) linked to an MTS. In another embodiment, the MTS forms one or more amphipathic helices. The amphipathic helix structure is recognized by the import machinery and is ultimately cleaved off after the protein enters the mitochondrial matrix by a mitochondrial processing peptidase. Protein import into the mitochondria is also described in, for example, Bolender et al., 2008, EMBO Rep. 9, 42-49; Dolezal et al., 2006, Science 313, 314-318; Gabriel and Pfanner, 2007, Methods Mol. Biol. 390, 99-117; Pfanner et al., 2004, Nat. Struct. Mol. Biol. 11, 1044-1048.

Some mitochondrial proteins do not have an N-terminal targeting sequence and an internal or C-terminal sequence may be used for localization. Mitochondrial targeting sequences may be enriched in positive, hydrophobic, and hydroxylated amino acids, while acidic residues are rare. While some proteins may lack a targeting sequence, others are dual targeted, e.g., targeted to the mitochondrion and to one or more additional subcellular compartments.

While multiple mitochondrial targeting sequences are effective at localizing exogenous protein to mitochondria, sequence and physiochemical characteristics of the amino acids determine the precise localization. In some embodiments, the mitochondrial targeting sequence is a sequence from a 5S rRNA, such as the fly 5S rRNA variant V. In one embodiment, the invention includes a composition of chondrisomes comprising an exogenous protein comprising a MTS from 5S rRNA. In some embodiments, the mitochondrial targeting sequence is from the RNA component of the endoribonuclease known as MRP, or the RNA component of the ribonucleoprotein known as RNAse P. In another embodiment, the invention includes a composition of chondrisomes comprising an exogenous protein comprising a MTS from RNAse P. In some embodiments, a mitochondrial targeting sequence may be designed to target the mitochondrial matrix by replicating the first 69 amino acids of the precursor of subunit 9 of the mitochondrial Fo-ATPase. In one embodiment, the invention includes a composition of chondrisomes comprising an exogenous protein comprising a MTS from precursor of subunit 9 of the mitochondrial Fo-ATPase. In some embodiments, a fusion of a mitochondrial targeting sequences, such as the first 69 amino acids of the precursor of subunit 9 of the mitochondrial Fo-ATPase, to dihydrofolate reductase (DHFR) imports the fusion protein into the mitochondrial matrix.

See, Kunze, M. & Berger, J. The similarity between N-terminal targeting signals for protein import into different organelles and its evolutionary relevance. Frontiers in Physiology, vol 6. 2015.

For example, e.g., the DSRed2 fluorescent protein is targeted to the mitochondrial matrix by appending the mitochondrial targeting sequence from subunit VIII of human cytochrome c oxidase (ATGTCCGTCCTG ACGCCGCTGCTGCTGCGGGGCTTGACAGGCTCGGC CCGGCGGCTCCCAGT GCCGCGCGCCAAGATCCAT-TCGTTG, SEQ ID NO:6) to the N-terminus of the protein. In one embodiment, the invention includes a composition of chondrisomes comprising DSRed2 fluorescent protein. In one embodiment, the invention includes a composition of chondrisomes comprising DSRed2 fluorescent protein with N-terminus mitochondrial targeting sequence, e.g., from subunit VIII of human cytochrome c oxidase. In one embodiment, the invention includes a composition of chondrisomes comprising an exogenous polypeptide fused to the mitochondrial targeting sequence from subunit VIII of human cytochrome c oxidase (SEQ ID NO:6).

In some embodiments, cytosolic proteins, such as proteases or enzymes, are modified for targeting to the mitochondria. Cytosolic proteins may be engineered to include a mitochondrial targeting sequence, e.g., first 69 amino acids of the precursor of subunit 9 of the mitochondrial Fo-ATPase. For example, cytosolic enzymes (e.g., proteases, phosphatases, kinases, demethylases, methyltransferases, acetylases) may be relocalized to the mitochondria. In one embodiment, the invention includes a composition of chondrisomes comprising cytosolic enzymes. In one embodiment, the invention includes a composition of chondrisomes comprising a cytosolic enzyme, e.g., a protease, phosphatase, kinase, demethylase, methyltransferase, acetylase, or any combination thereof.

In some embodiments, the source is modified to express nuclearly encoded proteins typically targeted to a mitochondrial space without their mitochondrial targeting sequence. For example, a mitochondrial translocase protein that is nuclearly encoded and cytosolically expressed is engineered in the source to lack a mitochondrial targeting sequence, thereby altering the mitochondrial to lack or have reduced mitochondrial translocase proteins. In one embodiment, the invention includes a composition of chondrisomes comprising a decreased level or a lack of a nuclearly encoded and cytosolically expressed mitochondrial protein, e.g., mitochondrial translocase protein. Mitochondria or chondrisome preparations that lack such mitochondrial translocase proteins have reduced protein translocation capacity.

Source Engineering

A source may be genetically modified using recombinant methods known in the art. A nucleic acid sequence coding for a desired gene can be obtained using recombinant methods known in the art, such as, for example by screening libraries from cells expressing the gene, by deriving the gene from a vector known to include the same, or by isolating directly from cells and tissues containing the same, using standard techniques. Alternatively, a gene of interest can be produced synthetically, rather than cloned.

Expression of natural or synthetic nucleic acids is typically achieved by operably linking a nucleic acid encoding the gene of interest to a promoter, and incorporating the construct into an expression vector. The vectors can be suitable for replication and integration in eukaryotes. Typical cloning vectors contain transcription and translation terminators, initiation sequences, and promoters useful for expression of the desired nucleic acid sequence.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter.

Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

The expression vector to be introduced into the source can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes may be used for identifying potentially transfected cells and for evaluating the functionality of regulatory sequences. In general, a reporter gene is a gene that is not present in or expressed by the recipient source and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479:79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In some embodiments, the source may be genetically modified to alter expression of one or more proteins. Expression of the one or more proteins may be modified for a specific time, e.g., development or differentiation state of the source. In one embodiment, the invention includes a composition of chondrisomes isolated from a source genetically modified to alter expression of one or more proteins, e.g., mitochondrial proteins or non-mitochondrial proteins that affect mitochondrial activity, structure or function. Expression of the one or more proteins may be restricted to a specific location(s) or widespread throughout the source. Alternative trans-splicing also creates variants that may be differentially targeted. In some embodiments, the source is engineered to create a long or a short spliced variant, e.g., trypanosomal isoleucyl-tRNA synthetase (IleRS), to differentially target the protein products, e.g., the longer spliced variant is found exclusively in mitochondria and the shorter spliced variant is translated to a cytosol-specific isoform. In some embodiments, a distribution of alternative splice variants, such as in the cytosol or the mitochondria, is altered by increasing the presence of one or more forms or decreasing the presence of one or more forms. In one embodiment, the invention includes a composition of chondrisomes isolated from a source genetically modified to alter expression of alternative splice variants, e.g., distribution of the splice variants or protein products from the splice variants. In one embodiment, the invention includes a composition of chondrisomes comprising modified expression of alternative splice variants, e.g., RNA or protein products from the splice variants.

In some embodiments, the expression of a structural gene is modified. For example, such structural gene may encode OMP25, (MNGRVDYLVTEEEINL-TRGPSGLGFNIVGGTDQQYVSNDSGIYVSRIKEN-GAAALDGRLQEGDK ILSVNGQDLKNLLHQDAVDL-FRNAGYAVSLRVQHRLQVQNGPIGHRGEGDPSGIPIF-MVLVPVF ALTMVAAWAFMRYRQQL, SEQ ID NO: 10) or a protein at least about 85%, 90%, 95%, 100% identical to SEQ ID NO:10. In one embodiment, the invention includes a composition of chondrisomes comprising modified expression of a structural gene, e.g., an increase or a decrease in expression of OMP25 by at least 10%, 15%, 20%, 30%, 40%, 50%, 60%, 75%, 80%, 90% or more.

In some embodiments, the expression of a membrane targeted protein is modified. In some embodiments, such membrane proteins can be chemical or ion transporters (e.g. MPC1/2 (Mitochondrial Pyruvate carrier) or UCP1, SEQ ID NO:1). In some embodiments, a decreased expression results in reduced flux of compounds transported across the membrane or an alteration of the source's ability to dynamically control said flux. In one embodiment, the invention includes a composition of chondrisomes comprising modified expression of a membrane targeted protein, e.g., an increase or a decrease in expression of a chemical or ion transporter by at least 10%, 15%, 20%, 30%, 40%, 50%, 60%, 75%, 80%, 90% or more.

In some embodiments, the expression of a translocase in the outer membrane (such as TOM22, MAAAVAAAGAGEPQSPDELLPKGDAEKPEEELEEDDDEELDETLSERLWGLTEMFPERVRSAA GATFDLSLFVAQKMYRFSRAALWIGTTSFMILVLPVVFETEKLQMEQQQQLQQRQILLGPNTGLS GGMPGALPSLPGKI, SEQ ID NO: 11) complex, a translocase in the inner membrane (such as TIM17A, MEEYAREPCPWRIVDDCGGAFTMGTIGGGIFQAIKGFRNSPVGVNHRLRGSLTAIKTRAPQLGGS FAVWGGLFSMIDCSMVQVRGKEDPWNSITSGALTGAILAARNGPVAMVGSAAMGGILLALIEG AGILLTRFASAQFPNGPQFAEDPSQLPSTQLPSSPFGDYRQYQ, SEQ ID NO: 12, or TIM17B, MEEYAREPCPWRIVDDCGGAFTMGVIGGGVFQAIKGFRNAPVGIRHRLRGSANAVRIRAPQIGG SFAVWGGLFSTIDCGLVRLRGKEDPWNSITSGALTGAVLAARSGPLAMVGSAMMGGILLALIEG VGILLTRYTAQQFRNAPPFLEDPSQLPPKDGTPAPGYPSYQQYH, SEQ ID NO: 13) complex, or a carrier translocase (such as TIM22, MAAAAPNAGGSAPETAGSAEAPLQYSLLLQYLVGDKRQPRLLEPGSLGGIPSPAKSEEQKMIEK AMESCAFKAALACVGGFVLGGAFGVFTAGIDTNVGFDPKDPYRTPTAKEVLKDMGQRGMSYA KNFAIVGAMFSCTECLIESYRGTSDWKNSVISGCITGGAIGFRAGLKAGAIGCGGFAAFSAAIDYY LR, SEQ ID NO: 14) is modified. In some embodiments, the source is engineered to express a protein at least 85%, 90%, 95%, 100% identical to SEQ ID NOs: 11, 12, 13, or 14. In one embodiment, the invention includes a composition of chondrisomes comprising modified expression of a translocase in the outer membrane complex, a translocase in the inner membrane complex, or a carrier translocase, e.g., an increase or a decrease in expression of the translocase by at least 10%, 15%, 20%, 30%, 40%, 50%, 60%, 75%, 80%, 90% or more.

In another embodiment, the expression of one or more metabolic conversion enzymes is altered to adjust the metabolic capacity of the chondrisome preparation. In some embodiments, such enzymes alter the capacity of the chondrisome preparation to alter a patient's metabolic concentration, e.g. OTC (ornithine transcarbamylase), such as by altering the ability to address urea cycle disorders. In some embodiments, such enzymes can be selected for their ability to adjust redox balancing and cycling, such as NADH oxidases (e.g. the heterologous LbNOX, see for example, Titov, D. V., et al., 2016, Science, 352 (6282): 231-235). In one embodiment, the invention includes a composition of chondrisomes comprising modified expression of one or more metabolic conversion enzymes, e.g., an increase or a decrease in expression of the metabolic conversion enzyme by at least 10%, 15%, 20%, 30%, 40%, 50%, 60%, 75%, 80%, 90% or more.

In some embodiments, the source may be engineered to express a cytosolic enzyme (e.g., proteases, phosphatases, kinases, demethylases, methyltransferases, acetylases) that targets a mitochondrial protein. In some embodiments, the source may be engineered to express one or more enzymes that is relocated to the mitochondria. In some embodiments, the enzyme affects one or more mitochondrial proteins (such as membrane transporters, intermediary metabolism enzymes, and the complexes of oxidative phosphorylation) by altering post-translational modifications. Post-translational protein modifications of proteins may affect responsiveness to nutrient availability and redox conditions, and protein-protein interactions. In one embodiment, the invention includes a composition of chondrisomes comprising proteins with altered post-translational modifications, e.g., an increase or a decrease in post-translational modifications by at least 10%, 15%, 20%, 30%, 40%, 50%, 60%, 75%, 80%, 90% or more on membrane transporters, intermediary metabolism enzymes, and the complexes of oxidative phosphorylation.

In some embodiments, a source is engineered to up- or down-regulate expression of an enzyme that controls a post-translational modification in the mitochondria. For example, PDH (pyruvate dehydrogenase) can be activated by deacetylation to alter the metabolic connection between glycolysis and the citric acid cycle by overexpression of SIRT3 or a protein at least 85%, 90%, 95%, 100% identical to SEQ ID NO:7 in the source. Similarly, phosphorylation of pyruvate dehydrogenase driven by increased expression pyruvate dehydrogenase kinase (MRLARLLRGAALAGPGPGLRAAGFSRSFSSDSGSSPASERGVPGQVDFYARFSPSPLSMKQFLDF GSVNACEKTSFMFLRQELPVRLANIMKEISLLPDNLLRTPSVQLVQSWYIQSLQELLDFKDKSAE DAKAIYDFTDTVIRIRNRHNDVIPTMAQGVIEYKESFGVDPVTSQNVQYFLDRFYMSRISIRMLLN QHSLLFGGKGKGSPSHRKHIGSINPNCNVLEVIKDGYENARRLCDLYYINSPELELEELNAKSPGQ PIQVVYVPSHLYHMVFELFKNAMRATMEHHANRGVYPPIQVHVTLGNEDLTVKMSDRGGGVPL RKIDRLFNYMYSTAPRPRVETSRAVPLAGFGYGLPISRLYAQYFQGDLKLYSLEGYGTDAVIYIK ALSTDSIERLPVYNKAAWKHYNTNHEADDWCVPSREPKDM TTFRSA, SEQ ID NO:8) in the source to inhibit PDH metabolic flux. In one embodiment, the invention includes a composition of chondrisomes comprising proteins with increased or decreased phosphorylation, e.g., an increase or a decrease in phosphorylation by at least 10%, 15%, 20%, 30%, 40%, 50%, 60%, 75%, 80%, 90% or more on membrane transporters, intermediary metabolism enzymes, and/or the complexes of oxidative phosphorylation. In another example, O-GlcNAc transferase (MASSVGNVADSTEPTKRMLSFQGLAELAHREYQAGDFEAAERHCMQLWRQEPDNTGVLLLLS SIHFQCRRLDRSAHFSTLAIKQNPLLAEAYSNLGNVYKERGQLQEAIEHYRHALRLKPDFIDGYIN LAAALVAAGDMEGAVQAYVSALQYNPDLYCVRSDLGNLLKALGRLEEAKACYLKAIETQPNF AVAWSNLGCVFNAQGEIWLAIHHFEKAVTLDPNFLDAYINLGNVLKEARIFDRAVAAYLRALSL SPNHAVVHGNLACVYYEQGLIDLAIDTYRRAIELQPHFPDAYCNLANALKEKGSVAEAEDCYNT ALRLCPTHADSLNNLANIKREQGNIEEAVRLYRKALEVFPEFAAAHSNLASVLQQQGKLQEALM HYKEAIRISPTFADAYSNMGNTLKEMQDVQGALQCYTRAIQINPAFADAHSNLASIHKDSGNIPE AIASYRTALKLKPDFPDAYCNLAHCLQIVCDWTDYDERMKKLVSIVADQLEKNRLPSVHPHHS MLYPLSHGFRKAIAERHGNLCLDKINVLHKPPYEHPKDLKLSDGRLRVGYVSSDFGNHPTSHLM QSIPGMHNPDKFEVFCYALSPDDGTNFRVKVMAEANHFIDLSQIPCNGKAADRIHQDGIHILVNM NGYTKGARNELFALRPAPIQAMWLGYPGTSGALFMDYIITDQETSPAEVAE- QYSEKLAYMPHTF FIGDHANMFPHLKK-KAVIDFKSNGHIYDNRIVLNGIDLKAFLD-SLPDVKIVKMKCPDGGDNADSS NTALNMPVIPMN-TIAEA VIEMINRGQIQITINGFSISNGLATTQINNKAAT-GEEVPRTIIVTTRSQYG LPEDAIVYCNFNQLYKIDP-STLQMWANILKRVPNSVLWLLRFPAVGEP-NIQQYAQNMGLPQNRII FSPVAPKEEHVRRGQLAD-VCLDTPLCNGHTTGMDVLWAGTPMVTMPGETLAS-RVAASQLTCLG CLELIAKNRQEYEDIAVKLGTDLEY-LKKVRGKVWKQRISSPLFNTKQYTMELERLYLQM-WEHY AAGNKPDHMIKPVEVTESA, SEQ ID NO:9 or a sequence at least about 85%, 90%, 95%, 100% identical to SEQ ID NO:9) is overexpressed in the source to reduce the ETC complex 1 activities by altering O-GlcNAcylation. In one embodiment, the invention includes a composition of chondrisomes comprising proteins with increased or decreased O-GlcNAcylation, e.g., an increase or a decrease in altering O-GlcNAcylation by at least 10%, 15%, 20%, 30%, 40%, 50%, 60%, 75%, 80%, 90% or more on membrane transporters, intermediary metabolism enzymes, and/or the complexes of oxidative phosphorylation.

In another embodiment, the source is modified to alter expression of kinases or phosphatases. Such alteration changes phosphorylation states in the mitochondria or chondrisome preparation. In some embodiments, one or more enzymes is selected that alters energy buffering, such as CKs (creatine kinase). By changing production levels of phosphocreatine, ATP buffering can be modified. In some embodiments, one or more kinases is selected based on a distribution of post-translational modifications that controls signaling and/or metabolic flux control, such as AMPK and its ability to alter fatty acid oxidation. In one embodiment, the invention includes a composition of chondrisomes comprising proteins with increased or decreased levels of phosphocreatine, e.g., an increase or a decrease in levels of phosphocreatine by at least 10%, 15%, 20%, 30%, 40%, 50%, 60%, 75%, 80%, 90% or more.

Mitochondria proteins have a strikingly high percentage of proteins that are acetylated on one or more lysines. Thousands of mitochondrial acetylation sites have now been identified and the mitochondrial protein deacetylase, Sirt3, is one of the enzymes that controls acetylation in mitochondria. In one embodiment, the mitochondria of the preparation are modified to express a protein deacetylase, e.g., SIRT3. In one embodiment, the source is engineered such that the mitochondria express a protein at least 85%, 90%, 95%, 100% identical to the sequence of human SIRT3 (or SEQ ID NO:7), wherein the protein has deacetylase activity in the mitochondria. In another embodiment, the invention includes a composition of chondrisomes comprising an exogenous protein at least 85%, 90%, 95%, 100% identical to the sequence of human SIRT3 (or SEQ ID NO:7). In another example, the source is modified to alter expression of a transcription factor, such as human TFAM (MA-FLRSMWGVLSALGRSGAELCTGCGSRLRSPFSFVYL-PRWFSSVLASCPKKPVSSYLRFSKEQ LPIFKAQNP-DAKTTELIRRIAQRWRELPDSKKKIYQDAYRAEWQ-VYKEEISRFKEQLTPSQIMSLE KEIMDKHLKRKA-MTKKKELTLLGKPKRPRSAYNVYVAERFQEAKGD-SPQEKLKTVKENWKNL SDSEKELYIQHAKEDE-TRYHNEMKSWEEQMIEVGRKDLLRRTIKKQRKYG-AEEC, SEQ ID NO: 15). In one embodiment, the source is engineered such that the mitochondria express a protein at least 85%, 90%, 95%, 100% identical to the sequence of human TFAM (or SEQ ID NO: 15). In another embodiment, the invention includes a composition of chondrisomes comprising an exogenous protein at least 85%, 90%, 95%, 100% identical to the sequence of human TFAM (or SEQ ID NO:15).

In some embodiments, one or more transcription factors is physically associated with the mitochondria. In some embodiments, one or more transcription factors alters a mitochondrial process, such as PGC-1alpha (peroxisome proliferator-activated receptor gamma coactivator 1-alpha, MAWDMCNQDSESVWSDIE-CAALVGEDQPLCPDLPELDLSELDVNDLDTDSFLG-GLKWCSDQSE IISNQYNNEPSNIFEKIDEENEANL-LAVLTETLDSLPVDEDGLPSFDALTDGDVTTDNEAS-PSSMPD GTPPPQEAEEPSLLKKLLLAPANTQLSYN-ECSGLSTQNHANHNHRIRTNPAIVKTENSWSNKAKSI CQQQKPQRRPCSELLKYLTTNDDPPHTKPTENRN-SSRDKCTSKKKSHTQSQSQHLQAKPTTLSLP LTPESPNDPKGSPFENKTIERTLSVELSGTA-GLTPPTTPPHKANQDNPFRASPKLKSSCKTVVPPPS KKPRYSESSGTQGNNSTKKGPEQSELYAQL-SKSSVLTGGHEERKTKRPSLRLFGDHDYCQSINSK TEILINISQELQDSRQLEN-KDVSSDWQGQICSSTDSDQCYLRETLEASKQVSPC-STRKQLQDQEIR AELNKHFGHPSQAVFDDEADKT-GELRDSDFSNEQFSKLPMFINSGLAMDGLFDDSEDE-SDKLSY PWDGTQSYSLFNVSP-SCSSFNSPCRDSVSPPKSLF-SQRPQRMRSRSRSFSRHRSCSRSPYSRSRSRS PGSRSSSRSCYYYESSHYRHRTHRNSPLYVRSRSR-SPYSRRPRYDSYEEYQHERLKREEYRREYE KRESER-AKQRERQRQKAIEERRVIYVGKIRPDTTRTELRDRFE-VFGEIEECTVNLRDDGDSYGFIT YRYTCDAFAALENGYTLRRSNETDFE-LYFCGRKQFFKSNYADLDSNSDDFDPASTKSKYD-SLDF DSLLKEAQRSLRR, SEQ ID NO:16) drives mitochondrial biogenesis. In some embodiments, the source is engineered such that the mitochondria express human PGC-1alpha or a protein at least 85%, 90%, 95%, 100% identical to SEQ ID NO:16. In one embodiment, the invention includes a composition of chondrisomes comprising an exogenous protein at least 85%, 90%, 95%, 100% identical to the sequence of human PGC-1alpha (or SEQ ID NO:16).

In another example, the source is modified to express an engineered affinity domain protein. In some embodiments, such an affinity domain, e.g., a FLAG tag (DYKDDDDK, SEQ ID NO:17) or tandem repeat of the FLAG tag, is tethered to a mitochondrial membrane protein, such as 3XFLAG-EGFP-OMP25 (see, for example, Chen, W. W., et al., Cell, 2016, 166 (5): 1324-1337). In some embodiments, such an affinity domain is cleavable so that it may be removed prior to therapeutic delivery of the chondrisome preparation. In one embodiment, the invention includes a composition of chondrisomes comprising a protein with a FLAG tag, e.g., a protein fusion with a FLAG tag, e.g., FLAG-OMP25.

In some embodiments, the source is engineered to lack a protein that affects a mitochondrial function, such as inhibiting the source's expression of a mitochondrial protein, or inhibiting a specific combination of endogenous genes that are targeted to the mitochondria (e.g. through inducible siRNA, through RNA CRISPR as described elsewhere herein). In one embodiment, the invention includes a composition of chondrisomes that lack one or more mitochondrial proteins, e.g., a membrane protein, a translocase, or a membrane complex protein.

Among ~1,500 mitochondrial proteins participate in mitochondrial biogenesis including the oxidative phosphorylation. Around 13 proteins are encoded from the mitochondrial genome and the rest of the mitochondrial proteins are expressed from the nuclear genome and actively transported to the mitochondria. In some embodiments, the source is engineered to express a mitochondrial protein at a modulated level, e.g., over-expression, under-expression or loss of nuclearly encoded mitochondrial proteins. In one embodiment, the source is engineered to express a protein that is at least 85%, 90%, 95%, 100% identical to a mitochondrial protein. In another embodiment, the invention includes a composition of chondrisomes comprising an exogenous protein that is at least 85%, 90%, 95%, or more identical to a mitochondrial protein. In another embodiment, the invention includes a composition of chondrisomes comprising a modulated level of one or more nuclearly encoded mitochondrial proteins, e.g., over-expression, under-expression or loss of a nuclearly encoded mitochondrial protein, such as a membrane protein, a translocase, or an enzyme that controls post-translational modification of mitochondrial proteins.

In some embodiments, the mitochondria are engineered to translate a nucleic acid, such as an exogenous nucleic acid, in the mitochondria. In some embodiments, the mitochondria of the preparation are modified to express a chemical transporter, e.g., UCP1, UCP2, UCP3, UCP4 or UCP5. The expressed transporter may be endogenous or exogenous to the source mitochondria (e.g., the transporter may be naturally expressed), or the mitochondria may be modified (e.g., genetically modified or loaded) to express or over-express the transporter. In one embodiment, the mitochondria are engineered to express a protein at least 85%, 90%, 95%, 100% identical to the sequence of human UCP1 (MGGLTASDVHPTLGVQLFSAGIAACLADVITFPLDTAKVRLQVQGECPTSSVIRYKGVLGTITAV VKTEGRMKLYSGLPAGLQRQISSASLRIGLYDTVQEFLTAGKETAPSLGSKILAGLTTGGVAVFIG QPTEVVKVRLQAQSHLHGIKPRYTGTYNAYRIIATTEGLTGLWKGTTPNLMRSVIINCTELVTYD LMKEAFVKNNILADDVPCHLVSALIAGFCATAMSSPVDVVKTRFINSPPGQYKSVPNCAMKVFT NEGPTAFFKGLVPSFLRLGSWNVIMFVCFEQLKRELSKSRQTMDCAT, SEQ ID NO:1), wherein the protein has transporter activity in the mitochondria. In another embodiment, the invention includes a composition of chondrisomes comprising an exogenous protein at least 85%, 90%, 95%, 100% identical to the sequence of human UCP1 (or SEQ ID NO:1).

In one embodiment, the mitochondria are engineered to express a protein at least 85%, 90%, 95%, 100% identical to the sequence of human UCP2 (MVGFKATDVPPTATVKFLGAGTAACIADLITFPLDTAKVRLQIQGESQGPVRATASAQYRGVM GTILTMVRTEGPRSLYNGLVAGLQRQMSFASVRIGLYDSVKQFYTKGSEHASIGSRLLAGSTTGA LAVAVAQPTDVVKVRFQAQARAGGGRRYQSTVNAYKTIAREEGFRGLWKGTSPNVARNAIVN CAELVTYDLIKDALLKANLMTDDLPCHFTSAFGAGFCTTVIASPVDVVKTRYMNSALGQYSSAG HCALTMLQKEGPRAFYKGFMPSFLRLGSWNVVMFVTYEQLKRALMAACTSREAPF, SEQ ID NO: 2), wherein the protein has transporter activity in the mitochondria. In another embodiment, the invention includes a composition of chondrisomes comprising an exogenous protein at least 85%, 90%, 95%, 100% identical to the sequence of human UCP2 (or SEQ ID NO:2).

In one embodiment, the mitochondria are engineered to express a protein at least 85%, 90%, 95%, 100% identical to the sequence of human UCP3 (MVGLKPSDVPPTMAVKFLGAGTAACFADLVTFPLDTAKVRLQIQGENQAVQTARLVQYRGVL GTILTMVRTEGPCSPYNGLVAGLQRQMSFASIRIGLYDSVKQVYTPKGADNSSLTTRILAGCTTG AMAVTCAQPTDVVKVRFQASIHLGPSRSDRKYSGTMDAYRTIAREEGVRGLWKGTLPNIMRNAI VNCAEVVTYDILKEKLLDYHLLTDNFPCHFVSAFGAGFCATVVASPVDVVKTRYMNSPPGQYFS PLDCMIKMVAQEGPTAFYKGFTPSFLRLGSWNVVMFVTYEQLKRALMKVQMLRESPF, SEQ ID NO: 3), wherein the protein has transporter activity in the mitochondria. In another embodiment, the invention includes a composition of chondrisomes comprising an exogenous protein at least 85%, 90%, 95%, 100% identical to the sequence of human UCP3 (or SEQ ID NO:3).

In one embodiment, the mitochondria are engineered to express a protein at least 85%, 90%, 95%, 100% identical to the sequence of human UCP4 (MSVPEEEERLLPLTQRWPRASKFLLSGCAATVAELATFPLDLTKTRLQMQGEAALARLGDGAR ESAPYRGMVRTALGIIEEEGFLKLWQGVTPAIYRHVVYSGGRMVTYEHLREVVFGKSEDEHYPL WKSVIGGMMAGVIGQFLANPTDLVKVQMQMEGKRKLEGKPLRFRGVHHAFAKILAEGGIRGL WAGWVPNIQRAALVNMGDLTTYDTVKHYLVLNTPLEDNIMTHGLSSLCSGLVASILGTPADVIK SRIMNQPRDKQGRGLLYKSSTDCLIQAVQGEGFMSLYKGFLPSWLRMTPWSMVFWLTYEKIRE MSGVSPF, SEQ ID NO:4), wherein the protein has transporter activity in the mitochondria. In one embodiment, the invention includes a composition of chondrisomes comprising an exogenous protein at least 85%, 90%, 95%, 100% identical to the sequence of human UCP4 (or SEQ ID NO:4).

In one embodiment, the mitochondria are engineered to express a protein at least 85%, 90%, 95%, 100% identical to the sequence of human UCP5 (MGIFPGIILIFLRVKFATAAVIVSGHQKSTTVSHEMSGLNWKPFVYGGLASIVAEFGTFPVDLTKT RLQVQGQSIDARFKEIKYRGMFHALFRICKEEGVLALYSGIAPALLRQASYGTIKIGIYQSLKRLF VERLEDETLLINMICGVVSGVISSTIANPTDVLKIRMQAQGSLFQGSMIGSFIDIYQQEGTRGLWR GVVPTAQRAAIVVGVELPVYDITKKHLILSGMMGDTILTHFVSSFTCGLAGALASNPVDVVRTR MMNQRAIVGHVDLYKGTVDGILKMWKHEGFFALYKGFWPNWLRLGPWNIIFFITYEQLKRLQI, SEQ ID NO:5), wherein the protein has transporter activity in the mitochondria. In another embodiment, the invention includes a composition of chondrisomes comprising an exogenous protein at least 85%, 90%, 95%, 100% identical to the sequence of human UCP5 (or SEQ ID NO:5).

A source may contain many hundreds of mitochondria with hundreds of copies of mitochondrial DNA. It is common for mutations to affect only some mitochondria, while leaving others unaffected, a state known as heteroplasmy. In one embodiment, the invention includes a composition of chondrisomes comprising heteroplasmic mtDNA. Detrimental heteroplasmic alleles can shift in percentage during both mitotic and meiotic cell division, leading to a potentially continuous array of defects, a process known as replicative segregation. As the percentage of mutant mtDNAs increases, the resulting defect becomes increasingly severe. Heteroplasmic alleles may be eliminated through differential cleavage (enzymes that recognize the heteroplasmic allele but not the wildtype or healthy allele). In some embodiments, a source is engineered to express an enzyme that specifically cleaves the heteroplasmic allele, thereby leaving the non-heteroplasmic allele intact. In one embodiment, the invention includes a composition of chondrisomes comprising heteroplasmic mtDNA, wherein a subset of the heteroplasmic mtDNA comprises an enzyme recognition sequence cleavable by an enzyme. In another embodiment, the invention includes a composition of chondrisomes comprising heteroplasmic mtDNA, wherein a subset of the heteroplasmic mtDNA is cleaved by an enzyme at an enzyme recognition sequence in the subset of mtDNA. In some embodiments, a source is treated with an enzyme that specifically cleaves the heteroplasmic allele, and leaving the non-heteroplasmic allele intact.

Mitochondrial diseases are commonly caused by mutations in the mitochondrial DNA. Pathogenic mtDNA mutations are heteroplasmic, and residual wild-type mtDNA can partially compensate for the mutated mtDNA. The levels of mutated mtDNA in affected tissues have to reach a high threshold, usually above 80%, for biochemical and clinical manifestations. In some embodiments, a source is engineered to express an enzyme that specifically cleaves the deleterious heteroplasmic allele, while leaving the non-heteroplasmic or wildtype allele intact. See, for example, mitoTALEN described in Bacman, et al., Nat. Med., vol. 19 (9): 1111-1113. In one embodiment, the invention includes a composition of chondrisomes comprising heteroplasmic mtDNA, wherein a subset of the heteroplasmic mtDNA comprises a deleterious mutation that is specifically recognized and cleaved by an enzyme. In another embodiment, the invention includes a composition of chondrisomes comprising a subset of mtDNA with a deleterious mutation, wherein only mtDNA with the deleterious mutation interacts with and activates an enzyme that cleaves the mtDNA with the deleterious mutation while leaving the mtDNA without the deleterious mutation intact. In another embodiment, the invention includes a composition of chondrisomes comprising mtDNA with about a 5 Kb deletion, m.8483_13459del4977. This mutation is known as the "common deletion" because it is present in approximately 30% of all patients with mtDNA deletions. The source may be engineered to express an enzyme, e.g., mitoTALEN, or treated with the enzyme that specifically cleaves the deleterious heteroplasmic allele, thereby leaving the non-deleterious heteroplasmic allele intact and capable of replication.

Mitochondria Modification

In one aspect, a modification is made to the chondrisome preparations as described herein to, e.g., produce chondrisomes with a heterologous function or induce a structural change in the chondrisomes.

Such modifications can be effective to, e.g., improve chondrisome activity, function or structure. Modifications to the chondrisomes can include, but are not limited to, changes to the mitochondrial or chondrisome metabolic state; changes to the mitochondrial or chondrisome respiratory state, and changes to the mitochondrial or chondrisome lipid and/or protein content. These changes can result in changing the distribution and quantity of chondrisome proteins.

Engineered Chondrisomes

In some embodiments, engineered chondrisomes with heterologous function are produced as a result of genetically engineering the endogenous mitochondrial genome prior to therapeutic delivery.

The human mitochondrial genome is a circular double stranded DNA molecule with a size of 16,569 bp. The mtDNA has no intron but retains compactly arranged 37 genes (13 proteins, 22 tRNAs and 2 rRNAs) critical for producing energy through OXPHOS. Major noncoding regions in the mtDNA genome involve the D-loop sequence and the origin of L-strand replication (OL), which controls mtDNA transcription and replication within mitochondria. The 13 protein-coding genes encode subunits of the OXPHOS enzyme complexes. The genes encoded in the mtDNA can be found in Table 2.

TABLE 2

Mitochondrial Genes.

| Gene ID | Start site in rCRS | End site in rCRS | Description |
|---|---|---|---|
| Mitochondrial encoded rRNA | | | |
| MT-RNR1 | 648 | 1601 | 12S ribosomal RNA |
| MT-RNR2 | 1671 | 3229 | 16S ribosomal RNA |
| MT-RNR3 | 3206 | 3229 | 5S-like sequence |
| Mitochondrial Encoded Proteins | | | |
| MT-ATP6 | 8527 | 9207 | ATP synthase F0 subunit 6 |
| MT-ATP8 | 8366 | 8572 | ATP synthase F0 subunit 8 |
| MT-CYB | 14747 | 15887 | Cytochrome b |
| MT-CO1 | 5904 | 7445 | Cytochrome c oxidase subunit I |
| MT-CO2 | 7586 | 8269 | Cytochrome c oxidase subunit II |
| MT-CO3 | 9207 | 9990 | Cytochrome c oxidase subunit III |
| MT-ND1 | 3307 | 4262 | NADH Dehydrogenase subunit 1 |
| MT-ND2 | 4470 | 5511 | NADH dehydrogenase subunit 2 |
| MT-ND3 | 10059 | 10404 | NADH dehydrogenase subunit 3 |
| MT-ND4 | 10760 | 12137 | NADH dehydrogenase subunit 4 |
| MT-ND4L | 10470 | 10766 | NADH dehydrogenase subunit 4L |
| MT-NDS | 12337 | 14148 | NADH dehydrogenase subunit 5 |
| MT-ND6 | 14149 | 14673 | NADH dehydrogenase subunit 6 |
| Mitochondrial Encoded Peptides | | | |
| HM | 2634 | 2707 | Humanin |
| SHLP1 | 2561 | 2490 | small humanin-like peptide 1 |
| SHLP2 | 2170 | 2092 | small humanin-like peptide 2 |
| SHLP3 | 1821 | 1707 | small humanin-like peptide 3 |
| SHLP4 | 2524 | 2446 | small humanin-like peptide 4 |
| SHLP5 | 2856 | 2785 | small humanin-like peptide 5 |
| SHLP6 | 2992 | 3051 | small humanin-like peptide 6 |
| MOTS-c | 1343 | 1392 | mitochondrial open reading frame of the 12S rRNA-c |
| Mitochondrial Encoded tRNA | | | |
| MT-TA | 5587 | 5655 | tRNA alanine |
| MT-TR | 10405 | 10469 | tRNA arginine |
| MT-TN | 5657 | 5729 | tRNA asparagine |
| MT-TD | 7518 | 7585 | tRNA aspartic acid |
| MT-TC | 5761 | 5826 | tRNA cysteine |
| MT-TE | 14674 | 14742 | tRNA glutamic acid |
| MT-TQ | 4329 | 4400 | tRNA glutamine |
| MT-TG | 9991 | 10058 | tRNA glycine |
| MT-TH | 12138 | 12206 | tRNA histidine |
| MT-TI | 4263 | 4331 | tRNA isoleucine |
| MT-TL1 | 3230 | 3304 | tRNA leucine 1 |
| MT-TL2 | 12266 | 12336 | tRNA leucine2 |
| MT-TK | 8295 | 8364 | tRNA lysine |
| MT-TM | 4402 | 4469 | tRNA methionine |
| MT-TF | 577 | 647 | tRNA phenylalanine |
| MT-TP | 15956 | 16023 | tRNA proline |
| MT-TS1 | 7446 | 7514 | tRNA serine 1 |
| MT-TS2 | 12207 | 12265 | tRNA serine2 |
| MT-TT | 15888 | 15953 | tRNA threonine |
| MT-TW | 5512 | 5579 | tRNA tryptophan |

TABLE 2-continued

| Mitochondrial Genes. | | | |
|---|---|---|---|
| Gene ID | Start site in rCRS | End site in rCRS | Description |
| MT-TY | 5826 | 5891 | tRNA tyrosine |
| MT-TV | 1602 | 1670 | tRNA valine |

The accepted consensus mitochondrial sequence is the revised Cambridge Reference Sequence (rCRS) (GenBank Accession NC_012920.1). However, every individual comprises a degree of sequence variability, potentially benign/healthy and/or disease/pathology linked, from this reference sequence. These changes are catalogued in a number of sequence databases, such as the Human Mitochondrial DataBase (www.hmtdb.uniba.it: 8080/hmdb/; see also, Rubino, F., et al., Nucleic Acid Res., 2012, 40: D1150-D1159).

Examples of mitochondrial engineering may include, but are not limited to, modifying the genome whereby one to all the bases in the mitochondrial genome are modified to a different nucleobase; deleting a defined region of the endogenous mitochondrial genome of any length between 1 base to the entire length of the genome (mtDNA removal); inserting novel genetic sequence into the genome; and changing the structure or order of the genetic components by inversion or rearrangement.

In some embodiments, the mitochondrial genome is modified such that between at least one to all the bases in the mitochondrial genome are modified to a different nucleobase. In one embodiment, the invention includes a composition of chondrisomes comprising at least 1 base to the entire length of the genome (mtDNA) is modified to a different nucleobase. In some embodiments, the mitochondrial genome is modified such that a defined region of the endogenous mitochondrial genome is removed. The length may be any length between at least 1 base to the entire length of the genome (mtDNA removal). In one embodiment, the invention includes a composition of mitochondria in a source or chondrisomes comprising at least 1 base to the entire length of the genome (mtDNA) is deleted.

In some embodiments, the mitochondrial genome is modified such that a novel genetic sequence is inserted into the genome. The length may be any length between at least 1 base to 100,000 bases. In one embodiment, the invention includes a composition of mitochondria in a source or chondrisomes comprising mtDNA with an insertion of at least 1 base to 100,000 bases.

In some embodiments, the mitochondrial genome is modified such that a structure of the genome is modified or the order of the genetic components is modified, such as by inversion or rearrangement. In some embodiments, the mitochondrial genome is modified such that a secondary or tertiary structure of the genome is modified or a genomic folding structure is modified that allows or inhibits genomic expression. In one embodiment, the invention includes a composition of mitochondria in a source or chondrisomes comprising mtDNA with a modified secondary or tertiary structure or a modified genomic folding structure.

In some embodiments, the mitochondria are modified with an exogenous nucleic acid that comprises a translation initiation sequence upstream (5') of a translational start codon. The mitochondrial translation initiation sequence can be any nucleic acid sequence that mediates the initiation of translation of an RNA in mitochondria. For example, suitable translation initiation sequences can be found upstream (5') of a translational start codon of a mitochondrial gene. In some embodiments, the mitochondrial translation initiation sequence is at least 80%, at least 85%, at least 90%, at least 95%, at least 96%, at least 97%, at least 98% or at least 99% identical to about 10 to about 40 nucleotides found upstream (5') of a translational start codon of a mitochondrial gene. In one embodiment, the invention includes a composition of mitochondria in a source or chondrisomes comprising an exogenous nucleic acid with a mitochondrial translation initiation sequence, e.g., at least 80%, at least 85%, at least 90%, at least 95%, at least 96%, at least 97%, at least 98% or at least 99% identical to about 10 to about 40 nucleotides found upstream (5') of a translational start codon of a mitochondrial gene.

Mitochondrial engineering can be performed either within the mitochondria by acting on the endogenous mitochondrial genome or in vitro. In vitro modification is on either through modification of isolated genetic material, or synthesis of genetic material or some combination thereof followed by reintroduction of the modified mitochondrial genome into the mitochondrial matrix. Transgenomic mitochondria are described, e.g., in US20070128726A1.

In some embodiments, tRNA sequences in the mitochondria are modified. For example, mitochondrial tRNA sequences may be modified to resemble cytosolic tRNA sequences. In another example, tRNA sequences are modified to alter the wobble position or third base position. In one embodiment, the invention includes a composition of mitochondria in a source or chondrisomes comprising one or more modified tRNA sequences, e.g., a tRNA sequence is modified to a cytosolic tRNA sequence or a tRNA sequence is modified to alter the wobble position or third base position.

In some embodiments, mitochondria are modified to reduce or eliminate pathogenic mtDNA mutations. In some embodiments, mitochondria are modified within a source to reduce the levels of mutated mtDNA in affected sources, e.g., below about 80% to reduce biochemical and clinical manifestations. In some embodiments, mitochondria are modified within a source with an enzyme that specifically cleaves the deleterious heteroplasmic allele, while leaving the non-heteroplasmic or wildtype allele intact. See, for example, mitoTALEN described in Bacman, et al., Nat. Med., vol. 19 (9): 1111-1113. In one embodiment, the invention includes a composition of mitochondria in a source or chondrisomes isolated from a source that comprises heteroplasmic mtDNA, wherein a subset of the heteroplasmic mtDNA comprises a deleterious mutation that is specifically recognized and cleaved by an enzyme. In another embodiment, the invention includes a composition of mitochondria in a source or chondrisomes isolated from a source that comprises a subset of mtDNA with a deleterious mutation, wherein only mtDNA with the deleterious mutation interacts with and activates an enzyme that cleaves the mtDNA with the deleterious mutation while leaving the mtDNA without the deleterious mutation intact. In another embodiment, the invention includes a composition of mitochondria in a source or chondrisomes isolated from a source that comprises mtDNA with the common deletion, e.g., about a 5 Kb deletion, m.8483_13459del4977. The source may be treated with the enzyme, e.g., mitoTALEN, to specifically cleave the mutant mtDNA while leaving the non-mutant mtDNA intact.

Protein Modification in Mitochondria

In some embodiments, mitochondria or chondrisomes are modified by loading the mitochondria with modified proteins (e.g. enable novel functionality, alter post-translational modifications, bind to the mitochondrial membrane and/or mitochondrial membrane proteins, form a cleavable protein with a heterologous function, form a protein destined for proteolytic degradation, assay the agent's location and levels, or deliver the agent via the mitochondria as a carrier). In one embodiment, the invention includes a composition of mitochondria in a source, or chondrisomes, loaded with modified proteins.

In some embodiments, an exogenous protein is non-covalently bound to the mitochondrial outer membrane and/or mitochondrial outer membrane proteins, loaded into a mitochondrial matrix, within the intermembrane space, or bound to the outer or inner membrane. In one embodiment, the invention includes a composition of mitochondria in a source or chondrisomes comprising an exogenous protein non-covalently bound to the mitochondrial outer membrane and/or mitochondrial outer membrane proteins, loaded into a mitochondrial matrix, within the intermembrane space, or bound to the outer or inner membrane. The protein may include a cleavable domain for release into the exterior, the matrix or the intermembrane space. In one embodiment, the invention includes a composition of mitochondria in a source or chondrisomes comprising an exogenous protein with a cleavable domain.

Mitochondrial peripheral membrane proteins are known to modulate actin binding. Altered distribution and concentration of mitochondrial peripheral membrane proteins can, among other behaviors and effects, alter the efficiency of mitochondrial uptake as demonstrated by the in vitro uptake assay outlined above. Candidate proteins include, but are not limited to, nuclear encoded, engineered, exogenous or xenogeneic proteins, and surface associating compounds can be used to modulate uptake, and behavior following delivery, e.g., lymphatic clearance, degradation, physiological stability intra and intercellularly. See Boldogh, I.R., Methods in Cell Biology, 2007, 80:683-706. In one embodiment, the invention includes a composition of mitochondria in a source or chondrisomes with modulated actin binding, e.g., altered distribution and/or concentration of mitochondrial peripheral membrane proteins that bind actin.

In some embodiments, one or more mitochondrial proteins (such as membrane transporters, intermediary metabolism enzymes, and the complexes of oxidative phosphorylation) are altered by post-translational modifications. Post-translational protein modifications of proteins located in the mitochondria affect responsiveness to nutrient availability and redox conditions, and protein-protein interactions to modify diverse mitochondrial functions. Examples of post-translational modifications include, but are not limited to, physiologic redox signaling via reactive oxygen and nitrogen species, phosphorylation, O-GlcNAcylation, S-nitrosylation, nitration, glutathionylation, acetylation, succinylation, and others. Key regulators are known for each of these pathways, e.g., Bckdha phosphorylation, Hmgcs2 acetylation and phosphorylation, and Acadl acetylation. In one embodiment, the invention includes a composition of mitochondria in a source or chondrisomes comprising one or more exogenous enzymes that regulate post-translational modifications. Interestingly, Acat1 Lys-265 was also recently identified as a prominent site of reversible succinylation, further suggesting that this is an unusually important site of post-translational regulation. In one embodiment, mitochondria in a source described herein are loaded with Acat1 (MAVLAALLRSGARSR-SPLLRRLVQEIRYVERSYVSKPTLKEVVIVSATRT-PIGSFLGSLSLLPATK LGSIAIQGAIEKAGIP-KEEVKEAYMGNVLQGGEGQAPTRQAVLGAGLPIST-PCTTINKVCASGMK AIMMAS-QSLMCGHQDVMVAGGMESMSNVPYVMNRG-STPYGGVKLEDLIVKDGLTDVYNKIH MGSCAEN-TAKKLNIARNEQDAYAINSYTRSKAAWEAGKFGNEV-IPVTVTVKGQPDVVVKEDEE YKRVDFSKVPKLKTVFQKENGTVTAANASTLND-GAAALVLMTADAAKRLNVTPLARIVAFADA AVE-PIDFPIAPVYAASMVLKDVGLKKEDIAMW-EVNEAFSLVVLANIKMLEIDPQKVNINGGAVS LGHPIGMSGARIVGHLTHALKQGEYGLASICNGGG-GASAMLIQKL, SEQ ID NO:18) acetylated at Lys-260 and Lys-265 to inhibit its activity by disrupting CoA binding. In one embodiment, the invention includes a composition of mitochondria in a source or chondrisomes comprising exogenous Acat1 acetylated at Lys-260 and Lys-265.

In some embodiments, a distribution of posttranslational modifications is altered in the mitochondria or chondrisomes by up or downregulating levels of enzymes (e.g., proteases, phosphatases, kinases, demethylases, methyltransferases, acetylases) that control the modifications in the mitochondria. For example, PDH (pyruvate dehydrogenase) can be activated by deacetylation to alter the metabolic connection between glycolysis and the citric acid cycle by increases levels of SIRT3. Similarly, increased activity of pyruvate dehydrogenase kinase results in the phosphorylation of pyruvate dehydrogenase to drive PDH metabolic flux. In another example, O-GlcNAcylation can be modified by O-GlcNAc transferase to control the electron transport chain by reducing ETC complex 1 activities.

In some embodiments, the mitochondria in the source or the chondrisomes are loaded with an agent that enables the mitochondria to have novel functionality within the source. In some embodiments, the mitochondria are loaded with an agent that binds the mitochondrial membrane and/or mitochondrial membrane proteins. For example, the source may be treated with an agent that loads the mitochondria, such as with a tag or marker, to assay the agent's location and levels, the mitochondria's location and activities within the source, e.g., DS-red.

As described herein, communication between the mitochondrion and the cytosol is dependent on numerous transporters. These transporters may be modulated via protein phosphorylation to affect the exchange of metabolites and signaling molecules, as well as proteins. In one embodiment, mitochondria in a source are loaded with dephosphorylated pyruvate dehydrogenase to catabolize glucose and gluconeogenesis precursors. In another embodiment, mitochondria in a source are loaded with phosphorylated pyruvate dehydrogenase to shift metabolism toward fat utilization.

Cleavable Proteins

In some embodiments, the mitochondria in a source or chondrisomes are modified with a cleavable protein. In some cases, proteins may be engineered to target to the inner membrane or outer membrane with a fused intermembrane domain that can be released by intermembrane proteases. The engineered fusion protein may bind any domain of a transmembrane mitochondrial proteins (e.g. GDP). The engineered fusion protein may be linked by a cleavage peptide to a protein domain located within the intermembrane space. The cleavage peptide may be cleaved by one or a combination of intermembrane proteases listed in Table 3 (e.g. HTRA2/OMI which requires a non-polar aliphatic amino acid-valine, isoleucine or methionine are preferred—at position P1, and hydrophilic residues-arginine is preferred—at the P2 and P3 positions).

TABLE 3

| Proteases | | |
|---|---|---|
| Location / Type / Protease Class / Enzyme | EC Number | Clevage Site |
| Cytosol | | |
| Endopeptidase | | |
| Serine Protease | | |
| Trypsin | E.C.3.4.21.4 | Arg-\|-Xaa and Lys-\|-Xaa |
| Thrombin | E.C.3.4.21.5 | Arg-\|-Gly |
| Cysteine Protease | | |
| Cathepsin B | E.C.3.4.22.1 | Arg-Arg-\|-Xaa |
| Calpain-1 | E.C.3.4.22.52 | Met-\|-Xaa, Tyr-\|-Xaa and Arg-\|-Xaa (with Leu or Val as the P2 residue) |
| Aspartic Acid Protease | | |
| Pepsin | E.C.3.4.23.1 | Preferentially Phe-\|-Xaa with Xaa = Phe, Trp, or Tyr |
| Cathepsin D | E.C.3.4.23.5 | Preferentially Phe-\|-Xaa, Tyr-\|-Xaa and Leu-\|-Xaa, ideally with Xaa /= Ala or Val |
| Metalloprotease | | |
| Neprilysin | E.C.3.4.24.11 | Xaa-\|-Tyr, Xaa-\|-Phe |
| Thimet oligopeptidase | E.C.3.4.24.15 | Xaa-\|-Arg, Xaa-\|-Ser |
| Exopeptidase | | |
| Amino peptidase | | |
| Leucyl-aminopeptidase | E.C.3.4.11.1 | Preferentially Leu-\|-Xaa, but not Arg-\|-Xaa and Lys-\|-Xaa |
| di/tri peptidyl peptidases | | |
| Prolyl tripeptyl-peptidase | E.C.3.4.14.12 | Xaa-Yaa-Pro-\|-Zaa if Zaa /= Pro |
| Peptidyl-dipeptidases | | |
| Peptidyl-dipeptidase A | E.C.3.4.15.1 | Xaa-\|-Yaa-Zaa, if Yaa /= Pro, or Zaa /= Asp or Glu |
| Metallo-carboxypeptidases | | |
| Carboxypeptidase U | E.C.3.4.17.20 | Xaa-\|-Arg and Xaa-\|-Lys |
| Mitochondrial Outer Membrane | | |
| Cysteine Protease | | |
| USP30 | EC:3.4.19.12 | |
| Mitochondrial Intermembrane | | |
| Metalloprotease | | |
| ATP23 | EC:3.4.24 | |
| Mitochondrial Inner Membrane | | |
| Metalloprotease | | |
| SPG7 | EC:3.4.24 | |
| Mitochondrial Matrix | | |
| Metalloprotease | | |
| PITRM1 | EC:3.4.24 | |

Proteolytic Degradation

In some embodiments, mitochondria in a source chondrisomes are modified with a protein destined for proteolytic degradation. Mitochondria contain a variety of proteases that recognize specific protein amino acid sequences and target the proteins for degradation. These protein degrading enzymes can be used to specifically degrade mitochondrial proteins having a proteolytic degradation sequence. In one embodiment, the invention includes a composition of mitochondria in a source or chondrisomes comprising modulated levels of one or more protein degrading enzymes, e.g., an increase or a decrease in protein degrading enzymes by at least 10%, 15%, 20%, 30%, 40%, 50%, 60%, 75%, 80%, 90% or more.

In some embodiments, mitochondrial proteins are engineered by any methods known in the art or any method described herein to comprise a proteolytic degradation sequence, e.g., a mitochondrial or cytosolic degradation sequence. Mitochondrial proteins may be engineered to include, but is not limited to a proteolytic degradation sequence, e.g., the preferred Capsase 2 protein sequence (Val-Asp-Val-Ala-Asp-|-) or other proteolytic sequences (see, for example, Gasteiger et al., The Proteomics Protocols Handbook; 2005:571-607), a modified proteolytic degradation sequence that has at least 75%, 80%, 85%, 90%, 95% or greater identity to the wildtype proteolytic degradation sequence, a cytosolic proteolytic degradation sequence, e.g., ubiquitin, or a modified cytosolic proteolytic degradation sequence that has at least 75%, 80%, 85%, 90%, 95% or greater identity to the wildtype proteolytic degradation sequence. In one embodiment, the invention includes a composition of mitochondria in a source or chondrisomes comprising a protein modified with a proteolytic degradation sequence, e.g., at least 75%, 80%, 85%, 90%, 95% or greater identity to the wildtype proteolytic degradation sequence, a cytosolic proteolytic degradation sequence, e.g., ubiquitin, or a modified cytosolic proteolytic degradation sequence that has at least 75%, 80%, 85%, 90%, 95% or greater identity to the wildtype proteolytic degradation sequence.

In some embodiments, mitochondria may be modified with a protein comprising a protease domain that recognizes specific mitochondrial proteins, e.g., over-expression of a mitochondrial protease, e.g., an engineered fusion protein with mitochondrial protease activity. For example, a protease or protease domain from a protease, such as mitochondrial processing peptidase, mitochondrial intermediate peptidase, inner membrane peptidase. In one embodiment, the invention includes a composition of mitochondria in a source or chondrisomes comprising an exogenous protein with a protease domain that recognizes specific mitochondrial proteins, e.g., over-expression of a mitochondrial protease, e.g., an engineered fusion protein with mitochondrial protease activity.

See, Alfonzo, J.D. & Soll, D. Mitochondrial tRNA import-the challenge to understand has just begun. Biological Chemistry 390:717-722. 2009; Langer, T. et al. Characterization of Peptides Released from Mitochondria. THE JOURNAL OF BIOLOGICAL CHEMISTRY. Vol. 280, No. 4. 2691-2699, 2005; Vliegh, P. et al. Synthetic therapeutic peptides: science and market. Drug Discovery Today. 15 (1/2). 2010; Quiros P.M.m et al., New roles for mitochondrial proteases in health, ageing and disease. Nature Reviews Molecular Cell Biology. V16, 2015; Weber-Lotfi, F. et al. DNA import competence and mitochondrial genetics. Biopolymers and Cell. Vol. 30. N 1. 71-73, 2014.

Chondrisome Modification

Cleavage of Heteroplasmic mtDNA

Pathogenic mtDNA mutations are heteroplasmic, and residual wild-type mtDNA can partially compensate for the mutated mtDNA. In some embodiments, chondrisomes are modified to reduce the levels of mutated mtDNA, e.g., below about 80% to reduce biochemical and clinical manifestations. In some embodiments, chondrisomes are modified with an enzyme that specifically cleaves the deleterious heteroplasmic allele, while leaving the non-heteroplasmic or wildtype allele intact. See, for example, mitoTALEN described in Bacman, et al., Nat. Med., vol. 19 (9): 1111-1113. In one embodiment, the invention includes a composition of chondrisomes comprising heteroplasmic mtDNA, wherein a subset of the heteroplasmic mtDNA comprises a deleterious mutation that is specifically recognized and cleaved by an enzyme. In another embodiment, the invention includes a composition of chondrisomes comprising a subset of mtDNA with a deleterious mutation, wherein only mtDNA with the deleterious mutation interacts with and activates an enzyme that cleaves the mtDNA with the deleterious mutation while leaving the mtDNA without the deleterious mutation intact. In another embodiment, the invention includes a composition of chondrisomes comprising mtDNA with the common deletion, e.g., about a 5 Kb deletion, m.8483_13459del4977. The chondrisomes may be treated with the enzyme, e.g., mitoTALEN, to specifically cleave the mutant mtDNA while leaving the non-mutant mtDNA intact.

Chondrisome Targeted Proteins

The MTS is recognized by the mitochondrial import complexes (translocases of the outer membrane (TOM) and the inner membrane (TIM)) and mediates mitochondrial localization, and subsequent delivery of mitochondrial proteins to the matrix compartment. In some embodiments, chondrisome preparations described herein are modified with a modifying agent, e.g., a biologic or drug, targeted to the chondrisome. The chondrisome preparation may be directly modified with the modifying agent targeted to the chondrisome by directly contacting the chondrisome preparation with the modifying agent. In some embodiments, the chondrisome preparation is modified with a modifying agent that is targeted to the chondrisome by any of the methods described herein. In one embodiment, the invention includes a composition of chondrisomes comprising a modifying agent, e.g., loaded with a modifying agent described herein.

Import into the chondrisome can be initiated by N-terminal targeting sequences (presequences) or internal targeting sequences. Import into the organelle may be mediated by a translocase in the outer membrane (TOM) complex, molecular chaperone proteins, and targeting sequences, a translocase in the inner membrane (TIM) complex to mediate transit from the intermembrane space into the mitochondrial matrix, as well as embedding proteins into the inner membrane, or a carrier translocase (TIM22) for embedding carrier proteins or N-terminal targeted inner membrane proteins. In some embodiments, the chondrisome preparation is modified by treating the preparation with a modifying agent that interferes with translocase function, e.g., an inhibitor of a translocase or a protease that directly targets molecular chaperone proteins, such that the number of proteins imported or the makeup of the proteins imported is altered. In one embodiment, the invention includes a composition of chondrisomes comprising decreased translocase activity or decreased levels of one or more chaperone proteins.

In some embodiments, the chondrisome preparation is modified with a protein targeted to, e.g., the DSRed2 fluorescent protein, the chondrisome matrix by appending the protein with a mitochondrial targeting sequence, e.g., from subunit VIII of human cytochrome c oxidase (ATGTCCGTCCTGACGCCGCTGCTGCTGCGGGGCTTGACAGGCTCGGCCCGGCGGCTCCCAGT GCCGCGCGCCAAGATCCATTCGTTG, SEQ ID NO:6), to the N-terminus of the protein.

In some embodiments, the chondrisome preparation is modified with a cytosolic protein, such as a protease or enzyme, that is targeted to the chondrisome. Cytosolic proteins may be produced with a mitochondrial targeting sequence, e.g., first 69 amino acids of the precursor of subunit 9 of the mitochondrial Fo-ATPase, then contacted with the chondrisome preparation to modify the chondrisomes with the retargeted cytosolic proteins.

Protein Modification in Chondrisome

In some embodiments, the chondrisome preparation is modified by loading with modified proteins to (e.g. enable novel functionality, alter post-translational modifications, bind to the chondrisome membrane and/or chondrisome membrane proteins, form a cleavable protein with a heterologous function, form a protein destined for proteolytic degradation, assay the agent's location and levels, or deliver the agent via the chondrisome as a carrier). In one embodiment, the invention includes a composition of chondrisomes loaded with modified proteins.

In some embodiments, the chondrisome preparations described herein are modified by a non-covalently bound protein to the chondrisome outer membrane and/or chondrisome outer membrane proteins. In one embodiment, the invention includes a composition of chondrisomes comprising an exogenous protein non-covalently bound to the mitochondrial outer membrane and/or mitochondrial outer membrane proteins, loaded into a mitochondrial matrix, within the intermembrane space, or bound to the outer or inner membrane. Altered distribution and/or concentration of peripheral membrane proteins can, among other behaviors and effects, alter the efficiency of protein uptake as demonstrated by the in vitro uptake assay described herein. Candidate proteins include, but are not limited to, nuclear encoded, engineered, exogenous or xenogeneic proteins, and surface associating compounds can be used to modulate uptake, and behavior following delivery, e.g., lymphatic clearance, degradation, physiological stability intra and intercellularly. See Boldogh, I.R. Cell-Free Assays for Mitochondria-Cytoskeleton Interactions. Methods in Cell Biology Vol 80 2007-b. In one embodiment, the invention includes a composition of chondrisomes comprising an altered distribution and/or concentration of one or more peripheral membrane proteins.

In some embodiments, the chondrisomes are loaded with a modifying agent, such as an antibody or transcription factor or drug, that utilizes the chondrisome as a carrier to deliver the agent. In one embodiment, the invention includes a composition of chondrisomes comprising an exogenous antibody or transcription factor or drug. Examples may include, but are not limited to, transcription factors such as GPS2: (MPALLERPKLSNAMARALHRHIMMERER-
KRQEEEEVDKMMEQKMKEEQERRKKKEMEERMS
LEETKEQILKLEEKLLALQEEKHQLFLQLKKVL-
HEEEKRRRKEQSDLTTLTSAAYQQSLTVHTGT
HLLSMQGSPGGHNRPGTLMAADRAKQMFGPQVLT-
TRHYVGSAAAFAGTPEHGQFQGSPGGAY GTAQPP-
PHYGPTQPAYSPSQQLRAP-
SAFPAVQYLSQPQPQPYAVHGHFQPTQTGFLQPGGA-
LSLQ KQMEHANQQTGFSDSSSLRPMHPQALH-
PAPGLLASPQLPVQMQPAGKSGFAATSQPGPRLPFIQ
HSQNPRFYHK, SEQ ID NO: 19 or a protein at least 85%, 90%, 95%, 98% identical to SEQ ID NO:19); or YBX1: (MSSEAETQQPPAAPPAAPAL-
SAADTKPGTTGSGAGSGGPGGLTSAAPAGGDKKVI-
ATKVLGTV KWFNVRNGYG-
FINRNDTKEDVFVHQTAIKKNNPRKYLRSVGDGET-
VEFDVVEGEKGAEAANVT GPGGVPVQGSKY-
AADRNHYRRYPRRRGPPRNYQQNYQNSESGEK-
NEGSESAPEGQAQQRRPYR RRRFP-
PYYMRRPYGRRPQYSNPPVQGEVMEGADNQGAGE-
QGRPVRQNMYRGYRPRFRRGPPR
QRQPREDGNEEDKENQGDETQGQQPPQR-
RYRRNFNYRRRRPENPKPQDGKETKAADPPAENSS
APEAEQGGAE, SEQ ID NO:20 or a protein at least 85%, 90%, 95%, 98% identical to SEQ ID NO:20), or structural control elements such as actin, OPA1: (MWRLRRAAVA-
CEVCQSLVKHSSGIKGSLPLQKLHLVSR-
SIYHSHHPTLKLQRPQLRTSFQQFSSL
TNLPLRKLKFSPIKYGYQPRRNFWPARLATRLLKL-
RYLILGSAVGGGYTAKKTFDQWKDMIPDL SEYK-
WIVPDIVWEIDEYIDFEKIRKALPSSEDLVKLAPDFD-
KIVESLSLLKDFFTSGSPEETAFRAT
DRGSESDKHFRKVSD-
KEKIDQLQEELLHTQLKYQRILERLEKEN-
KELRKLVLQKDDKGIHHRKL KKSLIDMY-
SEVLDVLSDYDASYNTQDHLPRVVVVGDQSAGKT-
SVLEMIAQARIFPRGSGEMMT
RSPVKVTLSEGPHHVALFKDSSREFDLTKEED-
LAALRHEIELRMRKNVKEGCTVSPETISLNVKG
PGLQRMVLVDLPGVINTVTSGMAPDTKETIFSIS-
KAYMQNPNAIILCIQDGSVDAERSIVTDLVSQ
MDPHGRRTIFVLTKVDLAEKN-
VASPSRIQQIIEGKLFPMKALGYFAVVTGKGNSSE-
SIEAIREYEE EFFQNSKLLKTSMLKAHQVT-
TRNLSLAVSDCFWKMVRESVEQQADSFKATRFNLE-
TEWKNNYP RLRELDRNELFEKAKNEILDEVIS-
LSQVTPKHWEEILQQSLWERVSTHVI-
ENIYLPAAQTMNSGTF
NTTVDIKLKQWTDKQLPNKAVEVAWETLQEEFSRF-
MTEPKGKEHDDIFDKLKEAVKEESIKRHK WND-
FAEDSLRVIQHNALEDRSISDKQQWDAAIYFMEE-
ALQARLKDTENAIENMVGPDWKKRW LYW-
KNRTQEQCVHNETKNELEKMLKCNEEHPAYLASDEI-
TTVRKNLESRGVEVDPSLIKDTWH
QVYRRHFLKTALNHCNLCRRGFYYYQRHFVDSE-
LECNDVVLFWRIQRMLAITANTLRQQLTNT EVRR-
LEKNVKEVLEDFAEDGEKKIKLLTGKRVQLAE-
DLKKVREIQEKLDAFIEALHQEK, SEQ ID NO: 21 or a protein at least 85%, 90%, 95%, 98% identical to SEQ ID NO:21), MFN1: (MAEPVSPLKHFVLAKKAI-
TAIFDQLLEFVTEGSHFVEATYKNPELDRIATED-
DLVEMQGYKDKL SIIGEVLSRRHMK-
VAFFGRTSSGKSSVINAMLWDKVLPSGIGHITNCFLS-
VEGTDGDKAYLMTEG SDEKKSVKTVNQLA-
HALHMDKDLKAGCLVRVFWPKAKCALLRD-
DLVLVDSPGTDVTTELDSW IDKFCLDADVFVLVANS-
ESTLMNTEKHFFHKVNERLSKPNIFILNNRWDASAS-
EPEYMEDVRRQ HMERCLHFLVEELKVVNALEAQN-
RIFFVSAKEVLSARKQKAQGMPESGVALAEGF-
HARLQEFQ NFEQIFEECISQSAVKTKFEQHTI-
RAKQILATVKNIMDSVNLAAEDKRHYSVEEREDQI-
DRLDFIR NQMNLLTLDVKKKIKEVTE-
EVANKVSCAMTDEICRLSVLVDEFCSEFHPNPDVL-
KIYKSELNKHI EDGMGRNLADRCT-
DEVNALVLQTQQEIIENLKPLLPAGIQDKLHTLIPCK-
KFDLSYNLNYHKLCS DFQEDI-
VFPFSLGWSSLVHRFLGPRNAQRVLLGLSEPIFQL-
PRSLASTPTAPTTPATPDNASQEELM ITLVT-
GLASVTSRTSMGIIIVGGVIWKTIGWKLLSVSLTMY-
GALYLYERLSWTTHAKERAFKQQF
VNYATEKLRMIVSSTSANCSHQVKQQIATT-
FARLCQQVDITQKQLEEEIARLPKEIDQLEKIQNNS
KLLRNKAVQLENELENFTKQFLPSSNEES, SEQ ID NO:22 or a protein at least 85%, 90%, 95%, 98% identical to SEQ ID NO:22) or MFN2: (MSLLFSRCNSIVTVK-
KNKRHMAEVNASPLKHFVTAKKKINGIFEQLGAY-
IQESATFLEDTYRNA ELDPVTTEEQVLDVKGYL-
SKVRGISEVLARRHMKVAFFGRTSNGKSTVINAML-
WDKVLPSGIGH TTNCFLRVEGTDGHEAFLLTEG-
SEEKRSAKTVNQLAHALHQDKQL-
HAGSLVSVMWPNSKCPLL KDDLVLMD-
SPGIDVTTELDSWIDKFCLDADVFVLVANSESTLMQ-
TEKHFFHKVSERLSRPNIFIL NNRW-
DASASEPEYMEEVRRQHMERCTSFLVDELGVVDR-
SQAGDRIFFVSAKEVLNARIQKAQG MPEGGGALAE-
GFQVRMFEFQNFERRFEECISQSAVKTKFEQHTVRA-
KQIAEAVRLIMDSLHMAA REQQVYCEEMREER-
QDRLKFIDKQLELLAQDYKLRIKQITEEVER-
QVSTAMAEEIRRLSVLVDDY QMDFHPSPVVLKVYK- NELHRHIEEGLGRNMSDRCSTAITNSLQTMQQDMI-DGLKPLLPVSVRSQI DMLVPRQCFSLNYDLNCDKL-CADFQEDIEFHFSLGWTMLVNRFLGPKNSR-RALMGYNDQVQRP IPLTPANPSMP-PLPQGSLTQEEFMVSMVTGLASLTSRTSMGILVVGG-VVWKAVGWRLIALSFGLY GLLYVYERLTWTTKAK-ERAFKRQFVEHASEKLQLVISYTG-SNCSHQVQQELSGTFAHLCQQVD VTRENLEQE-IAAMNKKIEVLDSLQSKAKLLRNKAGWLDSELNMF-THQYLQPSR, SEQ ID NO:23 or a protein at least 85%, 90%, 95%, 98% identical to SEQ ID NO:23).

In some embodiments, the chondrisome preparation is modified by contact with a cytosolic enzyme (e.g., protease, phosphatase, kinase, demethylase, methyltransferase, acetylase) to alter post-translational modification of proteins in the preparation. In some embodiments, one or more chondrisome proteins (such as membrane transporters, intermediary metabolism enzymes, and the complexes of oxidative phosphorylation) are altered by post-translational modifications. Post-translational protein modifications of proteins may affect responsiveness to nutrient availability and redox conditions, and protein-protein interactions. Examples of post-translational modifications include, but are not limited to, physiologic redox signaling via reactive oxygen and nitrogen species, phosphorylation, O-GlcNAcylation, S-nitrosylation, nitration, glutathionylation, acetylation, succinylation, and others. Key regulators are known for each of these pathways, e.g., Bckdha phosphorylation, Hmgcs2 acetylation and phosphorylation, and Acadl acetylation. In one embodiment, the invention includes a composition of chondrisomes comprising one or more exogenous enzymes that regulate post-translational modifications. Interestingly, Acat1 Lys-265 was also recently identified as a prominent site of reversible succinylation, further suggesting that this is an unusually important site of post-translational regulation. In one embodiment, chondrisomes in preparations described herein are loaded with Acat1 acetylated at Lys-260 and Lys-265 to inhibit its activity by disrupting CoA binding. In one embodiment, the invention includes a composition of chondrisomes comprising exogenous Acat1 acetylated at Lys-260 and Lys-265.

In another embodiment, the chondrisome preparation is modified by treatment with a kinase or phosphatase. Such treatment changes the phosphorylation state of the chondrisome preparation. In some embodiments, one or more enzymes is selected that alters energy buffering, such as CKs (creatine kinase). By changing production levels of phosphocreatine, ATP buffering can be modified. In some embodiments, one or more kinases is selected based on a distribution of post-translational modifications that controls signaling and/or metabolic flux control, such as AMPK and its ability to alter fatty acid oxidation. In one embodiment, the invention includes a composition of chondrisomes comprising one or more proteins with an altered phosphorylation state, e.g., an increase or a decrease in protein phosphorylation by at least 10%, 15%, 20%, 30%, 40%, 50%, 60%, 75%, 80%, 90% or more.

In one embodiment, the chondrisome preparation described herein is contacted with a dephosphorylated pyruvate dehydrogenase to catabolize glucose and gluconeogenesis precursors. In one embodiment, the invention includes a composition of chondrisomes comprising dephosphorylated pyruvate dehydrogenase. In another embodiment, the chondrisome preparation described herein is contacted with phosphorylated pyruvate dehydrogenase to shift metabolism toward fat utilization. In one embodiment, the invention includes a composition of chondrisomes comprising phosphorylated pyruvate dehydrogenase.

In another embodiment, the chondrisome preparation is contacted with one or more metabolic conversion enzymes to alter the metabolic capacity of the chondrisome preparation. In some embodiments, such enzymes can alter the capacity of the chondrisome preparation to alter a patient's metabolic concentration, e.g. OTC (ornithine transcarbamylase), such as by altering the ability to address urea cycle disorders. In some embodiments, such enzymes can be selected for their ability to adjust redox balancing and cycling, such as NADH oxidases (e.g. the heterologous LbNOX, see for example Titov, D. V., et al., 2016, Science, 352 (6282): 231-235). In one embodiment, the invention includes a composition of chondrisomes comprising NADH oxidase.

Alternative Spliced RNA

In some embodiments, a chondrisome preparation comprises a modified distribution of alternative splice variants, such as one or more variants is increased or decreased in the chondrisome preparation as compared to the splice variant that was present in the cytosol prior to preparing the chondrisome for isolation. As described herein, mitochondria import a certain number of RNAs (e.g., small noncoding RNAs, miRNAs, tRNAs, and possibly lncRNAs and viral RNAs). RNAs are processed within mitochondria and may have functions different from their cytosolic or nuclear counterparts. In some embodiments, the chondrisome preparation comprises RNA splice-variants that are differentially present in mitochondria or the cytosol. For example, in one embodiment, the short spliced variant of trypanosomal isoleucyl-tRNA synthetase (IleRS) lacking the presequence found exclusively in the cytosol is present in the chondrisome preparation. In one embodiment, the invention includes a composition of chondrisomes comprising RNA splice-variants that are differentially present in mitochondria or the cytosol, e.g., an increase or a decrease in RNA splice-variants by at least 10%, 15%, 20%, 30%, 40%, 50%, 60%, 75%, 80%, 90% or more. In another embodiment, the chondrisome preparation lacks the protein product of the longer spliced variant that is found exclusively in mitochondria.

Modifying Agent

The source, mitochondria in the source, or a chondrisome preparation may be modified or loaded with an agent, such as a nucleic acid (e.g., DNA, RNA), protein, or chemical compound. In some embodiment, the source, mitochondria in the source, or a chondrisome preparation is modified by two or more of the agents described herein, including mixtures, fusions, combinations and conjugates, of atoms, molecules, etc. For example, a nucleic acid may be combined with a polypeptide; two or more polypeptides may be conjugated to each other; a protein may be conjugated to a biologically active molecule (which may be a small molecule such as a prodrug); and the like.

TABLE 4

Agents for modifying or loading onto a source, mitochondria in a source or chondrisome preparation

| Compound<br>Small Molecules<br>Class<br>Molecule |
|---|
| Electron Transport Chain Modulator |
| Amiodarone (Complex 1) |
| b-Methoxyacrylate (Complex 3) |
| Malonate (complex 2) |
| n-Propylgallate (AOX) |

TABLE 4-continued

| Agents for modifying or loading onto a source, mitochondria in a source or chondrisome preparation |
|---|
| Compound |
| Small Molecules |
| Class |
| Molecule |
| ATPase Modulators |
| Aurovertin (Complex V) |
| Oligomycin (Complex V) |
| Uncouplers |
| FCCP |
| Valinomycin |
| 2,4-Dinitrophenol (DNP) |
| Myxobacterial products |
| melithiazol |
| Adipose Metabolism Modulating |
| Pioglitazone Hydrochloride |
| Nucleus/Mitochondrial Decouplers |
| podofilox |
| cycloheximide |
| thimerosal |
| pararosaniline |
| lycorine |
| Calcium transport modulation |
| CGP37157 |
| Mito Biogenesis Stimulation |
| Bezafibrate |
| Others |
| Cyclosporin A (CsA) |
| Dichloroacetate (DCA) |
| Surface associating compounds |
| Lipids |
| Lysobisphosphatidic acid |
| Sphingomyelin (SM) |
| Ganglioside GM3 |
| Phosphatidylserine (PS) |
| Phosphatidylinositol (PI) |
| Phosphatidylcholine (PC) |
| Phosphatidylethanolamine (PE) |
| Lysophosphatidylcholine (LPC) |
| Polypeptides |
| Enzymes |
| citrate synthase |
| cytochrome P450 (prenenolone processing) |
| Regulators |
| Nucleases |
| Zinc Finger Nucleases |
| Kinases |
| ABL2_HUMAN |
| Transporters |
| Type I protein transporter (Hy3B, HylD, TolC, HylA etc) |
| Porin (ompF) |
| Aminoacid exporter (eg yddG) |
| Methylases |
| DNMT1 |
| Surface associating compounds |
| Nucleic Acids |
| RNA |
| let-7b |
| miR-302a |
| miR-93 |
| miR-125b-1* |
| DNA |
| Oligonucleotide with homology |

Small Molecules

The source, mitochondria in the source, or a chondrisome preparation may be contacted with an exogenous agent, such as a small molecule or synthetic therapeutic agent, that modulates mitochondrial activity, function or structure. Examples of suitable small molecules include those described in, "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming organs; Hormones and Hormone Antagonists; Vitamins, Dermatology; and Toxicology, all incorporated herein by reference. In one embodiment, the invention includes a composition of chondrisomes comprising modulated mitochondrial activity, function or structure by a small molecule or synthetic therapeutic agent, e.g., a change in mitochondrial activity, function or structure by at least 10%, 15%, 20%, 30%, 40%, 50%, 60%, 75%, 80%, 90% or more.

The source, mitochondria in the source, or a chondrisome preparation may be loaded with a small molecule, including inorganic and organic chemicals, to enable novel functionality. Molecules<5 kDa can passively diffuse through the outer membrane of mitochondria (Benz 1985). In one embodiment, the invention includes a composition of mitochondria in the source or chondrisomes comprising a small molecule, e.g., an inorganic and organic chemical.

In some embodiments, the small molecule is a pharmaceutically active agent. In one embodiment, the small molecule is an inhibitor of a metabolic activity or component. Useful classes of pharmaceutically active agents include, but are not limited to, antibiotics, anti-inflammatory drugs, angiogenic or vasoactive agents, growth factors and chemotherapeutic (anti-neoplastic) agents (e.g., tumour suppressers). One or a combination of molecules from the categories and examples described herein or from (Orme-Johnson 2007, Methods Cell Biol. 2007; 80:813-26) can be used. In one embodiment, the invention includes a composition of mitochondria in the source or chondrisomes comprising an antibiotic, anti-inflammatory drug, angiogenic or vasoactive agent, growth factor or chemotherapeutic agent.

For example, small molecule drugs can be used to inhibit membrane targeted proteins. In some embodiments, such membrane proteins can be ion transporters (e.g. the sodium calucium exchanger), where the addition of CGP-37157, a benzothiazepine analogue of diltiazem, is able to decrease the calcium efflux from mitochondria (DOI: 10.1054/ceca.2000.0171). In one embodiment, the invention includes a composition of mitochondria in the source or chondrisomes comprising an ion transporter inhibitor, e.g., benzothiazepine analogue of diltiazem.

In some embodiments, a small molecule drug is used to inhibit a protein of the mitochondrial transport chain and/or reduce oxidative phosphorylation. In one embodiment, NADH dehydrogenase activity is decreased by the addition of metformin, a common type 2 diabetes drug, resulting in reduced proton gradient force in the treated cells. In one embodiment, the invention includes a composition of mitochondria in the source or chondrisomes comprising a mitochondrial transport chain inhibitor or oxidative phosphorylation inhibitor, e.g., metformin.

Biologics

The source, mitochondria in the source, or a chondrisome preparation may be treated with an exogenous agent, such as a biologic, that modulates mitochondrial activity, function or structure. In some embodiments, the biologic includes a metabolic enzyme, a transporter, a transcriptional regulator, a nuclease, a protein modifying enzyme (e.g., a kinase), and a nucleic acid modifying enzyme (e.g., a methylase). The biologic may be a polypeptide with at least 85%, 90%, 95%, 100% identity to an endogenous protein and retains at least one activity, function or structure of the endogenous protein. A large molecule biologic can comprise an amino acid or analogue thereof, which may be modified or unmodified or a non-peptide (e.g., steroid) hormone; a proteoglycan; a lipid; or a carbohydrate. If the large molecule biologic is a polypeptide, it can be loaded directly into a mitochondrion according to the methods described herein. In one embodiment, the invention includes a composition of mitochondria in the source or chondrisomes comprising an exogenous large molecule biologic, e.g., a hormone; a proteoglycan; a lipid; or a carbohydrate.

The source, mitochondria in the source, or a chondrisome preparation may be treated in vitro with purified protein. Prior to exogenous protein loading, the mitochondria in the source or in the preparation should be checked to ensure adequate maintenance of outer membrane integrity and membrane potential. In one embodiment, the invention includes a composition of mitochondria in the source or chondrisomes comprising an exogenous protein described herein.

The source, mitochondria in the source, or a chondrisome preparation may be treated with a protein that non-covalently or covalently binds to the mitochondrial outer membrane and/or mitochondrial outer membrane proteins. Mitochondrial peripheral membrane proteins are known to modulate actin binding. Altered distribution and concentration of mitochondrial peripheral membrane proteins can, among other behaviors and effects, alter the efficiency of mitochondrial uptake as demonstrated by the in vitro uptake assay outlined above. Candidate proteins include, but are not limited to, nuclear encoded, engineered, exogenous or xenogeneic proteins, and surface associating compounds can be used to modulate uptake, and behavior following delivery, e.g., lymphatic clearance, degradation, physiological stability intra and intercellularly. See Boldogh, I.R. Cell-Free Assays for Mitochondria-Cytoskeleton Interactions. Methods in Cell Biology Vol 80 2007-b.

Suitable biologics further include toxins, and biological and chemical warfare agents, see Somani, S. M. (ed.), Chemical Warfare Agents, Academic Press, New York (1992)).

The source, mitochondria in the source, or a chondrisome preparation may be treated with a cleavable protein that integrates into the mitochondrial membrane. The engineered fusion protein may include an anchoring domain selected from any of the transmembrane mitochondrial proteins (e.g. GDP). In one embodiment, the invention includes a composition of mitochondria in the source or chondrisomes comprising an engineered fusion protein described herein. The C-terminus or N-terminus of the protein may be attached to a protein domain located within the intermembrane space via a linker peptide. The linker peptide may be cleaved by one or a combination of intermembrane proteases listed in Table 3 (e.g. HTRA2/OMI which requires a non-polar aliphatic amino acid-valine, isoleucine or methionine are preferred—at position P1, and hydrophilic residues-arginine is preferred—at the P2 and P3 positions). The attached intermembrane domain can be selected from a variety of endogenous transmembrane proteins. In some embodiments, the exogenous protein is an engineered fusion protein, where the C-terminus or N-terminus of the protein is attached to a protein domain located within the cytosolic space via a linker peptide. For example, the linker peptide may be designed for cleavage by one or a combination of the cytosolic proteases outlined in Table 3 which requires the accompanying cleavage sequence also included in Table 3. The attached cytosolic domain can be selected from a variety of molecules as indicated in Table 4.

The source, mitochondria in the source, or a chondrisome preparation may be treated with a protein comprising a proteolytic degradation sequence. Mitochondria contain multiple proteases that recognize specific amino acid sequences and target the proteins for degradation. The source, mitochondria in the source, or a chondrisome preparation may be engineered to express mitochondrial proteins comprising a mitochondrial proteolytic degradation sequence, e.g. the preferred Capsase 2 protein sequence (Val-Asp-Val-Ala-Asp-|-) or other proteolytic sequences (see Gasteiger et al., The Proteomics Protocols Handbook; 2005:571-607) or a modified mitochondrial proteolytic degradation sequence that has at least 75%, 80%, 85%, 90%, 95% or greater identity to the wildtype proteolytic degradation sequence.

The source, mitochondria in the source, or a chondrisome preparation may be treated with a mitochondrial protein with a cytosolic proteolytic degradation sequence, e.g., ubiquitin, and a modified cytosolic proteolytic degradation sequence that has at least 75%, 80%, 85%, 90%, 95% or greater identity to the wildtype proteolytic degradation sequence.

The source, mitochondria in the source, or a chondrisome preparation may be treated with a protein comprising a protease domain that recognizes specific mitochondrial proteins. These protein degrading enzymes can be used to specifically degrade mitochondrial proteins. Depending on the sub-organellar location of the target proteins, these enzymes may be active in the mitochondrial matrix, the intermembrane space or in the cytoplasm if they are exported. Any mitochondrial protease, a modified mitochondrial protease that retains at least 10%, 15%, 20%, 30%, 40%, 50%, 60%, 75%, 80%, 90% or more protease activity, a cytosolic protease that specifically recognizes a mitochondrial protein (e.g., a modified mitochondrial protein with a cytosolic protease degradation sequence), and a cytosolic protease modified to specifically recognize a mitochondrial protein while retaining at least 10%, 15%, 20%, 30%, 40%, 50%, 60%, 75%, 80%, 90% or more protease activity may be useful with the invention described herein.

See, for example, Quiros P.M.m et al., New roles for mitochondrial proteases in health, ageing and disease. Nature Reveiws Molecular Cell Biology. V16, 2015; Langer, T. et al. Characterization of Peptides Released from Mitochondria. THE JOURNAL OF BIOLOGICAL CHEMISTRY. Vol. 280, No. 4. 2691-2699, 2005; and Vliegh, P. et al. Synthetic therapeutic peptides: science and market. Drug Discovery Today. 15 (1/2). 2010.

In some embodiments, the source, mitochondria in the source, or a chondrisome preparation may be treated with cytosolic proteins, such as proteases or enzymes, that are modified for targeting to the mitochondria. Cytosolic proteins may be engineered to include a mitochondrial localization sequence, e.g., a 5S rRNA, such as the fly 5S rRNA variant V, the RNA component of the endoribonuclease known as MRP, or the RNA component of the ribonucleoprotein known as RNAse P, or the first 69 amino acids of the precursor of subunit 9 of the mitochondrial Fo-ATPase.

Further examples of biologics may include, but are not limited to, metabolic enzymes, transporters, transcriptional regulators, nucleases, protein modifying enzymes (e.g., kinases), and nucleic acid modifying enzymes (e.g., methylases), such as those described in Table 4.

Nucleic Acids

The source, mitochondria in the source, or a chondrisome preparation may be treated with a nucleic acid, including, but not limited to, an oligonucleotide or modified oligonucleotide, an aptamer, a cDNA, genomic DNA, an artificial or natural chromosome (e.g., a yeast artificial chromosome) or a part thereof, RNA, including an siRNA, a shRNA, mRNA, tRNA, rRNA or a ribozyme, or a peptide nucleic acid (PNA); a virus or virus-like particles; a nucleotide or ribonucleotide or synthetic analogue thereof, which may be modified or unmodified.

In some embodiments, the source, mitochondria in the source, or a chondrisome preparation is treated with an exogenous nucleic acid, such as RNA. Mitochondria import several types of non-coding RNA, for example, microRNAs, tRNAs, RNA components of RNase P and MRP endonuclease, and 5S rRNA. The mitochondria may import RNA from the cytosol. For example, nucleus-encoded RNAs may be targeted to the mitochondria by using the 20-ribonucleotide stem-loop sequence of H1 RNA, the RNA component of the RNase P enzyme that regulates its import. When appended to a nonimported RNA, the H1 RNA import sequence, designated RP, enables the fusion transcript to be imported into mitochondria. See, for example, Wang, et al., (2012), PNAS, 109 (13): 4840-4845. In one embodiment, the invention includes a composition of mitochondria in a source or chondrisomes comprising an exogenous nucleic acid, such as RNA.

Mitochondria contain a smaller number of tRNA species than does the cytoplasm. The mitochondria may import tRNA from the cytosol for optimal protein synthesis. Precursor tRNAs can be imported into the mitochondria by, for example the protein import pathway (e.g., coimport with cytoplasmic aminoacyl-tRNA synthetase or other chaperone protein) or a pathway independent from protein import that does not require cytosolic factors. In one embodiment, the invention includes a composition of mitochondria in a source or chondrisomes comprising an exogenous tRNA.

In some embodiments, the source is engineered to express a DNA. The DNA may encode a polypeptide with at least 85%, 90%, 95%, 100% identity to an endogenous protein and retains at least one activity, function or structure of the endogenous protein. The DNA may encode a protein that aids a mitochondrial function or activity, or provides a new function or activity to the mitochondria, such as transcription or translation in the mitochondrial matrix. See, Weber-Lotfi, F. et al. DNA import competence and mitochondrial genetics. Biopolymers and Cell. Vol. 30. N 1. 71-73, 2014.

A nucleic acid sequences coding for a desired gene can be engineered using recombinant methods known in the art, such as, for example by screening libraries from cells expressing the gene, by deriving the gene from a vector known to include the same, or by isolating directly from cells and tissues containing the same, using standard techniques. Alternatively, a gene of interest can be produced synthetically, rather than cloned.

The nucleic acids may be operably linked to a promoter, or incorporate the nucleic acids into an expression vector. The vectors can be suitable for replication and integration in eukaryotes. Typical cloning vectors contain transcription and translation terminators, initiation sequences, and promoters useful for expression of the desired nucleic acid sequence.

Additional promoter elements, e.g., enhancers, may regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter.

Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

The expression vector to be introduced into the source can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes may be used for identifying potentially transfected cells and for evaluating the functionality of regulatory sequences. In general, a reporter gene is a gene that is not present in or expressed by the recipient source and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479:79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In some embodiments, the source may be genetically modified to alter expression of one or more proteins. Expression of the one or more proteins may be modified for a specific time, e.g., development or differentiation state of the source. Expression of the one or more proteins may be restricted to a specific location(s) or widespread throughout the source. Alternative trans-splicing also creates variants that may be differentially targeted. In some embodiments, the source is engineered to create a long or a short spliced variant, e.g., trypanosomal isoleucyl-tRNA synthetase (Il-eRS), to differentially target the protein products, e.g., the longer spliced variant is found exclusively in mitochondria and the shorter spliced variant is translated to a cytosol-specific isoform. In some embodiments, a distribution of alternative splice variants, such as in the cytosol or the mitochondria, is altered by increasing the presence of one or more forms or decreasing the presence of one or more forms.

In one embodiment, the source may be modified to over-express an endogenous nucleic acid or protein, or to express an exogenous nucleic acid or protein. The nucleic acid may include one or more mitochondrial genes, such as, a chemical transporter, e.g., UCP1, UCP2, UCP3, UCP4 or UCP5, or a nucleic acid that encodes SEQ ID NOs: 1, 2, 3, 4, or 5. The nucleic acid may include any one or more mitochondrial or cytosolic genes, such as, a protein deacetylase, e.g., Sirt3, or a nucleic acid that encodes SEQ ID NO:7, or others described herein. The nucleic acid may be a modified mitochondrial gene that has at least 75%, 80%, 85%, 90%, 95% or greater identity to the wildtype mitochondrial or cytosolic gene. The nucleic acid may include one or more of the exogenous genes described herein. The nucleic acid may be a modified exogenous gene, e.g., comprising a sequence for a mitochondrial targeting peptide, that has at least 75%, 80%, 85%, 90%, 95% or greater identity to the exogenous gene.

The nucleic acid encoding a polypeptide can be obtained using recombinant methods known in the art, such as, for example by screening libraries from cells expressing the gene, by deriving the gene from a vector known to include the same, or by isolating directly from cells and tissues containing the same, using standard techniques. Alternatively, a gene of interest can be produced synthetically, rather than cloned.

Expression of the nucleic acid may be achieved by direct introduction of the nucleic acid into the source, mitochondria in the source, or a chondrisome preparation by one of the methods described herein or by operably linking the nucleic acid encoding a polypeptide to a promoter, incorporating the construct into an expression vector and introducing the vector into the source, mitochondria in the source, or a chondrisome preparation by one of the methods described herein. Vectors useful with the invention should be suitable for replication and integration in eukaryotes. Typical cloning vectors contain transcription and translation terminators, initiation sequences, and promoters useful for expression of the desired nucleic acid sequence.

Additional promoter elements, e.g., enhancers, may regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, individual elements may function either cooperatively or independently to activate transcription.

A constitutive promoter sequence capable of driving high levels of expression of any polynucleotide sequence operatively linked thereto may be used, including, but not limited to the cytomegalovirus (CMV) promoter, simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In one embodiment, the source, mitochondria in the source, or a chondrisome preparation is treated with a nucleic acid comprising a gene that encodes a polypeptide, which the gene is operatively linked to transcriptional and translational regulatory elements active in a target cell or tissue at a target site Mitochondrial Biogenesis Agent The source, mitochondria in the source, or a chondrisome preparation may be treated with an agent that increases mitochondrial biogenesis. For example, the source, mitochondria in the source, or a chondrisome preparation may be contacted with a mitochondrial biogenesis (MB) agent in an amount and for a time sufficient to increase mitochondrial biogenesis in the source, mitochondria in the source, or a chondrisome preparation (e.g., by at least 10%, 15%, 20%, 30%, 40%, 50%, 60%, 75%, 80%, 90% or more). Such MB agents are described, e.g., in Cameron et al. 2016. Development of Therapeutics That Induce Mitochondrial Biogenesis for the Treatment of Acute and Chronic Degenerative Diseases. DOI: 10.1021/acs.jmedchem.6b00669.

In one embodiment, the MB agent is a an extract of a natural product or synthetic equivalent sufficient to increase mitochondrial biogenesis in the source, mitochondria in the source, or a chondrisome preparation. Examples of such natural products include resveratrol, epicatechin, curcumin, a phytoestrogen (e.g., genistein, daidzein, pyrroloquinoline, quinone, coumestrol and equol).

In another embodiment, the MB agent is a metabolite sufficient to increase mitochondrial biogenesis in the source, mitochondria in the source, or a chondrisome preparation, e.g., a primary or secondary metabolite. Such metabolites, e.g., primary metabolites include alcohols such as ethanol, lactic acid, and certain amino acids and secondary metabolites include organic compounds produced through the modification of a primary metabolite, are described in "Primary and Secondary Metabolites." Boundless Microbiology. Boundless, 26 May 2016.

In one embodiment, the MB agent is an energy source sufficient to increase mitochondrial biogenesis in the source, mitochondria in the source, or a chondrisome preparation, e.g., sugars, ATP, redox cofactors as NADH and FADH2. Such energy source, e.g., pyruvate or palmitate, are described in Mehlman, M. *Energy Metabolism and the Regulation of Metabolic Processes in Mitochondria*; Academic Press, 1972.

In one embodiment, the MB agent is a transcription factor modulator sufficient to increase mitochondrial biogenesis in the source, mitochondria in the source, or a chondrisome preparation. Examples of such transcription factor modulators include: thiazolidinediones (e.g., rosiglitazone, pioglitazone, troglitazone and ciglitazone), estrogens (e.g., 17β-Estradiol, progesterone) and estrogen receptor agonists; SIRTI Activators (e.g., SRT1720, SRT1460, SRT2183, SRT2104).

In one embodiment, the MB agent is a kinase modulator sufficient to increase mitochondrial biogenesis in the source, mitochondria in the source, or a chondrisome preparation. Examples include: AMPK and AMPK activators such as AICAR, metformin, phenformin, A769662; and ERK1/2 inhibitors, such as U0126, trametinib.

In one embodiment, the MB agent is a cyclic nucleotide modulator sufficient to increase mitochondrial biogenesis in the source, mitochondria in the source, or a chondrisome preparation. Examples include modulators of the NO-cGMP-PKG pathway (for example nitric oxide (NO) donors, such as sodium nitroprusside, (±)S-nitroso-N-acetylpenicillamine (SNAP), diethylamine NONOate (DEA-NONOate), diethylenetriamine-NONOate (DETA-NONOate); sGC stimulators and activators, such as cinaciguat, riociguat, and BAY 41-2272; and phosphodiesterase (PDE) inhibitors, such as zaprinast, sildenafil, udenafil, tadalafil, and vardenafil) and modulators of the cAMP-PKA-CREB Axis, such as phosphodiesterase (PDE) inhibitors such as rolipram.

In one embodiment, the MB agent is a modulator of a G protein coupled receptor (GPCR), such as a GPCR ligand, sufficient to increase mitochondrial biogenesis in the source, mitochondria in the source, or a chondrisome preparation.

In one embodiment, the MB agent is a modulator of a cannabinoid-1 receptor sufficient to increase mitochondrial biogenesis in the source, mitochondria in the source, or a chondrisome preparation. Examples include taranabant and rimonobant.

In one embodiment, the MB agent is a modulator of a 5-Hydroxytryptamine receptor sufficient to increase mitochondrial biogenesis in the source, mitochondria in the source, or a chondrisome preparation. Examples include alpha-methyl-5-hydroxytryptamine, DOI, CP809101, SB242084, serotonin reuptake inhibitors such as fluoxetine, alpha-methyl 5HT, 1-(2,5-dimethoxy-4-iodophenyl)-2-aminopropane, LY334370, and LY344864.

In one embodiment, the MB agent is a modulator of a beta adrenergic receptor sufficient to increase mitochondrial biogenesis in the source, mitochondria in the source, or a chondrisome preparation. Examples include epinephrine, norepinephrine, isoproterenol, metoprolol, formoterol, fenoterol and procaterol.

RNAi

In some embodiments, the source, mitochondria in the source, or a chondrisome preparation is modified with an RNA (of various sizes to include, but not limited to, siRNA, mRNA, gRNA) targeted to the mitochondrial intermembrane or matrix. For example, the source, mitochondria in the source, or a chondrisome preparation may be modified to under-express an endogenous nucleic acid or protein.

Certain RNA can inhibit gene expression through the biological process of RNA interference (RNAi). RNAi molecules comprise RNA or RNA-like structures typically containing 15-50 base pairs (such as about 18-25 base pairs) and having a nucleobase sequence identical (complementary) or nearly identical (substantially complementary) to a coding sequence in an expressed target gene within the cell. RNAi molecules include, but are not limited to: short interfering RNAs (siRNAs), double-strand RNAs (dsRNA), micro RNAs (miRNAs), short hairpin RNAs (shRNA), meroduplexes, and dicer substrates (U.S. Pat. Nos. 8,084,599 8,349,809 and 8,513,207). In one embodiment, the invention includes a composition of mitochondria in a source or chondrisomes comprising an exogenous nucleic acid, such as an RNAi molecule described herein.

RNAi molecules comprise a sequence substantially complementary, or fully complementary, to all or a fragment of a target gene. RNAi molecules may complement sequences at the boundary between introns and exons to prevent the maturation of newly-generated nuclear RNA transcripts of specific genes into mRNA for transcription. RNAi molecules complementary to specific genes can hybridize with the mRNA for that gene and prevent its translation. The antisense molecule can be DNA, RNA, or a derivative or hybrid thereof. Examples of such derivative molecules include, but are not limited to, peptide nucleic acid (PNA) and phosphorothioate-based molecules such as deoxyribonucleic guanidine (DNG) or ribonucleic guanidine (RNG).

RNAi molecules can be provided to the cell as "ready-to-use" RNA synthesized in vitro or as an antisense gene transfected into cells which will yield RNAi molecules upon transcription. Hybridization with mRNA results in degradation of the hybridized molecule by RNAse H and/or inhibition of the formation of translation complexes. Both result in a failure to produce the product of the original gene.

The length of the RNAi molecule that hybridizes to the transcript of interest should be around 10 nucleotides, between about 15 or 30 nucleotides, or about 15, 16, 17, 18, 19, 20, 21, 22, 23, 24, 25, 26, 27, 28, 29, 30 or more nucleotides. The degree of identity of the antisense sequence to the targeted transcript should be at least 75%, at least 80%, at least 85%, at least 90%, or at least 95.

RNAi molecules may also comprise overhangs, i.e. typically unpaired, overhanging nucleotides which are not directly involved in the double helical structure normally formed by the core sequences of the herein defined pair of sense strand and antisense strand. RNAi molecules may contain 3' and/or 5' overhangs of about 1-5 bases independently on each of the sense strands and antisense strands. In one embodiment, both the sense strand and the antisense strand contain 3' and 5' overhangs. In one embodiment, one or more of the 3' overhang nucleotides of one strand base pairs with one or more 5' overhang nucleotides of the other strand. In another embodiment, the one or more of the 3' overhang nucleotides of one strand base do not pair with the one or more 5' overhang nucleotides of the other strand. The sense and antisense strands of an RNAi molecule may or may not contain the same number of nucleotide bases. The antisense and sense strands may form a duplex wherein the 5' end only has a blunt end, the 3' end only has a blunt end, both the 5' and 3' ends are blunt ended, or neither the 5' end nor the 3' end are blunt ended. In another embodiment, one or more of the nucleotides in the overhang contains a thiophosphate, phosphorothioate, deoxynucleotide inverted (3' to 3' linked) nucleotide or is a modified ribonucleotide or deoxynucleotide.

Small interfering RNA (siRNA) molecules comprise a nucleotide sequence that is identical to about 15 to about 25 contiguous nucleotides of the target mRNA. In some embodiments, the siRNA sequence commences with the dinucleotide AA, comprises a GC-content of about 30-70% (about 30-60%, about 40-60%, or about 45%-55%), and does not have a high percentage identity to any nucleotide sequence other than the target in the genome of the mammal in which it is to be introduced, for example as determined by standard BLAST search.

siRNAs and shRNAs resemble intermediates in the processing pathway of the endogenous microRNA (miRNA) genes (Bartel, Cell 116:281-297, 2004). In some embodiments, siRNAs can function as miRNAs and vice versa (Zeng et al., Mol Cell 9:1327-1333, 2002; Doench et al., Genes Dev 17:438-442, 2003). MicroRNAs, like siRNAs, use RISC to downregulate target genes, but unlike siRNAs, most animal miRNAs do not cleave the mRNA. Instead, miRNAs reduce protein output through translational suppression or polyA removal and mRNA degradation (Wu et al., Proc Natl Acad Sci USA 103:4034-4039, 2006). Known miRNA binding sites are within mRNA 3' UTRs; miRNAs seem to target sites with near-perfect complementarity to nucleotides 2-8 from the miRNA's 5' end (Rajewsky, Nat Genet 38 Suppl: S8-13, 2006; Lim et al., Nature 433:769-773, 2005). This region is known as the seed region. Because siRNAs and miRNAs are interchangeable, exogenous siRNAs downregulate mRNAs with seed complementarity to the siRNA (Birmingham et al., Nat Methods 3:199-204, 2006. Multiple target sites within a 3' UTR give stronger downregulation (Doench et al., Genes Dev 17:438-442, 2003).

Lists of known miRNA sequences can be found in databases maintained by research organizations, such as Wellcome Trust Sanger Institute, Penn Center for Bioinformatics, Memorial Sloan Kettering Cancer Center, and European Molecule Biology Laboratory, among others. Known effective siRNA sequences and cognate binding sites are also well represented in the relevant literature. RNAi molecules are readily designed and produced by technologies known in the art. In addition, there are computational tools that increase the chance of finding effective and specific sequence motifs (Pei et al. 2006, Reynolds et al. 2004, Khvorova et al. 2003, Schwarz et al. 2003, Ui-Tei et al. 2004, Heale et al. 2005, Chalk et al. 2004, Amarzguioui et al. 2004).

The RNAi molecule modulates expression of RNA encoded by a gene. Because multiple genes can share some degree of sequence homology with each other, in some embodiments, the RNAi molecule can be designed to target a class of genes with sufficient sequence homology. In some embodiments, the RNAi molecule can contain a sequence that has complementarity to sequences that are shared amongst different gene targets or are unique for a specific gene target. In some embodiments, the RNAi molecule can be designed to target conserved regions of an RNA sequence having homology between several genes thereby targeting several genes in a gene family (e.g., different gene isoforms, splice variants, mutant genes, etc.). In some embodiments, the RNAi molecule can be designed to target a sequence that is unique to a specific RNA sequence of a single gene.

In some embodiments, the RNAi molecule targets a sequence in a mitochondrial or cytosol gene, e.g., an enzyme involved in post-translational modifications including, but are not limited to, physiologic redox signaling via reactive oxygen and nitrogen species, kinase, O-GlcNAcylation, S-nitrosylation, nitration, glutathionylation, acetylation, succinylation, and others. In one embodiment, the RNAi molecule targets a protein deacetylase, e.g., Sirt3. In one embodiment, the invention includes a composition of mitochondria in a source or chondrisomes comprising an RNAi that targets a mitochondrial or cytosol gene, e.g., an enzyme involved in post-translational modifications.

In some embodiments, the RNAi molecule targets a sequence in a gene, e.g., a membrane transport protein. In one embodiment, the RNAi molecule targets a chemical transporter, e.g., UCP1, UCP2, UCP3, UCP4 or UCP5. In one embodiment, the invention includes a composition of mitochondria in a source or chondrisomes comprising an RNAi that targets a chemical transporter gene, e.g., UCP1, UCP2, UCP3, UCP4 or UCP5.

Targeted Endonucleases

Mitochondria-targeted restriction endonucleases (REs) may also be a useful tool for mitochondrial genome manipulation. The source, mitochondria in a source, or a chondrisome preparation may be modified with recombinant REs with mitochondrial localization signals (MLSs) for import into the mitochondrial matrix where they can access mtDNA and create site-specific double-strand breaks. Cleavage of mtDNA in this manner leads primarily to the degradation of target mtDNA species and if present, expansion of heteroplasmic species lacking the cleavable sequence. Mitochondria-targeted endonucleases may recognize sequences only in specific mtDNA. Recognition and cleavage by the enzyme leads to a reduction in the relative levels of the target allele through cleavage stimulated mtDNA degradation. Only the uncleaved mtDNA can replicate and re-establishment of normal mtDNA levels results in an increased relative abundance of the mtDNA without the endonuclease recognition site.

Some available targeted REs include zinc-finger nucleases (ZFNs) and transcription activator-like effector nucleases (TALENs). Both systems share a common basic structure utilizing a sequencing-independent endonuclease domain from FokI coupled to a sequence-specific modular DNA-binding domain. As FokI creates double-strand breaks as a dimer, both enzyme systems require the design of pairs of monomers that bind the region of interest tail-tail in close proximity enabling the dimerization of FokI domains and double-strand cleavage between the monomer-binding sites. The principal differences between the systems are in the modularity of DNA sequence recognition. Both systems employ tandem repeats of modular DNA-binding domains to create sequence-specific DNA-binding domains. In ZFNs, each individual zincfinger domain recognizes 3 bp of DNA, and for TALENs, each TALE domain recognizes 1 bp. See, for example, mitoTALEN described in Bacman, et al., Nat. Med., vol. 19 (9): 1111-1113. In one embodiment, the invention includes a composition of mitochondria in a source or chondrisomes comprising a targeted RE, e.g., a zinc-finger nuclease (ZFN) or transcription activator-like effector nuclease (TALEN) described herein.

CRISPR

In one embodiment, a modification is made to the source, mitochondria in a source, or a chondrisome preparation to modulate one or more proteins targeted to the mitochondria, such as producing mitochondria with a heterologous function or structural changing the proteins in the mitochondria. One method for modulating proteins targeted to the mitochondria uses clustered regulatory interspaced short palindromic repeat (CRISPR) system for gene editing. CRISPR systems are adaptive defense systems originally discovered in bacteria and archaea. CRISPR systems use RNA-guided nucleases termed CRISPR-associated or "Cas" endonucleases (e.g., Cas9 or Cpf1) to cleave foreign DNA. In a typical CRISPR/Cas system, an endonuclease is directed to a target nucleotide sequence (e.g., a site in the genome that is to be sequence-edited) by sequence-specific, non-coding "guide RNAs" that target single- or double-stranded DNA sequences. Three classes (I-III) of CRISPR systems have been identified. The class II CRISPR systems use a single Cas endonuclease (rather than multiple Cas proteins). One class II CRISPR system includes a type II Cas endonuclease such as Cas9, a CRISPR RNA ("crRNA"), and a trans-activating crRNA ("tracrRNA"). The crRNA contains a "guide RNA", typically an about 20-nucleotide RNA sequence that corresponds to a target DNA sequence. The crRNA also contains a region that binds to the tracrRNA to form a partially double-stranded structure which is cleaved by RNase III, resulting in a crRNA/tracrRNA hybrid. The crRNA/tracrRNA hybrid then directs the Cas9 endonuclease to recognize and cleave the target DNA sequence. The target DNA sequence must generally be adjacent to a "protospacer adjacent motif" ("PAM") that is specific for a given Cas endonuclease; however, PAM sequences appear throughout a given genome. CRISPR endonucleases identified from various prokaryotic species have unique PAM sequence requirements; examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), and 5'-NNNGATT (*Neisseria meningiditis*). Some endonucleases, e.g., Cas9 endonucleases, are associated with G-rich PAM sites, e. g., 5'-NGG, and perform blunt-end cleaving of the target DNA at a location 3 nucleotides upstream from (5' from) the PAM site. Another class II CRISPR system includes the type V endonuclease Cpf1, which is smaller than Cas9; examples include AsCpf1 (from Acidaminococcus sp.) and LbCpf1 (from Lachnospiraceae sp.). Cpf1-associated CRISPR arrays are processed into mature crRNAs without the requirement of a tracrRNA; in other words a Cpf1 system requires only the Cpf1 nuclease and a crRNA to cleave the target DNA sequence. Cpf1 endonucleases, are associated with T-rich PAM sites, e.g., 5'-TTN. Cpf1 can also recognize a 5'-CTA PAM motif. Cpf1 cleaves the target DNA by introducing an offset or staggered double-strand break with a 4- or 5-nucleotide 5' overhang, for example, cleaving a target DNA with a 5-nucleotide offset or staggered cut located 18 nucleotides downstream from (3' from) from the PAM site on the coding strand and 23 nucleotides downstream from the PAM site on the complimentary strand; the 5-nucleotide overhang that results from such offset cleavage allows more precise genome editing by DNA insertion by homologous recombination than by insertion at blunt-end cleaved DNA. See, e.g., Zetsche et al. (2015) Cell, 163:759-771.

For the purposes of gene editing, CRISPR arrays can be designed to contain one or multiple guide RNA sequences corresponding to a desired target DNA sequence; see, for example, Cong et al. (2013) Science, 339:819-823; Ran et al. (2013) Nature Protocols, 8:2281-2308. At least about 16 or 17 nucleotides of gRNA sequence are required by Cas9 for DNA cleavage to occur; for Cpf1 at least about 16 nucleotides of gRNA sequence is needed to achieve detectable DNA cleavage. In practice, guide RNA sequences are generally designed to have a length of between 17-24 nucleotides (e.g., 19, 20, or 21 nucleotides) and complementarity to the targeted gene or nucleic acid sequence. Custom gRNA generators and algorithms are available commercially for use in the design of effective guide RNAs. Gene editing has also been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing). Chemically modified sgRNAs have also been demonstrated to be effective in genome editing; see, for example, Hendel et al. (2015) Nature Biotechnol., 985-991. In one embodiment, the invention includes a composition of mitochondria in a source or chondrisomes comprising a sgRNA.

Whereas wild-type Cas9 generates double-strand breaks (DSBs) at specific DNA sequences targeted by a gRNA, a number of CRISPR endonucleases having modified functionalities are available, for example: a "nickase" version of Cas9 generates only a single-strand break; a catalytically inactive Cas9 ("dCas9") does not cut the target DNA but interferes with transcription by steric hindrance. dCas9 can further be fused with an effector to repress (CRISPRi) or activate (CRISPRa) expression of a target gene. For example, Cas9 can be fused to a transcriptional repressor (e.g., a KRAB domain) or a transcriptional activator (e.g., a dCas9-VP64 fusion). A catalytically inactive Cas9 (dCas9) fused to FokI nuclease ("dCas9-FokI") can be used to generate DSBs at target sequences homologous to two gRNAs. See, e.g., the numerous CRISPR/Cas9 plasmids disclosed in and publicly available from the Addgene repository (Addgene, 75 Sidney St., Suite 550A, Cambridge, MA 02139; addgene.org/crispr/). A "double nickase" Cas9 that introduces two separate double-strand breaks, each directed by a separate guide RNA, is described as achieving more accurate genome editing by Ran et al. (2013) Cell, 154: 1380-1389. In one embodiment, the invention includes a composition of mitochondria in a source or chondrisomes comprising a CRISPR endonuclease.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1. CRISPR technology for generating mtDNA dysfunction in the mitochondrial genome with the CRISPR/Cas9 system is disclosed in Jo, A., et al., BioMed Res. Int'l, vol 2015, article ID 305716, 10 pages, dx.doi.org/10.1155/2015/305716.

In some embodiments, mitochondrial DNA is treated with mitochondrial targeted restriction endonuclease. Replication in mitochondria harboring mtDNA that is selectively cleaved by the restriction endonuclease is inhibited and thereby only non-cleaved mtDNA is allowed to propagate in the mitochondria.

In some embodiments, the desired genome modification involves homologous recombination, wherein one or more double-stranded DNA breaks in the target nucleotide sequence is generated by the RNA-guided nuclease and guide RNA(s), followed by repair of the break(s) using a homologous recombination mechanism ("homology-directed repair"). In such embodiments, a donor template that encodes the desired nucleotide sequence to be inserted or knocked-in at the double-stranded break is provided to the cell or subject; examples of suitable templates include single-stranded DNA templates and double-stranded DNA templates (e.g., linked to the polypeptide described herein). In general, a donor template encoding a nucleotide change over a region of less than about 50 nucleotides is provided in the form of single-stranded DNA; larger donor templates (e.g., more than 100 nucleotides) are often provided as double-stranded DNA plasmids. In some embodiments, the donor template is provided to the cell or subject in a quantity that is sufficient to achieve the desired homology-directed repair but that does not persist in the cell or subject after a given period of time (e.g., after one or more cell division cycles). In some embodiments, a donor template has a core nucleotide sequence that differs from the target nucleotide sequence (e.g., a homologous endogenous genomic region) by at least 1, at least 5, at least 10, at least 20, at least 30, at least 40, at least 50, or more nucleotides. This core sequence is flanked by "homology arms" or regions of high sequence identity with the targeted nucleotide sequence; in embodiments, the regions of high identity include at least 10, at least 50, at least 100, at least 150, at least 200, at least 300, at least 400, at least 500, at least 600, at least 750, or at least 1000 nucleotides on each side of the core sequence. In some embodiments where the donor template is in the form of a single-stranded DNA, the core sequence is flanked by homology arms including at least 10, at least 20, at least 30, at least 40, at least 50, at least 60, at least 70, at least 80, or at least 100 nucleotides on each side of the core sequence. In embodiments where the donor template is in the form of a double-stranded DNA, the core sequence is flanked by homology arms including at least 500, at least 600, at least 700, at least 800, at least 900, or at least 1000 nucleotides on each side of the core sequence. In one embodiment, two separate double-strand breaks are introduced into the cell or subject's target nucleotide sequence with a "double nickase" Cas9 (see Ran et al. (2013) Cell, 154:1380-1389), followed by delivery of the donor template.

In some embodiments, the composition comprising a gRNA and a targeted nuclease, e.g., a Cas9, e.g., a wild type Cas9, a nickase Cas9 (e.g., Cas9 D10A), a dead Cas9 (dCas9), eSpCas9, Cpf1, C2C1, or C2C3, or a nucleic acid encoding such a nuclease, are used to modulate mitochondrial gene expression. The choice of nuclease and gRNA(s) is determined by whether the targeted mutation is a deletion, substitution, or addition of nucleotides, e.g., a deletion, substitution, or addition of nucleotides to a targeted sequence. Fusions of a catalytically inactive endonuclease e.g., a dead Cas9 (dCas9, e.g., D10A; H840A) tethered with all or a portion of (e.g., biologically active portion of) an (one or more) effector domain create chimeric proteins that can be linked to the polypeptide to guide the composition to specific DNA sites by one or more RNA sequences (sgRNA) to modulate activity and/or expression of one or more target nucleic acids sequences (e.g., to methylate or demethylate a DNA sequence).

In some embodiments, one or more component of a CRISPR system described hereinabove. In embodiments, the methods described herein include a method of delivering one or more CRISPR system component described hereinabove to a source, e.g., to the nucleus of the source to modulate a mitochondrial protein, mitochondria in a source, e.g., to the nucleus of the source to modulate a mitochondrial protein, or a chondrisome preparation. In one embodiment, the invention includes a composition of mitochondria in a source or chondrisomes comprising CRISPR modified mtDNA.

In some embodiments, a zinc finger protein is engineered to bind a mitochondrial predetermined DNA sequence. Fusing a zinc finger protein to a nuclease domain creates a zinc-finger nuclease (ZFN) that can cleave DNA adjacent to the specific ZFP-binding site. By designing a single chain quasi-dimeric ZFN with a predetermined DNA binding domain, the ZFN can recognize a pathogenic point mutation in the mtDNA, selectively cleave and eliminate the mutant mtDNA and thereby increase the proportion of wild type mtDNA. In one embodiment, the invention includes a composition of mitochondria in a source or chondrisomes comprising ZFN cleaved mtDNA.

In some embodiments, the CRISPR components target any mitochondrial gene as described herein. In some embodiments, the CRISPR components target any cytosolic gene as described herein.

Targeting

In some embodiments, the modifying agent is designed for specific trafficking the mitochondria or chondrisome described herein to a target cell or tissue, e.g., cardiac tissue, or stem cells. The modifying agent may include a targeting group, e.g., a cell or tissue targeting agent, e.g., a lectin, glycoprotein, lipid or protein, e.g., an antibody, that binds to a specified cell type such as a cardiac cell or stem cell. In one embodiment, the invention includes a composition of mitochondria in a source or chondrisomes comprising a targeting agent, e.g., a cell or tissue targeting agent, e.g., a lectin, glycoprotein, lipid or protein, e.g., an antibody, that binds to a specified cell type such as a cardiac cell or stem cell. A targeting group may include, but is not limited to, a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide, RGD peptide mimetic, or other commonly used targeting group. In another embodiment, the invention includes a composition of mitochondria in a source or chondrisomes comprising the targeting group described herein.

In some embodiments, protofection is used to insert and express mitochondrial genomes into living cells. Protofection uses recombinant human mitochondrial transcription factor A (TFAM) engineered with an N-terminal protein transduction domain (PTD) followed by an MTS to deliver an agent to the mitochondria of living cells. For protocol, see Keeney P.M., et al., Hum Gene Ther 20:897-907 (2009). TFAM is a major mtDNA-binding protein with two high mobility group (HMG) domains. It binds to and organizes mtDNA into a mitochondrial nucleoid structure, which is necessary for mtDNA transcription and maintenance. The MTD-TFAM (MTD=PTD+MTS=mitochondrial transduction domain) recombinant protein would bind mtDNA by interacting with TFAM and rapidly transporting it across the plasma membranes into the mitochondria with the assistance of the MTD. In another embodiment, the invention includes a composition of mitochondria in a source or chondrisomes comprising recombinant MTD-TFAM as described herein.

Methods of Modifying Sources or Mitochondria

Methods of introducing a modifying agent into a source, mitochondria in the source, or a chondrisome preparation include physical, biological and chemical methods. See, for example, Geng. & Lu, Microfluidic electroporation for cellular analysis and delivery. Lab on a Chip. 13 (19): 3803-21. 2013; Sharei, A. et al. A vector-free microfluidic platform for intracellular delivery. PNAS vol. 110 no. 6. 2013; Yin, H. et al., Non-viral vectors for gene-based therapy. Nature Reviews Genetics. 15:541-555. 2014. Suitable methods for modifying a source, mitochondria in the source, or a chondrisome preparation described herein with such a modifying agent include, for example, diffusion, osmosis, osmotic pulsing, osmotic shock, hypotonic lysis, hypotonic dialysis, ionophoresis, electroporation, sonication, microinjection, calcium precipitation, membrane intercalation, lipid mediated transfection, detergent treatment, viral infection, receptor mediated endocytosis, use of protein transduction domains, particle firing, membrane fusion, freeze-thawing, mechanical disruption, and filtration.

Regardless of the method used to introduce the modifying agent into a source, mitochondria in the source, or a chondrisome preparation or otherwise expose the source, mitochondria in the source, or a chondrisome preparation to the modifying agent described herein of the present invention, in order to confirm the presence of the modifying agent in the source, mitochondria in the source, or a chondrisome preparation, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Physical Methods

Some examples of physical methods for introducing a modifying agent, e.g., protein, small molecule, or a polynucleotide, into a source, mitochondria in the source, or a chondrisome preparation include calcium phosphate precipitation, lipofection, particle bombardment, microinjection, electroporation, cell squeeze, and the like. The modifying agent can be introduced into a target source, mitochondria in the source, or a chondrisome preparation using commercially available methods which include diffusion, osmosis, osmotic pulsing, osmotic shock, hypotonic lysis, hypotonic dialysis, ionophoresis, sonication, microinjection, particle firing, membrane fusion, freeze-thawing, mechanical disruption, filtration, electroporation (Amaxa Nucleofector-II (Amaxa Biosystems, Cologne, Germany)), (ECM 830 (BTX) (Harvard Instruments, Boston, Mass.), microfluidic delivery (CellSqueeze, SQZ Biotech, Watertown, MA), Gene Pulser II (BioRad, Denver, Colo.), or multiporator (Eppendort, Hamburg Germany). See, for example, Geng. & Lu, Microfluidic electroporation for cellular analysis and delivery. Lab on a Chip. 13 (19): 3803-21. 2013; Sharei, A. et al. The modifying agent can also be introduced into a source, mitochondria in the source, or a chondrisome preparation using cationic liposome mediated transfection using lipofection, using polymer encapsulation, using peptide mediated transfection, or using biolistic particle delivery systems such as "gene guns" (see, for example, Nishikawa, et al. Hum Gene Ther., 12 (8): 861-70 (2001), and A vector-free microfluidic platform for intracellular delivery. PNAS vol. 110 no. 6. 2013; Yin, H. et al.

Biological Methods

Some examples of biological methods for introducing a modifying agent, e.g., protein, small molecule, or a polynucleotide, into a source, mitochondria in the source, or a chondrisome preparation include the use of DNA and RNA vectors, viral infection, receptor mediated endocytosis, and use of protein transduction domains. Viral vectors, and especially retroviral vectors, have become the most widely used method for inserting genes into mammalian, e.g., human cells. Vectors derived from retroviruses, such as the lentivirus, are suitable tools to achieve long-term gene transfer since they allow long-term, stable integration of a transgene and its propagation in daughter cells. Lentiviral vectors have the added advantage over vectors derived from onco-retroviruses, such as murine leukemia viruses, in that they can transduce non-proliferating cells. They also have the added advantage of low immunogenicity. Other viral vectors can be derived from Sendai virus, poxviruses, herpes simplex virus I, adenoviruses and adeno-associated viruses, and the like.

Some examples of biological methods for introducing a modifying agent, e.g., protein, small molecule, or a polynucleotide, into a source, mitochondria in the source, or a chondrisome preparation include physical association/contact. For example, a modifying agent may attach to the source, mitochondria in the source, or a chondrisome preparation by interacting with a protein domain, such as C2 domains (4) or PH domains (5), of the membrane surface. The interaction may be a covalent bond or a non-covalent interaction. In some embodiments, the modifying agent may bind to a surface protein or receptor.

Cell-penetrating peptides (CPPs) are short peptides that facilitate cellular intake/uptake of various molecular agents (from nanosize particles to small chemical molecules and large fragments of nucleic acids). The agent is associated with the CPP either through a chemical linkage via covalent bonds or through non-covalent interactions. The function of the CPPs is to deliver the agent into the cells via a process that commonly occurs through endocytosis. CPPs can generally be separated into three classes: peptides derived from proteins, chimeric peptides that are formed by the fusion of two natural sequences, and synthetic CPPs which are rationally designed sequences usually based on structure-activity studies. Other attempts to classify CPPs, in spite of their diversity, may be based on the physio-chemical characteristics of the sequences (e.g., their amphipathicity, or their hydrophobicity). Examples include, but are not limited to, TAT, dfTAT, penetratin, pVEC, transportan, MPG, Pep-1, polyarginines, MAP, and R6W3.

Chemical Methods

Some examples of chemical means for introducing a polynucleotide into a source, mitochondria in the source, or a chondrisome preparation include calcium precipitation, membrane intercalation, detergent treatment, colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Non-viral vectors for gene-based therapy. Nature Reviews Genetics. 15:541-555. 2014.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al, 1991 Glycobiology 5:505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Methods for Assaying Protein Modification

Modifications to the source, mitochondria in the source or chondrisome preparation can be assayed for loading levels. In the case where the modifying agent is a protein, quantification of modification kinetics is performed by using exogenous protein that has S35 radioisotope labeled methionine and cysteine amino acids (Sigma). Protein import is performed as described above with the addition that 5-mM methionine is included in the import buffer to prevent nonspecific binding of unincorporated radiolabeled amino acids and to reduce background noise in subsequent autoradiography. To determine kinetics of protein uptake, the uptake reaction is terminated by transferring the reaction to ice, followed by centrifugation after addition of the exogenous protein, the import reaction is removed for radiography analysis as previously described in Stojanovski, D., et al, Methods in Cell Biology, 80:783-806, 2007.

Modifications can be assayed for localization. Sequential disruption of mitochondrial membranes and analysis allows the localization of targeted modifying agents. In the case of exogenous protein loading, sequential treatment with proteases during membrane disruption allows determination of a protein's relative protection from protease between sample and untreated control. Protocols for these assays are detailed Stojanovski 2007, described herein, but briefly it is performed as follows. Aliquots of the isolated chondrisomes are prepared as following: one aliquot is retained as an untreated control; one aliquot is treated with protease directly to degrade any unincorporated of surface bound protein; one aliquot is incubated in hypotonic swelling buffer (10-mM MOPS-KOH, pH 7.2) to induce swelling, outer membrane rupture, and mitoplast formation. (This process should be monitored by immunodecoration of proteins that only become accessible to protease after swelling (e.g., cytochrome c heme lyase) and the integrity of the inner membrane should be assessed by comparing the protease resistance of the canonical citrate synthase matrix proteins in both whole chondrisomes and mitoplasts by Western blot analysis); finally, one aliquot is solubilized with Triton X-100 to assess matrix targeted proteins. Aliquots of the chondrisome samples are split and are subjected to proteinase K to degrade unprotected protein or a control buffer. The protease is then inhibited by phenylmethylsulfonyl fluoride treatment. Chondrisomes are then isolated by centrifugation, washed, TCA precipitated if required, solubilized in SDS-PAGE-loading dye, and subjected to SDS-PAGE and Western blots to determine the quantity of the target protein delivered to the various subcellular locations.

Alternatively, immunolabeling and microscopy is a classical approach that can be used to study the sub cellular localization of loaded. Methods to employ this technique in determining the sub-organelle localization of a delivered protein are described in the literature (Sambrook 2012) and should be performed whenever new cell types or protein targets are employed. Here, the approach to determine the localization of delivered protein is briefly outlined. First, the isolated mitochondria are added to poly(L-lysine)-coated (0.1%) coverslips where they are incubated in a wet-chamber at room temperature with protein target specific monoclonal antibody (Molecular Probes, Eugene, OR) in phosphate buffer saline (PBS) containing bovine serum albumin (BSA). To quantify background, control sections are incubated without the primary antibodies. Samples are rinsed with PBS. The samples are then incubated in a wet chamber with anti-rabbit IgG-fluorescein (or anti-mouse IgG-Texas red). The samples are once again rinsed three times with PBS and then mounted on slides for visualization. In the cases where primary antibodies for the protein of interest don't exist, an epitope tag (9-aa-long HAI hemagglutinin) is added to the coding region of the loaded protein (Pinton 2007). This allows immunolocalization of most delivered proteins. Stojanovski, D., et al., Methods in Cell Biology, 80:783-806, 2007; Sambrook, J. & Green, M.R. Molecular Cloning: A LABORATORY MANUAL. COLD SPRING HARBOR LABORATORY PRESS. 2012; and Pinton, P., et al., Methods in Cell Biology, 80:297-325, 2007.

Methods of Use

The chondrisome preparations and compositions described herein are useful in therapeutic (human) applications, or veterinary applications, in-vivo or ex-vivo.

In-vivo Applications

A chondrisome composition or preparation described herein may be delivered to a subject in an amount and for a time sufficient to enhance a cell or tissue function in a mammalian subject, e.g., a human. For example, the chondrisome composition or preparation is administered to the subject in an amount and for a time sufficient to improve function in the subject of a cell or tissue that is in an injured state (e.g., from trauma, disease or other damage).

A chondrisome composition or preparation described herein may be delivered to a subject in an amount and for a time sufficient to increase target tissue ATP levels, In some embodiments, target tissue ATP levels are increased by at least 5%, 10%, 20%, 30%, 40%, 50%, 60%, 70%, 80% or more.

A chondrisome composition or preparation described herein may be delivered to a subject in an amount and for a time sufficient to reduce ROS in a target tissue (e.g., cardiovascular tissue or neural tissue). In some embodiments, ROS levels are decreased by at least 5%, 10%, 20%, 30%, 40%, 50%, 60%, 70%, 80% or more in the target tissue.

In some embodiments, a chondrisome composition or preparation described herein may be delivered (in vivo or ex-vivo) to increase mitochondrial content and activity in a target cell or tissue. In a model system, citrate synthase activity can be used to assess mitochondrial quantity and activity to determine the increase in mitochondrial content as a result of delivered exogenous chondrisomes. Briefly, mitochondria extracted from cells are subjected to three rounds of freeze/thaw using a dry ice/ethanol slurry. 65 ul of assay reagent (100-mM Tris-HCl, pH 8.0; 100-uM DTNB; 50-uM acetyl coenzyme A; 0.1% (w/v) Triton X-100) is added to a cuvette and brought up to 0.5 ml with water. Processed mitochondria (15 ug of total protein) are added and the reaction is started by adding oxaloacetate to 50-uM and the reaction is followed for three minutes by monitoring absorbance at 412 nm. In some tissues (e.g. liver) there is significant background citrate synthase activity and a control reaction without the addition of oxaloacetate must be performed (Kirby et al., 1999). Relative or percent change in citrate synthase activity between an untreated control and a sample that has been treated with a chondrisome preparation described herein is used to determine the modulation of mitochondrial activity. Kirby et. Al. 2007. Biochemical Assays of Respiratory Chain Complex Activity. Methods in Cell Biology. Vol 80. In some embodiments, mitochondrial content and/or activity is increased in a target tissue by at least 5%, 10%, 20%, 30%, 40%, 50%, 60%, 70%, 80% or more.

In some embodiments, a chondrisome composition or preparation described herein is used to increase thermogenesis, modify adipocyte size and function, and/or modulate serum composition by delivering such preparations to a subject, e.g., to adipocytes (e.g., white adipocytes of a subject). In some embodiments, chondrisome preparations isolated from brown adipocytes are administered to white adipocytes of a subject. Such increase in thermogenesis and adipocyte function can result in increased fat burning ability and/or improved serum composition and/or weight loss in the subject.

In some embodiments, delivery of a chondrisome composition or preparation described herein may induce or block cellular differentiation, de-differentiation, or trans-differentiation. The target mammalian cell may be a precursor cell. Alternatively, the target mammalian cell may be a differentiated cell, and the cell fate alteration includes driving de-differentiation into a pluripotent precursor cell, or blocking such de-differentiation, such as the dedifferentiation of cancer cells into cancer stem cells. In situations where a change in cell fate is desired, effective amounts of a chondrisome preparation described herein encoding a cell fate inductive molecule or signal is introduced into a target cell under conditions such that an alteration in cell fate is induced. In some embodiments, a chondrisome preparation described herein is useful to reprogram a subpopulation of cells from a first phenotype to a second phenotype. Such a reprogramming may be temporary or permanent. Optionally, the reprogramming induces a target cell to adopt an intermediate phenotype.

Also provided are methods of reducing cellular differentiation in a target cell population. For example, a target cell population containing one or more precursor cell types is contacted with a a chondrisome composition or preparation described herein, under conditions such that the preparation reduces the differentiation of the precursor cell. In certain embodiments, the target cell population contains injured tissue in a mammalian subject or tissue affected by a surgical procedure. The precursor cell is, e.g., a stromal precursor cell, a neural precursor cell, or a mesenchymal precursor cell.

A chondrisome composition or preparation described herein, comprising a cargo or payload, may be used to deliver such payload (e.g., an agent listed in Table 4) to a cell tissue or subject. Delivery of a payload by administration of a chondrisome composition or preparation described herein may modify cellular protein expression levels. In certain embodiments, the administered preparation directs up-regulation of (via expression in the cell, delivery in the cell, or induction within the cell) of one or more payload (e.g., a polypeptide) that provide a functional activity which is substantially absent or reduced in the cell in which the polypeptide is delivered. For example, the missing functional activity may be enzymatic, structural, or regulatory in nature. In related embodiments, the administered chondrisome preparation directs up-regulation of one or more polypeptides that increases (e.g., synergistically) a functional activity which is present but substantially deficient in the cell in which the polypeptide is up-regulated.

The subject may have a disease or condition described herein.

Ex-vivo Applications

In embodiments, a chondrisome composition or preparation described herein is delivered ex-vivo to a cell or tissue, e.g., a human cell or tissue. In embodiments, the composition or preparation improves function of a cell or tissue ex-vivo, e.g., improves cell viability, respiration, or other function (e.g., another function described herein).

In some embodiments, the composition or preparation is delivered to an ex vivo tissue that is in an injured state (e.g., from trauma, disease, hypoxia, ischemia or other damage).

In some embodiments, the composition or preparation is delivered to an ex-vivo transplant (e.g., a tissue explant or tissue for transplantation, e.g., a human vein, a musculoskeletal graft such as bone or tendon, cornea, skin, heart valves, nerves; or an isolated or cultured organ, e.g., an organ to be transplanted into a human, e.g., a human heart, liver, lung, kidney, pancreas, intestine, thymus, eye). The preparation improves viability, respiration, or other function of the transplant. The composition or preparation can be delivered to the tissue or organ before, during and/or after transplantation.

In some embodiments, the composition or preparation is delivered, administered or contacted with a cell, e.g., a cell preparation. The cell preparation may be a cell therapy preparation (a cell preparation intended for administration to a human subject). In embodiments, the cell preparation is comprised of cells expressing a chimeric antigen receptor (CAR), e.g., expressing a recombinant CAR. The cells expressing the CAR may be, e.g., T cells, Natural Killer (NK) cells, cytotoxic T lymphocytes (CTL), regulatory T cells. In embodiments, the cell preparation is a neural stem cell preparation. In embodiments, the cell preparation is a mesenchymal stem cell (MSC) preparation. In embodiments, the cell preparation is a hemapoietic stem cell (HSC) preparation. In embodiments, the cell preparation is an islet cell preparation.

Therapeutic Use

The preparations of chondrisomes described herein can be used to treat a subject, e.g., a human, in need thereof. In such embodiments, the subject may be at risk, may have a symptom of, or may be diagnosed with or identified as having, a particular disease or condition (e.g., a disease or condition described herein).

In some embodiments, the source mitochondria are from the same subject that is treated with a chondrisome preparation or composition. In other embodiments they are different. For example, the source of mitochondria and recipient tissue may be autologous (from the same subject) or heterologous (from different subjects). In either case, the donor tissue for chondrisome compositions or preparations described herein may be a different tissue type than the recipient tissue. For example, the donor tissue may be muscular tissue and the recipient tissue may be connective tissue (e.g., adipose tissue). In other embodiments, the donor tissue and recipient tissue may be of the same or different type, but from different organ systems.

Diseases, disorders and conditions that may be treated or prevented by administering a chondrisome preparation described herein include those associated with but not limited to targets in the circulatory system, hepatic system, renal system, cardio-pulmonary system, central nervous system, musculoskeletal system, lymphatic system, immune system, sensory nervous systems (sight, hearing, smell, touch, taste), digestive system, endocrine systems (including adipose tissue metabolic regulation).

Mitochondrial Disease

Diseases, disorders and conditions that may be treated or prevented by administering a chondrisome preparation described herein include but are not limited to those associated with mutations of mitochondrial genes: 2-ketoglutarate dehydrogenase complex deficiency; Aminoglycoside-Induced Deafness; Ataxia, Friedreich Ataxia, progressive seizures, mental deterioration, and hearing loss; Autosomal Recessive Cardiomyopathy; Ophthalmoplegia; Autosomal recessive peripheral neuropathy (CMT4A); Beta-oxidation defects; Cerebellar ataxia, cataract and diabetes mellitus; Complex III deficiency; Complex V deficiency; Chronic progressive external ophthalmoplegia (CPEO); creatine deficiency syndromes; diabetes mellitus and deafness (DAD); Exercise intolerance; Hypertrophic cardiomyopathy; Kearns-Sayre Syndrome; LBSL-leukodystrophy; LCHAD; Leber's hereditary optic neuropathy; Leigh Disease or Syndrome; Luft Disease; MCAD; Maternally Inherited Diabetes and Deafness (MIDD); maternally inherited Leigh's syndrome (MILS); mitochondrial recessive ataxia syndrome (MIRAS); Mitochondrial encephalomyopathy, lactic acidosis and stroke-like episodes (MELAS); Myoclonic Epilepsy with Ragged Red Fibers (MERRF); Mitochondrial neurogastrointestinal encephalopathy disease (MNGIE); Myopathy and Diabetes; neuropathy, ataxia, retinitis, pigmentosa, and ptosis (NARP); Optic Atrophy; Pearson Syndrome; Progressive Myoclonus Epilepsy; Sensory Ataxia Neuropathy Dysarthia Ophthalmoplegia (SANDO); Short-chain acyl-CoA dehydrogenase deficiency (SCAD); Short Chain Hydroxy Acyl-CoA Dehydrogenase Deficiency (SCHAD); Nonsyndromic Hearing Loss and Deafness; SIDS; Hereditary spastic paraplegia; VLCAD etc.

Diseases, disorders and conditions that may be treated or prevented by administering preparation described herein include but are not limited to those associated with mutations of nuclear genes whose products are located or associated with the mitochondria: alpers Disease; carnitine-acyl-carnitine deficiency; Charcot-Marie-Tooth Disease (Type 2A)/Autosomal dominant peripheral neuropathy; Complex I deficiency; Complex II deficiency; Complex IV deficiency; CPT I Deficiency; CPT II Deficiency; Friedreich's ataxia; Fumarase Deficiency; MADD/Glutaric Aciduria Type II; Maple Syrup Urine Disease; Ornithine transcarbamylase deficiency; Rett Syndrome; Barth Syndrome;

Hemochromatosis; Batten Disease; Lesch-Nyhan Syndrome; Hurler Syndrome; Niemann-Pick Disease; Gaucher Disease; Glycogen Storage Disease; Zellweger Syndrome; Wilson's Disease; Menkes Disease; methylmalonic Acidemia; Huntington Disease.

Ischemia

The compositions and methods described herein may reduce the incidence, extent, and/or severity of ischemia (e.g., ischemic injury) in a subject who has one or more condition or disorder described herein.

Ischemia is the condition of an inadequate oxygen or blood supply to an organ or tissue. Tissue injury and/or death can occur as a result of an ischemic insult, and/or subsequent damage may be induced by reperfusion. During prolonged ischemia, ATP levels and intracellular pH decrease as a result of anaerobic metabolism and lactate accumulation. As a consequence, ATPase-dependent ion transport mechanisms become dysfunctional, contributing to increased intracellular and mitochondrial calcium levels (calcium overload), cell swelling and rupture, and cell death by necrotic, necroptotic, apoptotic, and autophagic mechanisms. Although oxygen levels are restored upon reperfusion, a surge in the generation of reactive oxygen species occurs and proinflammatory neutrophils infiltrate ischemic tissues to exacerbate ischemic injury. The pathologic events induced by ischemia or reperfusion may orchestrate the opening of the mitochondrial permeability transition pore (MPTP). (Kalogeris et al. 2012. Cell Biology of Ischmia/Reperfusion Injury. Int Rev Cell Mol Biol. 298:229-317). Ischemia/reperfusion (I/R) occurs, e.g., during hypovolemic shock, thrombolytic therapy, organ transplantation, coronary angioplasty, aortic cross-clamping, or cardiopulmonary bypass.

Ischemia may be caused by any mechanism including a partial or complete blockage (an obstruction), a narrowing (a constriction), a leak, a rupture or trauma of one or more blood vessels that supply blood to an organ or tissue. A subject may suffer from ischemia of the, e.g., brain, kidney, liver, arteries, heart, intestines, mesentery, skin, ovary, penis, mesenatry, bile ducts, extremities/limbs, or eye (e.g., the optic nerve).

The subject may have myocardial ischemia, cerebral ischemia (e.g., a transient ischemic attack), intestinal ischemia, hepatic ischemia, critical limb ischemia, testicular ischemia. A subject who has ischemia may have a blood clot (e.g., a thrombus or an embolus), vasculitis, atherosclerosis, coronary artery disease, peripheral artery disease. In some instances, ischemia is caused by a myocardial infarction, stroke, peripheral vascular disease. A subject may have acute injury ischemia, e.g., caused by aortic dissection, acute kidney injury, acute liver injury, acute lung injury, myocardial infarction, stroke, spinal cord injury, traumatic brain injury. Ischemia-induced injury (i.e., disease and/or damage) includes ischemic myelopathy, ischemic optic neuropathy, ischemic colitis, coronary heart disease, and/or cardiac heart disease (e.g., angina, heart attack, etc.), among others. A subject may have a developmental ischemia, such as Marfan Syndrome, Mitral Valve Stenosis, Tetralogy of Fallot, Ventricular Septal Defect.

Other disorders or conditions that may cause, may be caused by, or may be associated with, ischemia or I/R include: ischemic cholangiopathy, ischemic stroke, traumatic brain injury (TBI), subarachnoid hemorrhage, intracerebral hemorrhage, compartment syndrome, acute peripheral arterial occlusion, peripheral arterial disease, acute limb ischemia, frostbite, sixth cranial nerve palsy, diabetic or hypertensive retinopathy, ischemic optic neuropathy, retinal artery occlusion, acute coronary syndromes (acs), Takayasu Arteritis, intussusception, intestinal obstruction, renal atheroembolism, renal vein thrombosis, renal artery stenosis and occlusion, acute kidney injury, hepatic artery occlusion, postoperative hepatitis, ischemic hepatitis, pulmonary embolism, acute respiratory distress syndrome, pulmonary edema, acute mesenteric ischemia, adnexal torsion, priapism, preeclampsia and eclampsia, pressure ulcers, diabetic foot ulcers, burns, arterial gas embolism, shock, transplants. Methods of the invention can be performed with subjects having such disorders or conditions.

The compositions and methods described herein are useful to effect, in a subject in need thereof, one or more (e.g., 2 or more, 3 or more, 4 or more, 5 or more) of: (a) decreased reactive oxygen species (ROS) in a target tissue; (b) increased ATP levels in a target tissue; (c) increased intracellular pH in a target tissue; (d) decreased intracellular and/or mitochondrial calcium levels in a target tissue; (e) decreased cell death (e.g., decreased cell death by necrotic, necroptotic, apoptotic, ferroptotic or autophagic mechanisms) in a target tissue; (f) blocked or reduced mitochondrial permeability transition (MPT) in a target tissue; (g) reduction or clearance of pro-inflammatory neutrophil infiltrate in a target tissue. In some embodiments, a subject in need thereof is administered a preparation or composition described herein in an amount and for a time sufficient such that one or more of (a)-(g) are modulated in a target tissue of subject by at least 5%, 10%, 15%, 20%, 25%, 30%, 40%, 50%, 60%, 75%, 80%, 85%, or more, relative to a control tissue or subject that has not been treated, or relative to the same subject prior to administration.

In some embodiments, a subject having cardiac ischemia can be administered a chondrisome composition described herein in an amount and for a time sufficient such that: (a) blood flow is increased to an ischemic tissue of the subject, (b) infarct size is reduced in an ischemic tissue of the subject, (c) improved ejection fraction in the heart. In some embodiments, a subject who has ischemia is administered a chondrisome composition described herein in an amount and for a time sufficient such that one or more of (a)-(c) are modulated in an ischemic tissue of subject by at least 5%, 10%, 15%, 20%, 25%, 30%, 40%, 50%, 60%, 75%, 80%, 85%, or more, relative to a control tissue or subject that has not been treated, or relative to the same subject prior to administration.

A subject who has ischemia may be any person (a human subject) or animal (an animal subject) that has ischemia, I/R injury, an ischemia-related condition, a history of ischemia, and/or a significant chance of developing ischemia after a treatment begins and during a time period in which the treatment is still effective. An ischemic subject may be selected for treatment by any suitable criteria. Exemplary criteria include any detectable symptom of ischemia, a history of ischemia, an event that increases the risk of (or induces) ischemia (such as a surgical procedure, trauma, administration of a medication, etc.). A history of ischemia may involve one or more prior ischemic episodes. In some examples, a subject selected for treatment may have had an onset of ischemia that occurred at least about one, two, or three hours before treatment begins, or a plurality of ischemic episodes (such as transient ischemic attacks) that occurred less than about one day, twelve hours, or six hours prior to initiation of treatment. An ischemic subject may be a human, such as a human patient, or a non-human animal (such as an agricultural animal, e.g., a cow, a pig, a sheep, a chicken, a goat; or a companion animal, e.g., a dog or cat).

Combination Therapy for Ischemia

In some embodiments, a preparation described herein may be administered in combination with a second agent to treat ischemia. For example, the second agent may be aspirin; a nitrate; a beta blocker; a calcium channel blocker; a cholesterol-lowering agent; a steroid; an angiotensin-converting enzyme (ACE) inhibitor; ranolazine (Ranexa); a fibrinolytic agent, e.g., tissue plasminogen activator (tPA), streptokinase (SK), or urokinase. In some embodiments relating to I/R, a preparation described herein may be administered in combination with ischemic preconditioning, an antioxidant agent (e.g., superoxide dismutase, catalase, mannitol, allopurinol, vitamin E, N-acetylcysteine, iron chelating compounds (e.g., desferrioxamine), angiotensin-converting enzyme inhibitors, or calcium channel antagonists), an anticomplement agent (e.g., C3 convertase inhibitor, anti-C5 agent such as h5G1.1-scFv), an antileukocyte agent (e.g., leukocyte depletion/filtration, soluble interleukin-1 receptor antagonists, anti-TNF antibody, or platelet activation factor-leukotriene B4 antagonists).

In some embodiments, a preparation described herein may be administered in combination with a surgical or other procedure, e.g., angioplasty, thrombectomy, stenting, embolectomy, coronary artery bypass surgery or enhanced external counterpulsation.

Metabolic Conditions

Methods of the invention are useful in subjects in need of increasing thermogenesis, modulating serum composition (such as reducing serum cholesterol, or reducing serum triglycerides), and/or reducing adipocyte or fat volume. Subjects may have a disease or condition associated with undesirably high fat composition, such as overweight or obesity (e.g., a subject who has a BMI>25, >26, >27, >28, >29, >30, >31, >32, >33, >34, >35; a female subject who has a waist size greater than 35 in, a male subject who has a waist size greater than 40 in). A suitable subject may have a high cholesterol level (e.g., total cholesterol level>150 mg/dL, >160, 170, 180, 190, 200, 220, 240 mg/dL); high low-density-lipoprotein (LDL) levels (e.g., >80 mg/dL, >90, 100, 120, 140, 160, 180, 190 mg/dL), high triglyceride levels (e.g., >150 mg/dL, >200, 300, 400, 500, 600, 700, 800, 900 mg/dL); high blood pressure (systolic greater than 135, 140, 145, 150; diastolic greater than 85, 90, 95, 100), or has (or is at risk for) cancer, diabetes, or heart disease. The subject may have familial hypercholesterolemia.

In embodiments, a chondrisome preparation or composition useful in these methods is one wherein the source mitochondria or chondrisomes express an (endogenous or exogenous) uncoupling protein (e.g., UCP-1, UCP-2, UCP-3, UCP-4 or UCP-5).

The methods of the invention may include treating the subject with a combination of a preparation or composition described herein and one or more of: an agent for reducing cholesterol (e.g., a statin, a nicotinic acid, a fibric acid derivative, a bile acid sequestrant), an agent for reducing high blood pressure (e.g., a beta blocker, an ACE inhibitor, an angiotensin II receptor blocker; a calcium channel blocker, an alpha blocker, an alpha-2 receptor agonist, a central agonist, a peripheral adrenergic receptor inhibitor, a vasodilator); an obesity drug (e.g., a lipase inhibitor, a CNS stimulant, an anorexiant, a GLP-1 agonist, an antidepressant, a dopamine reuptake inhibitors, an opioid antagonist).

Other Conditions

Methods of the invention are useful in subjects who have a disease, disorder or condition such as: neurodegenerative disorders (e.g. Alzheimer's disease, Duchenne muscular dystrophy, Parkinson's Disease, amyotrophic lateral sclerosis (ALS), Huntington's disease); a disease associated with infectious agents or pathogens (e.g., bacterial, fungal, viral, parasitic infections); diseases associated with apoptosis, ferroptosis, necrosis; neoplasms, e.g., aberrant growths or cancer; metabolic diseases such as an acquired metabolic disease (e.g., diabetes, diabetic or hypertensive retinopathy, NASH/NAFLD, obesity, type 2 diabetes) or a rare metabolic disease (e.g., carnitine palmitoyltransferase deficiency, citrullinemia, ornithine transcarbomylase deficiency); disease associated with toxic proteins; diseases associated with the accumulation of lipids; clotting and anti-clotting diseases; one or more of the following: autoimmune disorders (e.g. diabetes, lupus, multiple sclerosis, psoriasis, rheumatoid arthritis); inflammatory disorders (e.g. arthritis, pelvic inflammatory disease); infectious diseases (e.g. viral infections (e.g., HIV, HCV, RSV), bacterial infections, fungal infections, sepsis); autism; cardiovascular disorders (e.g. atherosclerosis, hypercholesterolemia, thrombosis, clotting disorders, angiogenic disorders such as macular degeneration); proliferative disorders (e.g. cancer, benign neoplasms); respiratory disorders (e.g. chronic obstructive pulmonary disease); digestive disorders (e.g. inflammatory bowel disease, ulcers); musculoskeletal disorders (e.g. fibromyalgia, arthritis); endocrine, metabolic, and nutritional disorders (e.g. diabetes, osteoporosis); urological disorders (e.g. renal disease); psychological disorders (e.g. depression, schizophrenia); skin disorders (e.g. wounds, eczema); blood and lymphatic disorders (e.g. anemia, hemophilia); and degenerative diseases (e.g., osteoarthritis, sarcopenia, progeria, muscular dystrophy).

Non-Human Applications

Compositions described herein may also be used to similarly modulate the cell or tissue function or physiology of a variety of other organisms including but not limited to: farm or working animals (horses, cows, pigs, chickens etc.), pet or zoo animals (cats, dogs, lizards, birds, lions, tigers and bears etc.), aquaculture animals (fish, crabs, shrimp, oysters etc.), plants species (trees, crops, ornamentals flowers etc), fermentation species (*saccharomyces* etc.). Chondrisome preparations described herein can be made from such non-human sources and administered to a non-human target cell or tissue or subject. Chondrisome preparations can be autologous, allogeneic or xenogeneic to the target.

Formulation and Methods of Delivery

A preparation or composition described herein can be delivered via various routes. Parenteral routes include intramuscular (IM), subcutaneous (SC) and intravenous (IV), intramyocardial, intracoronary, intrathecal, epidural, intraarticular, intradermal, intravitreal, and intranasal routes or direct injection to fat tissue or the bone marrow. Enteral administration includes but is not limited to sublingual, buccal, oral and rectal routes. A preparation or composition described herein can also be delivered via transdermal delivery or topical application (applied to surface of any epidermis, skin, mouth, or GI tract). These routes of administration can be used as a method of either systemic delivery (e.g. systemic venous/arterial injection or profusion) or for tissue specific delivery of the payload via carefully selected points of administration (e.g. intravitreal or injection or perfusion to tissue with well-defined and isolated venous, arterial or lymphatic vasculature).

The compositions may be administered once to the subject or, alternatively, multiple administrations may be performed over a period of time. For example, two, three, four, five, or more administrations may be given to the subject during one treatment or over a period of time. In some embodiments, six, eight, ten, 12, 15 or 20 or more administrations may be given to the subject during one treatment or over a period of time as a treatment regimen.

In some embodiments, administrations may be given as needed, e.g., for as long as symptoms associated with the disease, disorder or condition persist. In some embodiments, repeated administrations may be indicated for the remainder of the subject's life. Treatment periods may vary and could be, e.g., one day, two days, three days, one week, two weeks, one month, two months, three months, six months, a year, or longer.

In some embodiments, the pharmaceutical composition is administered by a regimen sufficient to alleviate a symptom of the disease, disorder or condition.

In embodiments, a pharmaceutical composition or chondrisome preparation described herein is formulated for administration to a human subject. The chondrisome preparation may be formulated in a physiologically acceptable buffer for both storage and administration. In some embodiments, the chondrisome preparation is formulated for storage in a first formulation and formulated for administration with a second formulation (e.g., just before use). In some embodiments, the storage formulation may be frozen, and subsequently thawed and reformulated for administration to a subject. For example, a storage formulation may contain one or more of: an osmotic regulator, a sugar, a pH buffer, a salt. A formulation for administration to a subject may contain one or more of: an osmotic regulator, a sugar, a pH buffer, a salt, autologous serum (e.g., 5-50% autologous serum).

In embodiments of the methods described herein, the chondrisome composition or preparation is treated with an agent, and/or administered in combination with an agent, to modulate subcellular targeting of the administered preparation. In embodiments, the agent enables endosomal/lysosomal escape and/or enhances cytosolic or non-lysosomal delivery of the preparation. In embodiments, the agent is a peptide or protein that enhances cytosolic or non-lysosomal delivery of the preparation, e.g., haemagglutinin, diINF-7, penton base, gp41, gp41/polyethylenimine, TAT, L2 from Papillomavirus, envelope protein (E) of West Nile virus, listeriolysin O (LLO), Pneumococcal pneumolysin (PLO), Streptococcal streptolysin O (SLO), Diphtheria toxin (DT), *Pseudomonas aeruginosa* exotoxin A (ETA), Shiga toxin, cholera toxin, ricin, saporin, gelonin, human calcitonin derived peptide, fibroblast growth factors receptor (FGFR3), melittin, (R-Ahx-R) (4) AhxB, glycoprotein H (gpH) from herpes simplex, KALA, GALA, a synthetic surfactant, penetratin (pAntp), R6-Penetratin with arginine-residues, EB1, bovine prion protein (bPrPp), Poly(L-histidine), Sweet Arrow Peptide (SAP). In other embodiments, the agent is a chemical that enhances cytosolic or non-lysosomal delivery of the preparation, e.g., polyethylenimine (PEI), Poly(amidoamine) s (PAAs), poly(propylacrylic acid) (PPAA), ammonium chloride, chloroquine, methylamine. Other such agents are described, e.g., in Varkouhi et al. 2011. Endosomal escape pathways for delivery of biologicals. Journal of Controlled Release 151:220-228.

Effective doses of compositions and preparations described herein will vary depending on the mode of administration and the nature of the subject to be treated. In some instances, conventional methods of extrapolating human dosage based on doses administered to an animal model can be carried out. A unit dose useful in the methods described herein is between 2 μg/kg to 10 mg/kg, e.g., 2 μg/kg to 200 μg/kg, e.g., 2 μg/kg to 2 mg/kg, e.g., 2 μg/kg to 5 mg/kg, e.g., 2 μg/kg to 1 mg/kg, e.g., 5 μg/kg to 10 mg/kg, e.g., 5 μg/kg to 1 mg/kg, e.g., 5 μg/kg to 5 mg/kg, e.g., 5 μg/kg to 500 μg/kg, e.g., 5 μg/kg to 50 μg/kg, e.g., 5 μg/kg to 100 μg/kg, e.g., 5 μg/kg to 250 μg/kg.

Definitions

A used herein, a "mitochondrion" is an organelle capable of producing ATP through oxidative phosphorylation as it exists in a living cell or in its natural state in an organism.

As used herein, a "chondrisome" is a subcellular apparatus derived and isolated or purified from the mitochondrial network of a natural cell or tissue source. A "chondrisome preparation" has bioactivity (can interact with, or have an effect on, a cell or tissue) and/or pharmaceutical activity.

As used herein, "douncing" refers to a method of mechanically grinding tissue between two surfaces (typically between a container and a tightly fitting pestle) to obtain subcellular fractions.

As used herein, a chondrisome preparation described herein is "stable" when it maintains a predefined threshold level of its activity and structure over a defined period of time. In some embodiments, one or more (2 or more, 3 or more, 4 or more, 5 or more) structural and/or functional characteristics of a chondrisome preparation described can be used as defining metrics of stability for chondrisome preparations described herein. These metrics, whose assay protocols are outlined herein, are determined subsequent to preparation and prior to storage (e.g., at 4° C., 0° C., −4° C., −20° C., −80° C.) and following removal from storage. The characteristic of the preparation should not change by more than 95%, 90%, 85%, 80%, 75%, 60%, 50% (e.g., no more than 40%, 35%, 30%, 25%, 20%, 15%, 10%, 5%) over the course of 1, 2, 5, 8, 12, 24, 36, or 48 hours, 3 days, 7 days, 14 days, 21 days, 30 days, 60 days, 90 days, 4 months, 6 months, 9 months, a year or more of storage. In some embodiments, the characteristic of the chondrisome preparation described herein should not have changed by more than 50% (e.g., no more than 40%, 35%, 30%, 25%, 20%, 15%, 10%, 5%) over the course of 1, 2, 5, 8, 12, 24, 36, or 48 hours of storage. In some embodiments, the characteristic of the chondrisome preparation described herein should not change by more than 50% (e.g., no more than 40%, 35%, 30%, 25%, 20%, 15%, 10%, 5%) over the course of 1, 2, 5, 8, 12, 24, 36, or 48 hours, 3 days, 7 days, 14 days, 21 days, 30 days, 60 days, 90 days, 4 months, 6 months, 9 months, a year or more of storage.

As used herein, a "heterologous function" of a chondrisome preparation described herein is one or more biological activity different than the biological activity of the source mitochondria in its native parental cell. For example, a chondrisome preparation described herein may have an activity not present in the mitochondria in their native state, may be in a different metabolic state than the mitochondria in their native state, or a biological activity may be present at a higher or lower level than in the native state.

As used herein, "locally" or "local administration" means administration at a particular site of the body intended for a local effect. Examples of local administration include epicutaneous, inhalational, intra-articular, intrathecal, intravaginal, intravitreal, intrauterine, intra-lesional administration, lymph node administration, intratumoral administration, administration to a fat tissue or mucous membrane of the subject, wherein the administration is intended to have a local effect. Local administration may also include perfusion of the preparation into a target tissue. For example, a preparation described herein may be delivered locally to the cardiac tissue (i.e., myocardium, pericardium, or endocardium) by direct intracoronary injection, or by standard percutaneous catheter based methods or by perfusion into the cardiac tissue. In another example, the preparation is infused into the brain or cerebrospinal fluid using standard methods. In another example, the preparation is directly injected into adipose tissue of a subject.

As used herein, a chondrisome preparation is "pure" or "purified" when separated from its original cellular source and substantially free (>50%) of other cellular components. In some embodiments, the weight of the purified chondrisomes constitutes>50%, >60%, >70%, >80%, >90%, >95%, >98% of the combined weight of the chondrisomes and other sub-cellular fractions (see Hartwig et al., Proteomics, 2009, (9) 13209-3214)). In some embodiments, the weight of the purified chondrisomes constitutes between 50%-90%, between 50%-80%, between 60-90%, between 60-%-80%, between 80-95% of the combined weight of the chondrisomes and other sub-cellular fractions.

As used herein, "encapsulated" means surrounded by a protective structure. For example, a preparation of chondrisomes described herein may be encapsulated in a synthetic or natural membrane (e.g., an exosome, a vesicle, a host cell, a platelet) or another natural or synthetic biocompatible material.

As used herein, a "combination therapy" or "administered in combination" means that two (or more) different agents or treatments are administered to a subject as part of a defined treatment regimen for a particular disease or condition. The treatment regimen defines the doses and periodicity of administration of each agent such that the effects of the separate agents on the subject overlap. In some embodiments, the delivery of the two or more agents is simultaneous or concurrent and the agents may be co-formulated. In other embodiments, the two or more agents are not co-formulated and are administered in a sequential manner as part of a prescribed regimen. In some embodiments, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination may be administered by intravenous injection while a second therapeutic agent of the combination may be administered orally.

As used herein, the term "pharmaceutical composition" refers to a medicinal or pharmaceutical formulation for human therapeutic use that contains one or more active ingredient as well as one or more excipients and diluents to enable the active ingredient(s) suitable for the method of administration. The pharmaceutical composition of the invention includes pharmaceutically acceptable components that are compatible with the chondrisomes described herein. The pharmaceutical composition is typically in aqueous form for intravenous or subcutaneous administration. In embodiments, a pharmaceutical composition or pharmaceutical preparation is a composition or preparation produced under good manufacturing practices (GMP) conditions, having pharmacological activity or other direct effect in the mitigation, treatment, or prevention of disease, and/or a finished dosage form or formulation thereof and is for human use.

As used herein, the terms "increasing" and "decreasing" refer to modulating resulting in, respectively, greater or lesser amounts, function or activity of a metric relative to a reference. For example, subsequent to administration of a composition described herein, a functional output may be increased or decreased in a subject by at least 5%, 10%, 15%, 20%, 25%, 30%, 35%, 40%, 45%, 50%, 55%, 60%, 65%, 70%, 75%, 80%, 85%, 90%, 95% or 98% or more relative to prior to administration or relative to an untreated subject. Generally, the metric is measured subsequent to administration at a time that the administration has had the recited effect, e.g., at least one hour, one week, one month, 3 months, 6 months, after a treatment regimen (e.g., a therapy described herein) has begun.

As used herein, "percent identity" between two sequences can be determined by the BLAST 2.0 algorithm, which is described in Altschul et al., (1990) J. Mol. Biol. 215:403-410. Software for performing BLAST analyses is publicly available through the National Center for Biotechnology Information.

As used herein, "genetic quality" of a chondrisome preparation means, for all the loci described in Table 5, the percent of sequencing reads mapping to the wild type allele.

"Treatment" and "treating," as used herein, refer to the medical management of a subject with the intent to improve, ameliorate, stabilize, prevent or cure a disease, pathological condition, or disorder. This term includes active treatment (treatment directed to improve the disease, pathological condition, or disorder), causal treatment (treatment directed to the cause of the associated disease, pathological condition, or disorder), palliative treatment (treatment designed for the relief of symptoms), preventative treatment (treatment directed to minimizing or partially or completely inhibiting the development of the associated disease, pathological condition, or disorder); and supportive treatment (treatment employed to supplement another therapy).

As used herein, the term "autologous" refers to a preparation derived from the same individual to which the preparation is administered. "Allogeneic" refers to a preparation derived from a different animal of the same species. "Xenogeneic" refers to a preparation derived from an animal of a different species.

All references cited herein are hereby incorporated by reference in their entirety.

The following examples are provided to further illustrate some embodiments of the present invention, but are not intended to limit the scope of the invention; it will be understood by their exemplary nature that other procedures, methodologies, or techniques known to those skilled in the art may alternatively be used.

Examples

1 Production of Chondrisome preparation. 136
Example 1-1: production of chondrisome preparations from tissue culture cells 136
Example 1-2a: production of chondrisome preparation from skeletal muscle tissue 136
Example 1-2b: production of chondrisome preparations from skeletal muscle tissue for in vivo delivery 137
Example 1-3a: production of chondrisome preparations from blood cells 137
Example 1-3b: production of chondrisome preparations from platelet cells 138
Example 1-4: production of chondrisome preparation from brown adipose tissue 138
A Structural Characteristics of chondrisome preparations 139
Example A-1: average size 139
Example A-2: polydipersity. 139
Example A-3: outer membrane integrity 140
Example A-5: protein content 141
Example A-6: OXPHOS complex levels 141
Example A-7: genomic concentration 143
Example A-8: yield per cell 145
Example A-9: yield per unit mass of tissue 146
Example A-10: chondrisome count per protein mass 146
Example A-11: membrane potential state 147
B Bioenergetic Characteristics of chondrisome preparations 148
Example B-1: respiratory control ratio. 148
Example B-2a: individual respiratory complex activities (I-IV) 149
Example B-2b: complex V respiratory activities 150
Example B-3: reactive oxygen species production 151
Example B-4: enzymatic activity. 152
Example B-5: fatty acid oxidation level 154
Example B-6: electron transport chain efficiency 155
C Quality Characteristics 155
Example C-1: protein carbonyl level 155
Example C-2: lipid content 156
Example C-3: contaminating and non-contaminating protein levels 160
Example C-4: genetic quality 162
Example C-5: contaminating nuclear DNA levels 166
Example C-6: endotoxin levels 167
E Blood derived preps 168
Example E-1: preparation of chondrisome containing mitoparticles 168
Example E-2: concentration of chondrisome containing mitoparticles from platelets 168
Example E-3: membrane potential of chondrisome containing mitoparticles. 169
Example E-4: quantification of platelet derived chondrisome mitoparticle delivery to specific subcellular locations. 169
F Biological/Functional Characteristics 172
Example F-1: apoptosis induction level 172
Example F-2: enhancement of cellular respiration. 173
Example F-3: subcellular targeting levels 174
Example F-4: delivery of a loaded cargo 176
Example F-5: delivery of an engineered cargo. 177
Example F-6: chemical modulation of subcellular chondrisome targeting. 178
Example F-7: proportion of delivered chondrisomes maintain an active membrane potential 179
Example F-8: persistence of delivered chondrisomes 180
Example F-9: quantification of lipid utilization. 181
Example F-10: quantification of exogenous protein delivery 182
Example F-11: increase in uncoupled respiration 183
Example F-12: inhibition of MPTP opening following delivery of the chondrisome preparation 184
Example F-13: increased Akt activation 185
Example F-14: modulation of cellular nicotinamide adenine dinucleotide pools. 186
Example F-15: improved functional cardiac metrics 187
Example F-16: improved functional cardiac metrics 190
Example F-17: no acute immune effect 192
Example F-18: metabolic stimulation 193
Example F-19: no adaptive immune effect 194

1 Production of Chondrisome preparation

Example 1-1: Production of Chondrisome Preparations from Tissue Culture Cells Cell culture (primary or cell lines) were trypsinized with trypsin-EDTA 0.25%, followed by diluting the cells once trypsinized. Cells were pelleted by centrifugation at 200 g for 5 min at room temperature. Cells were then resuspended in phosphate-buffered saline to dilute remaining trypsin and re-centrifuged to obtain the cell pellet. The cells were then resuspended in 4-6 mL of MSHE (200 mM mannitol, 70 mM sucrose, 10 mM HEPES, 1 mM EDTA, adjust the pH to 7.4 with KOH)+0.5% BSA buffer and moved to a Potter Elvehjem homogenizer. Cell samples were homogenized with a glass Potter Elvehjem homogenizer using a Teflon pestle operated at 1600 rpm for 30-35 strokes, followed by further membrane disruption via syringe/needle transfer (sample drawn with 18-gauge needle and expeled with 30-gauge needle one time, followed by drawing with 18-gauge needle and expelling with 23-gauge needle four times).

The material was centrifuged at 600 g for 10 min at 4° C. The supernatant was centrifuged again at 600 g for 10 min at 4° C. The supernatant was then distributed into 2 mL microcentrifuge tubes and centrifuged at 10,000g for 10 min at 4° C. The resulting chondrisome pellets were resuspended in 2 mL of MSHE+0.5% BSA buffer and re-centrifuged at 10,000g for 10 min at 4° C. The final chondrisome pellet was resuspended in 100-500 μL MSHE buffer. Tissue and chondrisome solutions, including buffers, were kept on ice at all times. Final chondrisome suspensions were kept on ice and used within 3 hours of obtaining final pellet.

Example 1-2a: Production of Chondrisome Preparation from Skeletal Muscle Tissue

Tissue (human or mouse) was obtained by dissection or biopsy and washed in phosphate-buffered saline twice. Tissue and chondrisome samples, including buffers, were maintained at 4° C. throughout the process of subcellular apparatus isolation. Solid tissue was minced into small pieces in 2 ml MSHE (200 mM mannitol, 70 mM sucrose, 10 mM HEPES, 1 mM EDTA, adjust the pH to 7.4 with KOH)+ 0.5% BSA buffer (0.2-1g tissue per 8 mL of MSHE+0.5% BSA buffer) using scissors if necessary and then homogenized with a glass Potter Elvehjem homogenizer using Teflon pestle operated at 1600 rpm for 9-12 strokes.

The material was centrifuged at 600 g for 10 min at 4° C. The supernatant was centrifuged again at 600 g for 10 min at 4° C. The supernatant was then distributed into 2 mL microcentrifuge tubes and centrifuged at 10,000g for 10 min at 4° C. The resulting chondrisome pellets were resuspended in 2 mL of MSHE+0.5% BSA buffer and re-centrifuged at 10,000g for 10 min at 4° C. The final chondrisome pellet was resuspended in 100-500 μL MSHE buffer. Tissue and chondrisome solutions, including buffers, were kept on ice at all times. Final chondrisome suspensions were kept on ice and used within 3 hours of obtaining final pellet.

Example 1-2b: Production of Chondrisome Preparations from Skeletal Muscle Tissue for in Vivo Delivery Tissue was obtained by dissection or biopsy and washed in phosphate-buffered saline twice. Tissue and chondrisome samples, including buffers, were maintained at 4° C. throughout the process of subcellular apparatus isolation. Solid tissue was minced into small pieces in 2 ml MSHE (200 mM mannitol, 70 mM sucrose, 10 mM HEPES, 1 mM EDTA, adjust the pH to 7.4 with KOH)+0.5% BSA buffer using scissors (0.2-1g tissue per 8 mL of MSHE+0.5% BSA buffer) if necessary and then homogenized using source-specific homogenization protocol. Primary solid skeletal muscle tissue (human or mouse) samples were homogenized with a glass Potter Elvehjem homogenizer using Teflon pestle operated at 1600 rpm for 15 strokes.

The material was centrifuged at 1000 g for 10 min at 4° C. The supernatant was then distributed into 6 2 mL microcentrifuge tubes and centrifuged at 10,000g for 10 min at 4° C. The resulting chondrisome pellets were resuspended in 2 mL of MSHE+0.5% BSA buffer and re-centrifuged at 10,000g for 10 min at 4° C. The final chondrisome pellet was resuspended in 1 ml of delivery buffer (250 mM sucrose, 2 mM KH2PO4, 10 mM $MgCl_2$, 20 mM K-HEPES, 0.5 mM K-EGTA, pH 7.4) and then diluted 10× in the same buffer. Tissue and chondrisome solutions, including buffers, were kept on ice at all times. Final chondrisome suspensions were kept on ice and used within 1 hour of obtaining final pellet.

Example 1-3a: Production of Chondrisome Preparations from Blood Cells

Human blood was obtained commercially from ZenBio Inc. Blood cells were obtained by syringe draw (fluid tissue) and maintained at 4° C. throughout the process of chondrisome preparation. Samples were centrifuged at 2,500×g to pellet cells and the cell pellet was resuspended in 4-8 mL of MSHE (200 mM mannitol, 70 mM sucrose, 10 mM HEPES, 1 mM EDTA, adjust the pH to 7.4 with KOH)+0.5% BSA buffer and then homogenized using source-specific homogenization protocol. Primary human blood samples were homogenized with a glass Potter Elvehjem homogenizer using a Teflon pestle operated at 1600 rpm for 100 strokes, followed by further membrane disruption via syringe/needle transfer (draw sample with 18-gauge needle and expel with 30-gauge needle one time, followed by drawing with 18-gauge needle and expelling with 23-gauge needle four times).

The material was centrifuged at 600 g for 10 min at 4° C. The supernatant was centrifuged again at 600 g for 10 min at 4° C. The supernatant was then distributed into 2 mL microcentrifuge tubes and centrifuged at 10,000g for 10 min at 4° C. The resulting chondrisome pellets were resuspended in 2 mL of MSHE+0.5% BSA buffer and re-centrifuged at 10,000g for 10 min at 4° C. The final chondrisome pellet was resuspended in 100-500 μL MSHE buffer. Tissue and chondrisome solutions, including buffers, were kept on ice at all times. Final chondrisome preparations were kept on ice and used within 3 hours of obtaining final pellet.

Example 1-3b: Production of Chondrisome Preparations from Platelet Cells

Platelets were obtained commercially from ZenBio. Platelets were obtained by syringe draw (fluid tissue) and maintained at 4° C. throughout the process of subcellular apparatus isolation. Samples were centrifuged at 2,500×g to pellet cells and the cell pellet was resuspended in 4-8 mL of MSHE (200 mM mannitol, 70 mM sucrose, 10 mM HEPES, 1 mM EDTA, adjust the pH to 7.4 with KOH)+0.5% BSA buffer and then homogenized with a glass Potter Elvehjem homogenizer using a Teflon pestle operated at 1600 rpm for 100 strokes, followed by further membrane disruption via syringe/needle transfer (draw sample with 18-gauge needle and expel with 30-gauge needle one time, followed by drawing with 18-gauge needle and expelling with 23-gauge needle four times).

The material was centrifuged at 600 g for 10 min at 4° C. The supernatant was centrifuged again at 600 g for 10 min at 4° C. The supernatant was then distributed into 2 mL microcentrifuge tubes and centrifuged at 10,000g for 10 min at 4° C. The resulting chondrisome pellets were resuspended in 2 mL of MSHE (200 mM mannitol, 70 mM sucrose, 10 mM HEPES, 1 mM EDTA, adjust the pH to 7.4 with KOH)+0.5% BSA buffer and re-centrifuged at 10,000g for 10 min at 4° C. The final chondrisome pellet was resuspended in 100-500 μL MSHE buffer. Tissue and chondrisome solutions, including buffers, were kept on ice at all times. Final chondrisome preparations were kept on ice and used within 3 hours of obtaining final pellet.

Example 1-4: Production of Chondrisome Preparation from Brown Adipose Tissue

Mice were anesthetized and sacrificed using isoflurane, and then exsanguination was done by cardiac puncture prior to tissue dissection. Tissue was obtained by dissection or biopsy and washed in phosphate-buffered saline twice. Tissue and chondrisome samples, including buffers, were maintained at 4° C. throughout the process of isolation. Solid tissue was minced into small pieces in 2 ml SHE (Sucrose (250 mM), HEPES (5 mM), EGTA (2 mM), BSA 2%, PH=7.2 with KOH)+2% BSA buffer (0.8-1.6g tissue per 8 mL of SHE+2% BSA buffer) using scissors if necessary and then homogenized with a glass Potter Elvehjem homogenizer using Teflon pestle operated manually (by hand) for 9-12 strokes.

The material was centrifuged at 2100 rpm for 10 min at 4° C. The supernatant was centrifuged again at 2100g for 10 min at 4° C. The supernatant was then distributed into 2 mL microcentrifuge tubes and centrifuged at 9,000g for 10 min at 4° C. The resulting chondrisome pellets were resuspended in 2 mL of SHE+2% BSA buffer and re-centrifuged at 9,000g for 10 min at 4° C. This step was repeated in 2 ml SHE buffer with no BSA. The final chondrisome pellet was resuspended in 100-500 μL SHE buffer. Tissue and chondrisome solutions, including buffers, were kept on ice at all times. Final chondrisome suspensions were kept on ice and used within 3 hours of obtaining final pellet.

a Structural Characteristics of Chondrisome Preparations

Example A-1: Average Size

The chondrisome preparations were tested to determine the average size of particles using the commercially available qNANO GOLD sytstem. The qNANO GOLD with software version 3.3.2.194 was used according to manufacturer's instructions with the NP300 nanopore, which is designed to analyze particles within the 115 to 1150 nm size range. Chondrisome samples were diluted in phosphate-buffered saline (PBS) to a final concentration range of 0.01-0.1 μg protein/mL as outlined in Example A-5. Other instrument settings were adjusted as indicated in the following table:

| Measurement Parameter | Setting |
|---|---|
| Pressure | 6 |
| Nanopore type | NP300 |
| Calibration sample | CPC400_6P |
| Gold standard analysis | no |
| Capture assistant | none |

All chondrisome preparations were analyzed within 2 hours of isolation. The average size of the chondrisomes in the preparations tested was 175-950 nm. The minimum size range was 50-360 nm; the maximum size range was 1500-2300 nm.

Example A-2: Polydipersity

The chondrisome preparations were tested to determine the average size of particles using the commercially available qNANO GOLD system, using the same instrument settings as in Example A-1.

| Source tissue/cells | D10 (diameter in nm that 10% of the particles were below) | D50 (diameter in nm that 50% of the particles were below) | D90 (diameter in nm that 90% of the particles were below) | D90/D10 range |
|---|---|---|---|---|
| All tested | 150-375 | 225-550 | 575-1100 | 1.6-4.8 |
| Human platelets | 150-350 | 225-425 | 575-775 | 1.6-3.6 |
| Human fibroblasts | 175-375 | 350-550 | 900-1100 | 2.8-4.8 |

Example A-3: Outer Membrane Integrity

The chondrisome preparation was tested to verify the extent of outer membrane intactness following isolation. The integrity of the outer membrane can be evaluated to the degree by which respiration increases following provision of reduced cytochrome c, a 12-kDa protein that traverses compromised outer chondrisome membranes and donate electrons to cytochrome oxidase of the electron transport chain, leading to increased oxygen consumption (i.e., respiration).

Reduced cytochrome c was prepared using the method described in Spinazzi et al., Nature Protocols 7 (6): 1235-1246, 2012. Briefly, purified cytochrome c from bovine heart was acquired from Sigma-Aldrich (C3131) and suspended in 1.2 mL of 10 mM phosphate buffer. Then, 110 mg of ascorbic acid was dissolved in 1 mL of 10 mM phosphate buffer and adjusted to pH 6.5 using Tris base. Three hundred microliters of this solution was then added to the cytochrome c, followed by incubation at 4° C. for one hour. To remove excess ascorbic acid, the solution was passed through a PD10 disposable desalting column that had been equilibrated with 50 mL of 10 mM phosphate buffer. After elution with the phosphate buffer, the cytochrome c redox state was examined using a plate reader set to monitor absorbance at 550 nm. The presence of a peak at 550 nm that decayed following addition of a few granules of potassium ferricyanide (an oxidizing agent) indicated successful reduction of the purified cytochrome.

Chondrisomes were isolated from cultured human fibroblasts (see example 1-1) and protein content was assessed by BCA (example A-5) and the preparation remains on ice until the following quantification protocol was initiated (within 20 minutes from isolation). Isolated chondrisomes (0.125 to 1 mg/mL) were suspended in 1 mL respiration medium (0.3 mM mannitol, 10 mM KH2PO4, 5 mM $MgCl_2$, and 10 mM KCl (pH 7.2) in a Clark oxygen electrode chamber (Hansatech Instruments, Norfolk, United Kingdom) maintained at 37° C. Chondrisomes were allowed to equilibrate in the respiration buffer prior to addition of respiratory substrates.

First, the respiratory substrates (e.g. glutamate (5 mM) and malate (1 mM); succinate (5 mM) rotenone (2 μM)) were added to stimulate the production of NADH from the tricarboxylic acid cycle and deliver electrons to the electron transport chain. The resulting oxygen consumption rate was denoted as State 2 respiration, which was caused by a leak of electrons across the inner chondrisome membrane and the compensatory increased flux of electrons down the electron transport chain to maintain membrane potential equilibrium. Next, adenosine diphosphate (ADP) was added to a final concentration of 100 μM. In the presence of inorganic phosphate (10 mM) and the NADH-linked substrates, ADP causes a burst in respiration (termed State 3) as protons were utilized by the FoF1-ATPase to generate ATP. Upon consumption of the exogenous ADP, the chondrisomes returned to basal respiration (also termed State 4). After reaching this state, the reduced cytochrome c was added to the chondrisome suspension at a working concentration of 10 μM. Following addition of reduced cytochrome c, there was <5% increase in oxygen consumption rate over state 4 rate, indicative of an intact outer chondrisome membrane.

Example A-5: Protein Content

The chondrisome preparation was tested to determine the protein concentration using a standard BCA. Here a commercially available Pierce™ BCA Protein Assay Kit (Thermo Fischer product #23225) was used. As per the manufacturer's instructions, a standard curve was generated using the supplied BSA, from 0 to 20 μg of BSA per well (in triplicate). The chondrisome preparation was diluted such that the quantity measured was within the range of the standards. The chondrisome preparation was analyzed in triplicate and the mean value was used.

Example A-6: OXPHOS Complex Levels

An ELISA analysis approach was used to determine the concentration of the chondrisome oxidative phosphorylation complexes. Complex I levels were determined using a commercially available kit (Abcam, ab124539).

Immediately following generation of the chondrisome preparation the sample was split to quantify total protein levels (as outlined in example A-5) and to quantify specific complexes. As per the manufacturer's instructions all buffers were warmed to room temperature prior to the initiation of the analysis. Within 2 hours of isolation, 200 ug of the chondrisome preparation was pelleted and resuspended in 200 μL of supplied Extraction buffer with protease inhibitors added (Millipore, 539137). The chondrisome sample was then serially diluted 1/2 in 1× Incubation buffer. 50 ul of the samples dilution or 1× Incubation buffer (2 replicates of each) were added to the respective wells of the ELISA plate. The plate was sealed and incubated for 2 hour at room temperature on a plate shaker set to 300 rpm. The wells were washed twice by completely removing the fluid by aspiration and then dispensing 300 ul of 1× Wash buffer into each well. After the final wash the plate was inverted and blotted with paper to remove all excess liquid. Solutions of 1× Detector antibody provided with the kit were prepared and 50 ul of the Detector antibody solution was then added to each well used. The sealed plate was then incubated for 1 hour at room temperature on a plate shaker set to 300 rpm. The wells were washed 3 times by aspirating and adding 300 μL 1× Wash buffer as performed previously. Solutions of 1× HRP label provided with the kit were prepared and 50 ul of the 1× HRP label solution was then added to each well used. The sealed plate was then incubated for 1 hour at room temperature on a plate shaker set to 300 rpm. The wells were washed 3 times by aspirating and adding 300 μL 1× Wash buffer as performed previously. 100 ul of the Tetramethyl benzidine substrate solution (TMB buffer) was added to each well and the plate was immediately analyzed on a microplate reader by measuring absorbance at 600 nm every 1 minute for 30 minutes, with shaking between readings.

To calculate the complex levels, the OD reading for the 1× Incubation buffer only wells was subtracted from all the readings and then all duplicate readings were averaged for the 30-minute time-point. The chondrisome preparation was analyzed in duplicate and the mean value appropriately adjusted by the dilution factor used to determine the chondrisome preparation mOD level of each complex. Lastly the complex level was normalized to the total protein in the chondrisome preparation as determined by BCA. With this assay the chondrisome preparation was shown to have a complex I level of 36.4 mOD/ug total protein. The approach to determine the levels of the other complexes was analogous to the protocol described. Appropriate & specific commercially available kits and the complex levels obtained from them are outlined in the table below.

Human Platelet derived chondrisome preparations (produced via example 1-3b)

| OXPHOS Complex Measured | Commercial Kit Type | Kit ID | Complex Level Determined (mOD/ug total protein) |
|---|---|---|---|
| Complex I | Human Complex I ELISA kit | abcam, ab178011 | 5.74 ± 1.52 |
| Complex II | Human Succinate Dehydrogenase ELISA kit | abcam, ab124536 | 1.58 ± 0.65 |
| Complex III | Human Complex III ELISA kit | abcam, ab124537 | 22.3 ± 2.0 |
| Complex V | Human Complex V ELISA kit | abcam, ab124593 | 36.4 ± 3.5 |

Human Fibroblast derived chondrisome preparations (produced via example 1-1)

| OXPHOS Complex Measured | Commercial Kit Type | Kit ID | Complex Level Determined (mOD/ug total protein) |
|---|---|---|---|
| Complex I | Human Complex I ELISA kit | abcam, ab178011 | 2.44 ± 0.37 |
| Complex II | Human Succinate Dehydrogenase ELISA kit | abcam, ab124536 | 0.12 ± 0.06 |
| Complex III | Human Complex III ELISA kit | abcam, ab124537 | 2.43 ± 1.0 |
| Complex V | Human Complex V ELISA kit | abcam, ab124593 | 6.61 ± 2.4 |

Example A-7: Genomic Concentration

This example describes the determination of the mtDNA concentration of the chondrisome preparation relative to the total protein content of the preparation. Chondrisomes are isolated from human skeletal muscle punch biopsies, platelets, or cultured fibroblasts using the procedures explained in Examples 1-2a and 1-3b and 1-1 respectively. From these preparations, total DNA is isolated using a Qiagen DNeasy blood and tissue kit (catalog number 69504), followed by determination of DNA concentration using a Thermo Scientific NanoDrop. After completion of the DNA isolation procedure, a DNA standard is generated by producing an amplicon using the human mtDNA specific primers listed below and same the reaction protocol and machine as used for the semi-quantitative PCR described below. The PCR reaction is run on a resolving gel to confirm mtDNA specific amplification (single band and correct amplicon size). The PCR product is then cleaned to remove primers using a standard commercially available kit following the manufacturers recommendations (Zymo Research: DNA Clean & Concentrator™-5). The DNA concentration of this cleaned amplicon is determined using a Thermo Scientific NanoDrop and diluted to generate a 6-point standard curve over 4 orders of magnitude that is run during the semi-quantitative qPCR analysis. The standard curve is converted to total mitochondrial DNA by multiplying the NanoDrop measured quantity by 60.25 (amplicon is 60.25× smaller than mtDNA genome). A portion of the chondrisome preparation is devoted to the determination of total protein content of the chondrisome preparation quantified via BCA (example A-5).

RT-PCR is carried out using Applied Biosystems PCR Master Mix (catalog number 4309155) in a 20 μL total reaction volume using the following reaction template:

SYBR Green Master Mix: 10 μL
0.45 μM Forward Primer: 1 μL
0.45 μM Reverse Primer: 1 μL
DNA Template: 10 ng
PCR-Grade Water: Variable Forward and reverse primers are produced and acquired by Integrated DNA Technologies. The table below details the primer pairs and their associated sequences:

| Target | Forward Primer Sequence (5' → 3') | Reverse Primer Sequence (5' → 3') |
|---|---|---|
| Human mtDNA | CAC CCA AGA ACA GGG TTT GT (SEQ ID NO: 24) | TGG CCA TGG GTA TGT TGT TA (SEQ ID NO: 25) |
| Human nDNA | TGC TGT CTC CAT GTT TGA TGT ATC T (SEQ ID NO: 26) | TCT CTG CTC CCC ACC TCT AAG T (SEQ ID NO: 27) |

An Applied Biosystems 7900HT Real-Time PCR system is used to perform the amplification and detection with the following protocol:

| | |
|---|---|
| Denaturation, 94° C. | 2 min |
| 40 Cycles of the following sequence: | |
| Denaturation, 94° C. | 15 sec |
| Annealing, Extension, 60° C. | 1 min |

The Ct number denotes the cycle threshold for chondrisome mtDNA and the standard curve determined at a fluorescence level of 0.014179736. The Ct value is used to interpolate the DNA content of the chondrisome prep. Using this assay the expected ratio of mtDNA mass to protein mass of the prep is determined and outlined in the table below:

| Source: | mtDNA ug/mg protein |
|---|---|
| Human Fibroblast | 0.01-0.1 |
| Human Platelet | 0.01-0.05 |
| Human Muscle | 0.1-0.2 |

Example A-8: Yield Per Cell

The yield of chondrisomes derived from cell suspension starting material (tissue culture) was determined. Example A-5 has described the quantification of chondrisome protein content in the chondrisome preparation. This example defines the ratio between the starting cell amount and the resulting chondrisome protein yield (total ug protein) which can be used to characterize the preparation. Tissue culture produced cells were trypsinized from the culture flasks, and a 10 μL aliquot of cell solution was assayed on a Hemacytometer to count cell number with a minimum of 10e6 cells counted total. Using this assay the ranges of chondrisome yield per cell were are shown in the table below for each particular source material:

| Source cells | Preparation production example | Yield range (ug protein per $10^6$ cells) |
|---|---|---|
| Human fibroblasts | Example 1-1 | 10-70 |

The yield of chondrisomes derived from certain blood products was also determined. Example A-5 has described the quantification of chondrisome protein content in the chondrisome preparation. This example defines the ratio between the starting cell amount and the resulting chondrisome protein yield (total ug protein) which can be used to characterize the preparation. Total cellular content of human whole blood and human platelet concentrate was determined using a Drew Scientific Inc. Hemavet 950FS hematology analyzer. Total leukocyte, erythrocyte, and thrombocyte count was included in whole blood, while only total thrombocyte count was applicable to the platelet concentrate. Using this assay the ranges of chondrisome yield per cell were are shown in the table below for each particular source material:

| Source cells | Preparation production example | Yield range (ug protein per $10^6$ cells) |
|---|---|---|
| Human whole blood | Example 1-3a | 0.05-0.25 |
| Human platelets | Example 1-3b | 0.05-0.25 |

Example A-9: Yield Per Unit Mass of Tissue

This assay was used to determined yield of chondrisomes derived from weight of tissue starting material. Example A-5 has described the quantification of the protein content of the chondrisome preparation. Here this example defines the ratio between the starting dry tissue weight (grams) and the resulting chondrisome yield (total ug chondrisome protein) which can be used to characterize the preparation. Performing this assay on the chondrisome preparation produced from human skeletal muscle tissue (example 1-2a) the chondrisome yield per g tissue was 745 μg protein/g of tissue. (Range was 400-1200 μg/g of tissue).

Example A-10: Chondrisome Count Per Protein Mass

The chondrisome preparation was tested to determine the concentration of chondrisome particles using the commercially available qNANO GOLD sytstem. The qNANO GOLD with software version 3.3.2.194 was used according to manufacturer's instructions with the NP300 nanopore, which is designed to analyze particles within the 115 to 1150 nm size range. Chondrisome samples were diluted in phosphate-buffered saline (PBS) to a final concentration range of 0.01-0.1 μg/mL of protein determined by Example A-5. Other instrument settings were adjusted as indicated in the following table:

| Measurement Parameter | Setting |
|---|---|
| Pressure | 6 |
| Nanopore type | NP300 |

-continued

| Measurement Parameter | Setting |
|---|---|
| Calibration sample | CPC400_6P |
| Gold standard analysis | no |
| Capture assistant | none |

All chondrisome preparations were analyzed within 2 hours of isolation. The determined particle concentration (particles/mL) was normalized to the total protein content (mg/mL) as assessed by Example A-5. Particle concentrations are shown in the following table:

| Source tissue/cells | Production Method | Particle concentration (particles/mg total protein) |
|---|---|---|
| Human platelets | Example 1-3b | $2.51 \times 10^{10}$ |
| Human fibroblasts | Example 1-1 | $2.03 \times 10^{10}$ |

| Source tissue/cells | Particle concentration range (particles/mg total protein) |
|---|---|
| Human platelets | $0.5\text{-}20 \times 10^{10}$ |
| Human fibroblasts | $0.5\text{-}20 \times 10^{10}$ |

Example A-11: Membrane Potential State

The membrane potential of the chondrisome preparation was quantified using a commercially available dye TMRE for assessing chondrisome membrane potential (TMRE tetramethyl rhodamine, ethyl ester, perchlorate, Abcam, Cat #T669). Chondrisomes were isolated from mouse skeletal muscle (see example 1-2a) and the preparation remained on ice until the membrane assessment protocol was initiated (within 2 hours from isolation). While on ice, total protein content of the chondrisome preparation was quantified via BCA (see example A-5). The preparation was diluted in respiration buffer (250 mM sucrose, 2 mM KH2PO4, 10 mM $MgCl_2$, 20 mM K-HEPES and 0.5 mM K-EGTA, pH 7.4) to a final concentration of 10-100 μg protein/ml in 6×200 μL aliquots (untreated and FCCP-treated triplicates). Chondrisome respiratory substrates 5 mM glutamate and 1 mM malate were added to the samples, followed by 30 nM TMRE. For each sample, an unstained (no TMRE) sample was also prepared in parallel. Chondrisome samples were incubated at room temperature for 15 minutes. The samples were then analyzed on a BD FACScan flow cytometer with 488 nm argon laser excitation and emission was collected at 530+/−30 nm. For FCCP-treated samples, 2 μM FCCP was added to the samples and incubated for 5 minutes prior to analysis.

Membrane potential values (in millivolts, mV) were calculated based on the intensity of TMRE. All events were captured in the forward and side scatter channels (alternatively, a gate can be applied to select only the chondrisome population). The fluorescence intensity (FI) value for both the untreated and FCCP-treated samples, was normalized by subtracting the geometric mean of the fluorescence intensity of the unstained sample from the geometric mean of the untreated and FCCP-treated sample. The membrane potential state for each preparation was calculated using the normalized fluorescent intensity values with a modified Nernst equation (see below) that can be used to determine chondrisome membrane potential based on TMRE fluorescence (as TMRE accumulates in chondrisomes in a Nernstian fashion).

Chondrisome membrane potential (mV)=−61.5*log $(FI_{untreated\text{-}normalized}/FI_{FCCP\text{-}treated\text{-}normalized})$ . The membrane potential state of the chondrisome preparation was determined to be −65 mV (Range was −20 to −150 mV).

B Bioenergetic Characteristics of Chondrisome Preparations

Example B-1: Respiratory Control Ratio

This example describes the physiological respiration of the chondrisome preparation. Key functional capabilities of isolated chondrisomes were analyzed by the classical respiratory control experiments (Chance and Hollunger. *The interaction of energy and electron transfer reactions in chondrisomes. VI. The efficiency of the reaction. J Biol Chem* 236:1577-1584, 1961; Chance B and Williams G R. A simple and rapid assay of oxidative phosphorylation. Nature 175 (4469): 1120-1121, 1955). Chondrisomes were isolated (see appropriate example for each source material) and protein content was assessed by BCA (example A-5) and the preparation remained on ice until the following quantification protocol was initiated (within 20 minutes from isolation). Isolated chondrisomes (0.125 to 1 mg protein/mL) were suspended in 1 mL respiration medium (0.3 mM mannitol, 10 mM $KH_2PO_4$, 5 mM $MgCl_2$, and 10 mM KCl (pH 7.2) in a Clark oxygen electrode chamber (Hansatech Instruments, Norfolk, United Kingdom) maintained at 37° C. Chondrisomes were allowed to equilibrate in the respiration buffer prior to the addition of respiratory substrates.

First, the respiratory substrates (e.g. glutamate (5 mM) and malate (1 mM); succinate (5 mM) rotenone (2 μM)) were added to stimulate the production of NADH from the tricarboxylic acid cycle and deliver electrons to the electron transport chain. The resulting oxygen consumption rate was denoted as State 2 respiration, which was caused by a leak of electrons across the inner chondrisome membrane and the compensatory increased flux of electrons down the electron transport chain to maintain membrane potential equilibrium. Next, adenosine diphosphate (ADP) was added to a final concentration of 100 μM. In the presence of inorganic phosphate (10 mM) and the NADH-linked substrates, ADP causes a burst in respiration (termed State 3) as protons were utilized by the FoF1-ATPase to generate ATP. After ADP-stimulated respiration rate has plateaued, 5 μM oligomycin was added to inhibit ATPase and determine levels of respiration not coupled to ATP synthesis (state 40). Finally, maximally-stimulated respiration was induced via as addition of a chemical such uncoupler, carbonyl cyanide-p-trichloromethoxyphenylhydrazone (FCCP) at a concentration of 4 μM. The chemical uncoupler bypasses the F.F1-ATPase resistance and provides an indication of maximal electron flux through the electron transport chain. Respiratory control ratio 3/2 (RCR 3/2) was calculated by taking the ratio of State 3 to State 2 oxygen consumption rates. Respiratory control ratio 3/40 (RCR 3/40) was calculated by taking the ratio of State 3 to State 40 oxygen consumption rates. The RCRs obtained with this assay are indicated in the table below.

Human Fibroblast derived chondrisome preparations (produced via example 1-1)

| | Substrate | | | |
|---|---|---|---|---|
| | Glutamate/Malate | | Succinate/Rotenone | |
| | RCR | | | |
| | RCR 3/2 | RCR 3/4o | RCR 3/2 | RCR 3/4o |
| Ranges | 1-4 | 4-16 | 1.5-5 | 5-20 |

Human Platelet derived chondrisome preparations (produced via example 1-3b)

| | Substrate | | | |
|---|---|---|---|---|
| | Glutamate/Malate | | Succinate/Rotenone | |
| | RCR | | | |
| | RCR 3/2 | RCR 3/4o | RCR 3/2 | RCR 3/4o |
| Ranges | 1-4 | 4-13 | 1-4 | 1.5-5 |

Example B-2a: Individual Respiratory Complex Activities (I-IV)

This example describes electron transport chain complex activity of chondrisome preparations (here exemplified for Complex I) via spectrophotometry. Analogous methods can be used to assess the other Complex activities using immunocapture procedures and kinetic absorbance measurements.

Complex I activity can be measured in chondrisomes isolated from human tissue, whole blood, or cultured fibroblasts via UV-Vis spectrophotometry as described in Wibom R et al., Analytical Biochem 311:139-151, 2002. Chondrisomes are isolated and protein content is assessed by BCA (example A-5) and the preparation remains on ice until the following quantification protocol is initiated (within 20 minutes from isolation). Briefly, chondrisomes are solubilized with detergent and probed with a species-specific antibody to Complex I. The immunocaptured Complex in solution is then incubated in a reaction mixture containing 50 mM $KH_2PO_4$, 5 mM $MgCl_2$, 5 g/L bovine serum albumin, 0.20 mM KCN, 1.2 mg/L antimycin A, and 0.12 mM coenzyme $Q_1$. NADH is added to a final concentration of 0.15 mM, the oxidation of which can be followed at 340 nm before and after the addition of rotenone (2 mg/mL). The rotenone-sensitive activity can be calculated using an extinction coefficient of 6.81 L/mmol/cm. Complex I activity is then expressed as nmol NADH oxidized/min/mg chondrisome protein. Expected activity ranges for Complex I and for the other chondrisome respiratory chain complexes are indicated in the table below. Product numbers for the corresponding abcam MitoTox™ microplate assays have also been included.

Human chondrisomes derived from tissue, whole blood, blood-derived products, or cultured cells.

| Chondrisome Complex | abcam MitoTox ™ Microplate Assay | Activity (nmol/min/mg total protein) |
|---|---|---|
| Complex I | ab109903 | 0.5-10 |
| Complex II | ab109904 | 0.5-5 |
| Complex III | ab109905 | 0.5-10 |
| Complex IV | ab109906 | 0.5-10 |

Example B-2b: Complex V Respiratory Activities

ATP Synthase (or Complex V) activity can be assessed in chondrisomes isolated from whole tissue, blood, or blood-derived products using the abcam MitoTox™ Complex V OXPHOS Activity Microplate Assay. In the absence of an inner chondrisome membrane potential, the ATP Synthase operates in the reverse direction, hydrolyzing ATP to generate ADP in organic phosphate. The ADP produced can be coupled to the oxidation of NADH via the pyruvate kinase (PK), lactate dehydrogenase (LDH) enzymatic reactions.

Briefly, chondrisomes isolated from human tissue, whole blood, or blood derived products are solubilized in detergent and placed on ice for 30 min. The chondrisome suspension is centrifuged at 20,000×g for 20 min at 4° C. The resulting supernatant is used to perform a BCA protein assay, after which it is pipetted into the microplate coated with monoclonal antibodies against Complex V. The plate is allowed to incubate for two hours, consistent with the ELISA protocols outlined in Example A-6. To quantify the Complex V activity, the 96-well microplate is placed inside a plate reader set to monitor absorbance at 340 nm at 30° C. every 60 seconds. As mentioned, the activity of ATP Synthase is coupled to the oxidation of NADH over time (i.e., the conversion of NADH to $NAD^+$). The most linear oxidation rate of NADH occurs between 12-50 minutes of absorbance measurements. Using the rate of decrease in absorbance at 340 nm and the NADH extinction coefficient (6.22/mM/cm) and the amount of protein loaded into each well of the plate, the ATP Synthase activity is expressed as nmol/min/mg protein.

Chondrisome Preparations Derived from Human Tissue, Whole Blood, Blood-Derived Products, or Cultured Cells.

| Chondrisome Complex | Antibody Capture Kit | Activity (nmol/min/mg protein) |
|---|---|---|
| Complex V | ab109907 | 10-200 |

Example B-3: Reactive Oxygen Species Production

This example describes the measurement of reactive oxygen species (ROS) production in the chondrisome preparation. Chondrisome $H_2O_2$ production was quantified using a system containing horseradish peroxidase (HRP) in conjunction with Amplex Red reagent (10-acetyl-3,7-dihydroxyphenoxazine) (ThermoFisher, Cat #A22188).

Chondrisomes generate superoxide radicals at Complexes I, III, and IV of the electron transport chain. This superoxide quickly undergoes dismutation by MnSOD to form hydrogen peroxide ($H_2O_2$), which diffuses through the outer chondrisome membrane. In the assay, $H_2O_2$ was used as a substrate by HRP, leading to the oxidation of Amplex Red and the generation of a fluorescent product known as resorufin (Starkov 2010; Gram 2015). The assay was performed per the manufacturer's instructions, following a modified version of the protocol for Measuring $H_2O_2$ Released from Cells.

First, 100 μL of reaction mixture of 50 μM Amplex Red reagent and 0.1U/mL HRP in MAS buffer (70 mM Sucrose, 220 mM Mannitol, 5 mM $KH_2PO_4$, 5 mM $MgCl_2$, 1 mM EGTA, 0.1% BSA fatty acid-free, 2 mM HEPES, pH 7.4) with 5 mM glutamate and 5 mM malate as respiratory substrates was added into the appropriate number of wells of a 96-well plate for $H_2O_2$ standard curve and unknown samples. An $H_2O_2$ standard curve was prepared by adding $H_2O_2$ stock to final concentrations of 0, 1, 5, 10, and 50 μM in the appropriate wells. Chondrisome samples (in MSHE buffer) were added at 1, 5, 10, and 50 ug amounts to wells with reaction mixture for the unknown samples. The plate was then read on a fluorescence microplate reader with excitation of 545 nm and emission recorded at 590 nm with 20 nm bandwidths. The plate was initially measured 5 minutes after adding $H_2O_2$ standards and unknown samples to record baseline fluorescence. The plate was then incubated at 37° C. for 12 hours and fluorescence was read again. At 12 hours, the nmol of $H_2O_2$ for the unknown chondrisome samples was calculated by correlating the measured fluorescence values with a linear trendline fitted to the $H_2O_2$ standard curve. The moles of H2O2 production was normalized per ug protein of chondrisomes (example A-5) and per hour of reaction time.

With this assay the chondrisome preparation (produced as described in example 1-1) derived from human fibroblasts was shown to have a glutamate-malate H2O2 production in the range of 2-12 μmol H2O2/ug chondrisome protein/hr. In this specific experiment a H2O2 production level of 6.03 μmol H2O2/ug chondrisome protein/hr was measured.

With this assay the chondrisome preparation (produced as described in example 1-3b) derived from human platelets was shown to have a ROS production level in the range of 0.05-4 μmol H2O2/ug chondrisome protein/hr. In this specific experiment a H2O2 production level from of 0.40 μmol $H_2O_2$/ug chondrisome protein was measured.

Starkov AA. Measurement of mitochondrial ROS production. *Methods Mol Biol* 648:245-255, 2010.

Gram M et al. Skeletal muscle mitochondrial $H_2O_2$ emission increases with immobilization and decreases after aerobic training in young and older men. *J Physiol* 593 (17): 4011-4027, 2015.

Example B-4: Enzymatic Activity

This example describes the measurement of citrate synthase activity in the chondrisome preparation. Citrate synthase is an enzyme within the tricarboxylic acid (TCA) cycle that catalyzes the reaction between oxaloacetate (OAA) and acetyl-CoA to generate citrate. Upon hydrolysis of acetyl-CoA, there was a release of CoA with a thiol group (CoA-SH). The thiol group reacts with a chemical reagent, 5,5-Dithiobis-(2-nitrobenzoic acid) (DTNB), to form 5-thio-2-nitrobenzoic acid (TNB), which was a yellow product that can be measured spectrophotometrically at 412 nm (Green 2008). Commercially-available kits, such as the Abcam Human Citrate Synthase Activity Assay Kit (Product #ab119692) provide all the necessary reagents to perform this measurement.

The assay was performed as per the manufacturer's recommendations. Chondrisome preparation was prepared (see example 1-1 and 1-3b) and protein content was assessed by BCA (example A-5) and the preparation remains on ice until the following quantification protocol was initiated (within 120 minutes from isolation). Briefly, 2-20 ug of chondrisome samples were diluted in 1× Incubation buffer (final volume=100 μL) in the provided microplate wells, with one set of wells receiving only 1× Incubation buffer. The plate was sealed and incubated for 4 hours at room temperature with shaking at 300 rpm. The buffer was then aspirated from the wells and 300 μL of 1× Wash buffer was added. This washing step was repeated once more. Then, 100 μL of 1× Activity solution was added to each well, and the plate was analyzed on a microplate reader by measuring absorbance at 412 nm every 20 seconds for 30 minutes, with shaking between readings. Background values (wells with only 1× Incubation buffer) were subtracted from all wells, and the Citrate Synthase activity is expressed as the change in absorbance per minute per ug of chondrisomes sample loaded. Only the linear portion from 100-400 seconds of the kinetic measurement is used to calculate the activity. The output of this and analogous enzymatic activity assays are outlined in the table below.

Green H J et al. Metabolic, enzymatic, and transporter response in human muscle during three consecutive days of exercise and recovery. *Am J Physiol Regul Integr Comp Physiol* 295: R1238-R1250, 2008.

Human Fibroblast derived chondrisome preparations (produced via example 1-1)

| Enzymatic activity measured | Kit ID # | Enzymatic Activity Level |
|---|---|---|
| Citrate Synthase | Abcam, ab119692 | 1.96 ± 0.70 mOD/min/ug total protein |
| Alpha ketoglutarate dehydrogenase | abcam, ab185440 | 1.95 ± 0.89 mOD/min/ug total protein |
| Pyruvate dehydrogenase | Sigma-Aldrich Pyruvate Dehydrognease Assay Kit, product #MAK183 | 2.55 ± 0.15 mOD/min/ug total protein |
| Aconitase | abcam, ab83459 | 20.01 ± 3.00 mOD/min/ug total protein |
| Creatine Kinase | abcam, ab155901 | 10.00 ± 5.00 mOD/min/ug total protein (expected value) |

Human Platelet derived chondrisome preparations (produced via example 1-3b)

| Enzymatic activity measured | Kit ID # | Enzymatic Activity Level |
|---|---|---|
| Citrate Synthase | Abcam, ab119692 | 0.74 ± 0.30 mOD/min/ug total protein |
| Alpha ketoglutarate dehydrogenase | abcam, ab185440 | 3.19 ± 1.16 mOD/min/ug total protein |

-continued

| Enzymatic activity measured | Kit ID # | Enzymatic Activity Level |
|---|---|---|
| Pyruvate dehydrogenase | Sigma-Aldrich Pyruvate Dehydrognease Assay Kit, product #MAK183 | 4.54 ± 0.26 mOD/min/ug total protein |
| Aconitase | abcam, ab83459 | 1.07 ± 0.14 mOD/min/ug total protein |
| Creatine Kinase would similarly be expected to be: | abcam, ab155901 | 10.00 ± 5.00 mOD/min/ug total protein |

Example B-5: Fatty Acid Oxidation Level

This example describes the measurement of fatty oxidation acid in the chondrisome preparation. Chondrisome preparation was tested to determine fatty acid oxidation level using respiratory assay with Palmitoyl carnitine and malate as a substrate. Isolated chondrisomes (0.125 to 1 mg/mL) were suspended in 0.5 mL respiration medium (115 mM KCL, 10 mM KH2PO4, 2 mM MgCl2, 5 mM HEPES, 1 mM EGTA, BSA 0.1% (pH 7.2) plus substrate-Palmitoyl carnitine (25 μM) plus Malate (1 mM)-. Chondrisomes then will be loaded as 10 ug and 5 ug per well in a seahorse plate for human platelet and fibroblast isolated chondrisomes respectively. Respiration was measured by seahorse instrument maintained at 37° C. Chondrisomes were allowed to equilibrate in the respiration buffer prior to the addition of respiratory substrates.

Palmytolyl carnitine and Malate stimulate the production of FADH2 and NADH from the Beta oxidation pathway inside the chondrisomes and deliver electrons to the electron transport chain. The resulting oxygen consumption rate was denoted as State 2 respiration, which is caused by a leak of electrons across the inner chondrisome membrane and the compensatory increased flux of electrons down the electron transport chain to maintain membrane potential equilibrium. Next, adenosine diphosphate (ADP) was added to a final concentration of 4 mM. ADP causes a burst in respiration (termed State 3) as protons were utilized by the FoF1-ATPase to generate ATP. The increased respiration continues until all exogenous ADP has been consumed, after which the chondrisome respiration returns to a basal rate (defined as State 4). State 4 can also be artificially induced by adding Oligomycin (ATP synthase inhibitor). Finally, maximal fatty acid oxidation level of respiration was induced via addition of a chemical uncoupler, here using carbonyl cyanide-p-trichloromethoxyphenylhydrazone (FCCP) at a concentration of 4 μM. The chemical uncoupler bypasses the FoF1-ATPase resistance and provides an indication of maximal electron flux through the electron transport chain. The rate of respiration with the chondrisome preparation under palmitoyl carnitine as a substrate indicates the capacity of chondrisomes to oxidize fatty acid.

With this assay the chondrisome preparations derived from human platelet and fibroblast (produced as described in examples 1-3b and 1-1 respectively) were shown to have a maximal fatty acid oxidation level of 2.6+/−0.4 and 22.7+/−2.7 (pmolO2/min/ug chondrisome protein) respectively. The state 3/state 2 respiratory control ratio (RCR 3/2) calculated values were as 3.4+/−2.6 and 4.8+/−0.9 for human platelet and fibroblast isolated chondrisomes respectively.

Example B-6: Electron Transport Chain Efficiency

This example describes the measurement of chondrisome electron transport chain (ETC) efficiency, also referred to as ETC conductance. Isolated chondrisomes (0.125 to 1 mg/mL) are suspended in 1 mL respiration medium (0.3 mM mannitol, 10 mM KH2PO4, 5 mM $MgCl_2$, and 10 mM KCl (pH 7.2) in a Clark oxygen electrode chamber (Hansatech Instruments, Norfolk, United Kingdom) maintained at 37° C. Chondrisomes are allowed to equilibrate in the respiration buffer prior to the addition of glutamate (10 mM) and malate (1 mM).

Steady-state, intermediate oxygen consumption rates are attained using a creatine kinase energetic clamp as described by Glancy et al. *Effect of Calcium on the Oxidative Phosphorylation Cascade in Skeletal Muscle Mitochondria. Biochemistry* 52 (16): 2793-2809, 2013. Briefly, in the presence of a larger creatine pool, excess creatine kinase (CK), a known concentration of ATP, and the CK equilibrium constant, the free energy of ATP hydrolysis (i.e., the reverse driving force of chondrisome respiration) can be calculated after adding incremental amounts of phosphocreatine:

$$\Delta G_{ATP}=\Delta G^{\circ}_{ATP}-2.3*RT\log([PCr]*K_{CK}/([Cr]*[P_i])),$$

where $\Delta G^{\circ}_{ATP}$ is the standard $\Delta G_{ATP}$ (−7.592 kcal/mol), R is the gas constant (1.987 cal·K−1·mol−1), and T is temperature (310 K). Chondrisomes in the presence of 10 mM glutamate and 1 mM malate are provided 2.5 mM phosphocreatine (PCr), 5 mM creatine (Cr), 5 mM ATP, and 75 U/mL CK. Subsequent additions of PCr (to 3.75, 5, 7.5, and 10 mM) are made to slow chondrisome respiration. Upon completion of the respiration, the respiratory rates are plotted as a function of the reverse driving force, $\Delta G_{ATP}$. The resulting scatter plot is then fitted with a linear regression, the slope of the line indicating the conductance (L) of the chondrisome preparation, having a slope of $\Delta J_O$ (in nmol $O_2$/min/mg protein) divided by $\Delta G_{ATP}$ (in kcal/mol). The chondrisome preparations are expected to have 10-400 nmol $O_2$/min/mg protein/$\Delta G_{ATP}$ (in kcal/mol).

C Quality Characteristics

Example C-1: Protein Carbonyl Level

This example describes the quantification of chondrisome protein carbonyls, which are formed via reactive oxygen species-(ROS) induced protein damage. The commercially-available kit from Abcam, Protein Carbonyl Content Assay Kit (Product #ab126287) provides all the necessary reagents to perform this measurement. During the assay, the carbonyl groups are chemically derivatized with 2,4-dinitrophenylhydrazine (DNPH), resulting in stable hydrazine adducts that are detected via UV-Vis spectrophotometry at 375 nm.

Isolated chondrisomes were suspended in distilled $H_2O$ buffer at a concentration of 51, 2, or 4 μg/uL in a total volume of 100 μL per microcentrifuge tube. Since nucleic acids interfere with the assay, 1% streptozocin was added to each sample and incubated at room temperature for 15 minutes to degrade nucleic acids. Then, 100 μL of DNPH was added to each sample and was incubated at room temperature for 10 minutes. Next, 30 μL of 100% trichloroacetic acid (TCA) was added to each well and the plate was incubated on ice for 5 min. The samples were centrifuged at 13,000×g for 2 minutes, after which the supernatant was carefully removed. Ice-cold acetone (500 μL) was added to the pellets and the samples were placed in a sonicating bath for 2 minutes. The samples were then incubated for 5 min at −20° C. and centrifuged at 13,000×g. The acetone was removed from the pellet, followed by addition of 200 μL of 6 M guanidine to resolubilize the proteins. Then, 100 μL of each sample was transferred to a well (in duplicates) of 96-well plate. Lastly, the plate was read in a spectrophotometer with the detection wavelength set to 375 nm.

With this assay the chondrisome preparation (produced as described in example 1-3b) derived from human platelets was shown to have a protein carbonyl level in the range of 5-40 nmol carbonyl/mg chondrisome protein. In this specific experiment 19.7 nmol carbonyl/mg chondrisome protein was measured. Chondrisome preparations described herein are generally expected to have a protein carbonyl level less than 100 nmol carbonyl/mg chondrisome protein.

Example C-2: Lipid Content

Lipid extraction: Mass spectrometry-based lipid analysis was performed at Lipotype GmbH (Dresden, Germany) as described (1). Lipids were extracted using a two-step chloroform/methanol procedure (2). Samples were spiked with internal lipid standard mixture containing: cardiolipin 16: 1/15: 0/15: 0/15:0 (CL), ceramide 18:1;2/17:0 (Cer), diacylglycerol 17: 0/17:0 (DAG), hexosylceramide 18:1;2/12:0 (HexCer), lysophosphatidate 17:0 (LPA), lyso-phosphatidylcholine 12:0 (LPC), lyso-phosphatidylethanolamine 17:1 (LPE), lyso-phosphatidylglycerol 17:1 (LPG), lyso-phosphatidylinositol 17:1 (LPI), lyso-phosphatidylserine 17:1 (LPS), phosphatidate 17: 0/17:0 (PA), phosphatidylcholine 17: 0/17:0 (PC), phosphatidylethanolamine 17: 0/17:0 (PE), phosphatidylglycerol 17: 0/17:0 (PG), phosphatidylinositol 16: 0/16:0 (PI), phosphatidylserine 17: 0/17:0 (PS), cholesterol ester 20:0 (CE), sphingomyelin 18:1;2/12:0;0 (SM) and triacylglycerol 17: 0/17: 0/17:0 (TAG). After extraction, the organic phase was transferred to an infusion plate and dried in a speed vacuum concentrator. 1st step dry extract was re-suspended in 7.5 mM ammonium acetate in chloroform/methanol/propanol (1:2:4, V: V: V) and 2nd step dry extract in 33% ethanol solution of methylamine in chloroform/methanol (0.003:5:1; V: V: V). All liquid handling steps were performed using Hamilton Robotics STARlet robotic platform with the Anti Droplet Control feature for organic solvents pipetting.

MS data acquisition: Samples were analyzed by direct infusion on a QExactive mass spectrometer (Thermo Scientific) equipped with a TriVersa NanoMate ion source (Advion Biosciences). Samples were analyzed in both positive and negative ion modes with a resolution of Rm/z=200=280000 for MS and Rm/z=200=17500 for MSMS experiments, in a single acquisition. MSMS was triggered by an inclusion list encompassing corresponding MS mass ranges scanned in 1 Da increments (3). Both MS and MSMS data were combined to monitor CE, DAG and TAG ions as ammonium adducts; PC, PC O—, as acetate adducts; and CL, PA, PE, PE O—, PG, PI and PS as deprotonated anions. MS only was used to monitor LPA, LPE, LPE O—, LPI and LPS as deprotonated anions; Cer, HexCer, SM, LPC and LPC O— as acetate.

Data analysis and post-processing: Data were analyzed with in-house developed lipid identification software based on LipidXplorer as described in the following references (4,5). Only lipid identifications with a signal-to-noise ratio>5, and a signal intensity 5-fold higher than in corresponding blank samples were considered for further data analysis.

Sampaio JL, Gerl MJ, Klose C, Ejsing CS, Beug H, Simons K, et al. Membrane lipidome of an epithelial cell line. Proc Natl Acad Sci USA. 2011 Feb. 1;108 (5): 1903-7.

Ejsing CS, Sampaio JL, Surendranath V, Duchoslav E, Ekroos K, Klemm R W, et al. Global analysis of the yeast lipidome by quantitative shotgun mass spectrometry. Proc Natl Acad Sci USA. 2009 Mar. 17;106 (7): 2136-41.

Surma MA, Herzog R, Vasilj A, Klose C, Christinat N, Morin-Rivron D, et al. An automated shotgun lipidomics platform for high throughput, comprehensive, and quantitative analysis of blood plasma intact lipids. Eur J lipid Sci Technol. 2015 October; 117 (10): 1540-9.

Herzog R, Schwudke D, Schuhmann K, Sampaio JL, Bornstein SR, Schroeder M, et al. A novel informatics concept for high-throughput shotgun lipidomics based on the molecular fragmentation query language. Genome Biol. 2011 Jan. 19;12 (1): R8.

Herzog R, Schuhmann K, Schwudke D, Sampaio JL, Bornstein SR, Schroeder M, et al. LipidXplorer: a software for consensual cross-platform lipidomics. PLOS One. 2012 January;7 (1): e29851.

Using this assay the chondrisome preparations derived from human skeletal muscle (sourced from ReproCELL USA), human blood (sourced from ZenBio; SER—WB-SDS) and human fibroblast (sourced from National Disease Research Interchange) as described in examples 1-2a, 1-3a and 1-1 were analyzed for lipid contents. The protein content for these samples were also determined as detailed in example A-5 to be able to compare the lipid levels to protein content.

First general evaluation the lipid content of the preparations was determined. Total lipid content was calculated as the sum of the molar content of all lipids identified normalized to the protein content of the preparation. The degree of unsaturation of the lipids in the preparation was also determined by calculating the molar content of double bonds in found in the fatty acids of the lipids as a proportion of the total molar content of lipids (note that this quantity can be greater than 1 as lipids have more than 1 fatty acid chain which can each have more than 1 double bonds in the fatty acid backbone). This degree of unsaturation is expressed as "double bonds/total lipids". Lastly the proportion of two major classes of lipids was determined as a % of total lipids on a molar basis. These two classes were the phospholipids and the phosphosphingolipids. All four of the quantifications are measured in the table below for general chondrisome preparations and for preparations from specific tissue sources.

| Metric | Unit | General Chondrisome Preparation | Blood | Fibroblast | Muscle |
|---|---|---|---|---|---|
| total lipid | pmol/mg | 571382 ± 174496 | 216102 ± 66155 | 884050 ± 73422 | 613995 ± 37901 |
| double bonds/ total lipid | pmol/pmol | 2.86 ± 0.22 | 3 ± 0.03 | 2.6 ± 0.01 | 3 ± 0.027 |
| phospholipid/ total lipid | 100 * pmol/ pmol | 84.46 ± 18.96 | 95.7 ± 0.37 | 97.7 ± 0.07 | 60 ± 0.17 |

-continued

| Metric | Unit | General Chondrisome Preparation | Blood | Fibroblast | Muscle |
|---|---|---|---|---|---|
| phosphosphingolipid/ total lipid | 100 * pmol/ pmol | 5 ± 4.2 | 9.3 ± 0.17 | 4.6 ± 0.11 | 1 ± 0.012 |

The lipid content of relevant lipid classes was determined as a percentage of total lipids on a molar basis. This was calculated for general chondrisome preparations as detailed in the table below.

| Lipid Class (100 * pmol lipid class/pmol total lipid) | Quantity |
|---|---|
| Ceramide (Cer) content | 0.06-0.58 |
| Cardiolipin (CL) content | 0.6-3.91 |
| Lyso-Phosphatidylcholine (LPC) content | 0.05-0.47 |
| Lyso-Phosphatidylethanolamine (LPE) content | 0.03-0.14 |
| Phosphatidylcholine (PC) content | 25.97-56.7 |
| Phosphatidylcholine-ether (PC O-) content | 1.5-6.65 |
| Phosphatidylethanolamine (PE) content | 7.4-16.55 |
| Phosphatidylethanolamine-ether (PE O-) content | 8.72-14.97 |
| Phosphatidylinositol (PI) content | 4.1-5.36 |
| Phosphatidylserine (PS) content | 0.84-10.64 |
| Sphingomyelin (SM) content | 1.03-9.43 |
| Triacylglycerol (TAG) content | 0.25-38.9 |

Eicosanoids (e.g. prostaglandins, thromboxanes and leukotrienes) are potent cell signaling molecules that are produce by the metabolism of arachidonic acid. The source of this arachidonic acid for cells is the breakdown and removal of this fatty acid from phosphatidylethanolamine (PE) and/or phosphatidylcholine (PC). When these lipids are partially hydrolysed and stripped of one of the polyunsaturated arachidonic acid chains they become LPE and/or LPC respectively. The molar ratio of these two lipid metabolites is indicative of cellular arachidonic synthesis capability and this value was calculated and is displayed in the table below.

| metric | general chondrisome preparation | blood | fibroblast | muscle |
|---|---|---|---|---|
| PE:LPE | 151.32 ± 55.8 | 88.8 ± 0.64 | 145.9 ± 25.28 | 219.2 ± 13.125 |
| PC:LPC | 316.62 ± 103.88 | 103.9 ± 20.5 | 343.1 ± 35.68 | 502.8 ± 6.92 |

Lipid fatty acid chain length and degree of unsaturation play roles in the membrane fluidity, preferred membrane structural state and overall membrane morphology and fission/fusion capabilities. For these reasons the proportion of long and unsaturated fatty acids associated with PEs and PCs as a molar proportion for each respective class was calculated. Specifically, fatty acid chain lengths of 18 carbons with >0 double bonds and 20 carbons with 4 double bonds (arachidonic acid) were considered and their quantification is displayed in the table below.

| metric | unit | general chondrisome preparation | blood | fibroblast | muscle |
|---|---|---|---|---|---|
| PE 18:n (n > 0) content | pmol AA/pmol lipid class | 0.05 ± 0.03 | 0.04 ± 0.001 | 0.09 ± 0 | 0.04 ± 0.095 |
| PE 20:4 content | pmol AA/pmol lipid class | 0.05 ± 0.03 | 0.08 ± 0.004 | 0.03 ± 0 | 0.04 ± 0.034 |
| PC 18:n (n > 0) content | pmol AA/pmol lipid class | 0.31 ± 0.04 | 0.3 ± 0.02 | 0.3 ± 0.01 | 0.3 ± 0.005 |
| PC 20:4 content | pmol AA/pmol lipid class | 0.06 ± 0.04 | 0.1 ± 0.005 | 0.1 ± 0.005 | 0.013 ± 0.0002 |

Example C-3: Contaminating and Non-Contaminating Protein Levels

This assay was performed to determine the proteomics makeup of the sample preparation and to determine the proportion of proteins that come from non-mitochondrial sources and are thus labeled contaminants. Chondrisome preparations were generated from human skeletal muscle (sourced from ReproCELL USA), human blood (sourced from ZenBio; SER—WB-SDS), human platelets (sourced from ZenBio; SER—PRP-SDS) and human fibroblast (sourced from National Disease Research Interchange) as described in examples 1-2a, 1-3a, 1-3b and 1-1 respectively without final buffer resuspension. Rather, the chondrisome pellet was frozen for shipment to the proteomics analysis center.

The chondrisome samples were then thawed for protein extraction and analysis. First they were resuspended in 200 μl of lysis buffer (7M Urea, 2M Thiourea, 4% (w/v) Chaps in 50 mM Tris pH 8.0) and incubated for 15 minutes at room temperature with occasional vortexing. Mixtures were then lysed by sonication for 5 minutes in an ice bath and spun down for 5 minutes at 13000 RPM. Protein content was determined by Pierce 660 colorimetric assay and 100 μg protein of each sample was transferred to a new tube and the volume was adjusted to 100 μl with 50 mM Tris pH 8. Proteins were reduced for 15 minutes at 65° C. with 10 mM DTT and alkylated with 15 mM iodoacetamide for 30 minutes at room temperature in the dark. Proteins were precipitated with gradual addition of 6 volumes of cold (−20° C.) acetone and incubated over night at −80° C.. Protein pellets were washed 3 times with cold (−20° C.) methanol. Proteins were resuspended in 100 μl 50 mM Tris pH 8. 3.33 ug of Trypsin/LysC was added to the proteins for a first 4 h of digestion at 37° C. with agitation. Samples were diluted to 1 ml with 50 mM Tris pH 8 and 0.1% sodium deoxycholate was added with another 3.3 μg of Trypsin/LysC for digestion over night at 37° C. with agitation. Digestion was stopped and sodium deoxycholate was removed by the addition of 2% v/v formic acid. Samples were vortexed and cleared by centrifugation for 1 minute at 13 000 RPM. Peptides were purified by reversed phase solid phase extraction (SPE) and dried down. Samples were reconstituted in 20 μl of 3% DMSO, 0.2% formic acid in water and analyzed by LC-MS. To have quantitative measurements a protein standard was also run on the instrument. Standard peptides (Pierce™ 6 Protein Digest, equimolar, LC-MS grade, #88342) were diluted to 4, 8, 20, 40 and 100 fmol/ul and were analyzed by LC-MS/MS. The average AUC (area under the curve) of the 5 best peptides per protein (3 MS/MS transition/peptide) was calculated for each concentration to generate a standard curve.

Acquisition was performed with a ABSciex TripleTOF 5600 (ABSciex, Foster City, CA, USA) equipped with an electrospray interface with a 25 μm iD capillary and coupled to an Eksigent uUHPLC (Eksigent, Redwood City, CA, USA). Analyst TF 1.6 software was used to control the instrument and for data processing and acquisition. The source voltage was set to 5.2 kV and maintained at 225° C., curtain gas was set at 27 psi, gas one at 12 psi and gas two at 10 psi. Acquisition was performed in Information Dependant Acquisition (IDA) mode for the protein database and in SWATH acquisition mode for the samples. Separation was performed on a reversed phase HALO C18-ES column 0.3 μm i.d., 2.7 μm particles, 150 mm long (Advance Materials Technology, Wilmington, DE) which was maintained at 60° C. Samples were injected by loop overfilling into a 5 μL loop. For the 120 minute (samples) LC gradient, the mobile phase consisted of the following solvent A (0.2% v/v formic acid and 3% DMSO v/v in water) and solvent B (0.2% v/v formic acid and 3% DMSO in EtOH) at a flow rate of 3 μL/min.

For the absolute quantification of the proteins, we generated a standard curve (5 points, R2>0.99) using the sum of the AUC of the 5 best peptides (3 MS/MS ion per peptide) per protein. To generate a database for the analysis of the samples, we ran the DIAUmpire algorithm on each of the 12 samples and combined the output MGF files into one database. This database was used in the Peakview software (ABSciex) to quantify the proteins in each of the samples, using 5 transition/peptide and 5 peptide/protein maximum. A peptide was considered as adequately measured if the score computed by Peakview was superior to 1.5 or had a FDR<1%. The sum of the AUC of each of the adequately measured peptide was mapped on the standard curve, and is reported as fmol.

The resulting protein quantification data was then analyzed to determine protein levels and proportions of know classes of proteins as follows: enzymes were identified as proteins that were annotated with an Enzyme Commission (EC) number; ER associated proteins were identified as proteins that had a Gene Ontology (GO; www.geneontology.org) cellular compartment classification of ER and not mitochondria; exosome associated proteins were identified as proteins that had a Gene Ontology cellular compartment classification of exosomes and not mitochondria; MitoCarta proteins were identified as proteins that were identified as mitochondrial in the MitoCarta database (Calvo et al., NAR 20151 doi: 10.1093/nar/gkv1003); and lastly the mtDNA encoded protein content was determined from the 4 mtDNA encoded proteins that were observed in the data (MT-CO2, MT-ATP6, MT-ND5, and MT-ND6). The molar ratios of each of these categories were determined as the sum of the molar quantities of all the proteins in each class divided by the sum of the molar quantities of all identified proteins in each sample.

| Category | Unit | General Chondrisome Prep | Muscle | Blood | Platelet | Fibroblast |
|---|---|---|---|---|---|---|
| Enzyme | mol/mol | 0.13-0.33 | 0.324 ± 0.008 | 0.192 ± 0.006 | 0.137 ± 0.005 | 0.286 ± 0.004 |
| ER | mol/mol | 0.01-0.17 | 0.007 ± 0.0004 | 0.02 ± 0.002 | 0.037 ± 0.002 | 0.163 ± 0.009 |
| Exosome | mol/mol | 0.11-0.58 | 0.124 ± 0.009 | 0.547 ± 0.03 | 0.46 ± 0.004 | 0.346 ± 0.007 |
| Mitocarta | mol/mol | 0.04-0.62 | 0.6 ± 0.03 | 0.056 ± 0.02 | 0.09 ± 0.002 | 0.312 ± 0.008 |
| mtDNA encoded | mol/mol | 0.001-0.04 | 0.027 ± 0.01 | 0.001 ± 0.0002 | 0.002 ± 0.0001 | 0.002 ± 0.0008 |

Example C-4: genetic quality

This assay was performed to determine the substantial presence of known disease causing chondrisome mutations. This was done by generating a barcoded next generation sequencing library using commercially available kits and protocols (BiooScientific NEXTflex™ mtDNA-Seq Kit for Illumina Sequencing). Human fibroblasts were grown and chondrisomes were isolated as described in example 1-1. The sequencing library was prepared with the appropriate amplification ends for the next generation sequencing instrument to be used. Critically the average depth of coverage that as achieved over the entire chondrisome genome must be greater than 200× and at no single location should coverage drop below 100X. The output reads were filtered for quality where sequences with >10 consecutive nucleotides with Q<20 were eliminated. The disease associated mtDNA content of the chondrisome preparation was assessed by determining the proportion of reads that contained the wild type sequence at sites of confirmed disease associated tRNA, rRNA or protein coding mutation sites. These disease associations are based on Mitomap (MITOMAP: A Human Mitochondrial Genome Database. www.mitomap.org, 2016) determination of confirmed mutations and their position is based on the Revised Cambridge Reference Sequence (rCRS; GenBank accession number NC_012920). Using this assay the chondrisome preparation was determined to be substantially clear of known disease causing mutations with >90% of reads mapping to the WT sequence at all sites indicated in Table 5.

TABLE 5

Disease causing mutations.

| Position | Locus | Disease | WT | Mutant |
|---|---|---|---|---|
| | | tRNA and rRNA mutations | | |
| 583 | MT-TF | MELAS/MM & EXIT | G | A |
| 1494 | MT-RNR1 | DEAF | C | T |
| 1555 | MT-RNR1 | DEAF | A | G |
| 1606 | MT-TV | AMDF | G | A |
| 1644 | MT-TV | HCM + MELAS | G | A |
| 3243 | MT-TL1 | MELAS/LS/DMDF/MIDD/SNHL/CPEO/MM/ FSGS/ASD/Cardiac + multi-organ dysfunction | A | G |
| 3256 | MT- TL1 | MELAS | C | T |
| 3260 | MT- TL1 | MMC/MELAS | A | G |
| 3271 | MT- TL1 | MELAS/DM | T | C |
| 3291 | MT-TL1 | MELAS/Myopathy/Deafness + Cognitive Impairment | T | C |
| 3302 | MT- TL1 | MM | A | G |
| 3303 | MT- TL1 | MMC | C | T |
| 4298 | MT-TI | CPEO/MS | G | A |
| 4300 | MT-TI | MICM | A | G |
| 4308 | MT-TI | CPEO | G | A |
| 4332 | MT-TQ | Encephalopathy/MELAS | G | A |
| 5537 | MT-TW | Leigh Syndrome | A | AT |
| 5650 | MT-TA | Myopathy | G | A |
| 5703 | MT-TN | CPEO/MM | G | A |
| 7445 | MT-TS1 precursor | SNHL | A | G |
| 7471 | MT-TS1 | PEM/AMDF/Motor neuron disease-like | C | CC |
| 7497 | MT-TS1 | MM/EXIT | G | A |
| 7511 | MT-TS1 | SNHL | T | C |
| 8344 | MT-TK | MERRF; Other - LD/Depressive mood disorder/ leukoencephalopathy/HiCM | A | G |
| 8356 | MT-TK | MERRF | T | C |
| 8363 | MT-TK | MICM + DEAF/MERRF/Autism/LS/ Ataxia + Lipomas | G | A |
| 10010 | MT-TG | PEM | T | C |
| 12147 | MT-TH | MERRF-MELAS/Enchephalopathy | G | A |
| 12315 | MT-TL2 | CPEO/KSS | G | A |
| 14674 | MT-TE | Reversible COX deficiency myopathy | T | C |
| 14709 | MT-TE | MM + DMDF/Encephalomyopathy / Dementia + diabetes + ophthalmoplegia | T | C |
| | | Protein coding gene mutations | | |
| 3376 | MT-ND1 | LHON MELAS overlap | G | A |
| 3460 | MT-ND1 | LHON | G | A |
| 3635 | MT-ND1 | LHON | G | A |
| 3697 | MT-ND1 | MELAS/LS/LDYT | G | A |
| 3700 | MT-ND1 | LHON | G | A |
| 3733 | MT-ND1 | LHON | G | A |
| 3890 | MT-ND1 | Progressive encephalomyopathy/LS/optic atrophy | G | A |
| 4171 | MT-ND1 | LHON | C | A |
| 7445 | MT-001 | SNHL | A | G |
| 8528 | MT-ATP8/6 | Infantile cardiomyopathy | T | C |
| 8993 | MT-ATP6 | NARP/Leigh Disease/MILS/other | T | C |
| 8993 | MT-ATP6 | NARP/Leigh Disease/MILS/other | T | G |
| 9176 | MT-ATP6 | Leigh Disease/Spastic Paraplegia | T | G |
| 9176 | MT-ATP6 | FBSN/Leigh Disease | T | C |
| 9185 | MT-ATP6 | Leigh Disease/Ataxia syndromes/NARP-like disease | T | C |
| 10158 | MT-ND3 | Leigh Disease | T | C |
| 10191 | MT-ND3 | Leigh Disease/Leigh-like Disease/ESOC | T | C |
| 10197 | MT-ND3 | Leigh Disease/Dystonia/Stroke/LDYT | G | A |
| 10663 | MT-ND4L | LHON | T | C |
| 11777 | MT-ND4 | Leigh Disease | C | A |
| 11778 | MT-ND4 | LHON/Progressive Dystonia | G | A |
| 12706 | MT-NDS | Leigh Disease | T | C |
| 13051 | MT-NDS | LHON | G | A |
| 13513 | MT-NDS | Leigh Disease/MELAS/LHON-MELAS Overlap Syndrome | G | A |
| 13514 | MT-NDS | Leigh Disease/MELAS | A | G |
| 14459 | MT-ND6 | LDYT/Leigh Disease | G | A |
| 14482 | MT-ND6 | LHON | C | G |
| 14482 | MT-ND6 | LHON | C | A |
| 14484 | MT-ND6 | LHON | T | C |
| 14487 | MT-ND6 | Dystonia/Leigh Disease/Ataxia/Ptosis/Epilepsy | T | C |
| 14495 | MT-ND6 | LHON | A | G |
| 14568 | MT-ND6 | LHON | C | T |
| 14849 | MT-CYB | EXIT/Septo-Optic Dysplasia | T | C |

TABLE 5-continued

| Disease causing mutations. | | | | |
|---|---|---|---|---|
| Position | Locus | Disease | WT | Mutant |
| 14864 | MT-CYB | MELAS | T | C |
| 15579 | MT-CYB | Multisystem Disorder, EXIT | A | G |

The disease abbreviations refer to the following:

LHON Leber Hereditary Optic Neuropathy

AD Alzeimer's Disease

ADPD Alzeimer's Disease and Parkinsons's Disease

NARP Neurogenic muscle weakness, Ataxia, and Retinitis Pigmentosa; alternate phenotype at this locus is reported as Leigh Disease MELAS Mitochondrial Encephalomyopathy, Lactic Acidosis, and Stroke-like episodes

MERR

F Myoclonic Epilepsy and Ragged Red Muscle Fibers

CPEO Chronic Progressive External Ophthalmoplegia

DM Diabetes Mellitus

CIPO Chronic Intestinal Pseudoobstruction with myopathy and Ophthalmoplegia

PEM Progressive encephalopathy

MM Mitochondrial Myopathy

LIMM Lethal Infantile Mitochondrial Myopathy

MMC Maternal Myopathy and Cardiomyopathy

FICP Fatal Infantile Cardiomyopathy Plus, a MELAS-associated cardiomyopathy

LDYT Leber's hereditary optic neuropathy and DYsTonia

MHCM Maternally inherited Hypertrophic CardioMyopathy

KSS Kearns Sayre Syndrome

DMDF Diabetes Mellitus+DeaFness

DEAF Maternally inherited DEAFness or aminoglycoside-induced DEAFness

SNHL SensoriNeural Hearing Loss

Example C-5: Contaminating Nuclear DNA Levels

The amount of contaminating nuclear DNA (nDNA) in the chondrisome preparation was examined using semi-quantitative real-time PCR (RT-PCR). Chondrisomes were isolated from human skeletal muscle punch biopsies, platelets, or cultured fibroblasts using the procedures explained in Examples 1-2a and 1-3b and 1-1 respectively. From these preparations, total DNA was isolated using a Qiagen DNeasy blood and tissue kit (catalog number 69504), followed by determination of DNA concentration using a Thermo Scientific NanoDrop.

After completion of the DNA isolation procedure, RT-PCR was carried out using Applied Biosystems PCR Master Mix (catalog number 4309155) in a 20 μL total reaction volume using the following reaction template:

SYBR Green Master Mix: 10 μL 0.45 μM Forward Primer: 1 μL 0.45 μM Reverse Primer: 1 μL DNA Template: 10 ng PCR-Grade Water: Variable Forward and reverse primers were produced and acquired by Integrated DNA Technologies. The table below details the primer pairs and their associated sequences:

| Target | Forward Primer Sequence (5' → 3') | Reverse Primer Sequence (5' → 3') |
|---|---|---|
| Human mtDNA | CAC CCA AGA ACA GGG TTT GT (SEQ ID NO: 24) | TGG CCA TGG GTA TGT TGT TA (SEQ ID NO: 25) |
| Human nDNA | TGC TGT CTC CAT GTT TGA TGT ATC T (SEQ ID NO: 26) | TCT CTG CTC CCC ACC TCT AAG T (SEQ ID NO: 27) |

An Applied Biosystems 7900HT Real-Time PCR system was used to perform the amplification and detection with the following protocol:

| | |
|---|---|
| Denaturation, 94° C. | 2 min |
| 40 Cycles of the following sequence: | |
| Denaturation, 94° C. | 15 sec |
| Annealing, Extension, 60° C. | 1 min |

The ratio of mtDNA to nDNA was calculated using the relative cycle threshold values and the following formula:

$$\text{mtDNA}_{relative}=2\times2^{(Ct\ nuclear-Ct\ mito)}$$

where Ct nuclear denotes the cycle threshold for nDNA and Ct mito denotes mtDNA, respectively determined at a fluorescence level of 0.014179736. The following table presents the mtDNA copy number relative to the nuclear DNA copy number:

| Source: | Relative mtDNA level over nuclear DNA |
|---|---|
| Human Fibroblast | 64741 ± 23551 |
| Human Platelet | 246312 ± 151024 |
| Human Muscle | 2893 ± 773 |

Example C-6: Endotoxin Levels

This assay was performed using the commercially available kit for the determination of endotoxin levels (Pierce LAL Chromogenic Endotoxin Quantification Kit, ThermoFisher 88282). The manufacturer's protocols were followed and were briefly as follows. Critically, all materials (e.g., pipette tips, glass tubes, microcentrifuge tubes and disposable 96-well microplates) must be endotoxin-free. The assay microplate loaded in a heating block to maintain a temperature of 37° C. While at 37° C. 50 μL of each standard (X,Y,Z) or chondrisome preparation sample replicate was loaded into the appropriate wells. The plate was covered and incubated for 5 minutes at 37° C.50 μL of LAL buffer was added to each well and the plate was covered and gently shaken on a plate shaker for 10 seconds then incubated at 37° C. for 10 minutes. 100 μL of substrate solution was added to each well. Again cover, and shake for 10 seconds and incubate at 37° C. for 6 minutes. 50 μL of Stop Reagent (25% acetic acid) was added and then shake the plate on a plate mixer for 10 seconds. Absorbance was measured at 405-410 nm on a plate reader. Average absorbance of the blank replicates were subtracted from the average absorbance of all standard replicates and average of the chondrisome preparation replicates. A standard curve was generated by performing linear regression on the standards (The coefficient of determination, r2, must be ≥0.98) and the endo toxin level of the chondrisome preparation was interpolated. If the chondrisome preparation sample endotoxin concentration was >1.0EU/mL (out of range) dilute the sample five-fold in endotoxin-free water and re-test. Using this assay the endotoxin level of the chondrisome preparation (as prepared in example 1-1) derived from human fibroblasts was determined to be <0.02EU/ug chondrisome protein. (actual value 0.015 U/ug).

Using this assay the endotoxin level of the chondrisome preparation (as prepared in example 1-3a) derived from human blood was determined to be <0.03EU/ug chondrisome protein. (actual value 0.025 U/ug).

E Blood Derived Preps

Example E-1: Preparation of Chondrisome Containing Mitoparticles

Platelet samples were evaluated for starting concentration of platelets and then centrifuged and resuspended in Tyrodes buffer to a concentration of 1×10^8 platelets/mL. To release mitoparticles from platelets, platelets were activated with thrombin at 0.5 U/mL and incubated at room temperature in the dark for 4 hours. After activation, the preparation was centrifuged at 2000g to pellet platelets and the supernatant was collected. In this experiment, the supernatant was distributed into 2 mL Eppendorf tubes and spun at 18,000 g in bench top microcentrifuge for 90 minutes to pellet the mitoparticles containing chondrisomes. The pelleted mitoparticles were then resuspended in Tyrode's buffer and used for downstream applications.

Example E-2: Concentration of Chondrisome Containing Mitoparticles from Platelets In order to label platelet cellular membranes and chondrisomes, the resuspended platelets were stained in solution with 2 μM PKH67 fluorescent cell linker and 200 nM MitoTracker Deep Red, and incubated at 37° C. for 30 minutes. Appropriate unstained and single-stained controls were processed as well. Platelet solutions were then centrifuged at 2000g to pellet platelets. The supernatant was removed and the platelets were resuspended in the same volume of Tyrode's buffer. After thrombin-activation for 4 hours, fluorescence-activated cell sorting was performed on a Beckman Coulter MoFlo XDP instrument and the population of mitoparticles staining double-positive for PKH67 and Mito Tracker Deep Red we quantified. PKH67 was excited with a 488 nm laser and emission captured at 513+26 nm. Mito Tracker Deep Red was excited with a 640 nm laser and emission captured at 671+30 nm. Events double-positive for PKH67 and MitoTracker Deep Red were determined by gating at the minimum level for which each appropriately unstained sample showed<1% of events positive for the specific fluorescent marker (i.e. unstained and single-PKH67-stained samples show<1% events positive for Mito Tracker Deep Red). The number of double-positive events was counted and normalized to the volume of sample analyzed during the FACS assessment. The number of double-positive mitoparticles containing chondrisomes was expressed as the amount per platelet number. This assay determined that mitoparticles were identified at in the concentration range of 2-14 MPs per 10^10 platelets. In this specific experiment there was 7.8 MPs per 10^10 platelets in the preparation.

Example E-3: Membrane Potential of Chondrisome Containing Mitoparticles

The membrane potential of the chondrisome preparation is quantified using a commercially available dye, TMRE (tetramethylrhodamine ester, ThermoFisher #T669). Chondrisome-containing mitoparticles are prepared from human platelets as described in Example E-1, and stained for platelet cellular membranes and chondrisomes, followed by thrombin activation, as outlined in Example E-2. After thrombin activation for 4 hours, TMRE (30 nM) is added to the platelet solution and incubated at 37° C. for 30 minutes prior to analysis by FACS. A parallel set of samples is not stained with TMRE (unstained). Events double-positive for PKH67 and Mito Tracker Deep Red are determined by gating at the minimum level for which each appropriately unstained sample showed<1% of events positive for the specific fluorescent marker (i.e. unstained and single-PKH67-stained samples show<1% events positive for Mito Tracker Deep Red). The gated double-positive events are then assessed for TMRE intensity (TMRE excited with 543 nm laser and emission captured at 570±26 nm). A parallel sample of thrombin-stimulated platelets is treated with 2 μM FCCP for 5 minutes prior to FACS analysis.

Membrane potential values (in millivolts, mV) are calculated based on the intensity of TMRE. For both untreated and FCCP-treated samples, the corrected fluorescence intensity (FI) value is calculated by subtracting the geometric mean of TMRE fluorescence intensity for the unstained sample from the geometric mean of the untreated and FCCP-treated sample. The quantification of membrane potential of the chondrisomes-containing mitoparticle population is calculated using the modified Nernst equation below, which can be used to determine chondrisome membrane potential based on TMRE fluorescence (as TMRE accumulates in chondrisomes in a Nernstian fashion).

$$\text{Chondrisome membrane potential } (mV) = -61.5 * \log (FI_{untreated}/FI_{FCCP\text{-}treated})$$

Performing this assay on chondrisome preparations from mouse skeletal muscle chondrisomes (as described in example 1-2a) is expected to yield a membrane potential state of −65 mV (Range was −20 to −150 mV).

Example E-4: Quantification of Platelet Derived Chondrisome Mitoparticle Delivery to Specific Subcellular Locations This example describes delivery of mitoparticles to cultured cells.

Chondrisome-containing mitoparticles are generated from human platelet samples stained with Mito Tracker Deep Red and PKH67 Cell Linker and activated with thrombin for 4 hours (example E-2). The supernatant is distributed into 2 mL eppendorf tubes and spun at 18,000 g in bench top microcentrifuge for 90 minutes to pellet the mitoparticles containing chondrisomes. The pelleted mitoparticles are then resuspended in 200 μL of Tyrode's buffer. Chondrisome preparation protein content is assessed by BCA (example A-2) and the preparation remains on ice until the following protocol is initiated (within 120 minutes from isolation).

Leigh fibroblasts from Coriell Institute (GM01503) are cultured in DMEM media supplemented with 10% fetal bovine serum (ThermoFisher), and seeded at 25,000 cells per well in one well of a quadrant glass-bottom imaging dish (Greiner Bio-One). After 24 hours, cells are treated with 8 ug of chondrisome-containing mitoparticles per well in 500 μL media or an equivalent volume of Tyrode buffer as control. Cells are incubated with mitoparticles for 24 hours. Prior to imaging cells are incubated with 50 nM Lysotracker Red for 30 minutes. Cells are then imaged on a Zeiss LSM 710 confocal microscope with a 63× oil immersion objective while maintained at 37° C. and 5% CO2. PKH67 cell linker dye is subjected to 488 nm laser excitation and emission is recorded through a band pass 495-530 nm filter. Lysotracker red is subjected to 543 nm laser excitation and emission is recorded through a band pass 560 to 610 nm filter. Mito Tracker Deep Red is subjected to 633 nm helium/neon laser excitation and emission is recorded through a band-pass 650 to 710 nm filter. To observe individual chondrisomes Z-stack images are acquired in series of 6 slices per cell with a 1 airy unit pinhole ranging in thickness from 0.5-0.8 μm per slice.

Colocalization of donor chondrisomes (positive for MitoTracker Deep Red only) or chondrisome-containing mitoparticles (double-positive for MitoTracker Deep Red and PKH67) with recipient cell lysosomes (Lysotracker Red) is calculated by summing all events where there is greater than 80% pixel overlap between a given MitoTracker Deep Red-positive chondrisome region and a Lysotracker green-positive lysosomal regions within an analyzed z-plane. All z-plane images are processed in ImageJ (NIH) and mitoparticle, chondrisomes, and lysosomal regions are thresholded using the Moments threshold algorithm to identify regions after subtracting background. Using this imaging assay and colocalization calculation, >20% of the donor chondrisome-containing mitoparticles (Mito Tracker Deep Red and PKH67) are found to be targeted to endogenous cellular lysosomes. Analogous imaging and localization quantification protocols determine the expected targeting levels to other subcellular locations as detailed in the table below.

| Subcellular Target | Mitoparticle Preparation Stain | Target Cell Stain | Colocalization Quantification Method | Proportion |
|---|---|---|---|---|
| Cytosol | 200 nM MitoTracker Deep Red and PKH67 Cell Linker for 30 minutes at 37 C. in Tyrode's buffer at a concentration of 0.005-0.05 ug/uL. | 50 nM Lysotracker Red for 30 minutes | Fraction of MitoTracker Deep Red-positive events showing no significant colocalization (<80% pixel overlap) with Lysotracker Red regions. | >5% |
| Endogenous Mitochondrial Network | 200 nM MitoTracker Deep Red and PKH67 Cell Linker for 30 minutes at 37 C. in Tyrode's buffer at a concentration of 0.005-0.05 ug/uL. | 15 nM TMRE (ThermoFisher) for 60 minutes at 37C. | Fraction of MitoTracker Deep Red-positive events showing significant colocalization (>80% pixel overlap) with TMRE regions. | >5% |
| Lysosome | 200 nM MitoTracker Deep Red and PKH67 Cell Linker for 30 minutes at 37 C. in Tyrode's buffer at a concentration of 0.005-0.05 ug/uL. | 50 nM Lysotracker Red for 30 minutes | Fraction of MitoTracker Deep Red-positive events showing significant colocalization (>80% pixel overlap) with Lysotracker Red regions. | 5%-90% |
| Outer membrane | 200 nM MitoTracker Deep Red and PKH67 Cell Linker for 30 minutes at 37 C. in Tyrode's buffer at a concentration of 0.005-0.05 ug/uL. | Cells are fixed with 4% paraformaldehyde and stained with rabbit anti-TOMM20 antibody for outer chondrisome membrane, followed by anti-rabbit AlexaFluor 543 staining | Fraction of MitoTracker Deep Red-positive events showing significant colocalization (>80% pixel overlap) with TOMM20-AlexaFluor 543 (red) regions. | 5%-90% |

F Biological/Functional Characteristics

Example F-1: Apoptosis Induction Level

An approach to measuring apoptosis was via detection of fluorescent exclusion dye, propdium iodide. During late-stage apoptosis or necrosis, the cellular plasma membrane becomes permeable and propidium iodide is able to transverse the membrane and stain nuclear DNA of the cells. Live cells with an intact membrane do not allow propidium iodide uptake and thus show no nuclear DNA staining.

Though any cell type can be used for the assay, this examples pertains specifically to Leigh syndrome fibroblast cells acquired from Coriell Institute (GM01503) and cultured in DMEM media supplemented with 10% fetal bovine serum (ThermoFisher). Cells were seeded at a density of 10,000 cells/well in a 96-well plate in DMEM media supplemented with 10% FBS. The chondrisome preparation was generated (see example 1-1 and 1-3b) and the preparation remains on ice until the quantification assay was initiated (within 120 minutes from isolation). While on ice, total protein content of the chondrisome preparation was quantified via BCA (see example A-5). The chondrisome preparation was added to the wells at a concentration of 0, 0.5, 1, 2, or 4 μg/well. Cells were allowed to incubate for 124 hours with or without chondrisomes in DMEM media supplemented with 10% FBS.

Following the incubation period, cells were washed once in phosphate-buffered saline (PBS). PBS containing 1 ug/mL propidium iodide and 5 μM Hoescht 33342 was added to the wells (200 μL) according to the manufacturer's protocol (ThermoFisher Cat #P3566 and Cat #62249). Cells were incubated for 10-15 minutes and analyzed using Celigo Imaging Cell Cytometer (Brooks Life Science Systems). Blue (377/50 excitation; 470/22 emission) and red (531/40 excitation; 629/53 emission) fluorescence channels was imaged for each well. Analysis parameters for images acquired by Celigo Imaging Cell Cytometer were optimized to identify individual cells based on fluorescence (Algorithm 1, Threshold 1, Precision 2, Filter Size 25, Separate Touching Objects TRUE). The % cell death was calculated as the number of propidium iodide-positive cells normalized to the total number of cells (Hoescht-positive)×100. At least 1,000 cells were analyzed per well, with 3 well replicates per experiment. Cell death was measured at less than 3% for cells treated with up to 4 ug chondrisomes from human fibroblasts or human platelets.

Example F-2: Enhancement of Cellular Respiration

This assay pertains specifically to Leigh syndrome fibroblast cells acquired from Coriell Institute (GM01503) and cultured in DMEM media supplemented with 10% fetal bovine serum (ThermoFisher). Chondrisome preparations were generated (example 1-2a) from leg gastrocnemius muscle from C57bl/6 mice (Charles River Laboratories). The chondrisome preparation was resuspended in MSHE buffer (200 mM mannitol, 70 mM sucrose, 10 mM HEPES, 1 mM EDTA, adjust the pH to 7.4 with KOH). Chondrisome preparation protein content was assessed by BCA (example A-5) and the preparation remains on ice until the following protocol was initiated (within 120 minutes from isolation).

Leigh fibroblasts were seeded at 12,500 cells per well in a 96-well Seahorse plate (Agilent). After 24 hours, cells were treated with 4 or 16 ug of chondrisome preparation per well in 200 μL media or an equivalent volume of MSHE buffer as control. Cells were incubated with chondrisomes for 24 hours and oxygen consumption rates of fibroblast cells were subsequently measured by XF96 bioenergetic assay (Agilent).

Oxygen consumption assays were initiated by removing growth medium, replacing with low-buffered DMEM minimal medium containing 25 mM glucose and 2 mM glutamine (Agilent) and incubating at 37° C. for 60 minutes to allow temperature and pH to reach equilibrium. The microplate was then assayed in the XF96 Extracellular Flux Analyzer (Agilent) to measure extracellular flux changes of oxygen and pH in the media immediately surrounding adherent cells. After obtaining steady state oxygen consumption (basal respiration rate) and extracellular acidification rates, oligomycin (5 μM), which inhibits ATP synthase, and proton ionophore FCCP (carbonyl cyanide 4-(trifluoromethoxy)phenylhydrazone; 2 μM), which uncouples chondrisomes, were injected sequentially through reagent delivery chambers for each cell well in the microplate to obtain values for maximal oxygen consumption rates. Finally, 5 μM antimycin A (inhibitor of chondrisome complex III) was injected to confirm that respiration changes were due mainly to chondrisome respiration. The minimum rate of oxygen consumption after antimycin A injection was subtracted from all oxygen consumption measurements to remove the non-mitochondrial respiration component. Cell samples that do not appropriately respond to oligomycin (at least a 25% decrease in oxygen consumption rate from basal) or FCCP (at least a 50% increase in oxygen consumption rate after oligomycin) were excluded from the analysis. Using this assay the fold increase in basal respiration of the fibroblast from untreated to treated cells was 1.7-fold for cells treated with 4 ug chondrisomes and 2.1-fold for cells treated with 16 ug chondrisomes.

Example F-3: Subcellular Targeting Levels

This assay pertains specifically to Leigh syndrome fibroblast cells acquired from Coriell Institute (GM01503) and cultured in DMEM media supplemented with 10% fetal bovine serum (ThermoFisher). Chondrisome preparations were generated (example 1-1) from Hela cells. Prior to chondrisome isolation, Hela cells were transduced with adenovirus-mito-DsRed (250 viral particles/cell) and expression was enabled for 72 hours before chondrisome isolation. After chondrisome isolation, the chondrisome sample was resuspended in MSHE buffer (200 mM mannitol, 70 mM sucrose, 10 mM HEPES, 1 mM EDTA, adjust the pH to 7.4 with KOH). Chondrisome preparation protein content was assessed by BCA (example A-5) and the preparation remains on ice until the following protocol was initiated (within 120 minutes from isolation).

Leigh fibroblasts were seeded at 25,000 cells per well in one well of a quadrant glass-bottom imaging dish (Greiner Bio-One). After 24 hours, cells were treated with 8 ug of Mito-DsRED chondrisomes per well in 500 μL (described above) media or an equivalent volume of MSHE buffer as control. Cells were incubated with chondrisomes for 24 hours. Prior to imaging cells were incubated with 50 nM Lysotracker Green for 30 minutes. Cells were then imaged on a Zeiss LSM 710 confocal microscope with a 63× oil immersion objective while maintained at 37° C. and 5% $CO_2$. Lysotracker green was subjected to 488 nm argon laser excitation and emission was recorded through a band pass 500 to 550 nm filter. Mito-DsRED was subjected to 543 nm laser excitation and emission was recorded through a band-pass 550 to 610 nm filter. To observe individual chondrisomes Z-stack images were acquired in series of 6 slices per cell with a 1 airy unit pinhole ranging in thickness from 0.5-0.8 μm per slice. At least 3 different fields were imaged containing 4-30 cells per field, and the resulting analysis was conducted on 12-120 cells in total.

Colocalization of donor chondrisomes with recipient cell lysosomes was calculated by summing all events where there was greater than 80% pixel overlap between a given Mito-DsRED-positive chondrisome region and a Lysotracker green-positive lysosomal regions within an analyzed z-plane. All z-plane images were processed in ImageJ (NIH) and chondrisomes and lysosomal regions were thresholded using the Moments threshold algorithm to identify regions after subtracting background. Using this imaging assay and colocalization calculation, >70% of the donor chondrisomes (Mito-DsRED) were found to be targeted to endogenous cellular lysosomes. Analogous imaging and localization quantification protocols were used to determine targeting levels to other subcellular locations as detailed in the table below.

After staining, the chondrisome preparation was pelleted by centrifugation (10,000g for 10 minutes), resuspended in 1 mL of MSHE, and the centrifugation and resuspension was repeated an additional two times to wash away excess dye. After the last wash, chondrisomes were pelletd and resuspended in MSHE to a final concentration of 1 ug/uL, and applied to recipient Leigh fibroblast cells and to empty wells for control readings. The control wells were imaged immediately to quantify the signal level corresponding to the Mito Tracker loaded cargo.

Leigh fibroblasts were seeded at 25,000 cells per well in one well of a quadrant glass-bottom imaging dish (Greiner Bio-One). After 24 hours, cells were stained with 200 nM MitoTracker Green (ThermoFisher) for 60 minutes at 37° C., 5% CO2. Following staining, cells were washed with DMEM growth medium 3× followed by treatment with 8 ug of Mito Tracker Deep Red-stained muscle chondrisomes per well in 500 μL (described above) media or an equivalent volume of MSHE buffer as control. Cells were incubated

| Subcellular Target | Chondrisome preparation Stain | Target Cell Stain | Quantifying Colocalization Levels | Determined Colocalization Level |
|---|---|---|---|---|
| Cytosol | Expression of Mito-DsRED (250 MOI) in donor cell line. | 50 nM Lysotracker Green for 30 minutes | Fraction of Mito-DsRED-positive events showing no significant colocalization (<80% pixel overlap) with Lysotracker Red regions. | <30% |
| Endogenous Mitochondrial Network | Expression of Mito-DsRED (250 MOI) in donor cell line. | 200 nM MitoTracker Green (ThermoFisher) for 60 minutes at 37 C. | Fraction of Mito-DsRED-positive events showing significant colocalization (>80% pixel overlap) with MitoTracker Green regions. | <10% |
| Lysosome | Expression of Mito-DsRED (250 MOI) in donor cell line. | 50 nM Lysotracker Green for 30 minutes | Fraction of Mito-DsRED-positive events showing significant colocalization (>80% pixel overlap) with Lysotracker Red regions. | >70% |
| Outer membrane | Expression of Mito-DsRED (250 MOI) in donor cell line. | Cells are fixed with 4% paraformaldehyde and stained with rabbit anti-TOMM20 antibody for outer chondrisome membrane, followed by anti-rabbit AlexaFluor 488 staining. | Fraction of Mito-DsRED-positive events showing significant colocalization (>80% pixel overlap) with TOMM20-AlexaFluor 488 (green) regions. | <50% (expected) |

Example F-4: Delivery of a Loaded Cargo

This assay pertains specifically to Leigh syndrome fibroblast cells acquired from Coriell Institute (GM01503) and cultured in DMEM media supplemented with 10% fetal bovine serum (ThermoFisher). Chondrisome preparations were generated (example 1-2a) from leg gastrocnemius muscle from C57bl/6 mice (Charles River Laboratories). The chondrisome preparation was resuspended in MSHE buffer (200 mM mannitol, 70 mM sucrose, 10 mM HEPES, 1 mM EDTA, adjust the pH to 7.4 with KOH). Chondrisome preparation protein content was assessed by BCA (example A-5) and the preparation remains on ice until the following protocol was initiated (within 120 minutes from isolation). Chondrisome preparations were stained with 200 nM MitoTracker Deep Red (ThermoFisher) for 30 minutes at 37° C. in MSHE buffer at a concentration of 0.05 μg/uL.

with chondrisomes for 24 hours. Cells were then imaged on a Zeiss LSM 710 confocal microscope with a 63× oil immersion objective while maintained at 37° C. and 5% CO2. MitoTracker green was subjected to 488 nm argon laser excitation and emission was recorded through a band pass 500 to 550 nm filter. MitoTracker Deep Red was subjected to 633 nm helium/neon laser excitation and emission was recorded through a band-pass 650 to 710 nm filter. To observe individual chondrisomes Z-stack images were acquired in series of 6 slices per cell with a 1 airy unit pinhole ranging in thickness from 0.5-0.8 μm per slice. At least 3 different fields were imaged containing 4-30 cells per field, and the resulting analysis was conducted on 12-120 cells in total.

Delivery of the loaded chondrisome cargo was confirmed by observing MitoTracker Deep Red-positive chondrisome cargo within the recipient cell labeled with MitoTracker green. Images were processed in ImageJ (NIH) and donor/recipient cell chondrisome regions were thresholded using the Moments threshold algorithm to identify regions after subtracting background. Control Leigh fibroblast cells that did not receive Mito Tracker Deep Red-loaded chondrisome cargo were also imaged with identical settings and analyzed similarly to confirm that no MitoTracker Deep Red-positive signal was observed; thus the threshold was set appropriately so that the number of identified MitoTracker Deep Red-positive chondrisomes per cell was ≤1. Uptake of cargo loaded chondrisomes is defined as positive identification of ≥2 Mito Tracker Deep Red-positive chondrisomes) in a cell. Using this assay we determined that imaged recipient cells showed uptake of loaded chondrisomes. In this example we determined that 30% of the imaged recipient cells showed uptake of donor chondrisomes.

Example F-5: Delivery of an Engineered Cargo

This assay pertains specifically to Leigh syndrome fibroblast cells acquired from Coriell Institute (GM01503) and cultured in DMEM media supplemented with 10% fetal bovine serum (ThermoFisher). Chondrisome preparations were generated (example 1-1) from Hela cells. Prior to chondrisome isolation, Hela cells were transduced with adenovirus (250 viral particles/cell) for chonriosome-targeted DsRED fluorescent protein (mito-DsRED) and expression was enabled for 72 hours before chondrisome isolation. After chondrisome isolation, the chondrisome sample was resuspended in MSHE buffer (200 mM mannitol, 70 mM sucrose, 10 mM HEPES, 1 mM EDTA, adjust the pH to 7.4 with KOH). Chondrisome preparation protein content was assessed by BCA (example A-5) and the preparation remains on ice until the following protocol was initiated (within 120 minutes from isolation).

Leigh fibroblasts were seeded at 25,000 cells per well in one well of a quadrant glass-bottom imaging dish (Greiner Bio-One). After 24 hours, cells were treated with 8 ug of Mito-DsRED chondrisomes per well in 500 μL (described above) media or an equivalent volume of MSHE buffer as control. Cells were incubated with chondrisomes for 24 hours. Prior to imaging cells were incubated with 200 nM Mito Tracker Green for 60 minutes, followed by three media washes. Cells were then imaged on a Zeiss LSM 710 confocal microscope with a 63× oil immersion objective while maintained at 37° C. and 5% CO2. MitoTracker Green was subjected to 488 nm argon laser excitation and emission was recorded through a band pass 500 to 550 nm filter. Mito-DsRED was subjected to 543 nm laser excitation and emission was recorded through a band-pass 550 to 610 nm filter. To observe individual chondrisomes Z-stack images were acquired in series of 6 slices per cell with a 1 airy unit pinhole ranging in thickness from 0.5-0.8 μm per slice. At least 3 different fields were imaged containing 4-30 cells per field, and the resulting analysis was conducted on 12-120 cells in total.

Delivery of the engineered chondrisome cargo was confirmed by observing Mito-DsRED-positive chondrisome cargo within the recipient cell labeled with MitoTracker green. Images were processed in ImageJ (NIH) and donor/recipient cell chondrisome regions were thresholded using the Moments threshold algorithm to identify regions after subtracting background. Control Leigh fibroblast cells that did not receive Mito-DsRED-engineered chondrisome cargo were also imaged with identical settings and analyzed similarly to confirm that no Mito-DsRED-positive signal was observed; thus the threshold was set appropriately so that the number of identified Mito-DsRED-positive chondrisomes per cell was ≤1. Uptake of chondrisomes with engineered cargo is defined as positive identification of >2 Mito-DsRED-positive chondrisomes) in a cell. Using this assay we determined that imaged recipient cells showed uptake of chondrisomes with engineered cargo. In this example we determined that 30% of the imaged recipient cells showed uptake of donor chondrisomes.

Example F-6: Chemical Modulation of Subcellular Chondrisome Targeting

This assay pertains specifically to Leigh syndrome fibroblast cells acquired from Coriell Institute (GM01503) and cultured in DMEM media supplemented with 10% fetal bovine serum (ThermoFisher). Chondrisome preparations were generated (example 1-1) from Hela cells. Prior to chondrisome isolation, Hela cells were transduced with adenovirus (250 viral particles/cell) for chonriosome-targeted DsRED fluorescent protein (mito-DsRED) and expression was enabled for 72 hours before chondrisome isolation. After chondrisome isolation, the chondrisome sample was resuspended in MSHE buffer (200 mM mannitol, 70 mM sucrose, 10 mM HEPES, 1 mM EDTA, adjust the pH to 7.4 with KOH). Chondrisome preparation protein content was assessed by BCA (example A-5) and the preparation remains on ice until the following protocol was initiated (within 120 minutes from isolation).

Leigh fibroblasts were seeded at 25,000 cells per well in one well of a quadrant glass-bottom imaging dish (Greiner Bio-One). After 24 hours, cells were treated with 8 μg of Mito-DsRED chondrisomes per well in 500 μL (described above) media or an equivalent volume of MSHE buffer as control. Cells were incubated with chondrisomes for 24 hours. To enhance endosomal escape of the delivered chondrisome cargo, recipient Leigh fibroblasts were concomitantly treated with 30 μg/mL chloroquine in order to inhibit lysosomal acidification/degradation and reduce the fusion of endosomes with cargo to lysosomes. Cells were incubated with chondrisomes with or without chloroquine for 24 hours. Prior to imaging cells were incubated with 200 nM MitoTracker Green for 60 minutes, followed by three media washes. Cells were then imaged on a Zeiss LSM 710 confocal microscope with a 63× oil immersion objective while maintained at 37° C. and 5% CO2. MitoTracker Green was subjected to 488 nm argon laser excitation and emission was recorded through a band pass 500 to 550 nm filter. Mito-DsRED was subjected to 543 nm laser excitation and emission was recorded through a band-pass 550 to 610 nm filter. To observe individual chondrisomes Z-stack images were acquired in series of 6 slices per cell with a 1 airy unit pinhole ranging in thickness from 0.5-0.8 μm per slice.

Enhanced delivery of the chondrisome cargo was confirmed by observing Mito-DsRED-positive chondrisome cargo within the recipient cell labeled with MitoTracker green. Images were processed in ImageJ (NIH) and donor/recipient cell chondrisome regions were thresholded using the Moments threshold algorithm to identify regions after subtracting background. Control Leigh fibroblast cells that did not receive Mito-DsRED-engineered chondrisome cargo were also imaged with identical settings and analyzed similarly to confirm that no Mito-DsRED-positive signal was observed; thus the threshold was set appropriately so that the number of identified Mito-DsRED-positive chondrisomes per cell was ≤1. In this assay we define positive uptake by a recipient cell as identification of >2 Mito-DsRED-positive chondrisomes in a cell. At least 3 different fields were imaged containing 4-30 cells per field, and the resulting analysis was conducted on 12-120 cells in total. Using this assay, we determined there was a 15-45% increase in proportion of cells taking up chondrisomes from the non-treated to chloroquine treated groups. In this example we determined there was an increase in cellular uptake of chondrisomes following treatment with chloroquine: from 30% of non-chloroquine treated cells taking up donor chondrisomes to 40% in chloroquine treated, and a 4-fold increase in number of donor chondrisomes per recipient cell.

Example F-7: Proportion of Delivered Chondrisomes Maintain an Active Membrane Potential This assay pertains specifically to Leigh syndrome fibroblast cells acquired from Coriell Institute (GM01503) and cultured in DMEM media supplemented with 10% fetal bovine serum (ThermoFisher). Chondrisome preparations were generated (example 1-1) from Hela cells. Chondrisome preparation protein content was assessed by BCA (example A-5) and the preparation remains on ice until the following protocol was initiated (within 20 minutes from isolation). Prior to chondrisome isolation, Hela cells were transduced with adenovirus (250 viral particles/cell) for chonriosome-targeted DsRED fluorescent protein (mito-DsRED) and expression was enabled for 72 hours before chondrisome isolation. After chondrisome isolation, the chondrisome sample was resuspended in MSHE buffer (200 mM mannitol, 70 mM sucrose, 10 mM HEPES, 1 mM EDTA, adjust the pH to 7.4 with KOH). Protein concentration of the chondrisome sample was determined by BCA assay (Pierce).

Leigh fibroblasts were seeded at 25,000 cells per well in one well of a quadrant glass-bottom imaging dish (Greiner Bio-One). After 24 hours, cells were treated with 8 μg of mito-GFP chondrisomes from Hela cells per well in 500 μL media or an equivalent volume of MSHE buffer as control. Cells were incubated with chondrisomes for 24 hours, followed by washing with PBS three times and growth medium was replaced. Prior to imaging, cells were stained with tetramethylrhodamine ester (TMRE, 15 nM) for 1 hour. Cells were washed one time and growth medium with 15 nM TMRE was replaced. Cells were then imaged on a Zeiss LSM 710 confocal microscope with a 63× oil immersion objective while maintained at 37° C. and 5% CO2. Mito-GFP was subjected to 488 nm argon laser excitation and emission was recorded through a band pass 500 to 550 nm filter. TMRE was subjected to 5433 nm helium/neon laser excitation and emission was recorded through a band-pass 550 to 610 nm filter. To observe individual chondrisomes Z-stack images were acquired in series of 6 slices per cell with a 1 airy unit pinhole ranging in thickness from 0.5-0.8 μm per slice. At least 3 different fields were imaged containing 4-30 cells per field, and the resulting analysis was conducted on 12-120 cells in total.

Delivery of the chondrisomes with a significant membrane potential was quantified by measuring the average TMRE fluorescence intensity of mito-GFP-positive chondrisome cargo that were localized within the recipient cell network (identified with TMRE). Images were processed in ImageJ (NIH) and donor/recipient cell chondrisome regions were thresholded with the Moments threshold algorithm to identify regions after subtracting background. Mito-GFP-positive chondrisome regions (donor) were determined to have a significantly active membrane potential if the average TMRE fluorescence intensity for the mito-GFP region was >50% of the average TMRE fluorescence intensity for the entire cell. Control Leigh fibroblast cells that did not receive mito-GFP-engineered chondrisome cargo were also imaged with identical settings to verify that no mito-GFP-positive signal was observed; thus the threshold was set appropriately so that the number of identified Mito-DsRED-positive chondrisomes per cell was ≤1. Using this assay, we determined that delivery of the chondrisome preparation resulted in 0.1%-10% of the total delivered chondrisomes having an active membrane potential.

Example F-8: Persistence of Delivered Chondrisomes

This assay pertains specifically to Leigh syndrome fibroblast cells acquired from Coriell Institute (GM01503) and cultured in DMEM media supplemented with 10% fetal bovine serum (ThermoFisher). Chondrisome preparations were generated (example 1-1) from Hela cells. Prior to chondrisome isolation, Hela cells were transduced with adenovirus (250 viral particles/cell) for chonriosome-targeted DsRED fluorescent protein (mito-DsRED) and expression was enabled for 72 hours before chondrisome isolation. After chondrisome isolation, the chondrisome sample was resuspended in MSHE buffer (200 mM mannitol, 70 mM sucrose, 10 mM HEPES, 1 mM EDTA, adjust the pH to 7.4 with KOH). Chondrisome preparation protein content was assessed by BCA (example A-5) and the preparation remains on ice until the following protocol was initiated (within 120 minutes from isolation).

Leigh fibroblasts were seeded at 25,000 cells per well in one well of a quadrant glass-bottom imaging dish (Greiner Bio-One). After 24 hours, cells were treated with 8 μg of Mito-DsRED chondrisomes per well in 500 μL (described above) media or an equivalent volume of MSHE buffer as control. Cells were incubated with chondrisomes for 24 hours. Prior to imaging cells were incubated with 200 nM Mito Tracker Green for 60 minutes, followed by three media washes. Cells were then imaged on a Zeiss LSM 710 confocal microscope with a 63× oil immersion objective while maintained at 37° C. and 5% CO2. Mito Tracker Green was subjected to 488 nm argon laser excitation and emission was recorded through a band pass 500 to 550 nm filter. Mito-DsRED was subjected to 543 nm laser excitation and emission was recorded through a band-pass 550 to 610 nm filter. To observe individual chondrisomes Z-stack images were acquired in series of 6 slices per cell with a 1 airy unit pinhole ranging in thickness from 0.5-0.8 μm per slice. Cells were imaged at 24 hr time intervals over the course of 5 days. At least 3 different fields were imaged containing 4-30 cells per field, and the resulting analysis was conducted on 12-120 cells in total.

Residence time of the delivered chondrisome cargo was confirmed by observing Mito-DsRED-positive chondrisome cargo within the recipient cell labeled with MitoTracker green. Images were processed in ImageJ (NIH) and donor/recipient cell chondrisome regions were thresholded using the Moments threshold algorithm to identify regions after subtracting background. Control Leigh fibroblast cells that did not receive Mito-DsRED-engineered chondrisome cargo were also imaged with identical settings and analyzed similarly to confirm that no Mito-DsRED-positive signal was observed; thus the threshold was set appropriately so that the number of identified Mito-DsRED-positive chondrisomes per cell was ≤1. The presence of recipient cells showing uptake of donor chondrisomes (defined as positive identification of >2 Mito-DsRED-positive chondrisomes) was observable up to 5 days after application of donor chondrisomes to recipient cells.

Example F-9: Quantification of Lipid Utilization

This assay pertains specifically to INS1 cells cultured in RPMI media supplemented with 10% fetal bovine serum (ThermoFisher), 11 mM glucose with 500 μM Oleate+ Palmitate. Chondrisome preparations were generated (example 1-4) from brown adipose tissue from C57bl/6 mice (Charles River Laboratories). Chondrisome preparation protein content was assessed by BCA (example A-5) and the preparation remains on ice until the following protocol was initiated (within 20 minutes from isolation). The chondrisome sample was resuspended in SHE buffer (250 mM sucrose, 5 mM HEPES, 2 mM EDTA, adjust the pH to 7.2 with KOH). Chondrisomes were subsequently pelleted by centrifugation (10,000g for 10 minutes), resuspended in RPMI media, and applied to recipient INS1 cell at a concentration of 40 μg per 100,000 cells.

INS1 cells were seeded at 30,000 cells per well in 96 well plate. After 24 hours, BAT chondrisome preparations were applied to the cells. Cells were incubated with or without chondrisomes for 48 hours at 37° C. and 5% CO2. Prior to imaging lipid droplets, cells were incubated with 3.1 μM Nile Red for 15 minutes in RPMI media while maintained at 37° C. and 5% CO2. Cells were then washed with PBS and imaged on Celigo Imaging Cell Cytometer (Brooks Life Science Systems). Cellular lipid levels were determined by average integrated intensity of Nile red signals across the cells over the entire well. To quantify red fluorescence intensity per cell in INSIs, cells were imaged using red (531/40 excitation; 629/53 emission) fluorescence channel in each well. Analysis parameters for images acquired by Celigo Imaging Cell Cytometer were optimized to identify individual INS1 cells based on fluorescence, and the average red fluorescence intensity per cell was determined. Analysis settings were determined to identify fluorescent cells distinguishable from background fluorescence. Exposure and analysis settings were kept constant for each condition. Average fluorescence intensity per cell values were determined by the average integrated intensity per cell values in order to exclude error from background pixels included in identified cell regions. At least 5,000 cells were analyzed per well, with 3 well replicates per experiment. Using this assay, we find that the delivery of the chondrisome preparation results in a decrease in cellular lipid levels by 15-45% relative to the control group that did not receive chondrisomes (see FIG. 1).

Example F-10: Quantification of Exogenous Protein Delivery

This assay pertains specifically to HEPG2 cells cultured in DMEM media supplemented with 10% fetal bovine serum (ThermoFisher). Chondrisome preparations were generated (example 1-4) from brown adipose tissue from C57bl/6 mice (Charles River Laboratories). Chondrisome preparation protein content was assessed by BCA (example A-5) and the preparation remained on ice until the following protocol was initiated (within 20 minutes from isolation). The chondrisome sample was resuspended in SHE buffer (250 mM sucrose, 5 mM HEPES, 2 mM EDTA, adjust the pH to 7.2 with KOH). Chondrisomes were subsequently pelleted by centrifugation (10,000g for 10 minutes), resuspended in DMEM media, and applied to recipient HEPG2 cell at a concentration 20 μg per 100,000 cells.

HEPG2 cells were seeded at 100,000 cells per well in 12 well plate. After 24 hours, BAT chondrisomes were applied to the cells. Cells were incubated with chondrisomes for 24 and 48 hours at 37° C. and 5% CO2. Prior to lysing the HEPG2 cells and extracting protein, DMEM media was collected from each well, cells were detached from wells by using 0.25% Trypsin. Cells were pelleted by centrifugation (1500g for 10 min) and the supernatant media was collected to remove any exogenous brown adipocyte chondrisomes that had not been internalized into the recipient HEPG2 cells. The cell pellet was lysed using RIPA buffer plus protease inhibitor (1:100) on ice. Cell pellet was incubated on ice for 15-30 minutes before being centrifuged at 12,000g for 10 min at 4° C. Cell lysate was then collected maintained at −20° C. for western blot assay.

Figure 2:
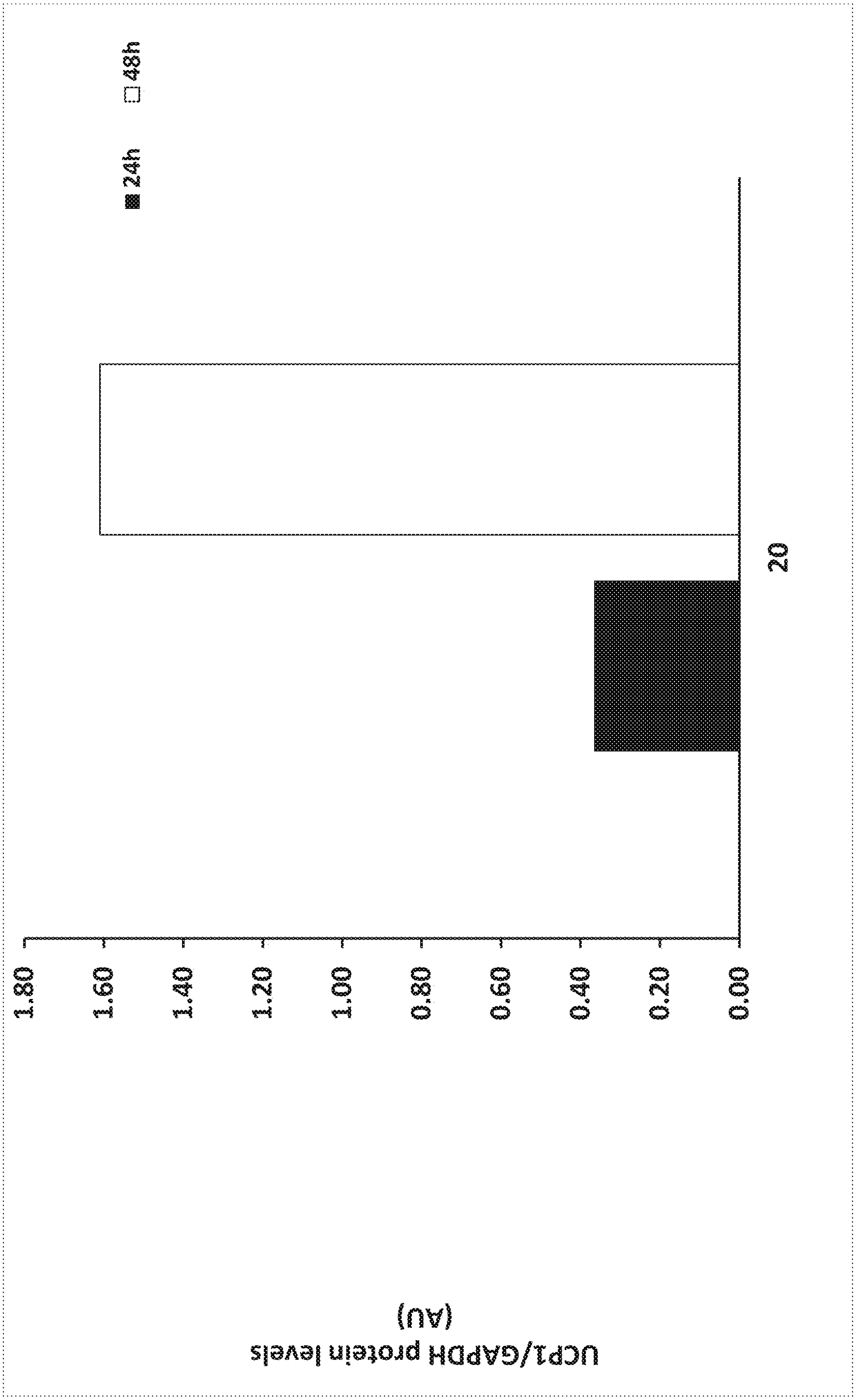
FIG. 2 is a graph showing quantification of UCP1 protein levels normalized to their corresponding loading control (GAPDH) in HEPG2 cells 24 h and 48 h after receiving 20 ug of BAT chondrisome protein/100K cells. Bar graphs represent average #SD.

Protein samples were made and run through the 4-12% gradient gel via a standard western blot assay (Trudeau et al., The Journal of Cell Biologyl; 214 (1): 25). Membranes were probed for UCP1 (abcam ab10983) and GAPDH antibodies (Cell Signaling 2118S). UCP1 protein level were measured by densitometery relative to GAPDH protein level, using ImageJ software. FIG. 2 shows that the recipient cells took up the exogenous proteins. Using this assay we determined 0.37+/−0.2 and 1.61+/−0.8 of UCP1/GAPDH protein levels (AU) at 24 hrs and 48 hrs after application of the chondrisomes respectively.

Example F-11: Increase in Uncoupled Respiration

This assay pertains specifically to HEPG2 cells cultured in DMEM media supplemented with 10% fetal bovine serum (ThermoFisher). Chondrisome preparations were generated (example 1-4) from brown adipose tissue from C57bl/6 mice (Charles River Laboratories). Chondrisome preparation protein content was assessed by BCA (example A-5) and the preparation remained on ice until the following protocol was initiated (within 20 minutes from isolation). The chondrisome sample was resuspended in SHE buffer (250 mM sucrose, 5 mM HEPES, 2 mM EDTA, adjust the pH to 7.2 with KOH).

HEPG2 cells were seeded at 12,000 cells per well in a 96-well Seahorse plate (Agilent). After 24 hours, cells were treated with 4-90-ug of BAT chondrisome protein per 100,000 cell in 200 μL media. Cells were incubated with chondrisomes for 48 hours and oxygen consumption rates of HEPG2 cells were subsequently measured by XF96 bioenergetic assay (Agilent).

Figure 3:
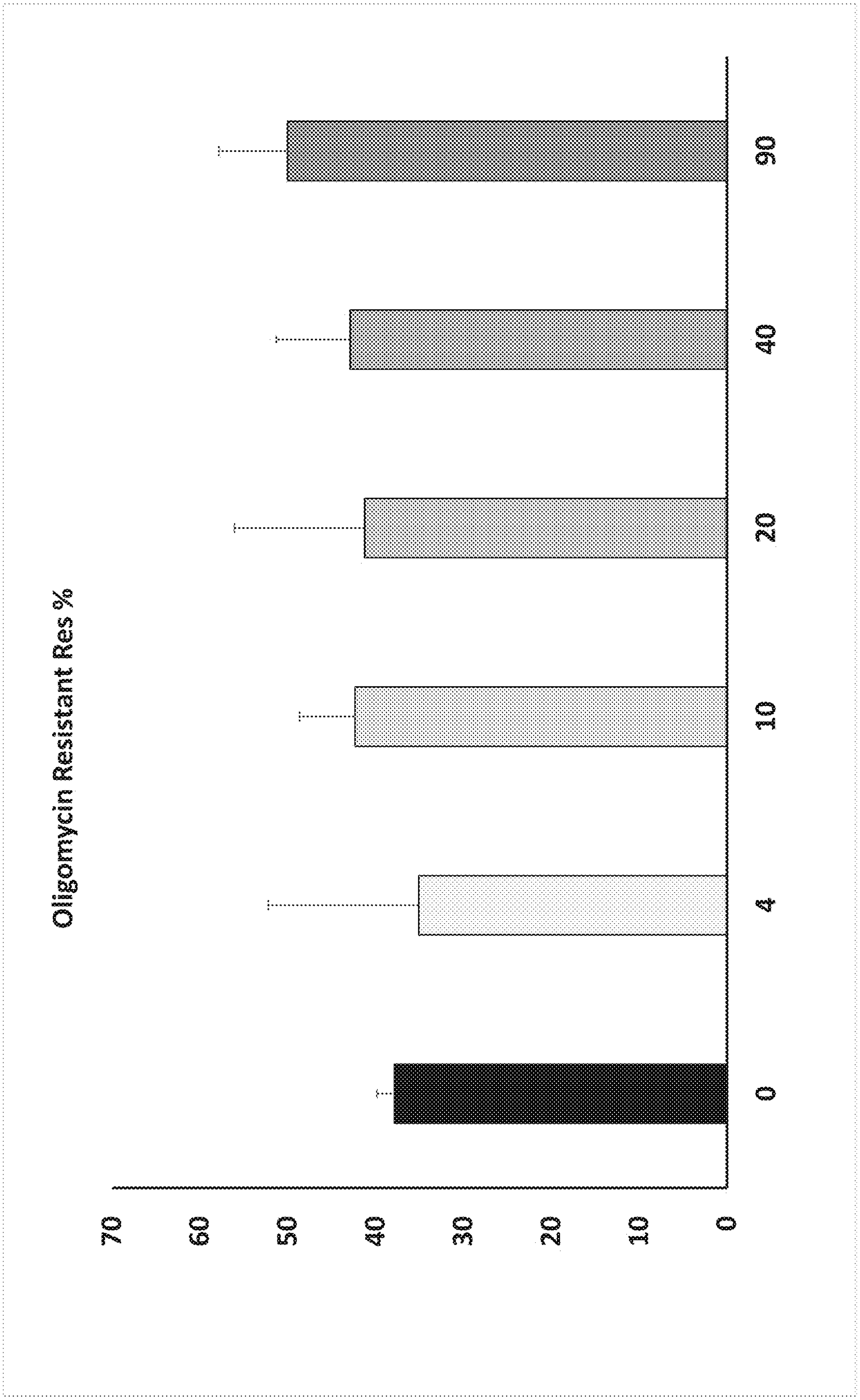
FIG. 3 is a graph showing quantification of uncoupled mitochondrial respiration after oligomycin injection in control HEPG2 cells and HEPG2 cells that received 4 to 90 μg BAT chondrisome protein/100K cells. Bar graphs represent average±SD.

Oxygen consumption assays were initiated by removing growth medium, replacing with low-buffered DMEM minimal medium containing 2.5 mM glucose and 1 mM glutamine (Agilent) and incubating at 37° C. for 30 minutes to allow temperature and pH to reach equilibrium. The microplate was then assayed in the XF96 Extracellular Flux Analyzer (Agilent) to measure extracellular flux changes of oxygen and pH in the media immediately surrounding adherent cells. After obtaining steady state oxygen consumption and extracellular acidification rates, Palmitate & BSA (0.3 mM palmitate; 1.2 mM BSA) plus carnitine (0.5 mM), oligomycin (2 μM), which inhibits ATP synthase, and proton ionophore FCCP (carbonyl cyanide 4-(trifluoromethoxy)phenylhydrazone; 2 μM), which uncouples chondrisomes, were injected sequentially through reagent delivery chambers for each well in the microplate to obtain values for maximal oxygen consumption rates. Finally, 4 μM antimycin A (inhibitor of chondrisome complex III) was injected in order to confirm that respiration changes were due mainly to chondrisome respiration. The uncoupled respiration ratio (expressed as %) of anitimycin A normalized oligomycin respiration rate and antimycin normalized fatty acid respiration rate (100* (Oligomycin OCR-Antimycin A OCR)/(Palmitate-BSA OCR-Antimycin A OCR)) was calculated for both cells treated with chondrisomes and control cells that were untreated. Treated HEPG2 cells were shown to have an increase in the uncoupled respiration ratio of 10-30% over untreated cells, see FIG. 3. In this example the increase was shown to be >10%.

Example F-12: Inhibition of MPTP Opening Following Delivery of the Chondrisome Preparation Quantification of the impact of delivery of chondrisome preparation to a cell's MPTP state was achieved with a commercially available kit (MitoProbe Transition Pore Assay Kit, Molecular Probes M34153). Chondrisome preparations were generated from human fibroblast (example 1-1) or human platelets (example 1-3b). Chondrisome preparation protein content was assessed by BCA (example A-5) and the preparation remains on ice until the following protocol was initiated (within 120 minutes from isolation). The assay was performed following the manufacturer's recommendations but briefly described here.

Though any cell type can be used for the assay, this example pertains specifically to Leigh syndrome fibroblast cells acquired from Coriell Institute (GM01503) and cultured in DMEM media supplemented with 10% fetal bovine serum (ThermoFisher). Cells were seeded at a density of 40,000 cells/well in a 24-well plate in DMEM media supplemented with 10% FBS. 3 wells were for each of: chondrisome preparation, no chondrisome preparation control. The chondrisome preparation was added to the 3 test article wells at a concentration of 2 μg/well. Cells were allowed to incubate for 24 hours in DMEM media supplemented with 10% FBS. Following the incubation period, cells were washed in phosphate-buffered saline (PBS). Cells were trypsinized to remove from the cell culture plate and centrifuged for 200×g for 5 minutes at room temperature. The supernatant was discarded and the cells were resuspended in prewarmed HBSS/Ca. Cell density was determined via hemocytometer and adjusted to $10^6$ cells/mL. The final volume can be divided into 3×1 ml aliquots in flow cytometry tubes per replicate to enable 3 chemical treatments for each: one will receive calcein AM only (tube 1), one will contain calcein AM and CoCl2 (tube 2), and the final one will contain calcein AM, CoCl2, and ionomycin (tube 3). A sample of the cells containing no added reagents was also prepared for instrument set up. Tubes 1, 2, and 3, receive 5 μL of the 2 μM working solution of calcein AM. Tubes 2 and 3 receive 5 μL of CoCl2 (supplied with the kit). Tube 3 receives 5 μL of ionomycin. All tubes were mixed well and incubated at 37° C. for 15 minutes, protected from light.~3.5 mL of HBSS/Ca buffer was added to the tubes and the cells were pelleted by centrifugation. This step serves to remove excess staining and quenching reagents. The pellet was resuspended in ~400 μL of flow cytometric analysis buffer. After staining, samples on ice and analyzed within one hour.

The samples were analyzed using a flow cytometer with 488 nm excitation and emission filters appropriate for fluorescein. The change in fluorescence intensity between tubes 2 and 3 indicates the continuous activation of chondrisome permeability transition pores. The pore state was quantified by the ratio of the ratio of tube 3 fluorescence (open pore): tube 2 fluorescence (chondrisome signal only), with higher values indicating a more open pore. Using this assay, a 2 μg dose of chondrisomes showed<10% increase in pore opening relative to untreated cells.

Example F-13: Increased Akt Activation

Quantification of the impact of delivery of chondrisome preparation to a cell's AKT activation state was achieved with a commercially available kit (Akt Activity Assay kit, Abcam, ab65786). Chondrisome preparations were generated from human fibroblasts (example 1-1) or human platelets (1-3b). Chondrisome preparation protein content was assessed by BCA (example A-5) and the preparation remains on ice until the following protocol was initiated (within 20 minutes from isolation). The assay was performed following the manufacturer's recommendations but briefly described here.

Though any cell type can be used for this assay, this particular example pertains specifically to Leigh syndrome fibroblast cells acquired from Coriell Institute (GM01503) and cultured in DMEM media supplemented with 10% fetal bovine serum (ThermoFisher). Cells were seeded at a density of 80,000 cells/well in a 12-well plate in DMEM media supplemented with 10% FBS. Duplicate wells were for each of: chondrisome preparation, no chondrisome preparation control. The chondrisome preparation was added to the 2 test article wells at a concentration of 8 and 32 μg/well. Cells were allowed to incubate for 24 hours in DMEM media supplemented with 10% FBS. Following the incubation period, cells were washed in ice-cold phosphate-buffered saline (PBS). Cells were lysed by adding 100 μL of ice-cold Kinase Extraction Buffer and scraping with a cell scraper to collect the lysate. The collected samples were incubated on ice for 5 minutes followed by centrifugation at 13,000 rpm for 10 minutes at 4° C. The supernatant was transferred to a new tube as the cell lysate, and duplicate samples were combined to make one sample per group.

2 μL of Akt Specific Antibody was added to the 200 μL of cell lysate and incubated at room temperature on a rotator for 45 minutes. Next, 50 μL of Protein A-Sepharose slurry was added to each sample followed by incubation at room temperature on a rotator for 1 hour. The samples were centrifuged at 15,000 rpm for 2 minutes, and the supernatant was aspirated. The pelleted beads were washed once by adding 0.5 mL of Kinase Extraction buffer, followed by centrifugation to pellet the beads and aspiration of the supernatant. The pelleted beads were washed once more by adding 0.5 mL Kinase Assay buffer, followed by centrifugation to pellet the beads and aspiration of the supernatant. 50 μL of Kinase Assay Buffer was added to the pelleted beads to resuspend. Subsequently 2 μL of GSK-3α Protein/ATP Mixture was added and the sample was incubated at 30° C. for 2 hours. The beads were pelleted by centrifugation and 45 μL of 1× NuPAGE LDS Sample Buffer (ThermoFisher #NP0007, diluted in Kinase Assay Buffer) was added to the beads to resuspend them. The samples were then boiled at 95° C. for 3 minutes, followed by centrifugation to pellet the beads. The supernatant was transferred to a new microcentrifuge tube and used as the protein samples for Western blot analysis.

Figure 4:
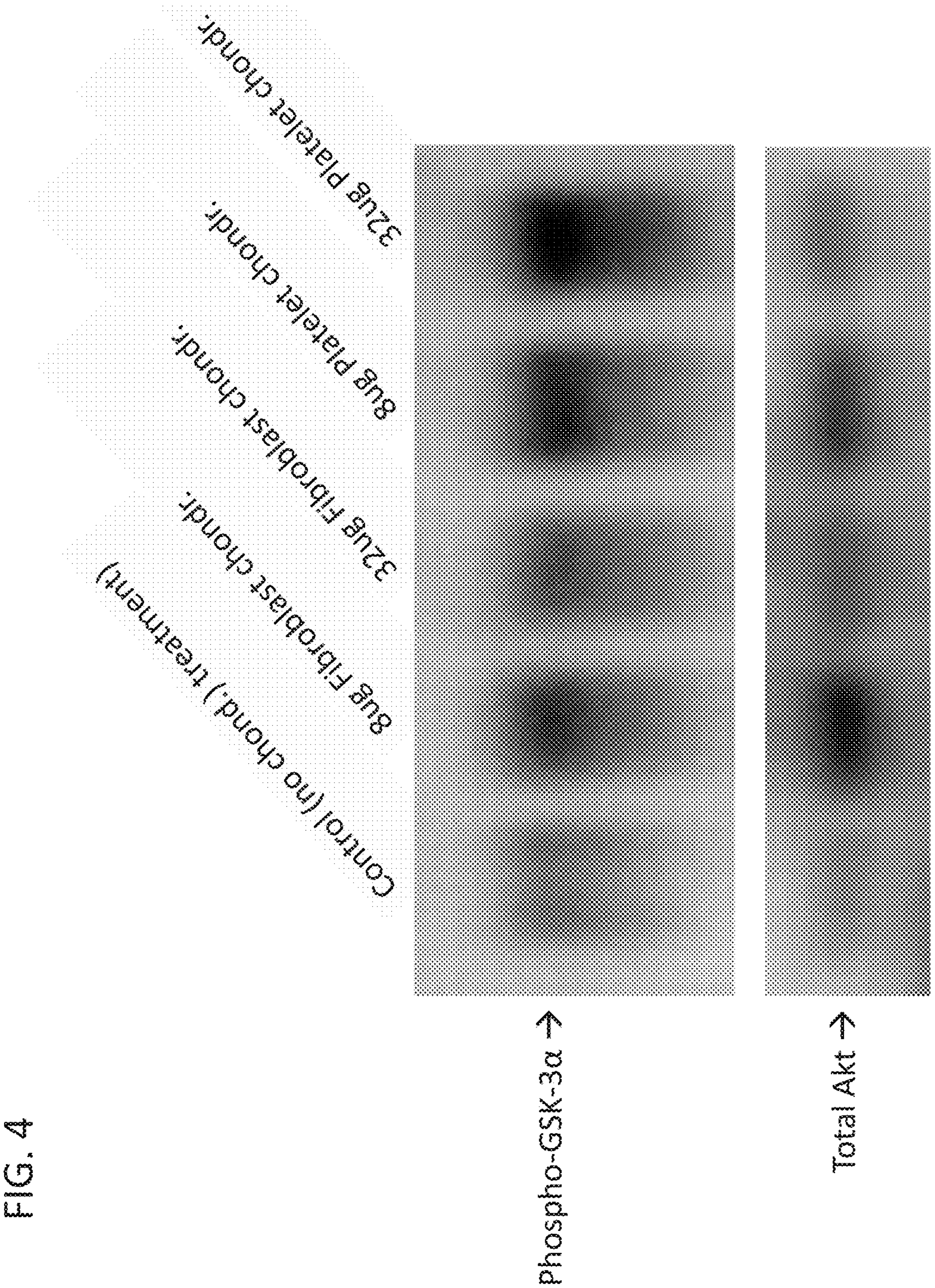
FIG. 4 is an image showing Leigh fibroblasts treated with 8 or 32 ug of human fibroblast or human platelet chondrisomes (chondr.) and assessed for phospho-GSK-3a and total Akt levels with Akt activity assay kit and western blot analysis. Representative bands for phospho-GSK-3a and total Akt are shown for the indicated conditions.

Protein samples were run through the 4-12% gradient gel via a standard western blot assay (see Example F-10) and transferred to a PVDF membrane. After blocking in 3% BSA in tris-buffered saline with 0.2% Tween-20 (TBST), the membrane was probed with rabbit anti-Phospho-GSK–3a (Ser 21) Specific Antibody at a 1:1000 dilution in blocking buffer. Following three washes with TBST, the membrane was incubated with 1:3000 anti-rabbit IgG, HRP-linked antibody (Cell Signaling #7074S) diluted in blocking buffer and then washed three times with TBST before exposing to a chemiluminescent SuperSignal West Femto Maximum Sensitivity Substrate (Thermo Scientific #34095) to detect the protein signals. Total Akt levels in the samples was confirmed by stripping the membrane with 6.2M guanidinium hydrochloride and reprobing with Akt antibody (provided with kit). The densitometric values were used for adjustment of any differences in loading. Densitometric analysis of the Western blot signals was performed at non-saturating exposures and analyzed using the ImageJ gel analyzer function. Representative bands are shown from Leigh fibroblasts treated with 8 or 32 μg of human fibroblast or platelet chondrisomes for 24 hours. Treatment with 32 μg isolated chondrisomes increased phospho-GSK−3a/total Akt levels in Leigh fibroblast cells 200+80% (see FIG. 4).

Example F-14: Modulation of Cellular Nicotinamide Adenine Dinucleotide Pools

Modulation of reductive stress in cells that have been treated with donor chondrisomes can be determined using commercially-available NAD/NADH kits, such as the abcam colorimetric assay (catalog number ab65348). Briefly, cells can be treated with chondrisomes isolated from human tissue, whole blood, blood-derived products, or cultured fibroblasts for 24-72 hours, as described in previous examples. Upon cessation of treatment, cells are harvested, washed in PBS, and pelleted by centrifuging at 2,000×g for 5 min. The supernatant is discarded, and the cell pellet is treated with the provided NAD/NADH extraction buffer and two freeze/thaw cycles (20 minutes on dry ice followed by 10 minutes at room temperature). The extract is then centrifuged at 12,000×g for 5 minutes at 4° C. to pellet any insoluble material. The resulting supernatant contains the extracted NAD/NADH, which is then transferred to a separate microcentrifuge tube.

Within the cellular extract, there are potentially numerous NADH-consuming enzymes that need to be removed prior to proceeding with the assay. To accomplish this removal, the extracts are filtered through 10 kDa spin columns, also available through abcam (catalog number ab93349). The samples are pipetted into the spin colums, followed by centrifugation at 10,000×g for 10 minutes at 4° C. The filtrate is then collected and placed on ice.

In order to measure total nicotinamide adenine dinucleotide pools (i.e., $NAD^+$+NADH), the filtrate can be assayed as is. However, in order to assay NADH alone, all $NAD^+$ must be decomposed from the sample. To accomplish this, an aliquot (200 μL) of the cellular extract is pipetted into a microcentrifuge tube and heated at 60° C. for 30 minutes in a heating block, leading to the selective decomposition of $NAD^+$. Samples are then cooled on ice.

The total nicotinamide adenine dinucleotide and NADH samples are pipetted into a 96-well microplate (1-50 μL/well) along with a NADH standard curve and incubated with the provided NAD Cycling Buffer and Cycling Enzyme Mix for 5 minutes. The NADH Develop is then added to each well, followed by incubation at room temperature for 1-4 hours. During this incubation, multiple readings can be acquired in a plate-reading spectrophotometer set to measure absorbance at 450 nm in kinetic mode. The sample will reach a plateau absorbance value, which can be used in subsequent calculations.

To perform the analysis, the absorbance from the sample alone (no treatment with NADH Developer) should be subtracted from the Developer-treated sample. The corrected absorbance values for the samples are compared against the standard curve and the concentration of total nicotinamide adenine dinucleotide pools and NADH calculated as follows:

$$\text{Total } NAD \text{ Concentration} = (\text{Total } NAD/\text{Sample Volume}) \times Dil.\text{Factor}$$

$$\text{NADH Concentration} = (\text{NADH}/\text{Sample Volume}) \times Dil.\text{Factor}$$

The total NAD and NADH concentrations are then be normalized to the amount of cellular protein, derived from the BCA assay performed following the freeze/thaw extraction step. Treatment with donor chondrisomes should decrease total NAD/NADH ratio compared to the untreated control cells by 5-25%.

Example F-15: Improved Functional Cardiac Metrics

This example assesses the impact of a chondrisome preparation on acute myocardial ischemia in a rabbit model.

The chondrisome preparation was generated as follows: pectoral muscle tissue was obtained from 2 6 mm biopsy samples from a healthy donor rabbit and kept at 4° C. throughout the protocol. Solid tissue was minced into small pieces in PBS without any chelators (e.g EGTA) and then tissue pieces were transferred into isolation buffer (IB; 300 mM sucrose, 10 mM K-HEPES, and 1 mM K-EGTA). The tissue was then homogenized using the "m-mitotissue" mitochondrial isolation program on the Miltenyl GentleMACS Dissociator. 1 mg of bacterial protease (subtilisin A) was added to the homogenate and then incubated on ice for 10 minutes. The solution was then centrifuged at 750g for 4 minutes and the supernatant was sequentially filtered through to 40 μm, 40 μm and 10 μm filters. The filtrate was then centrifuged at 10,000g for 10 minutes to concentrate the chondrisomes. The filtrate was removed and the resulting chondrisome pellet was resuspended in respiration buffer (RB; 250 mM sucrose, 2 mM KH PO 10 mM MgCl 20 mM K-HEPES Buffer (pH 7.2) and 0.5 mM KEGTA (pH 8.0)) and then diluted 10× in the same RB. No BSA was used in any part of the isolation process.

The rabbit model of acute myocardial ischemia was prepared as follows: Male New Zealand White rabbits (2-2.5 kg) were anesthetized with isoflurane and anesthesia depth checked to ensure ear pinch and blink reflex, and jaw tone were lost. Rabbits were intubated and mechanically ventilated with room air. Core temperature was monitored continually and maintained at >36° C. using a heating pad. To define baseline cardiovascular function and hemodynamic parameters, a Doppler echocardiography and electrocardiograms (ECGs) were be recorded. Blood draws for biomarkers quantification were be taken at 0 hrs, 6 hrs and 24 hrs. Pulse oximetry probe on the ear measures heart rate and level of oxygenation. Following baseline acquisitions, surgery was initiated by making a 2-3 cm left intercostal thoracotomy (4th intercostal space) to expose the heart. A snare occluder was be placed around the first antero-lateral branch of the LAD 5 to 10 mm distal from the apex (to obtain as close as possible to 30% of LV AAR required). Heparin was injected (3 mg/kg IV) via a catheter placed in the marginal ear vein before snaring the LAD to prevent the forming of blood clots inside the coronary artery while temporarily occluded. The coronary artery was occluded at time 0, defined by ECG ST segment elevation indicative of myocardial ischaemia (MI).

Experimental protocol: Following 29 min of regional ischemia the chondrisome preparation (or vehicle) was injected into the area at risk in a consistent pattern that covers the blanched area. The chondrisome preparation (between 50-75 minutes following tissue biopsy) was injected at a dose of 6 μg/kg+/−2 μg/kg. Hearts received 8×0.1 ml injections via a sterile 1-ml insulin syringe with a 28-gauge needle. After 30 minutes of acute MI, the occluder was be re-opened to allow reperfusion for a period of 24 h. All closures performed under anesthesia. Animals were weaned from anesthesia and allowed to recover on a warming pad until fully recovered (awake and able to walk on their own). Thirty minutes prior to the end of the procedure, pain prophylaxis medication was administered. At the end of the 24 h reperfusion period, the rabbits were re-anesthetized with isoflurane. Cardiovascular and hemodynamic parameters were measured via Doppler echocardiography, and ECG recording, and blood draws performed. At the end of those procedures, the rabbits were sacrificed and the hearts excised and mounted into a Langendorff apparatus to allow retrograde perfusion of the heart with stains and dyes. Once the blood was flushed out, the LAD was re-occluded with the snare and Evans blue was perfused through the aorta to stain the perfused zone with deep blue color, hence delineating the "At risk" zone as the non-stained area. The hearts were then removed from the Langendorff device. The hearts were cut into transverse slices sections and incubated in TTC for 15 minutes at 37° C. The surviving tissue will turn deep red. Dead tissue will be grey-white. The area at risk of the myocardium was determined by negative staining with Evan's blue, and the infarcted myocardium was gray-white. Morphometric readouts were used to calculate the left ventricular area, risk area, and infarct. Infarct size was then expressed as a percentage of the risk area.

Mean values were calculated for the 8 animals per group (vehicle and chondrisome preparation). Using this model the following efficacy signals were observed with the delivery of the chondrisome preparation:

- Echocardiography measures of cardiac function, Chondrisome vs. vehicle:
  - Improvement of fractional shortening relative to baseline
  - No change in end diastolic volume relative to baseline
  - Improvement of end systolic volume relative to baseline
  - Improvement of stroke volume relative to baseline
  - Improvement of ejection fraction relative to baseline
  - Improvement of cardiac output relative to baseline
  - Improvement of cardiac index relative to baseline

| | % change from baseline | |
|---|---|---|
| | Vehicle | Chondrisome |
| Fractional Shortening | −27 ± 9 | −17 ± 14 |
| End diastolic volume | −9 ± 22 | −10 ± 19 |
| End systolic volume | 48 ± 39 | 37 ± 62 |
| Stroke Volume | −41 ± 19 | −31 ± 22 |
| Ejection Fraction | −36 ± 15 | −23 ± 23 |
| Cardiac Output | −36 ± 22 | −29 ± 20 |
| Cardiac Index | −36 ± 22 | −29 ± 20 |

- Staining assessment of infarcted area:
  - Decrease in infarcted area relative to area at risk
    - Vehicle: group Infarct area as % of area at risk of the left ventricle: 46%±12%
    - Chondrisome group: Infarct area as % of area at risk of the left ventricle: 27%±7%
- Serum markers of cardiac injury:
  - Decreased CKNB levels relative to vehicle at 6 hrs and 24 hrs
  - Decreased cTnI at 6 hrs relative to vehicle

| | 6 hr | | 24 hr | |
|---|---|---|---|---|
| | Vehicle | Chondrisome | Vehicle | Chondrisome |
| CKMB (U/L) | 500 ± 285 | 295 ± 63 | 624 ± 335 | 358 ± 143 |
| cTnI (ng/ml) | 5 ± 2 | 3 ± 2 | 2 ± 2 | 2 ± 2 |

Example F-16: Improved Functional Cardiac Metrics

This example assesses the impact of a chondrisome preparation on acute myocardial ischemia in a rabbit model.

Chondrisome preparation: Pectoral muscle tissue was obtained from 2 6 mm biopsy samples from a healthy rabbit and kept at 4° C. throughout the protocol. Solid tissue was minced into small pieces in 2 ml MSHE (200 mM mannitol, 70 mM sucrose, 10 mM HEPES, 1 mM EDTA, adjust the pH to 7.4 with KOH)+0.5% BSA buffer (0.2-1g tissue per 8 mL of MSHE+0.5% BSA buffer) using scissors if necessary and then homogenized with a glass Potter Elvehjem homogenizer using Teflon pestle operated at 1600 rpm for 15 strokes. The material was centrifuged at 1000 g for 10 min at 4° C. The supernatant was then distributed into 6 2 mL microcentrifuge tubes and centrifuged at 10,000g for 10 min at 4° C. The resulting chondrisome pellets were resuspended in 2 mL of MSHE+0.5% BSA buffer and re-centrifuged at 10,000g for 10 min at 4° C. The final chondrisome pellet was resuspended in 1 ml of delivery buffer (250 mM sucrose, 2 mM KH2PO4, 10 mM MgCl2, 20 mM K-HEPES, 0.5 mM K-EGTA, pH 7.4) and then diluted 10× in the same buffer. Tissue and chondrisome solutions, including buffers, were kept on ice at all times.

Animal model: Male New Zealand White rabbits (2-2.5 kg) were anesthetized with isoflurane and anesthesia depth checked to ensure ear pinch and blink reflex, and jaw tone were lost. Rabbits were intubated and mechanically ventilated with room air. Core temperature was monitored continually and maintained at >36° C. using a heating pad. To define baseline cardiovascular function and hemodynamic parameters, a Doppler echocardiography and electrocardiograms (ECGs) were be recorded. Blood draws for biomarkers quantification were be taken at 0 hrs, 6 hrs and 24 hrs. Pulse oximetry probe on the ear measures heart rate and level of oxygenation. Following baseline acquisitions, surgery was initiated by making a 2-3 cm left intercostal thoracotomy (4th intercostal space) to expose the heart. A snare occluder was placed around the first antero-lateral branch of the LAD 5 to 10 mm distal from the apex (to obtain as close as possible to 30% of LV AAR required). Heparin was injected (3 mg/kg IV) via a catheter placed in the marginal ear vein before snaring the LAD to prevent the forming of blood clots inside the coronary artery while temporarily occluded. The coronary artery was occluded at time 0, defined by ECG ST segment elevation indicative of myocardial ischaemia (MI). Following 29 min of regional ischemia the chondrisome preparation (or vehicle) was injected into the area at risk in a consistent pattern that covers the blanched area.

Experiment: The chondrisome preparation (between 50-75 minutes following tissue biopsy) was injected at a dose of 36+/−5 μg/kg. Hearts received 8×0.1 ml injections via a sterile 1-ml insulin syringe with a 28-gauge needle. After 30 minutes of acute MI, the occluder was re-opened to allow reperfusion for a period of 24 h. All closures performed under anesthesia. Animals were weaned from anesthesia and allowed to recover on a warming pad until fully recovered (awake and able to walk on their own). Thirty minutes prior to the end of the procedure, pain prophylaxis medication was administered.

At the end of the 24 h reperfusion period, the rabbits were re-anesthetized with isoflurane. Cardiovascular and hemodynamic parameters were measured via Doppler echocardiography, and ECG recording, and blood draws performed. At the end of those procedures, the rabbits were sacrificed and the hearts excised and mounted into a Langendorff apparatus to allow retrograde perfusion of the heart with stains and dyes. Once the blood was flushed out, the LAD was re-occluded with the snare and Evans blue was perfused through the aorta to stain the perfused zone with deep blue color, hence delineating the "At risk" zone as the non-stained area. The hearts were then removed from the Langendorff device. The hearts were cut into transverse slices sections and incubated in TTC for 15 minutes at 37° C. The surviving tissue will turn deep red. Dead tissue will be grey-white. The area at risk of the myocardium was determined by negative staining with Evan's blue, and the infarcted myocardium was gray-white. Morphometric readouts were used to calculate the left ventricular area, risk area, and infarct. Infarct size was then expressed as a percentage of the risk area.

Mean values were calculated for the 8 animals per group (vehicle and chondrisome preparation). Using this model the following efficacy signals were observed with the delivery of the chondrisome preparation:

- Echocardiography measures of cardiac function, Chondrisome vs. vehicle:
  - No change in fractional shortening relative to baseline
  - No change in end diastolic volume relative to baseline
  - Smaller volume of end systolic volume relative to baseline for treatment
  - Improvement of stroke volume relative to baseline
  - Improvement of ejection fraction relative to baseline
  - Improvement of cardiac output relative to baseline
  - Improvement of cardiac index relative to baseline

| | % change from baseline | |
|---|---|---|
| | Vehicle | Chondrisome |
| Fractional Shortening | −14 ± 15 | −13 ± 10 |
| End diastolic volume | −18 ± 19 | −22 ± 12 |
| End systolic volume | 17 ± 37 | −18 ± 31 |
| Stroke Volume | −36 ± 21 | −24 ± 12 |
| Ejection Fraction | −25 ± 17 | 0 ± 14 |
| Cardiac Output | −34 ± 30 | −24 ± 17 |
| Cardiac Index | −38 ± 25 | −24 ± 17 |

- Staining assessment of infarcted area:
  - No change in infarcted area relative to area at risk
    - Vehicle: group Infarct area as % of area at risk of the left ventricle: 54%=18%
    - Chondrisome group: Infarct area as % of area at risk of the left ventricle: 50%+24%
- Serum markers of cardiac injury:
  - No improvement in CKNB levels relative to vehicle at 6 hrs and 24 hrs
  - No improvement in cTnl at 6 hrs relative to vehicle at 6 hrs and 24 hrs
  - Greatly reduced serum hydrogen peroxide at 15-minutes post reperfusion:
    - Vehicle group: 146+146 μM
    - Chondrisome group: 18+40 μM

| | 6 hr | | 24 hr | |
|---|---|---|---|---|
| | Vehicle | Chondrisome | Vehicle | Chondrisome |
| CKMB (U/L) | 394 ± 122 | 455 ± 166 | 325 ± 89 | 666 ± 565 |
| cTnI (ng/ml) | 476 ± 188 | 588 ± 290 | 412 ± 387 | 702 ± 802 |

Example F-17: No Acute Immune Effect

This example assesses the acute immune response of delivery of a chondrisome preparation.

7.25 mg of chondrisomes (as measured by protein concentration via the BCA assay in example A-5) per kg of mouse weight diluted in MSHE (200 mM mannitol, 70 mM sucrose, 10 mM HEPES, 1 mM EDTA, adjust the pH to 7.4 with KOH) or vehicle control without chondrisomes were injected intravenously into the tail vein or subcutaneously into the intrascapular area of 5 week old female C57Bl/6 mice in a single injection. Mice were monitored continuously for the first 30 minutes after injection, every 20 minutes for the four subsequent hours, and then 4 times per day for the next 24 hours. Animals exhibited no adverse reaction to chondrisomes over this time.

Figure 6:
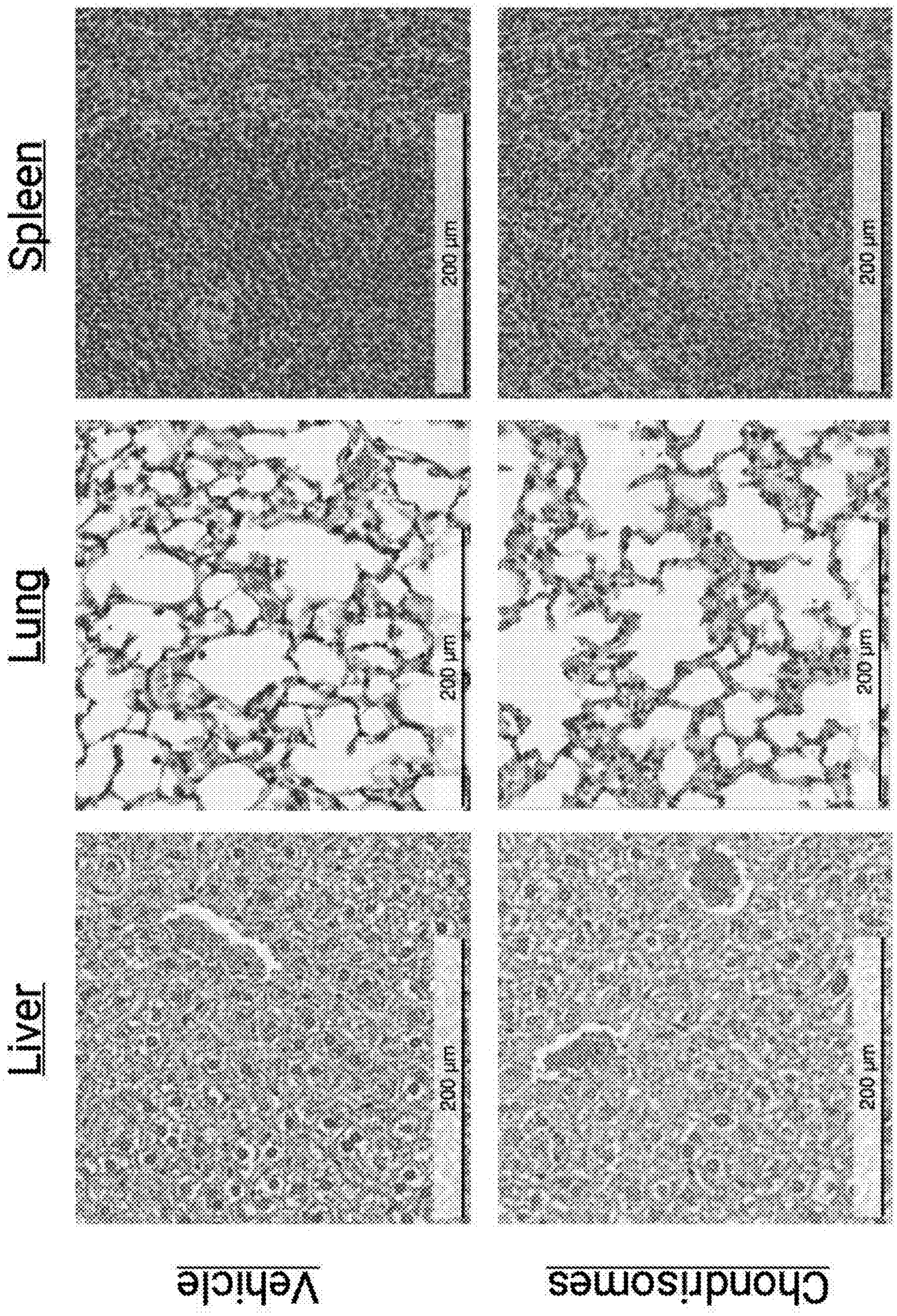
FIG. 6 is a panel of images showing representative hematoxylin and eosin (H&E) stained slides of the liver, lung, and spleen from animals treated intravenously with chondrisomes or vehicle. There is no elevated level of immune cell infiltration in the chondrisome treatment compared to the vehicle treatment in any of the three organs.

24 hours after injection, mice were euthanized via CO2 inhalation. Following euthanasia, blood was collected via cardiac puncture in $K_2$EDTA and processed to plasma. Lungs, liver, and spleen were harvested and fixed in buffered formalin. The plasma was evaluated for an innate immune reaction via ELISA using the Life Technologies Mouse Inflammatory 4-Plex kit on a Luminex Magpix machine. The ELISA measured the concentrations of IL-1-beta, IL-6, GM-CSF, and TNF-alpha. The concentration of these cytokines in the plasma was measured by establishing a standard curve with serial dilutions of known concentrations of the cytokines supplied by the manufacturer in the kit. The concentration of cytokines in both chondrisomes-treated and vehicle-treated animals at each route of administration was below the level of detection for the ELISA kit, and thus were not elevated by the chondrisomes or vehicle treatment (FIG. 5). Specifically, the ELISA kit measured less than 23.56 μg IL-1-beta, less than 28.13 μg IL-6, less than 15.33 μg GM-CSF, and less than 23.26 μg TNF-alpha per ml of plasma. Lungs, liver, and spleen fixed in buffered formalin were processed to 5 micron-thick histology slides and stained with hematoxylin and eosin stain (H&E). The histology slides were analyzed for elevated immune-cell infiltration into the tissue, and there was no difference between animals injected with chondrisomes or vehicle (representative images in FIG. 6).

Example F-18: Metabolic Stimulation

This example assesses the effect of in-vivo delivery of chondrisomes isolated from brown adipose tissue.

Vehicle or 1-2 mg of chondrisomes (as measured by protein concentration via the BCA assay in example A-5)

derived from the brown adipose tissue of C57BL/6J mice (as described in example 1-4) incubated at 4 degrees for 7 days were injected into the left periogonadal white adipose pad of 24-week old diet-induced obese C57BL/6J mice purchased from Jackson Laboratory via 4 injections of 25 μl each. Immediately following the administration of chondrisomes, the mice were placed into a Comprehensive Lab Animal Monitoring System (CLAMS). The CLAMS system measures the oxygen consumption, carbon dioxide production, respiratory exchange ratio, energy expenditure, food consumption, total activity, and ambulatory activity of each mouse. The animals were treated with chondrisomes or vehicle then placed back into the CLAMS chamber each day for 5 days, and remain in the CLAMS chamber and not injected for a $6^{th}$ and $7^{th}$ day. Prior to injections on the first day, the percent fat and percent lean body composition of each mouse was measured via MRI, and the body weight was measured on a weight scale. Over the course of the experiment the animals were fed a diet that was 60% fat (Diet D12492 made by Research Diets). At the end of the $7^{th}$ day, the animals were removed from the CLAMS chamber, the percent fat and percent lean body composition of each mouse was measured via MRI, and the body weight was measured on a weight scale. The animals were then sacrificed via cervical dislocation. Blood was drawn via cardiac puncture and processed to serum. The serum was processed by centrifuging blood samples at 1.6 g for 10 min at 4° C. The perigonadal white adipose pad from both the left and right side of the animal were removed and weighed on an weight scale. The fat pad was cut in half. Half of the fat pad was fixed in formalin and half was snap-frozen at −80 degrees. The liver of the animals was also removed and cut in half. Half of the liver fixed in formalin and half was snap-frozen at −80 degrees. To determine whether the chondrisome treatment affected the mass of the injected perigonadal fat pad, the mass of the fat pad was divided by the mass of the uninjected fat pad from the same animal.

Figure 7:
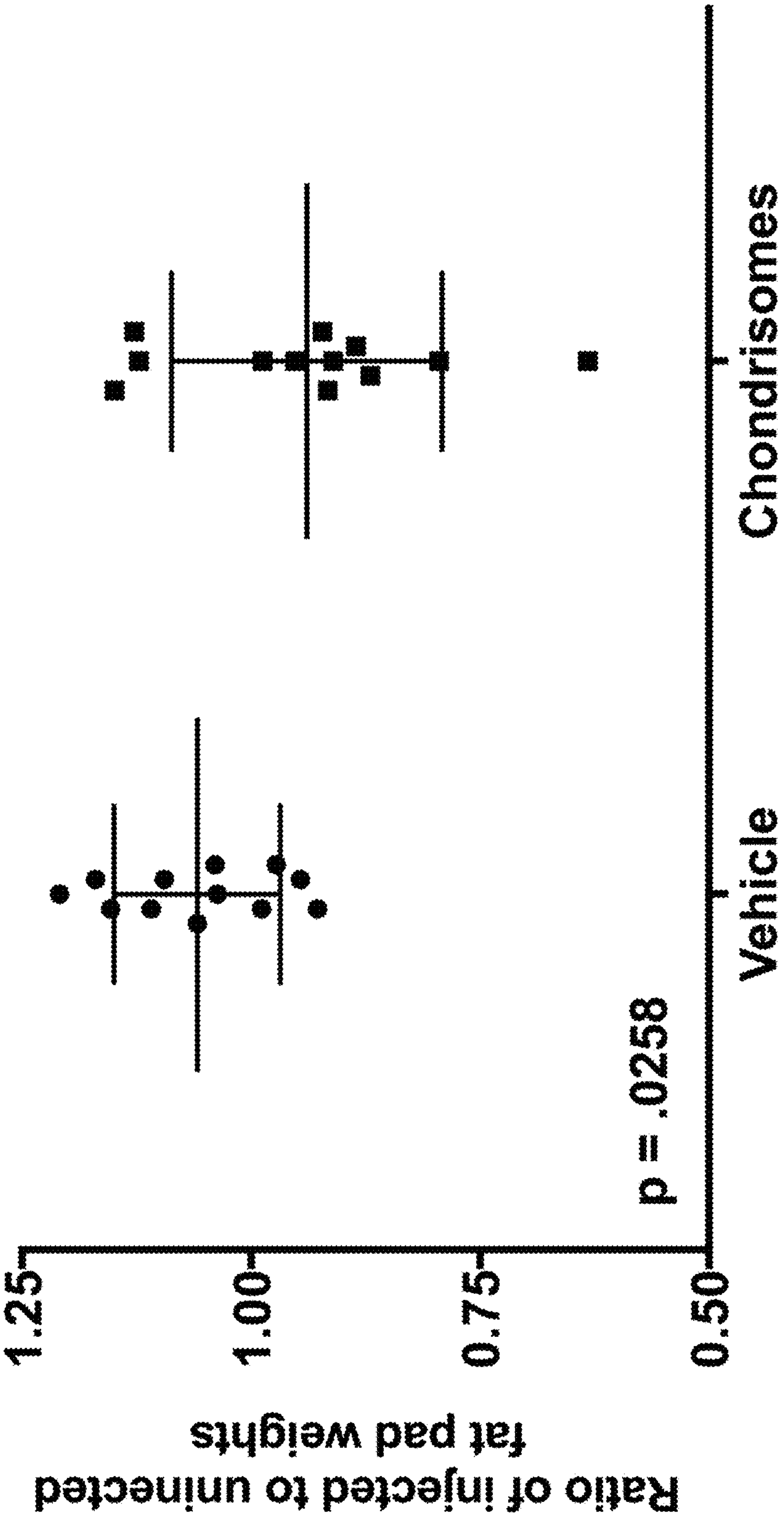
FIG. 7 is a graph showing the ratio of the weights of the treated to untreated perigondal fat pads of animals that received chondrisomes or vehicle injections. The ratio is significantly lower in animals that received chondrisome treatment as assessed via an unpaired t test.

Results:

Mice that received chondrisomes had a lower ratio of injected to un-injected fat pad mass than mice that received vehicle control (FIG. 7).

Figure 8:
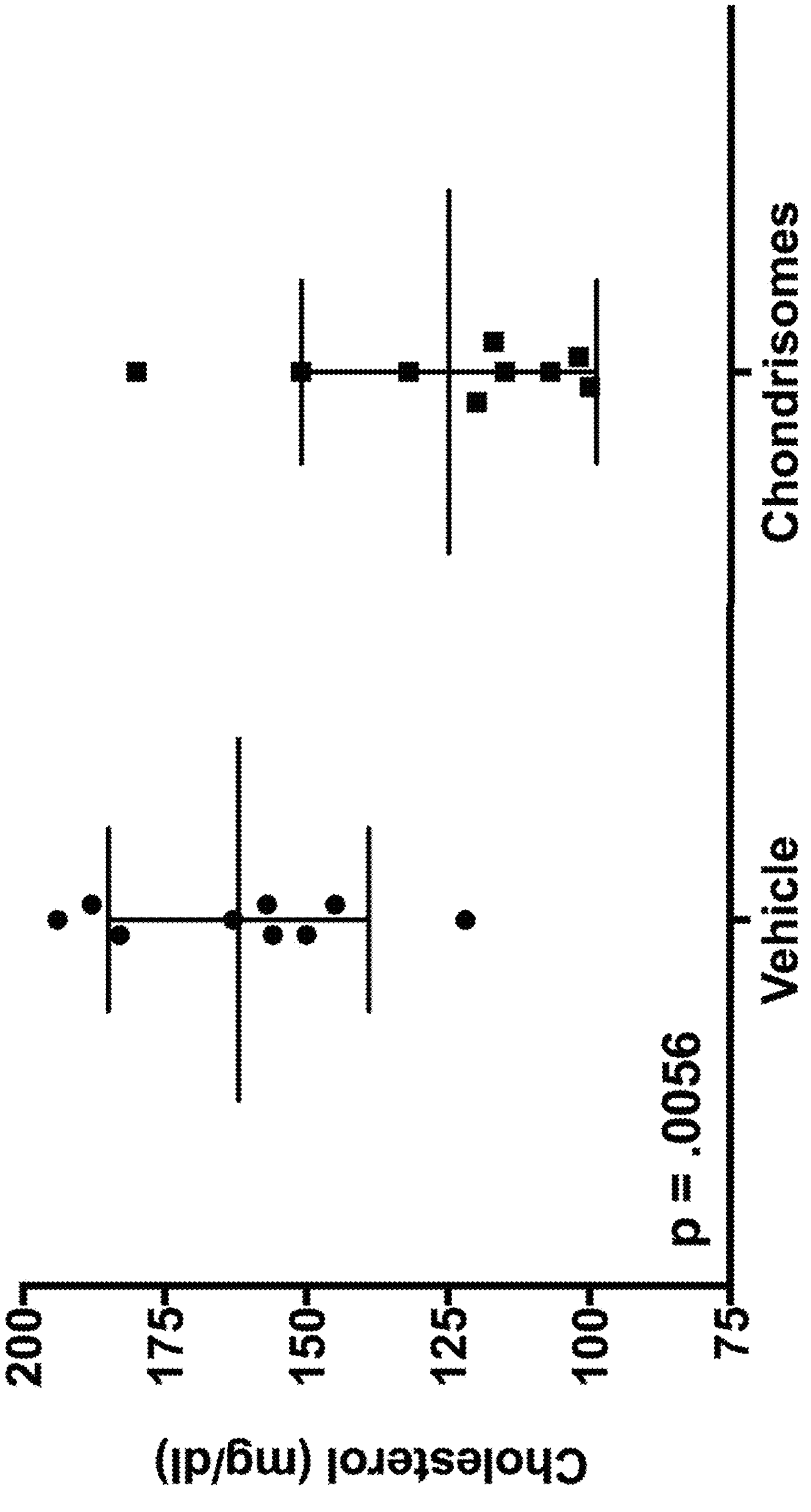
FIG. 8 is a graph showing the serum concentration of total cholesterol in animals that received chondrisomes or vehicle injections. The ratio is significantly lower in animals that received chondrisome treatment as assessed via Welch's t test.
Figure 9:
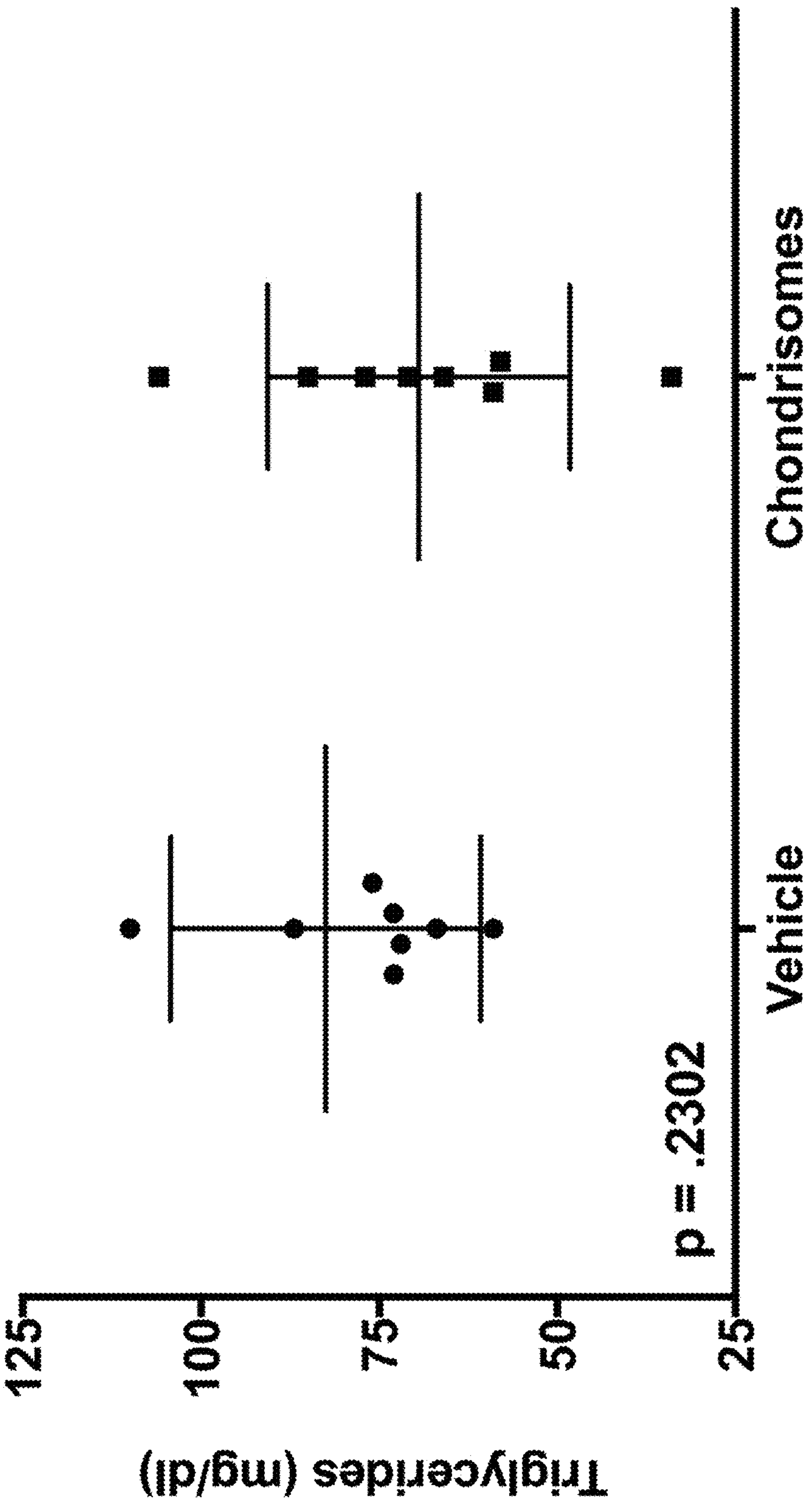
FIG. 9 is a graph showing the serum concentration of total triglycerides in animals that received chondrisomes or vehicle injections. The ratio is trending to be lower in animals that received chondrisome treatment.

The concentration of total cholesterol and total triglycerides in the serum of animals injected in the periogondal fat pad with brown adipose tissue chondrisomes or vehicle was measured using IDEXX Dry-Slide Technology. 70 μl of serum was loaded onto catalyst sample cups and measured on a IDEXX Catalyst DX Chemistry Analyzer. Animals treated with chondrisomes had decreased serum cholesterol and serum triglycerides relative to vehicle treated animals (FIG. 8; FIG. 9).

Example F-19: No Adaptive Immune Effect

This example assesses the adaptive immune response of delivery of a chondrisome preparation.

5 mg of chondrisomes (as measured by protein concentration via BCA assay) per kg of mouse weight diluted in MSHE buffer (200 mM mannitol, 70 mM sucrose, 10 mM HEPES, 1 mM EDTA, pH adjusted to 7.4 with KOH) was injected in a volume of 25 μl into the left footpad of a 5-week old female C57BL/6J mouse, and 25 μl of the vehicle (MSHE) control was injected into the right footpad of the same mouse. Chondrisomes were isolated from leg gastrocnemius muscle from C57bl/6 mice (syngeneic) or Balb/c mice (allogenic) using the isolation protocol described in example 1-2a. 7 days after the injection, half of the mice were sacrificed via CO2 asphyxiation followed by cervical dislocation and their popliteal lymph node proximal to each paw was removed and weighed on an analytical scale.

The ratio of the weight of chondrisomes-injected to vehicle-injected popliteal lymph nodes was calculated as a measure of the immunogenicity of a single treatment. The average ratio of the weight of lymph nodes from the mice that received syngeneic chondrisomes was 1.03 and from the mice that received the allogeneic chondrisomes was 2.09 (FIG. 10). 14 days later (21 days after the initial injection), 5 mg of chondrisomes (as measured by protein concentration via the BCA assay) per kg of mouse weight diluted in MSHE buffer was injected in a volume of 25 μl into the left footpad of the remaining live mice, and 25 ul of the vehicle control were injected into the right footpad of the same mouse. 5 days later (on the $26^{th}$ day of the experiment), the mice were sacrificed via CO2 asphyxiation followed by cervical dislocation and their popliteal lymph node was removed and weighed on an analytical scale.

Figure 10:
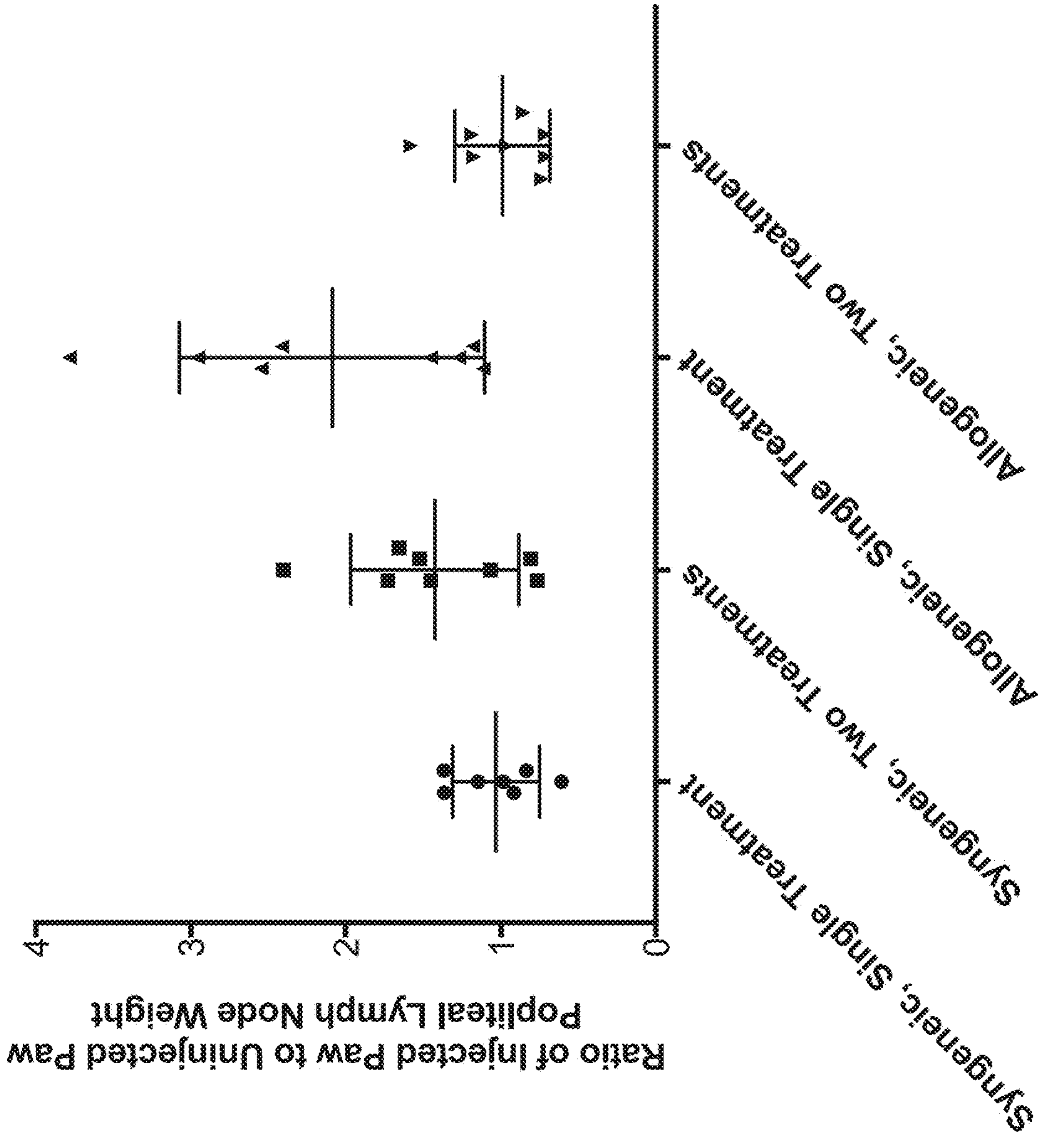
FIG. 10 is a graph showing the ratio of the weight of chondrisome-injected to vehicle-injected paw lymph nodes for animals that received a single or multiple treatments of syngeneic chondrisomes or allogeneic chondrisomes.

The ratio of the weight of chondrisomes-injected to vehicle-injected paw lymph nodes was calculated to measure whether there was an adaptive immune response to the treatment as indicated by an increased weight ratio as compared to the single treatment. The average ratio of the weight of lymph nodes from the mice that received syngeneic chondrisomes after the second injection was 1.43 and from the mice that received the allogeneic chondrisomes was 0.99 (FIG. 10). The increase in the ratio of injected to uninjected lymph node weights observed between the first and second injection for mice that received syngeneic chondrisomes was not statistically significant, and the ratio decreased for mice the received allogeneic chondrisomes. Thus, there was not an adaptive immune response to chondrisomes.

SEQUENCES

Human UCP1:

(SEQ ID NO: 1)

MGGLTASDVHPTLGVQLFSAGIAACLADVITFPLDTAKVRLQVQGECPTSSVIRYKGVLG

TITAVVKTEGRMKLYSGLPAGLQRQISSASLRIGLYDTVQEFLTAGKETAPSLGSKILAG

LTTGGVAVFIGQPTEVVKVRLQAQSHLHGIKPRYTGTYNAYRIIATTEGLTGLWKGTTPN

LMRSVIINCTELVTYDLMKEAFVKNNILADDVPCHLVSALIAGFCATAMSSPVDVVKTRF

INSPPGQYKSVPNCAMKVFTNEGPTAFFKGLVPSFLRLGSWNVIMFVCFEQLKRELSKSR

QTMDCAT

-continued

Human UCP2:

(SEQ ID NO: 2)

MVGFKATDVP PTATVKFLGA GTAACIADLI TFPLDTAKVR LQIQGESQGP

VRATASAQYR GVMGTILTMV RTEGPRSLYN GLVAGLQRQM SFASVRIGLY

DSVKQFYTKG SEHASIGSRL LAGSTTGALA VAVAQPTDVV KVRFQAQARA

GGGRRYQSTV NAYKTIAREE GFRGLWKGTS PNVARNAIVN CAELVTYDLI

KDALLKANLM TDDLPCHFTS AFGAGFCTTV IASPVDVVKT RYMNSALGQY

SSAGHCALTM LQKEGPRAFY KGFMPSFLRL GSWNVVMFVT YEQLKRALMA

ACTSREAPF

Human UCP3:

(SEQ ID NO: 3)

MVGLKPSDVP PTMAVKFLGA GTAACFADLV TFPLDTAKVR LQIQGENQAV

QTARLVQYRG VLGTILTMVR TEGPCSPYNG LVAGLQRQMS FASIRIGLYD

SVKQVYTPKG ADNSSLTTRI LAGCTTGAMA VTCAQPTDVV KVRFQASIHL

GPSRSDRKYS GTMDAYRTIA REEGVRGLWK GTLPNIMRNA IVNCAEVVTY

DILKEKLLDY HLLTDNFPCH FVSAFGAGFC ATVVASPVDV VKTRYMNSPP

GQYFSPLDCM IKMVAQEGPT AFYKGFTPSF LRLGSWNVVM FVTYEQLKRA

LMKVQMLRES PF

Human UCP4:

(SEQ ID NO: 4)

MSVPEEEERL LPLTQRWPRA SKFLLSGCAA TVAELATFPL DLTKTRLQMQ

GEAALARLGD GARESAPYRG MVRTALGIIE EEGFLKLWQG VTPAIYRHVV

YSGGRMVTYE HLREVVFGKS EDEHYPLWKS VIGGMMAGVI GQFLANPTDL

VKVQMQMEGK RKLEGKPLRF RGVHHAFAKI LAEGGIRGLW AGWVPNIQRA

ALVNMGDLTT YDTVKHYLVL NTPLEDNIMT HGLSSLCSGL VASILGTPAD

VIKSRIMNQP RDKQGRGLLY KSSTDCLIQA VQGEGFMSLY KGFLPSWLRM

TPWSMVFWLT YEKIREMSGV SPF

Human UCP5

(SEQ ID NO: 5)

MGIFPGIILI FLRVKFATAA VIVSGHQKST TVSHEMSGLN WKPFVYGGLA

SIVAEFGTFP VDLTKTRLQV QGQSIDARFK EIKYRGMFHA LFRICKEEGV

LALYSGIAPA LLRQASYGTI KIGIYQSLKR LFVERLEDET LLINMICGVV

SGVISSTIAN PTDVLKIRMQ AQGSLFQGSM IGSFIDIYQQ EGTRGLWRGV

VPTAQRAAIV VGVELPVYDI TKKHLILSGM MGDTILTHFV SSFTCGLAGA

LASNPVDVVR TRMMNQRAIV GHVDLYKGTV DGILKMWKHE GFFALYKGFW

PNWLRLGPWN IIFFITYEQL KRLQI subunit VIII of human cytochrome c oxidase:

(SEQ ID NO: 6)

ATGTCCGTCC TGACGCCGCT GCTGCTGCGG GGCTTGACAG GCTCGGCCCG

GCGGCTCCCA GTGCCGCGCG CCAAGATCCA TTCGTTG human Sirt3:

(SEQ ID NO: 7)

MVGAGISTPS GIPDFRSPGS GLYSNLQQYD LPYPEAIFEL PFFFHNPKPF FTLAKELYPG

NYKPNVTHYF LRLLHDKGLL LRLYTQNIDG LERVSGIPAS KLVEAHGTFA SATCTVCQRP

FPGEDIRADV MADRVPRCPV CTGVVKPDIV FFGEPLPQRF LLHVVDFPMA DLLLILGTSL

EVEPFASLTE AVRSSVPRLL INRDLVGPLA WHPRSRDVAQ LGDVVHGVES LVELLGWTEE

MRDLVQRETG KLDGPDK

-continued human pyruvate dehydrogenase kinase:

(SEQ ID NO: 8)

MRLARLLRGA ALAGPGPGLR AAGFSRSFSS DSGSSPASER GVPGQVDFYA

RFSPSPLSMK QFLDFGSVNA CEKTSFMFLR QELPVRLANI MKEISLLPDN

LLRTPSVQLV QSWYIQSLQE LLDFKDKSAE DAKAIYDFTD TVIRIRNRHN

DVIPTMAQGV IEYKESFGVD PVTSQNVQYF LDRFYMSRIS IRMLLNQHSL

LFGGKGKGSP SHRKHIGSIN PNCNVLEVIK DGYENARRLC DLYYINSPEL

ELEELNAKSP GQPIQVVYVP SHLYHMVFEL FKNAMRATME HHANRGVYPP

IQVHVTLGNE DLTVKMSDRG GGVPLRKIDR LFNYMYSTAP RPRVETSRAV

PLAGFGYGLP ISRLYAQYFQ GDLKLYSLEG YGTDAVIYIK ALSTDSIERL

PVYNKAAWKH YNTNHEADDW CVPSREPKDM TTFRSA human O-GlcNAc transferase:

(SEQ ID NO: 9)

MASSVGNVAD STEPTKRMLS FQGLAELAHR EYQAGDFEAA ERHCMQLWRQ

EPDNTGVLLL LSSIHFQCRR LDRSAHFSTL AIKQNPLLAE AYSNLGNVYK

ERGQLQEAIE HYRHALRLKP DFIDGYINLA AALVAAGDME GAVQAYVSAL

QYNPDLYCVR SDLGNLLKAL GRLEEAKACY LKAIETQPNF AVAWSNLGCV

FNAQGEIWLA IHHFEKAVTL DPNFLDAYIN LGNVLKEARI FDRAVAAYLR

ALSLSPNHAV VHGNLACVYY EQGLIDLAID TYRRAIELQP HFPDAYCNLA

NALKEKGSVA EAEDCYNTAL RLCPTHADSL NNLANIKREQ GNIEEAVRLY

RKALEVFPEF AAAHSNLASV LQQQGKLQEA LMHYKEAIRI SPTFADAYSN

MGNTLKEMQD VQGALQCYTR AIQINPAFAD AHSNLASIHK DSGNIPEAIA

SYRTALKLKP DFPDAYCNLA HCLQIVCDWT DYDERMKKLV SIVADQLEKN

RLPSVHPHHS MLYPLSHGFR KAIAERHGNL CLDKINVLHK PPYEHPKDLK

LSDGRLRVGY VSSDFGNHPT SHLMQSIPGM HNPDKFEVFC YALSPDDGTN

FRVKVMAEAN HFIDLSQIPC NGKAADRIHQ DGIHILVNMN GYTKGARNEL

FALRPAPIQA MWLGYPGTSG ALFMDYIITD QETSPAEVAE QYSEKLAYMP

HTFFIGDHAN MFPHLKKKAV IDFKSNGHIY DNRIVLNGID LKAFLDSLPD

VKIVKMKCPD GGDNADSSNT ALNMPVIPMN TIAEAVIEMI NRGQIQITIN

GFSISNGLAT TQINNKAATG EEVPRTIIVT TRSQYGLPED AIVYCNFNQL

YKIDPSTLQM WANILKRVPN SVLWLLRFPA VGEPNIQQYA QNMGLPQNRI

IFSPVAPKEE HVRRGQLADV CLDTPLCNGH TTGMDVLWAG TPMVTMPGET

LASRVAASQL TCLGCLELIA KNRQEYEDIA VKLGTDLEYL KKVRGKVWKQ

RISSPLFNTK QYTMELERLY LQMWEHYAAG NKPDHMIKPV EVTESA human OMP25:

SEQ ID NO: 10

MNGRVDYLVTEEEINLTRGPSGLGFNIVGGTDQQYVSNDSGIYVSRIKENGAAALDGRLQEGDKI

LSVNGQDLKNLLHQDAVDLFRNAGYAVSLRVQHRLQVQNGPIGHRGEGDPSGIPIFMVLVPVFA

LTMVAAWAFMRYRQQL, human TOM22:

SEQ ID NO: 11

MAAAVAAAGAGEPQSPDELLPKGDAEKPEEELEEDDDEELDETLSERLWGLTEMFPERVRSAA

GATFDLSLFVAQKMYRFSRAALWIGTTSFMILVLPVVFETEKLQMEQQQQLQQRQILLGPNTGLS

GGMPGALPSLPGKI,

-continued human TIM17A:

SEQ ID NO: 12
MEEYAREPCPWRIVDDCGGAFTMGTIGGGIFQAIKGFRNSPVGVNHRLRGSLTAIKTRAPQLGGS

FAVWGGLFSMIDCSMVQVRGKEDPWNSITSGALTGAILAARNGPVAMVGSAAMGGILLALIEG

AGILLTRFASAQFPNGPQFAEDPSQLPSTQLPSSPFGDYRQYQ, human TIM17B:

SEQ ID NO: 13
MEEYAREPCPWRIVDDCGGAFTMGVIGGGVFQAIKGFRNAPVGIRHRLRGSANAVRIRAPQIGG

SFAVWGGLFSTIDCGLVRLRGKEDPWNSITSGALTGAVLAARSGPLAMVGSAMMGGILLALIEG

VGILLTRYTAQQFRNAPPFLEDPSQLPPKDGTPAPGYPSYQQYH, human TIM22:

SEQ ID NO: 14
MAAAAPNAGGSAPETAGSAEAPLQYSLLLQYLVGDKRQPRLLEPGSLGGIPSPAKSEEQKMIEK

AMESCAFKAALACVGGFVLGGAFGVFTAGIDTNVGFDPKDPYRTPTAKEVLKDMGQRGMSYA

KNFAIVGAMFSCTECLIESYRGTSDWKNSVISGCITGGAIGFRAGLKAGAIGCGGFAAFSAAIDYY

LR, human TFAM:

SEQ ID NO: 15
MAFLRSMWGVLSALGRSGAELCTGCGSRLRSPFSFVYLPRWFSSVLASCPKKPVSSYLRFSKEQL

PIFKAQNPDAKTTELIRRIAQRWRELPDSKKKIYQDAYRAEWQVYKEEISRFKEQLTPSQIMSLEK

EIMDKHLKRKAMTKKKELTLLGKPKRPRSAYNVYVAERFQEAKGDSPQEKLKTVKENWKNLS

DSEKELYIQHAKEDETRYHNEMKSWEEQMIEVGRKDLLRRTIKKQRKYGAEEC, human PGC-lalpha (peroxisome proliferator-activated receptor gamma coactivator 1-alpha):

SEQ ID NO: 16
MAWDMCNQDSESVWSDIECAALVGEDQPLCPDLPELDLSELDVNDLDTDSFLGGLKWCSDQSE

IISNQYNNEPSNIFEKIDEENEANLLAVLTETLDSLPVDEDGLPSFDALTDGDVTTDNEASPSSMPD

GTPPPQEAEEPSLLKKLLLAPANTQLSYNECSGLSTQNHANHNHRIRTNPAIVKTENSWSNKAKSI

CQQQKPQRRPCSELLKYLTTNDDPPHTKPTENRNSSRDKCTSKKKSHTQSQSQHLQAKPTTLSLP

LTPESPNDPKGSPFENKTIERTLSVELSGTAGLTPPTTPPHKANQDNPFRASPKLKSSCKTVVPPPS

KKPRYSESSGTQGNNSTKKGPEQSELYAQLSKSSVLTGGHEERKTKRPSLRLFGDHDYCQSINSK

TEILINISQELQDSRQLENKDVSSDWQGQICSSTDSDQCYLRETLEASKQVSPCSTRKQLQDQEIR

AELNKHFGHPSQAVFDDEADKTGELRDSDFSNEQFSKLPMFINSGLAMDGLFDDSEDESDKLSY

PWDGTQSYSLFNVSPSCSSFNSPCRDSVSPPKSLFSQRPQRMRSRSRSFSRHRSCSRSPYSRSRSRS

PGSRSSSRSCYYYESSHYRHRTHRNSPLYVRSRSRSPYSRRPRYDSYEEYQHERLKREEYRREYE

KRESERAKQRERQRQKAIEERRVIYVGKIRPDTTRTELRDRFEVFGEIEECTVNLRDDGDSYGFIT

YRYTCDAFAALENGYTLRRSNETDFELYFCGRKQFFKSNYADLDSNSDDFDPASTKSKYDSLDF

DSLLKEAQRSLRR,

FLAG tag:

(SEQ ID NO: 17)
DYKDDDDK human Acat1:

SEQ ID NO: 18
MAVLAALLRSGARSRSPLLRRLVQEIRYVERSYVSKPTLKEVVIVSATRTPIGSFLGSLSLLPATKL

GSIAIQGAIEKAGIPKEEVKEAYMGNVLQGGEGQAPTRQAVLGAGLPISTPCTTINKVCASGMKA

IMMASQSLMCGHQDVMVAGGMESMSNVPYVMNRGSTPYGGVKLEDLIVKDGLTDVYNKIHM

GSCAENTAKKLNIARNEQDAYAINSYTRSKAAWEAGKFGNEVIPVTVTVKGQPDVVVKEDEEY

KRVDFSKVPKLKTVFQKENGTVTAANASTLNDGAAALVLMTADAAKRLNVTPLARIVAFADAA

-continued

VEPIDFPIAPVYAASMVLKDVGLKKEDIAMWEVNEAFSLVVLANIKMLEIDPQKVNINGGAVSL

GHPIGMSGARIVGHLTHALKQGEYGLASICNGGGGASAMLIQKL, human GPS2:

SEQ ID NO: 19

MPALLERPKLSNAMARALHRHIMMERERKRQEEEEVDKMMEQKMKEEQERRKKKEMEERMS

LEETKEQILKLEEKLLALQEEKHQLFLQLKKVLHEEEKRRRKEQSDLTTLTSAAYQQSLTVHTGT

HLLSMQGSPGGHNRPGTLMAADRAKQMFGPQVLTTRHYVGSAAAFAGTPEHGQFQGSPGGAY

GTAQPPPHYGPTQPAYSPSQQLRAPSAFPAVQYLSQPQPQPYAVHGHFQPTQTGFLQPGGALSLQ

KQMEHANQQTGFSDSSSLRPMHPQALHPAPGLLASPQLPVQMQPAGKSGFAATSQPGPRLPFIQ

HSQNPRFYHK,

Human YBX1:

SEQ ID NO: 20

MSSEAETQQPPAAPPAAPALSAADTKPGTTGSGAGSGGPGGLTSAAPAGGDKKVIATKVLGTVK

WFNVRNGYGFINRNDTKEDVFVHQTAIKKNNPRKYLRSVGDGETVEFDVVEGEKGAEAANVTG

PGGVPVQGS KYAADRNHYRRYPRRRGPPRNYQQNYQNSESGEKNEGSESAPEGQAQQRRPYRR

RRFPPYYMRRPYGRRPQYSNPPVQGEVMEGADNQGAGEQGRPVRQNMYRGYRPRFRRGPPRQ

RQPREDGNEEDKENQGDETQGQQPPQRRYRRNFNYRRRRPENPKPQDGKETKAADPPAENSSA

PEAEQGGAE,

Human OPA1:

SEQ ID NO: 21

MWRLRRAAVACEVCQSLVKHSSGIKGSLPLQKLHLVSRSIYHSHHPTLKLQRPQLRTSFQQFSSL

TNLPLRKLKFSPIKYGYQPRRNFWPARLATRLLKLRYLILGSAVGGGYTAKKTFDQWKDMIPDL

SEYKWIVPDIVWEIDEYIDFEKIRKALPSSEDLVKLAPDFDKIVESLSLLKDFFTSGSPEETAFRAT

DRGSESDKHFRKVSDKEKIDQLQEELLHTQLKYQRILERLEKENKELRKLVLQKDDKGIHHRKL

KKSLIDMYSEVLDVLSDYDASYNTQDHLPRVVVVGDQSAGKTSVLEMIAQARIFPRGSGEMMT

RSPVKVTLSEGPHHVALFKDSSREFDLTKEEDLAALRHEIELRMRKNVKEGCTVSPETISLNVKG

PGLQRMVLVDLPGVINTVTSGMAPDTKETIFSISKAYMQNPNAIILCIQDGSVDAERSIVTDLVSQ

MDPHGRRTIFVLTKVDLAEKNVASPSRIQQIIEGKLFPMKALGYFAVVTGKGNSSESIEAIREYEE

EFFQNSKLLKTSMLKAHQVTTRNLSLAVSDCFWKMVRESVEQQADSFKATRFNLETEWKNNYP

RLRELDRNELFEKAKNEILDEVISLSQVTPKHWEEILQQSLWERVSTHVIENIYLPAAQTMNSGTF

NTTVDIKLKQWTDKQLPNKAVEVAWETLQEEFSRFMTEPKGKEHDDIFDKLKEAVKEESIKRHK

WNDFAEDSLRVIQHNALEDRSISDKQQWDAAIYFMEEALQARLKDTENAIENMVGPDWKKRW

LYWKNRTQEQCVHNETKNELEKMLKCNEEHPAYLASDEITTVRKNLESRGVEVDPSLIKDTWH

QVYRRHFLKTALNHCNLCRRGFYYYQRHFVDSELECNDVVLFWRIQRMLAITANTLRQQLTNT

EVRRLEKNVKEVLEDFAEDGEKKIKLLTGKRVQLAEDLKKVREIQEKLDAFIEALHQEK, human MFN1:

SEQ ID NO: 22

MAEPVSPLKHFVLAKKAITAIFDQLLEFVTEGSHFVEATYKNPELDRIATEDDLVEMQGYKDKLS

IIGEVLSRRHMKVAFFGRTSSGKSSVINAMLWDKVLPSGIGHITNCFLSVEGTDGDKAYLMTEGS

DEKKSVKTVNQLAHALHMDKDLKAGCLVRVFWPKAKCALLRDDLVLVDSPGTDVTTELDSWI

DKFCLDADVFVLVANSESTLMNTEKHFFHKVNERLSKPNIFILNNRWDASASEPEYMEDVRRQH

MERCLHFLVEELKVVNALEAQNRIFFVSAKEVLSARKQKAQGMPESGVALAEGFHARLQEFQN

FEQIFEECISQSAVKTKFEQHTIRAKQILATVKNIMDSVNLAAEDKRHYSVEEREDQIDRLDFIRN

QMNLLTLDVKKKIKEVTEEVANKVSCAMTDEICRLSVLVDEFCSEFHPNPDVLKIYKSELNKHIE

DGMGRNLADRCTDEVNALVLQTQQEIIENLKPLLPAGIQDKLHTLIPCKKFDLSYNLNYHKLCSD

-continued

FQEDIVFPFSLGWSSLVHRFLGPRNAQRVLLGLSEPIFQLPRSLASTPTAPTTPATPDNASQEELMI

TLVTGLASVTSRTSMGIIIVGGVIWKTIGWKLLSVSLTMYGALYLYERLSWTTHAKERAFKQQFV

NYATEKLRMIVS STSANCSHQVKQQIATTFARLCQQVDITQKQLEEEIARLPKEIDQLEKIQNNSK

LLRNKAVQLENELENFTKQFLPSSNEES,

Human MFN2:

SEQ ID NO: 23

MSLLFSRCNSIVTVKKNKRHMAEVNASPLKHFVTAKKKINGIFEQLGAYIQESATFLEDTYRNAE

LDPVTTEEQVLDVKGYLSKVRGISEVLARRHMKVAFFGRTSNGKSTVINAMLWDKVLPSGIGHT

TNCFLRVEGTDGHEAFLLTEGSEEKRSAKTVNQLAHALHQDKQLHAGSLVSVMWPNSKCPLLK

DDLVLMDSPGIDVTTELDSWIDKFCLDADVFVLVANSESTLMQTEKHFFHKVSERLSRPNIFILN

NRWDASASEPEYMEEVRRQHMERCTSFLVDELGVVDRSQAGDRIFFVSAKEVLNARIQKAQGM

PEGGGALAEGFQVRMFEFQNFERRFEECISQSAVKTKFEQHTVRAKQIAEAVRLIMDSLHMAAR

EQQVYCEEMREERQDRLKFIDKQLELLAQDYKLRIKQITEEVERQVSTAMAEEIRRLSVLVDDY

QMDFHPSPVVLKVYKNELHRHIEEGLGRNMSDRCSTAITNSLQTMQQDMIDGLKPLLPVSVRSQI

DMLVPRQCFSLNYDLNCDKLCADFQEDIEFHFSLGWTMLVNRFLGPKNSRRALMGYNDQVQRP

IPLTPANPSMPPLPQGSLTQEEFMVSMVTGLASLTSRTSMGILVVGGVVWKAVGWRLIALSFGLY

GLLYVYERLTWTTKAKERAFKRQFVEHASEKLQLVISYTGSNCSHQVQQELSGTFAHLCQQVD

VTRENLEQEIAAMNKKIEVLDSLQSKAKLLRNKAGWLDSELNMFTHQYLQPSR,

We claim:

1. A method of reducing fat tissue mass or volume in the fat tissue of a subject, comprising: administering to the fat tissue of the subject a pharmaceutical preparation comprising isolated, modified chondrisomes derived from a cellular source of mitochondria, wherein the pharmaceutical preparation comprises a therapeutically effective amount of the isolated chondrisomes.

2. The method according to claim 1, wherein the therapeutically effective amount of the isolated chondrisomes is between 2 μg/kg to 10 mg/kg based on subject's weight.

3. The method according to claim 1, wherein the isolated chondrisomes are modified chondrisomes.

4. The method according to claim 1, wherein the pharmaceutical preparation comprising isolated chondrisomes is formulated for local administration to the fat tissue of the subject or systemic administration to the subject.

5. The method according to claim 1, wherein the pharmaceutical preparation comprising isolated chondrisomes is directly injected into the fat tissue of the subject.

6. The method according to claim 1, wherein the reduction of fat tissue mass or volume of the subject is of at least 5% compared to fat tissue mass or volume of the subject prior to the administration of the preparation.

7. The method according to claim 1, wherein the mitochondrial source is a source tissue or cell type different from the fat tissue or adipocyte of the subject.

8. The method according to claim 1, wherein the isolated chondrisomes of the preparation are isolated from a mitochondrial source selected from the group of consisting of: circulating cells, muscle cells, epidermal cell, dermal cells, hypodermal cells, stem cells, liver cells, kidney cells, pancreas cells, and spleen cells.

9. The method according to claim 1, wherein the isolated chondrisomes of the preparation are isolated at least in part from brown adipocytes.

10. The method of claim 1, wherein the chondrisomes of the composition express a protein having 100% identity to UCP1 (SEQ ID NO: 1).

11. The method of claim 1, wherein the chondrisomes of the preparation are isolated from brown adipocytes.

12. The method of claim 1, wherein the chondrisomes of the preparation are autologous to the target tissue or subject.

13. The method of claim 1, wherein the chondrisomes of the preparation are allogeneic to the target tissue or subject.

14. The method of claim 1, wherein the subject is a human.

15. The method of claim 1, wherein the subject is an agriculturally important animal.

16. The method of claim 1, wherein the preparation is administered to white adipocytes.

17. The method according to claim 1, wherein the modification of the chondrisome arises from exposing the cellular source of mitochondria to an external stress condition or agent.

18. The method according to claim 1, wherein the modified chondrisomes are engineered to overexpress or knock-down or knock-out an endogenous gene product.

19. The method according to claim 1, wherein the modified chondrisomes are engineered to express a heterologous gene product.

20. The method according to claim 1, wherein the modified chondrisomes are loaded with a heterologous cargo agent.

21. The method according to claim 1, wherein the modified chondrisomes are engineered to express a protein having 100% identity to the sequence of human UCP1 (SEQ ID NO:1), UCP2 (SEQ ID NO: 2), UCP3 (SEQ ID NO:3), UCP4 (SEQ ID NO:4), UCP5 (SEQ ID NO:5), SIRT3 (SEQ ID NO: 7), or pyruvate dehydrogenase kinase (SEQ ID NO:8).

22. The method according to claim 1, wherein the modified chondrisomes are loaded with an exogenous agent selected from a nucleic acid, a polypeptide, or chemical compound.

* * * * *

SEQUENCE LISTING

<160> NUMBER OF SEQ ID NOS: 27

<210> SEQ ID NO 1
<211> LENGTH: 307
<212> TYPE: PRT
<213> ORGANISM: homo sapien

<400> SEQUENCE: 1

Met Gly Gly Leu Thr Ala Ser Asp Val His Pro Thr Leu Gly Val Gln
1 5 10 15

Leu Phe Ser Ala Gly Ile Ala Ala Cys Leu Ala Asp Val Ile Thr Phe
20 25 30

Pro Leu Asp Thr Ala Lys Val Arg Leu Gln Val Gln Gly Glu Cys Pro
35 40 45

Thr Ser Ser Val Ile Arg Tyr Lys Gly Val Leu Gly Thr Ile Thr Ala
50 55 60

Val Val Lys Thr Glu Gly Arg Met Lys Leu Tyr Ser Gly Leu Pro Ala
65 70 75 80

Gly Leu Gln Arg Gln Ile Ser Ser Ala Ser Leu Arg Ile Gly Leu Tyr
85 90 95

Asp Thr Val Gln Glu Phe Leu Thr Ala Gly Lys Glu Thr Ala Pro Ser
100 105 110

Leu Gly Ser Lys Ile Leu Ala Gly Leu Thr Thr Gly Gly Val Ala Val
115 120 125

Phe Ile Gly Gln Pro Thr Glu Val Val Lys Val Arg Leu Gln Ala Gln
130 135 140

Ser His Leu His Gly Ile Lys Pro Arg Tyr Thr Gly Thr Tyr Asn Ala
145 150 155 160

Tyr Arg Ile Ile Ala Thr Thr Glu Gly Leu Thr Gly Leu Trp Lys Gly 165 170 175

Thr Thr Pro Asn Leu Met Arg Ser Val Ile Ile Asn Cys Thr Glu Leu
180 185 190

Val Thr Tyr Asp Leu Met Lys Glu Ala Phe Val Lys Asn Asn Ile Leu
195 200 205

Ala Asp Asp Val Pro Cys His Leu Val Ser Ala Leu Ile Ala Gly Phe
210 215 220

Cys Ala Thr Ala Met Ser Ser Pro Val Asp Val Val Lys Thr Arg Phe
225 230 235 240

Ile Asn Ser Pro Pro Gly Gln Tyr Lys Ser Val Pro Asn Cys Ala Met
245 250 255

Lys Val Phe Thr Asn Glu Gly Pro Thr Ala Phe Phe Lys Gly Leu Val
260 265 270

Pro Ser Phe Leu Arg Leu Gly Ser Trp Asn Val Ile Met Phe Val Cys
275 280 285

Phe Glu Gln Leu Lys Arg Glu Leu Ser Lys Ser Arg Gln Thr Met Asp
290 295 300

Cys Ala Thr
305

<210> SEQ ID NO 2
<211> LENGTH: 309
<212> TYPE: PRT
<213> ORGANISM: homo sapien

<400> SEQUENCE: 2

Met Val Gly Phe Lys Ala Thr Asp Val Pro Pro Thr Ala Thr Val Lys
1 5 10 15

Phe Leu Gly Ala Gly Thr Ala Ala Cys Ile Ala Asp Leu Ile Thr Phe
20 25 30

Pro Leu Asp Thr Ala Lys Val Arg Leu Gln Ile Gln Gly Glu Ser Gln
35 40 45

Gly Pro Val Arg Ala Thr Ala Ser Ala Gln Tyr Arg Gly Val Met Gly
50 55 60

Thr Ile Leu Thr Met Val Arg Thr Glu Gly Pro Arg Ser Leu Tyr Asn
65 70 75 80

Gly Leu Val Ala Gly Leu Gln Arg Gln Met Ser Phe Ala Ser Val Arg
85 90 95

Ile Gly Leu Tyr Asp Ser Val Lys Gln Phe Tyr Thr Lys Gly Ser Glu
100 105 110

His Ala Ser Ile Gly Ser Arg Leu Leu Ala Gly Ser Thr Thr Gly Ala
115 120 125

Leu Ala Val Ala Val Ala Gln Pro Thr Asp Val Val Lys Val Arg Phe
130 135 140

Gln Ala Gln Ala Arg Ala Gly Gly Gly Arg Arg Tyr Gln Ser Thr Val
145 150 155 160

Asn Ala Tyr Lys Thr Ile Ala Arg Glu Glu Gly Phe Arg Gly Leu Trp
165 170 175

Lys Gly Thr Ser Pro Asn Val Ala Arg Asn Ala Ile Val Asn Cys Ala
180 185 190

Glu Leu Val Thr Tyr Asp Leu Ile Lys Asp Ala Leu Leu Lys Ala Asn
195 200 205

Leu Met Thr Asp Asp Leu Pro Cys His Phe Thr Ser Ala Phe Gly Ala
210 215 220

```
Gly Phe Cys Thr Thr Val Ile Ala Ser Pro Val Asp Val Val Lys Thr
225                 230                 235                 240

Arg Tyr Met Asn Ser Ala Leu Gly Gln Tyr Ser Ser Ala Gly His Cys
                245                 250                 255

Ala Leu Thr Met Leu Gln Lys Glu Gly Pro Arg Ala Phe Tyr Lys Gly
            260                 265                 270

Phe Met Pro Ser Phe Leu Arg Leu Gly Ser Trp Asn Val Val Met Phe
        275                 280                 285

Val Thr Tyr Glu Gln Leu Lys Arg Ala Leu Met Ala Ala Cys Thr Ser
    290                 295                 300

Arg Glu Ala Pro Phe
305


<210> SEQ ID NO 3
<211> LENGTH: 312
<212> TYPE: PRT
<213> ORGANISM: homo sapien

<400> SEQUENCE: 3

Met Val Gly Leu Lys Pro Ser Asp Val Pro Pro Thr Met Ala Val Lys
1               5                   10                  15

Phe Leu Gly Ala Gly Thr Ala Ala Cys Phe Ala Asp Leu Val Thr Phe
            20                  25                  30

Pro Leu Asp Thr Ala Lys Val Arg Leu Gln Ile Gln Gly Glu Asn Gln
        35                  40                  45

Ala Val Gln Thr Ala Arg Leu Val Gln Tyr Arg Gly Val Leu Gly Thr
    50                  55                  60

Ile Leu Thr Met Val Arg Thr Glu Gly Pro Cys Ser Pro Tyr Asn Gly
65                  70                  75                  80

Leu Val Ala Gly Leu Gln Arg Gln Met Ser Phe Ala Ser Ile Arg Ile
                85                  90                  95

Gly Leu Tyr Asp Ser Val Lys Gln Val Tyr Thr Pro Lys Gly Ala Asp
            100                 105                 110

Asn Ser Ser Leu Thr Thr Arg Ile Leu Ala Gly Cys Thr Thr Gly Ala
        115                 120                 125

Met Ala Val Thr Cys Ala Gln Pro Thr Asp Val Val Lys Val Arg Phe
    130                 135                 140

Gln Ala Ser Ile His Leu Gly Pro Ser Arg Ser Asp Arg Lys Tyr Ser
145                 150                 155                 160

Gly Thr Met Asp Ala Tyr Arg Thr Ile Ala Arg Glu Glu Gly Val Arg
                165                 170                 175

Gly Leu Trp Lys Gly Thr Leu Pro Asn Ile Met Arg Asn Ala Ile Val
            180                 185                 190

Asn Cys Ala Glu Val Val Thr Tyr Asp Ile Leu Lys Glu Lys Leu Leu
        195                 200                 205

Asp Tyr His Leu Leu Thr Asp Asn Phe Pro Cys His Phe Val Ser Ala
    210                 215                 220

Phe Gly Ala Gly Phe Cys Ala Thr Val Val Ala Ser Pro Val Asp Val
225                 230                 235                 240

Val Lys Thr Arg Tyr Met Asn Ser Pro Pro Gly Gln Tyr Phe Ser Pro
                245                 250                 255

Leu Asp Cys Met Ile Lys Met Val Ala Gln Glu Gly Pro Thr Ala Phe
            260                 265                 270

Tyr Lys Gly Phe Thr Pro Ser Phe Leu Arg Leu Gly Ser Trp Asn Val
        275                 280                 285
```

Val Met Phe Val Thr Tyr Glu Gln Leu Lys Arg Ala Leu Met Lys Val
290 295 300

Gln Met Leu Arg Glu Ser Pro Phe
305 310

<210> SEQ ID NO 4
<211> LENGTH: 323
<212> TYPE: PRT
<213> ORGANISM: homo sapien

<400> SEQUENCE: 4

Met Ser Val Pro Glu Glu Glu Glu Arg Leu Leu Pro Leu Thr Gln Arg
1 5 10 15

Trp Pro Arg Ala Ser Lys Phe Leu Leu Ser Gly Cys Ala Ala Thr Val
20 25 30

Ala Glu Leu Ala Thr Phe Pro Leu Asp Leu Thr Lys Thr Arg Leu Gln
35 40 45

Met Gln Gly Glu Ala Ala Leu Ala Arg Leu Gly Asp Gly Ala Arg Glu
50 55 60

Ser Ala Pro Tyr Arg Gly Met Val Arg Thr Ala Leu Gly Ile Ile Glu
65 70 75 80

Glu Glu Gly Phe Leu Lys Leu Trp Gln Gly Val Thr Pro Ala Ile Tyr
85 90 95

Arg His Val Val Tyr Ser Gly Gly Arg Met Val Thr Tyr Glu His Leu
100 105 110

Arg Glu Val Val Phe Gly Lys Ser Glu Asp Glu His Tyr Pro Leu Trp
115 120 125

Lys Ser Val Ile Gly Gly Met Met Ala Gly Val Ile Gly Gln Phe Leu
130 135 140

Ala Asn Pro Thr Asp Leu Val Lys Val Gln Met Gln Met Glu Gly Lys
145 150 155 160

Arg Lys Leu Glu Gly Lys Pro Leu Arg Phe Arg Gly Val His His Ala
165 170 175

Phe Ala Lys Ile Leu Ala Glu Gly Gly Ile Arg Gly Leu Trp Ala Gly
180 185 190

Trp Val Pro Asn Ile Gln Arg Ala Ala Leu Val Asn Met Gly Asp Leu
195 200 205

Thr Thr Tyr Asp Thr Val Lys His Tyr Leu Val Leu Asn Thr Pro Leu
210 215 220

Glu Asp Asn Ile Met Thr His Gly Leu Ser Ser Leu Cys Ser Gly Leu
225 230 235 240

Val Ala Ser Ile Leu Gly Thr Pro Ala Asp Val Ile Lys Ser Arg Ile
245 250 255

Met Asn Gln Pro Arg Asp Lys Gln Gly Arg Gly Leu Leu Tyr Lys Ser
260 265 270

Ser Thr Asp Cys Leu Ile Gln Ala Val Gln Gly Glu Gly Phe Met Ser
275 280 285

Leu Tyr Lys Gly Phe Leu Pro Ser Trp Leu Arg Met Thr Pro Trp Ser
290 295 300

Met Val Phe Trp Leu Thr Tyr Glu Lys Ile Arg Glu Met Ser Gly Val
305 310 315 320

Ser Pro Phe

<210> SEQ ID NO 5

<211> LENGTH: 325
<212> TYPE: PRT
<213> ORGANISM: homo sapien

<400> SEQUENCE: 5

Met Gly Ile Phe Pro Gly Ile Ile Leu Ile Phe Leu Arg Val Lys Phe
1 5 10 15

Ala Thr Ala Ala Val Ile Val Ser Gly His Gln Lys Ser Thr Thr Val
20 25 30

Ser His Glu Met Ser Gly Leu Asn Trp Lys Pro Phe Val Tyr Gly Gly
35 40 45

Leu Ala Ser Ile Val Ala Glu Phe Gly Thr Phe Pro Val Asp Leu Thr
50 55 60

Lys Thr Arg Leu Gln Val Gln Gly Gln Ser Ile Asp Ala Arg Phe Lys
65 70 75 80

Glu Ile Lys Tyr Arg Gly Met Phe His Ala Leu Phe Arg Ile Cys Lys
85 90 95

Glu Glu Gly Val Leu Ala Leu Tyr Ser Gly Ile Ala Pro Ala Leu Leu
100 105 110

Arg Gln Ala Ser Tyr Gly Thr Ile Lys Ile Gly Ile Tyr Gln Ser Leu
115 120 125

Lys Arg Leu Phe Val Glu Arg Leu Glu Asp Glu Thr Leu Leu Ile Asn
130 135 140

Met Ile Cys Gly Val Val Ser Gly Val Ile Ser Ser Thr Ile Ala Asn
145 150 155 160

Pro Thr Asp Val Leu Lys Ile Arg Met Gln Ala Gln Gly Ser Leu Phe
165 170 175

Gln Gly Ser Met Ile Gly Ser Phe Ile Asp Ile Tyr Gln Gln Glu Gly
180 185 190

Thr Arg Gly Leu Trp Arg Gly Val Val Pro Thr Ala Gln Arg Ala Ala
195 200 205

Ile Val Val Gly Val Glu Leu Pro Val Tyr Asp Ile Thr Lys Lys His
210 215 220

Leu Ile Leu Ser Gly Met Met Gly Asp Thr Ile Leu Thr His Phe Val
225 230 235 240

Ser Ser Phe Thr Cys Gly Leu Ala Gly Ala Leu Ala Ser Asn Pro Val
245 250 255

Asp Val Val Arg Thr Arg Met Met Asn Gln Arg Ala Ile Val Gly His
260 265 270

Val Asp Leu Tyr Lys Gly Thr Val Asp Gly Ile Leu Lys Met Trp Lys
275 280 285

His Glu Gly Phe Phe Ala Leu Tyr Lys Gly Phe Trp Pro Asn Trp Leu
290 295 300

Arg Leu Gly Pro Trp Asn Ile Ile Phe Phe Ile Thr Tyr Glu Gln Leu
305 310 315 320

Lys Arg Leu Gln Ile
325

<210> SEQ ID NO 6
<211> LENGTH: 87
<212> TYPE: DNA
<213> ORGANISM: homo sapien

<400> SEQUENCE: 6
atgtccgtcc tgacgccgct gctgctgcgg ggcttgacag gctcggcccg gcggctccca 60
gtgccgcgcg ccaagatcca ttcgttg 87

<210> SEQ ID NO 7
<211> LENGTH: 257
<212> TYPE: PRT
<213> ORGANISM: homo sapien

<400> SEQUENCE: 7

Met Val Gly Ala Gly Ile Ser Thr Pro Ser Gly Ile Pro Asp Phe Arg
1 5 10 15

Ser Pro Gly Ser Gly Leu Tyr Ser Asn Leu Gln Gln Tyr Asp Leu Pro
20 25 30

Tyr Pro Glu Ala Ile Phe Glu Leu Pro Phe Phe Phe His Asn Pro Lys
35 40 45

Pro Phe Phe Thr Leu Ala Lys Glu Leu Tyr Pro Gly Asn Tyr Lys Pro
50 55 60

Asn Val Thr His Tyr Phe Leu Arg Leu Leu His Asp Lys Gly Leu Leu
65 70 75 80

Leu Arg Leu Tyr Thr Gln Asn Ile Asp Gly Leu Glu Arg Val Ser Gly
85 90 95

Ile Pro Ala Ser Lys Leu Val Glu Ala His Gly Thr Phe Ala Ser Ala
100 105 110

Thr Cys Thr Val Cys Gln Arg Pro Phe Pro Gly Glu Asp Ile Arg Ala
115 120 125

Asp Val Met Ala Asp Arg Val Pro Arg Cys Pro Val Cys Thr Gly Val
130 135 140

Val Lys Pro Asp Ile Val Phe Phe Gly Glu Pro Leu Pro Gln Arg Phe
145 150 155 160

Leu Leu His Val Val Asp Phe Pro Met Ala Asp Leu Leu Leu Ile Leu
165 170 175

Gly Thr Ser Leu Glu Val Glu Pro Phe Ala Ser Leu Thr Glu Ala Val
180 185 190

Arg Ser Ser Val Pro Arg Leu Leu Ile Asn Arg Asp Leu Val Gly Pro
195 200 205

Leu Ala Trp His Pro Arg Ser Arg Asp Val Ala Gln Leu Gly Asp Val
210 215 220

Val His Gly Val Glu Ser Leu Val Glu Leu Leu Gly Trp Thr Glu Glu
225 230 235 240

Met Arg Asp Leu Val Gln Arg Glu Thr Gly Lys Leu Asp Gly Pro Asp
245 250 255

Lys

<210> SEQ ID NO 8
<211> LENGTH: 436
<212> TYPE: PRT
<213> ORGANISM: homo sapien

<400> SEQUENCE: 8

Met Arg Leu Ala Arg Leu Leu Arg Gly Ala Ala Leu Ala Gly Pro Gly
1 5 10 15

Pro Gly Leu Arg Ala Ala Gly Phe Ser Arg Ser Phe Ser Ser Asp Ser
20 25 30

Gly Ser Ser Pro Ala Ser Glu Arg Gly Val Pro Gly Gln Val Asp Phe
35 40 45

Tyr Ala Arg Phe Ser Pro Ser Pro Leu Ser Met Lys Gln Phe Leu Asp
50 55 60

```
Phe Gly Ser Val Asn Ala Cys Glu Lys Thr Ser Phe Met Phe Leu Arg
65                  70                  75                  80

Gln Glu Leu Pro Val Arg Leu Ala Asn Ile Met Lys Glu Ile Ser Leu
                85                  90                  95

Leu Pro Asp Asn Leu Leu Arg Thr Pro Ser Val Gln Leu Val Gln Ser
            100                 105                 110

Trp Tyr Ile Gln Ser Leu Gln Glu Leu Leu Asp Phe Lys Asp Lys Ser
        115                 120                 125

Ala Glu Asp Ala Lys Ala Ile Tyr Asp Phe Thr Asp Thr Val Ile Arg
    130                 135                 140

Ile Arg Asn Arg His Asn Asp Val Ile Pro Thr Met Ala Gln Gly Val
145                 150                 155                 160

Ile Glu Tyr Lys Glu Ser Phe Gly Val Asp Pro Val Thr Ser Gln Asn
                165                 170                 175

Val Gln Tyr Phe Leu Asp Arg Phe Tyr Met Ser Arg Ile Ser Ile Arg
            180                 185                 190

Met Leu Leu Asn Gln His Ser Leu Leu Phe Gly Gly Lys Gly Lys Gly
        195                 200                 205

Ser Pro Ser His Arg Lys His Ile Gly Ser Ile Asn Pro Asn Cys Asn
    210                 215                 220

Val Leu Glu Val Ile Lys Asp Gly Tyr Glu Asn Ala Arg Arg Leu Cys
225                 230                 235                 240

Asp Leu Tyr Tyr Ile Asn Ser Pro Glu Leu Glu Leu Glu Glu Leu Asn
                245                 250                 255

Ala Lys Ser Pro Gly Gln Pro Ile Gln Val Val Tyr Val Pro Ser His
            260                 265                 270

Leu Tyr His Met Val Phe Glu Leu Phe Lys Asn Ala Met Arg Ala Thr
        275                 280                 285

Met Glu His His Ala Asn Arg Gly Val Tyr Pro Pro Ile Gln Val His
    290                 295                 300

Val Thr Leu Gly Asn Glu Asp Leu Thr Val Lys Met Ser Asp Arg Gly
305                 310                 315                 320

Gly Gly Val Pro Leu Arg Lys Ile Asp Arg Leu Phe Asn Tyr Met Tyr
                325                 330                 335

Ser Thr Ala Pro Arg Pro Arg Val Glu Thr Ser Arg Ala Val Pro Leu
            340                 345                 350

Ala Gly Phe Gly Tyr Gly Leu Pro Ile Ser Arg Leu Tyr Ala Gln Tyr
        355                 360                 365

Phe Gln Gly Asp Leu Lys Leu Tyr Ser Leu Glu Gly Tyr Gly Thr Asp
    370                 375                 380

Ala Val Ile Tyr Ile Lys Ala Leu Ser Thr Asp Ser Ile Glu Arg Leu
385                 390                 395                 400

Pro Val Tyr Asn Lys Ala Ala Trp Lys His Tyr Asn Thr Asn His Glu
                405                 410                 415

Ala Asp Asp Trp Cys Val Pro Ser Arg Glu Pro Lys Asp Met Thr Thr
            420                 425                 430

Phe Arg Ser Ala
        435
```

<210> SEQ ID NO 9
<211> LENGTH: 1046
<212> TYPE: PRT
<213> ORGANISM: homo sapien

<400> SEQUENCE: 9

```
Met Ala Ser Ser Val Gly Asn Val Ala Asp Ser Thr Glu Pro Thr Lys
1               5                   10                  15

Arg Met Leu Ser Phe Gln Gly Leu Ala Glu Leu Ala His Arg Glu Tyr
            20                  25                  30

Gln Ala Gly Asp Phe Glu Ala Ala Glu Arg His Cys Met Gln Leu Trp
        35                  40                  45

Arg Gln Glu Pro Asp Asn Thr Gly Val Leu Leu Leu Leu Ser Ser Ile
    50                  55                  60

His Phe Gln Cys Arg Arg Leu Asp Arg Ser Ala His Phe Ser Thr Leu
65                  70                  75                  80

Ala Ile Lys Gln Asn Pro Leu Leu Ala Glu Ala Tyr Ser Asn Leu Gly
                85                  90                  95

Asn Val Tyr Lys Glu Arg Gly Gln Leu Gln Glu Ala Ile Glu His Tyr
            100                 105                 110

Arg His Ala Leu Arg Leu Lys Pro Asp Phe Ile Asp Gly Tyr Ile Asn
        115                 120                 125

Leu Ala Ala Ala Leu Val Ala Ala Gly Asp Met Glu Gly Ala Val Gln
    130                 135                 140

Ala Tyr Val Ser Ala Leu Gln Tyr Asn Pro Asp Leu Tyr Cys Val Arg
145                 150                 155                 160

Ser Asp Leu Gly Asn Leu Leu Lys Ala Leu Gly Arg Leu Glu Glu Ala
                165                 170                 175

Lys Ala Cys Tyr Leu Lys Ala Ile Glu Thr Gln Pro Asn Phe Ala Val
            180                 185                 190

Ala Trp Ser Asn Leu Gly Cys Val Phe Asn Ala Gln Gly Glu Ile Trp
        195                 200                 205

Leu Ala Ile His His Phe Glu Lys Ala Val Thr Leu Asp Pro Asn Phe
    210                 215                 220

Leu Asp Ala Tyr Ile Asn Leu Gly Asn Val Leu Lys Glu Ala Arg Ile
225                 230                 235                 240

Phe Asp Arg Ala Val Ala Ala Tyr Leu Arg Ala Leu Ser Leu Ser Pro
                245                 250                 255

Asn His Ala Val Val His Gly Asn Leu Ala Cys Val Tyr Tyr Glu Gln
            260                 265                 270

Gly Leu Ile Asp Leu Ala Ile Asp Thr Tyr Arg Arg Ala Ile Glu Leu
        275                 280                 285

Gln Pro His Phe Pro Asp Ala Tyr Cys Asn Leu Ala Asn Ala Leu Lys
    290                 295                 300

Glu Lys Gly Ser Val Ala Glu Ala Glu Asp Cys Tyr Asn Thr Ala Leu
305                 310                 315                 320

Arg Leu Cys Pro Thr His Ala Asp Ser Leu Asn Asn Leu Ala Asn Ile
                325                 330                 335

Lys Arg Glu Gln Gly Asn Ile Glu Glu Ala Val Arg Leu Tyr Arg Lys
            340                 345                 350

Ala Leu Glu Val Phe Pro Glu Phe Ala Ala Ala His Ser Asn Leu Ala
        355                 360                 365

Ser Val Leu Gln Gln Gln Gly Lys Leu Gln Glu Ala Leu Met His Tyr
    370                 375                 380

Lys Glu Ala Ile Arg Ile Ser Pro Thr Phe Ala Asp Ala Tyr Ser Asn
385                 390                 395                 400

Met Gly Asn Thr Leu Lys Glu Met Gln Asp Val Gln Gly Ala Leu Gln
                405                 410                 415
```

```
Cys Tyr Thr Arg Ala Ile Gln Ile Asn Pro Ala Phe Ala Asp Ala His
            420                 425                 430

Ser Asn Leu Ala Ser Ile His Lys Asp Ser Gly Asn Ile Pro Glu Ala
        435                 440                 445

Ile Ala Ser Tyr Arg Thr Ala Leu Lys Leu Lys Pro Asp Phe Pro Asp
    450                 455                 460

Ala Tyr Cys Asn Leu Ala His Cys Leu Gln Ile Val Cys Asp Trp Thr
465                 470                 475                 480

Asp Tyr Asp Glu Arg Met Lys Lys Leu Val Ser Ile Val Ala Asp Gln
                485                 490                 495

Leu Glu Lys Asn Arg Leu Pro Ser Val His Pro His His Ser Met Leu
            500                 505                 510

Tyr Pro Leu Ser His Gly Phe Arg Lys Ala Ile Ala Glu Arg His Gly
        515                 520                 525

Asn Leu Cys Leu Asp Lys Ile Asn Val Leu His Lys Pro Pro Tyr Glu
    530                 535                 540

His Pro Lys Asp Leu Lys Leu Ser Asp Gly Arg Leu Arg Val Gly Tyr
545                 550                 555                 560

Val Ser Ser Asp Phe Gly Asn His Pro Thr Ser His Leu Met Gln Ser
                565                 570                 575

Ile Pro Gly Met His Asn Pro Asp Lys Phe Glu Val Phe Cys Tyr Ala
            580                 585                 590

Leu Ser Pro Asp Asp Gly Thr Asn Phe Arg Val Lys Val Met Ala Glu
        595                 600                 605

Ala Asn His Phe Ile Asp Leu Ser Gln Ile Pro Cys Asn Gly Lys Ala
    610                 615                 620

Ala Asp Arg Ile His Gln Asp Gly Ile His Ile Leu Val Asn Met Asn
625                 630                 635                 640

Gly Tyr Thr Lys Gly Ala Arg Asn Glu Leu Phe Ala Leu Arg Pro Ala
                645                 650                 655

Pro Ile Gln Ala Met Trp Leu Gly Tyr Pro Gly Thr Ser Gly Ala Leu
            660                 665                 670

Phe Met Asp Tyr Ile Ile Thr Asp Gln Glu Thr Ser Pro Ala Glu Val
        675                 680                 685

Ala Glu Gln Tyr Ser Glu Lys Leu Ala Tyr Met Pro His Thr Phe Phe
    690                 695                 700

Ile Gly Asp His Ala Asn Met Phe Pro His Leu Lys Lys Lys Ala Val
705                 710                 715                 720

Ile Asp Phe Lys Ser Asn Gly His Ile Tyr Asp Asn Arg Ile Val Leu
                725                 730                 735

Asn Gly Ile Asp Leu Lys Ala Phe Leu Asp Ser Leu Pro Asp Val Lys
            740                 745                 750

Ile Val Lys Met Lys Cys Pro Asp Gly Gly Asp Asn Ala Asp Ser Ser
        755                 760                 765

Asn Thr Ala Leu Asn Met Pro Val Ile Pro Met Asn Thr Ile Ala Glu
    770                 775                 780

Ala Val Ile Glu Met Ile Asn Arg Gly Gln Ile Gln Ile Thr Ile Asn
785                 790                 795                 800

Gly Phe Ser Ile Ser Asn Gly Leu Ala Thr Thr Gln Ile Asn Asn Lys
                805                 810                 815

Ala Ala Thr Gly Glu Glu Val Pro Arg Thr Ile Ile Val Thr Thr Arg
            820                 825                 830
```

-continued

```
Ser Gln Tyr Gly Leu Pro Glu Asp Ala Ile Val Tyr Cys Asn Phe Asn
        835                 840                 845

Gln Leu Tyr Lys Ile Asp Pro Ser Thr Leu Gln Met Trp Ala Asn Ile
    850                 855                 860

Leu Lys Arg Val Pro Asn Ser Val Leu Trp Leu Leu Arg Phe Pro Ala
865                 870                 875                 880

Val Gly Glu Pro Asn Ile Gln Gln Tyr Ala Gln Asn Met Gly Leu Pro
                885                 890                 895

Gln Asn Arg Ile Ile Phe Ser Pro Val Ala Pro Lys Glu Glu His Val
            900                 905                 910

Arg Arg Gly Gln Leu Ala Asp Val Cys Leu Asp Thr Pro Leu Cys Asn
        915                 920                 925

Gly His Thr Thr Gly Met Asp Val Leu Trp Ala Gly Thr Pro Met Val
    930                 935                 940

Thr Met Pro Gly Glu Thr Leu Ala Ser Arg Val Ala Ala Ser Gln Leu
945                 950                 955                 960

Thr Cys Leu Gly Cys Leu Glu Leu Ile Ala Lys Asn Arg Gln Glu Tyr
                965                 970                 975

Glu Asp Ile Ala Val Lys Leu Gly Thr Asp Leu Glu Tyr Leu Lys Lys
            980                 985                 990

Val Arg Gly Lys Val Trp Lys Gln  Arg Ile Ser Ser Pro  Leu Phe Asn
        995                 1000                1005

Thr Lys  Gln Tyr Thr Met Glu  Leu Glu Arg Leu Tyr  Leu Gln Met
    1010                1015                1020

Trp Glu  His Tyr Ala Ala Gly  Asn Lys Pro Asp His  Met Ile Lys
    1025                1030                1035

Pro Val  Glu Val Thr Glu Ser  Ala
    1040                1045
```

<210> SEQ ID NO 10
<211> LENGTH: 145
<212> TYPE: PRT
<213> ORGANISM: homo sapien

<400> SEQUENCE: 10

```
Met Asn Gly Arg Val Asp Tyr Leu Val Thr Glu Glu Glu Ile Asn Leu
1               5                   10                  15

Thr Arg Gly Pro Ser Gly Leu Gly Phe Asn Ile Val Gly Gly Thr Asp
            20                  25                  30

Gln Gln Tyr Val Ser Asn Asp Ser Gly Ile Tyr Val Ser Arg Ile Lys
        35                  40                  45

Glu Asn Gly Ala Ala Ala Leu Asp Gly Arg Leu Gln Glu Gly Asp Lys
    50                  55                  60

Ile Leu Ser Val Asn Gly Gln Asp Leu Lys Asn Leu Leu His Gln Asp
65                  70                  75                  80

Ala Val Asp Leu Phe Arg Asn Ala Gly Tyr Ala Val Ser Leu Arg Val
                85                  90                  95

Gln His Arg Leu Gln Val Gln Asn Gly Pro Ile Gly His Arg Gly Glu
            100                 105                 110

Gly Asp Pro Ser Gly Ile Pro Ile Phe Met Val Leu Val Pro Val Phe
        115                 120                 125

Ala Leu Thr Met Val Ala Ala Trp Ala Phe Met Arg Tyr Arg Gln Gln
    130                 135                 140

Leu
145
```

<210> SEQ ID NO 11
<211> LENGTH: 142
<212> TYPE: PRT
<213> ORGANISM: homo sapien

<400> SEQUENCE: 11

```
Met Ala Ala Ala Val Ala Ala Ala Gly Ala Gly Glu Pro Gln Ser Pro
1               5                   10                  15

Asp Glu Leu Leu Pro Lys Gly Asp Ala Glu Lys Pro Glu Glu Glu Leu
            20                  25                  30

Glu Glu Asp Asp Asp Glu Glu Leu Asp Glu Thr Leu Ser Glu Arg Leu
        35                  40                  45

Trp Gly Leu Thr Glu Met Phe Pro Glu Arg Val Arg Ser Ala Ala Gly
    50                  55                  60

Ala Thr Phe Asp Leu Ser Leu Phe Val Ala Gln Lys Met Tyr Arg Phe
65                  70                  75                  80

Ser Arg Ala Ala Leu Trp Ile Gly Thr Thr Ser Phe Met Ile Leu Val
                85                  90                  95

Leu Pro Val Val Phe Glu Thr Glu Lys Leu Gln Met Glu Gln Gln Gln
            100                 105                 110

Gln Leu Gln Gln Arg Gln Ile Leu Leu Gly Pro Asn Thr Gly Leu Ser
        115                 120                 125

Gly Gly Met Pro Gly Ala Leu Pro Ser Leu Pro Gly Lys Ile
    130                 135                 140
```

<210> SEQ ID NO 12
<211> LENGTH: 171
<212> TYPE: PRT
<213> ORGANISM: homo sapien

<400> SEQUENCE: 12

```
Met Glu Glu Tyr Ala Arg Glu Pro Cys Pro Trp Arg Ile Val Asp Asp
1               5                   10                  15

Cys Gly Gly Ala Phe Thr Met Gly Thr Ile Gly Gly Gly Ile Phe Gln
            20                  25                  30

Ala Ile Lys Gly Phe Arg Asn Ser Pro Val Gly Val Asn His Arg Leu
        35                  40                  45

Arg Gly Ser Leu Thr Ala Ile Lys Thr Arg Ala Pro Gln Leu Gly Gly
    50                  55                  60

Ser Phe Ala Val Trp Gly Gly Leu Phe Ser Met Ile Asp Cys Ser Met
65                  70                  75                  80

Val Gln Val Arg Gly Lys Glu Asp Pro Trp Asn Ser Ile Thr Ser Gly
                85                  90                  95

Ala Leu Thr Gly Ala Ile Leu Ala Ala Arg Asn Gly Pro Val Ala Met
            100                 105                 110

Val Gly Ser Ala Ala Met Gly Gly Ile Leu Leu Ala Leu Ile Glu Gly
        115                 120                 125

Ala Gly Ile Leu Leu Thr Arg Phe Ala Ser Ala Gln Phe Pro Asn Gly
    130                 135                 140

Pro Gln Phe Ala Glu Asp Pro Ser Gln Leu Pro Ser Thr Gln Leu Pro
145                 150                 155                 160

Ser Ser Pro Phe Gly Asp Tyr Arg Gln Tyr Gln
                165                 170
```

<210> SEQ ID NO 13

<211> LENGTH: 172
<212> TYPE: PRT
<213> ORGANISM: homo sapien

<400> SEQUENCE: 13

```
Met Glu Glu Tyr Ala Arg Glu Pro Cys Pro Trp Arg Ile Val Asp Asp
1               5                   10                  15

Cys Gly Gly Ala Phe Thr Met Gly Val Ile Gly Gly Gly Val Phe Gln
            20                  25                  30

Ala Ile Lys Gly Phe Arg Asn Ala Pro Val Gly Ile Arg His Arg Leu
        35                  40                  45

Arg Gly Ser Ala Asn Ala Val Arg Ile Arg Ala Pro Gln Ile Gly Gly
    50                  55                  60

Ser Phe Ala Val Trp Gly Gly Leu Phe Ser Thr Ile Asp Cys Gly Leu
65                  70                  75                  80

Val Arg Leu Arg Gly Lys Glu Asp Pro Trp Asn Ser Ile Thr Ser Gly
                85                  90                  95

Ala Leu Thr Gly Ala Val Leu Ala Ala Arg Ser Gly Pro Leu Ala Met
            100                 105                 110

Val Gly Ser Ala Met Met Gly Gly Ile Leu Leu Ala Leu Ile Glu Gly
        115                 120                 125

Val Gly Ile Leu Leu Thr Arg Tyr Thr Ala Gln Gln Phe Arg Asn Ala
    130                 135                 140

Pro Pro Phe Leu Glu Asp Pro Ser Gln Leu Pro Pro Lys Asp Gly Thr
145                 150                 155                 160

Pro Ala Pro Gly Tyr Pro Ser Tyr Gln Gln Tyr His
                165                 170
```

<210> SEQ ID NO 14
<211> LENGTH: 194
<212> TYPE: PRT
<213> ORGANISM: homo sapien

<400> SEQUENCE: 14

```
Met Ala Ala Ala Ala Pro Asn Ala Gly Gly Ser Ala Pro Glu Thr Ala
1               5                   10                  15

Gly Ser Ala Glu Ala Pro Leu Gln Tyr Ser Leu Leu Leu Gln Tyr Leu
            20                  25                  30

Val Gly Asp Lys Arg Gln Pro Arg Leu Leu Glu Pro Gly Ser Leu Gly
        35                  40                  45

Gly Ile Pro Ser Pro Ala Lys Ser Glu Glu Gln Lys Met Ile Glu Lys
    50                  55                  60

Ala Met Glu Ser Cys Ala Phe Lys Ala Ala Leu Ala Cys Val Gly Gly
65                  70                  75                  80

Phe Val Leu Gly Gly Ala Phe Gly Val Phe Thr Ala Gly Ile Asp Thr
                85                  90                  95

Asn Val Gly Phe Asp Pro Lys Asp Pro Tyr Arg Thr Pro Thr Ala Lys
            100                 105                 110

Glu Val Leu Lys Asp Met Gly Gln Arg Gly Met Ser Tyr Ala Lys Asn
        115                 120                 125

Phe Ala Ile Val Gly Ala Met Phe Ser Cys Thr Glu Cys Leu Ile Glu
    130                 135                 140

Ser Tyr Arg Gly Thr Ser Asp Trp Lys Asn Ser Val Ile Ser Gly Cys
145                 150                 155                 160

Ile Thr Gly Gly Ala Ile Gly Phe Arg Ala Gly Leu Lys Ala Gly Ala
                165                 170                 175
```

```
Ile Gly Cys Gly Gly Phe Ala Ala Phe Ser Ala Ala Ile Asp Tyr Tyr
            180                 185                 190

Leu Arg


<210> SEQ ID NO 15
<211> LENGTH: 246
<212> TYPE: PRT
<213> ORGANISM: homo sapien

<400> SEQUENCE: 15

Met Ala Phe Leu Arg Ser Met Trp Gly Val Leu Ser Ala Leu Gly Arg
1               5                   10                  15

Ser Gly Ala Glu Leu Cys Thr Gly Cys Gly Ser Arg Leu Arg Ser Pro
            20                  25                  30

Phe Ser Phe Val Tyr Leu Pro Arg Trp Phe Ser Ser Val Leu Ala Ser
        35                  40                  45

Cys Pro Lys Lys Pro Val Ser Ser Tyr Leu Arg Phe Ser Lys Glu Gln
    50                  55                  60

Leu Pro Ile Phe Lys Ala Gln Asn Pro Asp Ala Lys Thr Thr Glu Leu
65                  70                  75                  80

Ile Arg Arg Ile Ala Gln Arg Trp Arg Glu Leu Pro Asp Ser Lys Lys
                85                  90                  95

Lys Ile Tyr Gln Asp Ala Tyr Arg Ala Glu Trp Gln Val Tyr Lys Glu
            100                 105                 110

Glu Ile Ser Arg Phe Lys Glu Gln Leu Thr Pro Ser Gln Ile Met Ser
        115                 120                 125

Leu Glu Lys Glu Ile Met Asp Lys His Leu Lys Arg Lys Ala Met Thr
    130                 135                 140

Lys Lys Lys Glu Leu Thr Leu Leu Gly Lys Pro Lys Arg Pro Arg Ser
145                 150                 155                 160

Ala Tyr Asn Val Tyr Val Ala Glu Arg Phe Gln Glu Ala Lys Gly Asp
                165                 170                 175

Ser Pro Gln Glu Lys Leu Lys Thr Val Lys Glu Asn Trp Lys Asn Leu
            180                 185                 190

Ser Asp Ser Glu Lys Glu Leu Tyr Ile Gln His Ala Lys Glu Asp Glu
        195                 200                 205

Thr Arg Tyr His Asn Glu Met Lys Ser Trp Glu Glu Gln Met Ile Glu
    210                 215                 220

Val Gly Arg Lys Asp Leu Leu Arg Arg Thr Ile Lys Lys Gln Arg Lys
225                 230                 235                 240

Tyr Gly Ala Glu Glu Cys
                245


<210> SEQ ID NO 16
<211> LENGTH: 798
<212> TYPE: PRT
<213> ORGANISM: Homo sapiens

<400> SEQUENCE: 16

Met Ala Trp Asp Met Cys Asn Gln Asp Ser Glu Ser Val Trp Ser Asp
1               5                   10                  15

Ile Glu Cys Ala Ala Leu Val Gly Glu Asp Gln Pro Leu Cys Pro Asp
            20                  25                  30

Leu Pro Glu Leu Asp Leu Ser Glu Leu Asp Val Asn Asp Leu Asp Thr
        35                  40                  45
```

-continued

```
Asp Ser Phe Leu Gly Gly Leu Lys Trp Cys Ser Asp Gln Ser Glu Ile
    50                  55                  60

Ile Ser Asn Gln Tyr Asn Asn Glu Pro Ser Asn Ile Phe Glu Lys Ile
65                  70                  75                  80

Asp Glu Glu Asn Glu Ala Asn Leu Leu Ala Val Leu Thr Glu Thr Leu
                85                  90                  95

Asp Ser Leu Pro Val Asp Glu Asp Gly Leu Pro Ser Phe Asp Ala Leu
            100                 105                 110

Thr Asp Gly Asp Val Thr Thr Asp Asn Glu Ala Ser Pro Ser Ser Met
        115                 120                 125

Pro Asp Gly Thr Pro Pro Pro Gln Glu Ala Glu Glu Pro Ser Leu Leu
    130                 135                 140

Lys Lys Leu Leu Leu Ala Pro Ala Asn Thr Gln Leu Ser Tyr Asn Glu
145                 150                 155                 160

Cys Ser Gly Leu Ser Thr Gln Asn His Ala Asn His Asn His Arg Ile
                165                 170                 175

Arg Thr Asn Pro Ala Ile Val Lys Thr Glu Asn Ser Trp Ser Asn Lys
            180                 185                 190

Ala Lys Ser Ile Cys Gln Gln Gln Lys Pro Gln Arg Arg Pro Cys Ser
        195                 200                 205

Glu Leu Leu Lys Tyr Leu Thr Thr Asn Asp Asp Pro Pro His Thr Lys
    210                 215                 220

Pro Thr Glu Asn Arg Asn Ser Ser Arg Asp Lys Cys Thr Ser Lys Lys
225                 230                 235                 240

Lys Ser His Thr Gln Ser Gln Ser Gln His Leu Gln Ala Lys Pro Thr
                245                 250                 255

Thr Leu Ser Leu Pro Leu Thr Pro Glu Ser Pro Asn Asp Pro Lys Gly
            260                 265                 270

Ser Pro Phe Glu Asn Lys Thr Ile Glu Arg Thr Leu Ser Val Glu Leu
        275                 280                 285

Ser Gly Thr Ala Gly Leu Thr Pro Pro Thr Thr Pro Pro His Lys Ala
    290                 295                 300

Asn Gln Asp Asn Pro Phe Arg Ala Ser Pro Lys Leu Lys Ser Ser Cys
305                 310                 315                 320

Lys Thr Val Val Pro Pro Pro Ser Lys Lys Pro Arg Tyr Ser Glu Ser
                325                 330                 335

Ser Gly Thr Gln Gly Asn Asn Ser Thr Lys Lys Gly Pro Glu Gln Ser
            340                 345                 350

Glu Leu Tyr Ala Gln Leu Ser Lys Ser Ser Val Leu Thr Gly Gly His
        355                 360                 365

Glu Glu Arg Lys Thr Lys Arg Pro Ser Leu Arg Leu Phe Gly Asp His
    370                 375                 380

Asp Tyr Cys Gln Ser Ile Asn Ser Lys Thr Glu Ile Leu Ile Asn Ile
385                 390                 395                 400

Ser Gln Glu Leu Gln Asp Ser Arg Gln Leu Glu Asn Lys Asp Val Ser
                405                 410                 415

Ser Asp Trp Gln Gly Gln Ile Cys Ser Ser Thr Asp Ser Asp Gln Cys
            420                 425                 430

Tyr Leu Arg Glu Thr Leu Glu Ala Ser Lys Gln Val Ser Pro Cys Ser
        435                 440                 445

Thr Arg Lys Gln Leu Gln Asp Gln Glu Ile Arg Ala Glu Leu Asn Lys
    450                 455                 460

His Phe Gly His Pro Ser Gln Ala Val Phe Asp Asp Glu Ala Asp Lys
```

```
465                 470                 475                 480

Thr Gly Glu Leu Arg Asp Ser Asp Phe Ser Asn Glu Gln Phe Ser Lys
                485                 490                 495

Leu Pro Met Phe Ile Asn Ser Gly Leu Ala Met Asp Gly Leu Phe Asp
            500                 505                 510

Asp Ser Glu Asp Glu Ser Asp Lys Leu Ser Tyr Pro Trp Asp Gly Thr
        515                 520                 525

Gln Ser Tyr Ser Leu Phe Asn Val Ser Pro Ser Cys Ser Ser Phe Asn
    530                 535                 540

Ser Pro Cys Arg Asp Ser Val Ser Pro Pro Lys Ser Leu Phe Ser Gln
545                 550                 555                 560

Arg Pro Gln Arg Met Arg Ser Arg Ser Arg Ser Phe Ser Arg His Arg
                565                 570                 575

Ser Cys Ser Arg Ser Pro Tyr Ser Arg Ser Arg Ser Arg Ser Pro Gly
            580                 585                 590

Ser Arg Ser Ser Ser Arg Ser Cys Tyr Tyr Tyr Glu Ser Ser His Tyr
        595                 600                 605

Arg His Arg Thr His Arg Asn Ser Pro Leu Tyr Val Arg Ser Arg Ser
    610                 615                 620

Arg Ser Pro Tyr Ser Arg Arg Pro Arg Tyr Asp Ser Tyr Glu Glu Tyr
625                 630                 635                 640

Gln His Glu Arg Leu Lys Arg Glu Glu Tyr Arg Arg Glu Tyr Glu Lys
                645                 650                 655

Arg Glu Ser Glu Arg Ala Lys Gln Arg Glu Arg Gln Arg Gln Lys Ala
            660                 665                 670

Ile Glu Glu Arg Arg Val Ile Tyr Val Gly Lys Ile Arg Pro Asp Thr
        675                 680                 685

Thr Arg Thr Glu Leu Arg Asp Arg Phe Glu Val Phe Gly Glu Ile Glu
    690                 695                 700

Glu Cys Thr Val Asn Leu Arg Asp Asp Gly Asp Ser Tyr Gly Phe Ile
705                 710                 715                 720

Thr Tyr Arg Tyr Thr Cys Asp Ala Phe Ala Ala Leu Glu Asn Gly Tyr
                725                 730                 735

Thr Leu Arg Arg Ser Asn Glu Thr Asp Phe Glu Leu Tyr Phe Cys Gly
            740                 745                 750

Arg Lys Gln Phe Phe Lys Ser Asn Tyr Ala Asp Leu Asp Ser Asn Ser
        755                 760                 765

Asp Asp Phe Asp Pro Ala Ser Thr Lys Ser Lys Tyr Asp Ser Leu Asp
    770                 775                 780

Phe Asp Ser Leu Leu Lys Glu Ala Gln Arg Ser Leu Arg Arg
785                 790                 795


<210> SEQ ID NO 17
<211> LENGTH: 8
<212> TYPE: PRT
<213> ORGANISM: Artificial Sequence
<220> FEATURE:
<223> OTHER INFORMATION: Synthetic sequence

<400> SEQUENCE: 17

Asp Tyr Lys Asp Asp Asp Asp Lys
1               5


<210> SEQ ID NO 18
<211> LENGTH: 427
<212> TYPE: PRT
```

<213> ORGANISM: homo sapien

<400> SEQUENCE: 18

Met Ala Val Leu Ala Ala Leu Leu Arg Ser Gly Ala Arg Ser Arg Ser
1 5 10 15

Pro Leu Leu Arg Arg Leu Val Gln Glu Ile Arg Tyr Val Glu Arg Ser
20 25 30

Tyr Val Ser Lys Pro Thr Leu Lys Glu Val Val Ile Val Ser Ala Thr
35 40 45

Arg Thr Pro Ile Gly Ser Phe Leu Gly Ser Leu Ser Leu Leu Pro Ala
50 55 60

Thr Lys Leu Gly Ser Ile Ala Ile Gln Gly Ala Ile Glu Lys Ala Gly
65 70 75 80

Ile Pro Lys Glu Glu Val Lys Glu Ala Tyr Met Gly Asn Val Leu Gln
85 90 95

Gly Gly Glu Gly Gln Ala Pro Thr Arg Gln Ala Val Leu Gly Ala Gly
100 105 110

Leu Pro Ile Ser Thr Pro Cys Thr Thr Ile Asn Lys Val Cys Ala Ser
115 120 125

Gly Met Lys Ala Ile Met Met Ala Ser Gln Ser Leu Met Cys Gly His
130 135 140

Gln Asp Val Met Val Ala Gly Gly Met Glu Ser Met Ser Asn Val Pro
145 150 155 160

Tyr Val Met Asn Arg Gly Ser Thr Pro Tyr Gly Gly Val Lys Leu Glu
165 170 175

Asp Leu Ile Val Lys Asp Gly Leu Thr Asp Val Tyr Asn Lys Ile His
180 185 190

Met Gly Ser Cys Ala Glu Asn Thr Ala Lys Lys Leu Asn Ile Ala Arg
195 200 205

Asn Glu Gln Asp Ala Tyr Ala Ile Asn Ser Tyr Thr Arg Ser Lys Ala
210 215 220

Ala Trp Glu Ala Gly Lys Phe Gly Asn Glu Val Ile Pro Val Thr Val
225 230 235 240

Thr Val Lys Gly Gln Pro Asp Val Val Val Lys Glu Asp Glu Glu Tyr
245 250 255

Lys Arg Val Asp Phe Ser Lys Val Pro Lys Leu Lys Thr Val Phe Gln
260 265 270

Lys Glu Asn Gly Thr Val Thr Ala Ala Asn Ala Ser Thr Leu Asn Asp
275 280 285

Gly Ala Ala Ala Leu Val Leu Met Thr Ala Asp Ala Ala Lys Arg Leu
290 295 300

Asn Val Thr Pro Leu Ala Arg Ile Val Ala Phe Ala Asp Ala Ala Val
305 310 315 320

Glu Pro Ile Asp Phe Pro Ile Ala Pro Val Tyr Ala Ala Ser Met Val
325 330 335

Leu Lys Asp Val Gly Leu Lys Lys Glu Asp Ile Ala Met Trp Glu Val
340 345 350

Asn Glu Ala Phe Ser Leu Val Val Leu Ala Asn Ile Lys Met Leu Glu
355 360 365

Ile Asp Pro Gln Lys Val Asn Ile Asn Gly Gly Ala Val Ser Leu Gly
370 375 380

His Pro Ile Gly Met Ser Gly Ala Arg Ile Val Gly His Leu Thr His
385 390 395 400

```
Ala Leu Lys Gln Gly Glu Tyr Gly Leu Ala Ser Ile Cys Asn Gly Gly
                405                 410                 415

Gly Gly Ala Ser Ala Met Leu Ile Gln Lys Leu
            420                 425


<210> SEQ ID NO 19
<211> LENGTH: 327
<212> TYPE: PRT
<213> ORGANISM: homo sapien

<400> SEQUENCE: 19

Met Pro Ala Leu Leu Glu Arg Pro Lys Leu Ser Asn Ala Met Ala Arg
1               5                   10                  15

Ala Leu His Arg His Ile Met Met Glu Arg Glu Arg Lys Arg Gln Glu
            20                  25                  30

Glu Glu Glu Val Asp Lys Met Met Glu Gln Lys Met Lys Glu Glu Gln
        35                  40                  45

Glu Arg Arg Lys Lys Lys Glu Met Glu Glu Arg Met Ser Leu Glu Glu
    50                  55                  60

Thr Lys Glu Gln Ile Leu Lys Leu Glu Glu Lys Leu Leu Ala Leu Gln
65                  70                  75                  80

Glu Glu Lys His Gln Leu Phe Leu Gln Leu Lys Lys Val Leu His Glu
                85                  90                  95

Glu Glu Lys Arg Arg Arg Lys Glu Gln Ser Asp Leu Thr Thr Leu Thr
            100                 105                 110

Ser Ala Ala Tyr Gln Gln Ser Leu Thr Val His Thr Gly Thr His Leu
        115                 120                 125

Leu Ser Met Gln Gly Ser Pro Gly Gly His Asn Arg Pro Gly Thr Leu
    130                 135                 140

Met Ala Ala Asp Arg Ala Lys Gln Met Phe Gly Pro Gln Val Leu Thr
145                 150                 155                 160

Thr Arg His Tyr Val Gly Ser Ala Ala Ala Phe Ala Gly Thr Pro Glu
                165                 170                 175

His Gly Gln Phe Gln Gly Ser Pro Gly Gly Ala Tyr Gly Thr Ala Gln
            180                 185                 190

Pro Pro Pro His Tyr Gly Pro Thr Gln Pro Ala Tyr Ser Pro Ser Gln
        195                 200                 205

Gln Leu Arg Ala Pro Ser Ala Phe Pro Ala Val Gln Tyr Leu Ser Gln
    210                 215                 220

Pro Gln Pro Gln Pro Tyr Ala Val His Gly His Phe Gln Pro Thr Gln
225                 230                 235                 240

Thr Gly Phe Leu Gln Pro Gly Gly Ala Leu Ser Leu Gln Lys Gln Met
                245                 250                 255

Glu His Ala Asn Gln Gln Thr Gly Phe Ser Asp Ser Ser Ser Leu Arg
            260                 265                 270

Pro Met His Pro Gln Ala Leu His Pro Ala Pro Gly Leu Leu Ala Ser
        275                 280                 285

Pro Gln Leu Pro Val Gln Met Gln Pro Ala Gly Lys Ser Gly Phe Ala
    290                 295                 300

Ala Thr Ser Gln Pro Gly Pro Arg Leu Pro Phe Ile Gln His Ser Gln
305                 310                 315                 320

Asn Pro Arg Phe Tyr His Lys
                325


<210> SEQ ID NO 20
```

<211> LENGTH: 324
<212> TYPE: PRT
<213> ORGANISM: homo sapien

<400> SEQUENCE: 20

Met Ser Ser Glu Ala Glu Thr Gln Gln Pro Pro Ala Ala Pro Pro Ala
1 5 10 15

Ala Pro Ala Leu Ser Ala Ala Asp Thr Lys Pro Gly Thr Thr Gly Ser
20 25 30

Gly Ala Gly Ser Gly Gly Pro Gly Gly Leu Thr Ser Ala Ala Pro Ala
35 40 45

Gly Gly Asp Lys Lys Val Ile Ala Thr Lys Val Leu Gly Thr Val Lys
50 55 60

Trp Phe Asn Val Arg Asn Gly Tyr Gly Phe Ile Asn Arg Asn Asp Thr
65 70 75 80

Lys Glu Asp Val Phe Val His Gln Thr Ala Ile Lys Lys Asn Asn Pro
85 90 95

Arg Lys Tyr Leu Arg Ser Val Gly Asp Gly Glu Thr Val Glu Phe Asp
100 105 110

Val Val Glu Gly Glu Lys Gly Ala Glu Ala Ala Asn Val Thr Gly Pro
115 120 125

Gly Gly Val Pro Val Gln Gly Ser Lys Tyr Ala Ala Asp Arg Asn His
130 135 140

Tyr Arg Arg Tyr Pro Arg Arg Arg Gly Pro Pro Arg Asn Tyr Gln Gln
145 150 155 160

Asn Tyr Gln Asn Ser Glu Ser Gly Glu Lys Asn Glu Gly Ser Glu Ser
165 170 175

Ala Pro Glu Gly Gln Ala Gln Gln Arg Arg Pro Tyr Arg Arg Arg Arg
180 185 190

Phe Pro Pro Tyr Tyr Met Arg Arg Pro Tyr Gly Arg Arg Pro Gln Tyr
195 200 205

Ser Asn Pro Pro Val Gln Gly Glu Val Met Glu Gly Ala Asp Asn Gln
210 215 220

Gly Ala Gly Glu Gln Gly Arg Pro Val Arg Gln Asn Met Tyr Arg Gly
225 230 235 240

Tyr Arg Pro Arg Phe Arg Arg Gly Pro Pro Arg Gln Arg Gln Pro Arg
245 250 255

Glu Asp Gly Asn Glu Glu Asp Lys Glu Asn Gln Gly Asp Glu Thr Gln
260 265 270

Gly Gln Gln Pro Pro Gln Arg Arg Tyr Arg Arg Asn Phe Asn Tyr Arg
275 280 285

Arg Arg Arg Pro Glu Asn Pro Lys Pro Gln Asp Gly Lys Glu Thr Lys
290 295 300

Ala Ala Asp Pro Pro Ala Glu Asn Ser Ser Ala Pro Glu Ala Glu Gln
305 310 315 320

Gly Gly Ala Glu

<210> SEQ ID NO 21
<211> LENGTH: 960
<212> TYPE: PRT
<213> ORGANISM: homo sapien

<400> SEQUENCE: 21

Met Trp Arg Leu Arg Arg Ala Ala Val Ala Cys Glu Val Cys Gln Ser
1 5 10 15

```
Leu Val Lys His Ser Ser Gly Ile Lys Gly Ser Leu Pro Leu Gln Lys
            20                  25                  30

Leu His Leu Val Ser Arg Ser Ile Tyr His Ser His His Pro Thr Leu
        35                  40                  45

Lys Leu Gln Arg Pro Gln Leu Arg Thr Ser Phe Gln Gln Phe Ser Ser
    50                  55                  60

Leu Thr Asn Leu Pro Leu Arg Lys Leu Lys Phe Ser Pro Ile Lys Tyr
65                  70                  75                  80

Gly Tyr Gln Pro Arg Arg Asn Phe Trp Pro Ala Arg Leu Ala Thr Arg
                85                  90                  95

Leu Leu Lys Leu Arg Tyr Leu Ile Leu Gly Ser Ala Val Gly Gly Gly
            100                 105                 110

Tyr Thr Ala Lys Lys Thr Phe Asp Gln Trp Lys Asp Met Ile Pro Asp
        115                 120                 125

Leu Ser Glu Tyr Lys Trp Ile Val Pro Asp Ile Val Trp Glu Ile Asp
    130                 135                 140

Glu Tyr Ile Asp Phe Glu Lys Ile Arg Lys Ala Leu Pro Ser Ser Glu
145                 150                 155                 160

Asp Leu Val Lys Leu Ala Pro Asp Phe Asp Lys Ile Val Glu Ser Leu
                165                 170                 175

Ser Leu Leu Lys Asp Phe Phe Thr Ser Gly Ser Pro Glu Glu Thr Ala
            180                 185                 190

Phe Arg Ala Thr Asp Arg Gly Ser Glu Ser Asp Lys His Phe Arg Lys
        195                 200                 205

Val Ser Asp Lys Glu Lys Ile Asp Gln Leu Gln Glu Glu Leu Leu His
    210                 215                 220

Thr Gln Leu Lys Tyr Gln Arg Ile Leu Glu Arg Leu Glu Lys Glu Asn
225                 230                 235                 240

Lys Glu Leu Arg Lys Leu Val Leu Gln Lys Asp Asp Lys Gly Ile His
                245                 250                 255

His Arg Lys Leu Lys Lys Ser Leu Ile Asp Met Tyr Ser Glu Val Leu
            260                 265                 270

Asp Val Leu Ser Asp Tyr Asp Ala Ser Tyr Asn Thr Gln Asp His Leu
        275                 280                 285

Pro Arg Val Val Val Val Gly Asp Gln Ser Ala Gly Lys Thr Ser Val
    290                 295                 300

Leu Glu Met Ile Ala Gln Ala Arg Ile Phe Pro Arg Gly Ser Gly Glu
305                 310                 315                 320

Met Met Thr Arg Ser Pro Val Lys Val Thr Leu Ser Glu Gly Pro His
                325                 330                 335

His Val Ala Leu Phe Lys Asp Ser Ser Arg Glu Phe Asp Leu Thr Lys
            340                 345                 350

Glu Glu Asp Leu Ala Ala Leu Arg His Glu Ile Glu Leu Arg Met Arg
        355                 360                 365

Lys Asn Val Lys Glu Gly Cys Thr Val Ser Pro Glu Thr Ile Ser Leu
    370                 375                 380

Asn Val Lys Gly Pro Gly Leu Gln Arg Met Val Leu Val Asp Leu Pro
385                 390                 395                 400

Gly Val Ile Asn Thr Val Thr Ser Gly Met Ala Pro Asp Thr Lys Glu
                405                 410                 415

Thr Ile Phe Ser Ile Ser Lys Ala Tyr Met Gln Asn Pro Asn Ala Ile
            420                 425                 430

Ile Leu Cys Ile Gln Asp Gly Ser Val Asp Ala Glu Arg Ser Ile Val
```

```
        435                 440                 445

Thr Asp Leu Val Ser Gln Met Asp Pro His Gly Arg Arg Thr Ile Phe
    450                 455                 460

Val Leu Thr Lys Val Asp Leu Ala Glu Lys Asn Val Ala Ser Pro Ser
465                 470                 475                 480

Arg Ile Gln Gln Ile Ile Glu Gly Lys Leu Phe Pro Met Lys Ala Leu
                485                 490                 495

Gly Tyr Phe Ala Val Val Thr Gly Lys Gly Asn Ser Ser Glu Ser Ile
            500                 505                 510

Glu Ala Ile Arg Glu Tyr Glu Glu Glu Phe Phe Gln Asn Ser Lys Leu
        515                 520                 525

Leu Lys Thr Ser Met Leu Lys Ala His Gln Val Thr Thr Arg Asn Leu
    530                 535                 540

Ser Leu Ala Val Ser Asp Cys Phe Trp Lys Met Val Arg Glu Ser Val
545                 550                 555                 560

Glu Gln Gln Ala Asp Ser Phe Lys Ala Thr Arg Phe Asn Leu Glu Thr
                565                 570                 575

Glu Trp Lys Asn Asn Tyr Pro Arg Leu Arg Glu Leu Asp Arg Asn Glu
            580                 585                 590

Leu Phe Glu Lys Ala Lys Asn Glu Ile Leu Asp Glu Val Ile Ser Leu
        595                 600                 605

Ser Gln Val Thr Pro Lys His Trp Glu Glu Ile Leu Gln Gln Ser Leu
    610                 615                 620

Trp Glu Arg Val Ser Thr His Val Ile Glu Asn Ile Tyr Leu Pro Ala
625                 630                 635                 640

Ala Gln Thr Met Asn Ser Gly Thr Phe Asn Thr Thr Val Asp Ile Lys
                645                 650                 655

Leu Lys Gln Trp Thr Asp Lys Gln Leu Pro Asn Lys Ala Val Glu Val
            660                 665                 670

Ala Trp Glu Thr Leu Gln Glu Glu Phe Ser Arg Phe Met Thr Glu Pro
        675                 680                 685

Lys Gly Lys Glu His Asp Asp Ile Phe Asp Lys Leu Lys Glu Ala Val
    690                 695                 700

Lys Glu Glu Ser Ile Lys Arg His Lys Trp Asn Asp Phe Ala Glu Asp
705                 710                 715                 720

Ser Leu Arg Val Ile Gln His Asn Ala Leu Glu Asp Arg Ser Ile Ser
                725                 730                 735

Asp Lys Gln Gln Trp Asp Ala Ala Ile Tyr Phe Met Glu Glu Ala Leu
            740                 745                 750

Gln Ala Arg Leu Lys Asp Thr Glu Asn Ala Ile Glu Asn Met Val Gly
        755                 760                 765

Pro Asp Trp Lys Lys Arg Trp Leu Tyr Trp Lys Asn Arg Thr Gln Glu
    770                 775                 780

Gln Cys Val His Asn Glu Thr Lys Asn Glu Leu Glu Lys Met Leu Lys
785                 790                 795                 800

Cys Asn Glu Glu His Pro Ala Tyr Leu Ala Ser Asp Glu Ile Thr Thr
                805                 810                 815

Val Arg Lys Asn Leu Glu Ser Arg Gly Val Glu Val Asp Pro Ser Leu
            820                 825                 830

Ile Lys Asp Thr Trp His Gln Val Tyr Arg Arg His Phe Leu Lys Thr
        835                 840                 845

Ala Leu Asn His Cys Asn Leu Cys Arg Arg Gly Phe Tyr Tyr Tyr Gln
    850                 855                 860
```

```
Arg His Phe Val Asp Ser Glu Leu Glu Cys Asn Asp Val Val Leu Phe
865                 870                 875                 880

Trp Arg Ile Gln Arg Met Leu Ala Ile Thr Ala Asn Thr Leu Arg Gln
                885                 890                 895

Gln Leu Thr Asn Thr Glu Val Arg Arg Leu Glu Lys Asn Val Lys Glu
            900                 905                 910

Val Leu Glu Asp Phe Ala Glu Asp Gly Glu Lys Lys Ile Lys Leu Leu
        915                 920                 925

Thr Gly Lys Arg Val Gln Leu Ala Glu Asp Leu Lys Lys Val Arg Glu
    930                 935                 940

Ile Gln Glu Lys Leu Asp Ala Phe Ile Glu Ala Leu His Gln Glu Lys
945                 950                 955                 960


<210> SEQ ID NO 22
<211> LENGTH: 741
<212> TYPE: PRT
<213> ORGANISM: homo sapien

<400> SEQUENCE: 22

Met Ala Glu Pro Val Ser Pro Leu Lys His Phe Val Leu Ala Lys Lys
1               5                   10                  15

Ala Ile Thr Ala Ile Phe Asp Gln Leu Leu Glu Phe Val Thr Glu Gly
            20                  25                  30

Ser His Phe Val Glu Ala Thr Tyr Lys Asn Pro Glu Leu Asp Arg Ile
        35                  40                  45

Ala Thr Glu Asp Asp Leu Val Glu Met Gln Gly Tyr Lys Asp Lys Leu
    50                  55                  60

Ser Ile Ile Gly Glu Val Leu Ser Arg Arg His Met Lys Val Ala Phe
65                  70                  75                  80

Phe Gly Arg Thr Ser Ser Gly Lys Ser Ser Val Ile Asn Ala Met Leu
                85                  90                  95

Trp Asp Lys Val Leu Pro Ser Gly Ile Gly His Ile Thr Asn Cys Phe
            100                 105                 110

Leu Ser Val Glu Gly Thr Asp Gly Asp Lys Ala Tyr Leu Met Thr Glu
        115                 120                 125

Gly Ser Asp Glu Lys Lys Ser Val Lys Thr Val Asn Gln Leu Ala His
    130                 135                 140

Ala Leu His Met Asp Lys Asp Leu Lys Ala Gly Cys Leu Val Arg Val
145                 150                 155                 160

Phe Trp Pro Lys Ala Lys Cys Ala Leu Leu Arg Asp Asp Leu Val Leu
                165                 170                 175

Val Asp Ser Pro Gly Thr Asp Val Thr Thr Glu Leu Asp Ser Trp Ile
            180                 185                 190

Asp Lys Phe Cys Leu Asp Ala Asp Val Phe Val Leu Val Ala Asn Ser
        195                 200                 205

Glu Ser Thr Leu Met Asn Thr Glu Lys His Phe Phe His Lys Val Asn
    210                 215                 220

Glu Arg Leu Ser Lys Pro Asn Ile Phe Ile Leu Asn Asn Arg Trp Asp
225                 230                 235                 240

Ala Ser Ala Ser Glu Pro Glu Tyr Met Glu Asp Val Arg Arg Gln His
                245                 250                 255

Met Glu Arg Cys Leu His Phe Leu Val Glu Glu Leu Lys Val Val Asn
            260                 265                 270

Ala Leu Glu Ala Gln Asn Arg Ile Phe Phe Val Ser Ala Lys Glu Val
```

```
        275                 280                 285

Leu Ser Ala Arg Lys Gln Lys Ala Gln Gly Met Pro Glu Ser Gly Val
    290                 295                 300

Ala Leu Ala Glu Gly Phe His Ala Arg Leu Gln Glu Phe Gln Asn Phe
305                 310                 315                 320

Glu Gln Ile Phe Glu Glu Cys Ile Ser Gln Ser Ala Val Lys Thr Lys
                325                 330                 335

Phe Glu Gln His Thr Ile Arg Ala Lys Gln Ile Leu Ala Thr Val Lys
            340                 345                 350

Asn Ile Met Asp Ser Val Asn Leu Ala Ala Glu Asp Lys Arg His Tyr
        355                 360                 365

Ser Val Glu Glu Arg Glu Asp Gln Ile Asp Arg Leu Asp Phe Ile Arg
    370                 375                 380

Asn Gln Met Asn Leu Leu Thr Leu Asp Val Lys Lys Lys Ile Lys Glu
385                 390                 395                 400

Val Thr Glu Glu Val Ala Asn Lys Val Ser Cys Ala Met Thr Asp Glu
                405                 410                 415

Ile Cys Arg Leu Ser Val Leu Val Asp Glu Phe Cys Ser Glu Phe His
            420                 425                 430

Pro Asn Pro Asp Val Leu Lys Ile Tyr Lys Ser Glu Leu Asn Lys His
        435                 440                 445

Ile Glu Asp Gly Met Gly Arg Asn Leu Ala Asp Arg Cys Thr Asp Glu
    450                 455                 460

Val Asn Ala Leu Val Leu Gln Thr Gln Gln Glu Ile Ile Glu Asn Leu
465                 470                 475                 480

Lys Pro Leu Leu Pro Ala Gly Ile Gln Asp Lys Leu His Thr Leu Ile
                485                 490                 495

Pro Cys Lys Lys Phe Asp Leu Ser Tyr Asn Leu Asn Tyr His Lys Leu
            500                 505                 510

Cys Ser Asp Phe Gln Glu Asp Ile Val Phe Pro Phe Ser Leu Gly Trp
        515                 520                 525

Ser Ser Leu Val His Arg Phe Leu Gly Pro Arg Asn Ala Gln Arg Val
    530                 535                 540

Leu Leu Gly Leu Ser Glu Pro Ile Phe Gln Leu Pro Arg Ser Leu Ala
545                 550                 555                 560

Ser Thr Pro Thr Ala Pro Thr Thr Pro Ala Thr Pro Asp Asn Ala Ser
                565                 570                 575

Gln Glu Glu Leu Met Ile Thr Leu Val Thr Gly Leu Ala Ser Val Thr
            580                 585                 590

Ser Arg Thr Ser Met Gly Ile Ile Ile Val Gly Gly Val Ile Trp Lys
        595                 600                 605

Thr Ile Gly Trp Lys Leu Leu Ser Val Ser Leu Thr Met Tyr Gly Ala
    610                 615                 620

Leu Tyr Leu Tyr Glu Arg Leu Ser Trp Thr Thr His Ala Lys Glu Arg
625                 630                 635                 640

Ala Phe Lys Gln Gln Phe Val Asn Tyr Ala Thr Glu Lys Leu Arg Met
                645                 650                 655

Ile Val Ser Ser Thr Ser Ala Asn Cys Ser His Gln Val Lys Gln Gln
            660                 665                 670

Ile Ala Thr Thr Phe Ala Arg Leu Cys Gln Gln Val Asp Ile Thr Gln
        675                 680                 685

Lys Gln Leu Glu Glu Glu Ile Ala Arg Leu Pro Lys Glu Ile Asp Gln
    690                 695                 700
```

Leu Glu Lys Ile Gln Asn Asn Ser Lys Leu Leu Arg Asn Lys Ala Val
705 710 715 720

Gln Leu Glu Asn Glu Leu Glu Asn Phe Thr Lys Gln Phe Leu Pro Ser
725 730 735

Ser Asn Glu Glu Ser
740

<210> SEQ ID NO 23
<211> LENGTH: 757
<212> TYPE: PRT
<213> ORGANISM: homo sapien

<400> SEQUENCE: 23

Met Ser Leu Leu Phe Ser Arg Cys Asn Ser Ile Val Thr Val Lys Lys
1 5 10 15

Asn Lys Arg His Met Ala Glu Val Asn Ala Ser Pro Leu Lys His Phe
20 25 30

Val Thr Ala Lys Lys Lys Ile Asn Gly Ile Phe Glu Gln Leu Gly Ala
35 40 45

Tyr Ile Gln Glu Ser Ala Thr Phe Leu Glu Asp Thr Tyr Arg Asn Ala
50 55 60

Glu Leu Asp Pro Val Thr Thr Glu Glu Gln Val Leu Asp Val Lys Gly
65 70 75 80

Tyr Leu Ser Lys Val Arg Gly Ile Ser Glu Val Leu Ala Arg Arg His
85 90 95

Met Lys Val Ala Phe Phe Gly Arg Thr Ser Asn Gly Lys Ser Thr Val
100 105 110

Ile Asn Ala Met Leu Trp Asp Lys Val Leu Pro Ser Gly Ile Gly His
115 120 125

Thr Thr Asn Cys Phe Leu Arg Val Glu Gly Thr Asp Gly His Glu Ala
130 135 140

Phe Leu Leu Thr Glu Gly Ser Glu Glu Lys Arg Ser Ala Lys Thr Val
145 150 155 160

Asn Gln Leu Ala His Ala Leu His Gln Asp Lys Gln Leu His Ala Gly
165 170 175

Ser Leu Val Ser Val Met Trp Pro Asn Ser Lys Cys Pro Leu Leu Lys
180 185 190

Asp Asp Leu Val Leu Met Asp Ser Pro Gly Ile Asp Val Thr Thr Glu
195 200 205

Leu Asp Ser Trp Ile Asp Lys Phe Cys Leu Asp Ala Asp Val Phe Val
210 215 220

Leu Val Ala Asn Ser Glu Ser Thr Leu Met Gln Thr Glu Lys His Phe
225 230 235 240

Phe His Lys Val Ser Glu Arg Leu Ser Arg Pro Asn Ile Phe Ile Leu
245 250 255

Asn Asn Arg Trp Asp Ala Ser Ala Ser Glu Pro Glu Tyr Met Glu Glu
260 265 270

Val Arg Arg Gln His Met Glu Arg Cys Thr Ser Phe Leu Val Asp Glu
275 280 285

Leu Gly Val Val Asp Arg Ser Gln Ala Gly Asp Arg Ile Phe Phe Val
290 295 300

Ser Ala Lys Glu Val Leu Asn Ala Arg Ile Gln Lys Ala Gln Gly Met
305 310 315 320

Pro Glu Gly Gly Gly Ala Leu Ala Glu Gly Phe Gln Val Arg Met Phe

```
                325                 330                 335

Glu Phe Gln Asn Phe Glu Arg Arg Phe Glu Glu Cys Ile Ser Gln Ser
            340                 345                 350

Ala Val Lys Thr Lys Phe Glu Gln His Thr Val Arg Ala Lys Gln Ile
        355                 360                 365

Ala Glu Ala Val Arg Leu Ile Met Asp Ser Leu His Met Ala Ala Arg
    370                 375                 380

Glu Gln Gln Val Tyr Cys Glu Glu Met Arg Glu Glu Arg Gln Asp Arg
385                 390                 395                 400

Leu Lys Phe Ile Asp Lys Gln Leu Glu Leu Leu Ala Gln Asp Tyr Lys
                405                 410                 415

Leu Arg Ile Lys Gln Ile Thr Glu Glu Val Glu Arg Gln Val Ser Thr
            420                 425                 430

Ala Met Ala Glu Glu Ile Arg Arg Leu Ser Val Leu Val Asp Asp Tyr
        435                 440                 445

Gln Met Asp Phe His Pro Ser Pro Val Val Leu Lys Val Tyr Lys Asn
    450                 455                 460

Glu Leu His Arg His Ile Glu Glu Gly Leu Gly Arg Asn Met Ser Asp
465                 470                 475                 480

Arg Cys Ser Thr Ala Ile Thr Asn Ser Leu Gln Thr Met Gln Gln Asp
                485                 490                 495

Met Ile Asp Gly Leu Lys Pro Leu Leu Pro Val Ser Val Arg Ser Gln
            500                 505                 510

Ile Asp Met Leu Val Pro Arg Gln Cys Phe Ser Leu Asn Tyr Asp Leu
        515                 520                 525

Asn Cys Asp Lys Leu Cys Ala Asp Phe Gln Glu Asp Ile Glu Phe His
    530                 535                 540

Phe Ser Leu Gly Trp Thr Met Leu Val Asn Arg Phe Leu Gly Pro Lys
545                 550                 555                 560

Asn Ser Arg Arg Ala Leu Met Gly Tyr Asn Asp Gln Val Gln Arg Pro
                565                 570                 575

Ile Pro Leu Thr Pro Ala Asn Pro Ser Met Pro Pro Leu Pro Gln Gly
            580                 585                 590

Ser Leu Thr Gln Glu Glu Phe Met Val Ser Met Val Thr Gly Leu Ala
        595                 600                 605

Ser Leu Thr Ser Arg Thr Ser Met Gly Ile Leu Val Val Gly Gly Val
    610                 615                 620

Val Trp Lys Ala Val Gly Trp Arg Leu Ile Ala Leu Ser Phe Gly Leu
625                 630                 635                 640

Tyr Gly Leu Leu Tyr Val Tyr Glu Arg Leu Thr Trp Thr Thr Lys Ala
                645                 650                 655

Lys Glu Arg Ala Phe Lys Arg Gln Phe Val Glu His Ala Ser Glu Lys
            660                 665                 670

Leu Gln Leu Val Ile Ser Tyr Thr Gly Ser Asn Cys Ser His Gln Val
        675                 680                 685

Gln Gln Glu Leu Ser Gly Thr Phe Ala His Leu Cys Gln Gln Val Asp
    690                 695                 700

Val Thr Arg Glu Asn Leu Glu Gln Glu Ile Ala Ala Met Asn Lys Lys
705                 710                 715                 720

Ile Glu Val Leu Asp Ser Leu Gln Ser Lys Ala Lys Leu Leu Arg Asn
                725                 730                 735

Lys Ala Gly Trp Leu Asp Ser Glu Leu Asn Met Phe Thr His Gln Tyr
            740                 745                 750
```

```
Leu Gln Pro Ser Arg
        755


<210> SEQ ID NO 24
<211> LENGTH: 20
<212> TYPE: DNA
<213> ORGANISM: Homo sapiens
<220> FEATURE:
<223> OTHER INFORMATION: Human mtDNA Forward Primer

<400> SEQUENCE: 24

cacccaagaa cagggtttgt                                                  20


<210> SEQ ID NO 25
<211> LENGTH: 20
<212> TYPE: DNA
<213> ORGANISM: Homo sapiens
<220> FEATURE:
<223> OTHER INFORMATION: Human mtDNA Reverse Primer

<400> SEQUENCE: 25

tggccatggg tatgttgtta                                                  20


<210> SEQ ID NO 26
<211> LENGTH: 25
<212> TYPE: DNA
<213> ORGANISM: Homo sapiens
<220> FEATURE:
<223> OTHER INFORMATION: Human nDNA Forward Primer

<400> SEQUENCE: 26

tgctgtctcc atgtttgatg tatct                                            25


<210> SEQ ID NO 27
<211> LENGTH: 22
<212> TYPE: DNA
<213> ORGANISM: Homo sapiens
<220> FEATURE:
<223> OTHER INFORMATION: Human nDNA Reverse Primer

<400> SEQUENCE: 27

tctctgctcc ccacctctaa gt                                               22
```